United States Patent
Soli et al.

(10) Patent No.: US 11,950,916 B2
(45) Date of Patent: Apr. 9, 2024

(54) USER INTERFACES FOR HEALTH MONITORING

(71) Applicant: Apple Inc., Cupertino, CA (US)

(72) Inventors: Christopher D. Soli, San Francisco, CA (US); Roxanne B. Brittain, San Francisco, CA (US); Gary Ian Butcher, Los Gatos, CA (US); Matthew W. Crowley, Sunnyvale, CA (US); Bradley W. Griffin, Aptos, CA (US); Heather E. Daniel, San Jose, CA (US); Stephen O. Lemay, Palo Alto, CA (US)

(73) Assignee: Apple Inc., Cupertino, CA (US)

( * ) Notice: Subject to any disclaimer, the term of this patent is extended or adjusted under 35 U.S.C. 154(b) by 380 days.

(21) Appl. No.: 17/135,710

(22) Filed: Dec. 28, 2020

(65) Prior Publication Data

US 2021/0113137 A1  Apr. 22, 2021

Related U.S. Application Data

(63) Continuation of application No. 16/144,030, filed on Sep. 27, 2018, now Pat. No. 11,039,778.

(Continued)

(51) Int. Cl.
*A61B 5/332* (2021.01)
*A61B 5/02* (2006.01)
(Continued)

(52) U.S. Cl.
CPC ............... *A61B 5/332* (2021.01); *A61B 5/02* (2013.01); *A61B 5/339* (2021.01); *G06F 1/163* (2013.01);
(Continued)

(58) Field of Classification Search
CPC ......... A61B 5/0404; A61B 5/02; G06F 9/453; G06F 1/163; G06F 3/017
See application file for complete search history.

(56) References Cited

U.S. PATENT DOCUMENTS 4,205,628 A  6/1980 Null
4,842,266 A  6/1989 Sweeney et al.
(Continued)

FOREIGN PATENT DOCUMENTS

AU  2013201390 B2  5/2015
CA  2815518 A1  5/2012
(Continued)

OTHER PUBLICATIONS

Notice of Acceptance received for Australian Patent Application No. 2022202459, dated May 11, 2023, 3 pages.
(Continued)

*Primary Examiner* — Scott Luan
(74) *Attorney, Agent, or Firm* — DLA Piper LLP (US)

(57) ABSTRACT

The present disclosure generally relates to user interfaces for health monitoring. Exemplary user interfaces for initial setup of health monitoring using a first electronic device and a second electronic device is described. Exemplary user interfaces for recording biometric information for use in health monitoring is described. Exemplary user interfaces for using an input device while recording biometric information for health monitoring is described. Exemplary user interfaces for viewing and managing aspects of health monitoring is described.

33 Claims, 76 Drawing Sheets

Related U.S. Application Data

(60) Provisional application No. 62/657,870, filed on Apr. 15, 2018, provisional application No. 62/657,881, filed on Apr. 15, 2018, provisional application No. 62/643,699, filed on Mar. 15, 2018, provisional application No. 62/641,994, filed on Mar. 12, 2018.

(51) Int. Cl.
　　A61B 5/339　　(2021.01)
　　G06F 1/16　　(2006.01)
　　G06F 3/01　　(2006.01)
　　G06F 3/0485　　(2022.01)
　　G06F 9/451　　(2018.01)
　　G06T 13/80　　(2011.01)

(52) U.S. Cl.
　　CPC ............ G06F 3/017 (2013.01); G06F 3/0485 (2013.01); G06F 9/453 (2018.02); G06T 13/80 (2013.01)

(56) References Cited

U.S. PATENT DOCUMENTS

| | | |
|---|---|---|
| 5,423,863 A | 6/1995 | Felblinger et al. |
| 5,458,548 A | 10/1995 | Crossing et al. |
| 5,474,077 A | 12/1995 | Suga |
| 5,515,344 A | 5/1996 | Ng |
| 5,642,731 A | 7/1997 | Kehr |
| 5,788,655 A | 8/1998 | Yoshimura et al. |
| 6,013,008 A | 1/2000 | Fukushima |
| 6,095,949 A | 8/2000 | Arai |
| 6,095,984 A | 8/2000 | Amano et al. |
| 6,097,371 A | 8/2000 | Siddiqui et al. |
| 6,097,385 A | 8/2000 | Robinson |
| 6,244,988 B1 | 6/2001 | Delman |
| 6,302,789 B2 | 10/2001 | Harada et al. |
| 6,416,471 B1 | 7/2002 | Kumar et al. |
| 6,600,696 B1 | 7/2003 | Lynn |
| 6,603,477 B1 | 8/2003 | Tittle |
| 6,639,584 B1 | 10/2003 | Li |
| 6,705,972 B1 | 3/2004 | Takano et al. |
| 6,837,827 B1 | 1/2005 | Lee |
| 6,866,613 B1 | 3/2005 | Brown et al. |
| 6,950,839 B1 | 9/2005 | Green et al. |
| 7,020,514 B1 | 3/2006 | Wiesel |
| 7,111,157 B1 | 9/2006 | Hooper |
| 7,128,693 B2 | 10/2006 | Brown et al. |
| 7,166,078 B2 | 1/2007 | Saini et al. |
| 7,251,454 B2 | 7/2007 | White |
| 7,302,272 B2 | 11/2007 | Ackley |
| 7,313,435 B2 | 12/2007 | Nakada et al. |
| 7,662,065 B1 | 2/2010 | Kahn et al. |
| 7,695,406 B2 | 4/2010 | Waters |
| 7,739,148 B2 | 6/2010 | Suzuki et al. |
| 7,771,320 B2 | 8/2010 | Riley et al. |
| 8,060,229 B2 | 11/2011 | Gupta et al. |
| 8,105,208 B2 | 1/2012 | Oleson et al. |
| 8,152,694 B2 | 4/2012 | Srinivasan et al. |
| 8,200,323 B2 | 6/2012 | Dibenedetto et al. |
| 8,321,006 B1 | 11/2012 | Snyder et al. |
| 8,341,557 B2 | 12/2012 | Pisula et al. |
| 8,475,339 B2 | 7/2013 | Hwang et al. |
| 8,496,563 B2 | 7/2013 | Komatsu et al. |
| 8,676,170 B2 | 3/2014 | Porrati et al. |
| 8,725,527 B1 | 5/2014 | Kahn et al. |
| 8,758,262 B2 | 6/2014 | Rhee et al. |
| 8,784,115 B1 | 7/2014 | Chuang |
| 8,825,445 B2 | 9/2014 | Hoffman et al. |
| 8,888,707 B2 | 11/2014 | Shirasaki et al. |
| 8,934,963 B1 | 1/2015 | Farazi |
| 8,990,006 B1 | 3/2015 | Wallace et al. |
| 9,011,292 B2 | 4/2015 | Weast et al. |
| 9,020,538 B1 | 4/2015 | White et al. |
| 9,026,927 B2 | 5/2015 | Brumback et al. |
| 9,224,291 B2 | 12/2015 | Moll-carrillo et al. |
| 9,230,076 B2 | 1/2016 | King et al. |
| 9,490,763 B2 | 11/2016 | Taniguchi et al. |
| 9,557,881 B1 | 1/2017 | Jain et al. |
| 9,579,060 B1 | 2/2017 | Lisy et al. |
| 9,589,445 B2 | 3/2017 | White et al. |
| 9,606,695 B2 | 3/2017 | Matas |
| 9,672,715 B2 | 6/2017 | Roberts et al. |
| 9,712,629 B2 | 7/2017 | Molettiere et al. |
| 9,721,066 B1 | 8/2017 | Funaro et al. |
| 9,730,621 B2 | 8/2017 | Cohen et al. |
| 9,801,562 B1 | 10/2017 | Host-madsen |
| 9,808,206 B1 | 11/2017 | Zhao et al. |
| 9,813,642 B1 | 11/2017 | Chen et al. |
| 9,854,653 B1 | 12/2017 | Ackmann et al. |
| 9,940,682 B2 | 4/2018 | Hoffman et al. |
| 10,004,451 B1 | 6/2018 | Proud |
| 10,056,006 B1 | 8/2018 | Hsu-hoffman et al. |
| 10,150,002 B2 | 12/2018 | Kass et al. |
| 10,175,781 B2 | 1/2019 | Karagozler et al. |
| 10,220,258 B2 | 3/2019 | Gu et al. |
| 10,226,195 B2 | 3/2019 | Briante et al. |
| 10,254,911 B2 | 4/2019 | Yang |
| 10,275,262 B1 | 4/2019 | Bull et al. |
| 10,339,830 B2 | 7/2019 | Han et al. |
| 10,365,811 B2 | 7/2019 | Robinson et al. |
| 10,398,381 B1 | 9/2019 | Heneghan et al. |
| 10,437,962 B2 | 10/2019 | Soni et al. |
| 10,568,533 B2 | 2/2020 | Soli et al. |
| 10,576,327 B2 | 3/2020 | Kim et al. |
| 10,592,088 B2 | 3/2020 | Robinson et al. |
| 10,602,964 B2 | 3/2020 | Kerber |
| 10,635,267 B2 | 4/2020 | Williams |
| 10,674,942 B2 | 6/2020 | Williams et al. |
| 10,685,090 B2 | 6/2020 | Petterson et al. |
| 10,736,543 B2 | 8/2020 | Chen et al. |
| 10,762,990 B1 | 9/2020 | Schilling et al. |
| 10,764,700 B1 | 9/2020 | Felton |
| 10,796,549 B2 | 10/2020 | Roberts et al. |
| 11,073,942 B2 | 7/2021 | Lee et al. |
| 11,107,569 B1 | 8/2021 | Devoto |
| 11,107,580 B1 | 8/2021 | Felton et al. |
| 11,209,957 B2 | 12/2021 | Dryer et al. |
| 2001/0049470 A1 | 12/2001 | Mault et al. |
| 2002/0045960 A1 | 4/2002 | Phillips et al. |
| 2002/0086774 A1 | 7/2002 | Warner |
| 2002/0095292 A1 | 7/2002 | Mittal et al. |
| 2002/0118121 A1 | 8/2002 | Lehrman et al. |
| 2003/0023178 A1 | 1/2003 | Bischoff et al. |
| 2003/0064860 A1 | 4/2003 | Yamashita et al. |
| 2003/0134714 A1 | 7/2003 | Oishi et al. |
| 2003/0179229 A1 | 9/2003 | Van et al. |
| 2003/0181291 A1 | 9/2003 | Ogawa |
| 2003/0191609 A1 | 10/2003 | Bernardi et al. |
| 2003/0200483 A1 | 10/2003 | Sutton |
| 2003/0216971 A1 | 11/2003 | Sick et al. |
| 2003/0226695 A1 | 12/2003 | Mault |
| 2004/0017300 A1 | 1/2004 | Kotzin et al. |
| 2004/0077958 A1 | 4/2004 | Kato et al. |
| 2004/0190729 A1 | 9/2004 | Yonovitz et al. |
| 2004/0193069 A1 | 9/2004 | Takehara |
| 2004/0210117 A1 | 10/2004 | Ueno et al. |
| 2004/0236189 A1 | 11/2004 | Hawthorne et al. |
| 2005/0010117 A1 | 1/2005 | Agutter et al. |
| 2005/0027208 A1 | 2/2005 | Shiraishi et al. |
| 2005/0075214 A1 | 4/2005 | Brown et al. |
| 2005/0079905 A1 | 4/2005 | Martens |
| 2005/0113650 A1 | 5/2005 | Pacione et al. |
| 2005/0124324 A1 | 6/2005 | Thomas et al. |
| 2005/0149362 A1 | 7/2005 | Peterson et al. |
| 2005/0165627 A1 | 7/2005 | Fotsch et al. |
| 2005/0228735 A1 | 10/2005 | Duquette |
| 2005/0244013 A1 | 11/2005 | Battenberg et al. |
| 2005/0272564 A1 | 12/2005 | Pyles et al. |
| 2006/0052727 A1 | 3/2006 | Palestrant |
| 2006/0094969 A1 | 5/2006 | Nissila |
| 2006/0098109 A1 | 5/2006 | Ooki |
| 2006/0106741 A1 | 5/2006 | Janarthanan |
| 2006/0136173 A1 | 6/2006 | Case, Jr. et al. |

(56) References Cited

U.S. PATENT DOCUMENTS

| | | |
|---|---|---|
| 2006/0149144 A1 | 7/2006 | Lynn et al. |
| 2006/0152372 A1 | 7/2006 | Stout |
| 2006/0160090 A1 | 7/2006 | Macina et al. |
| 2006/0182287 A1 | 8/2006 | Schulein et al. |
| 2006/0184800 A1 | 8/2006 | Rosenberg |
| 2006/0195039 A1 | 8/2006 | Panken et al. |
| 2006/0205564 A1 | 9/2006 | Peterson |
| 2006/0235319 A1 | 10/2006 | Belohlavek et al. |
| 2006/0240959 A1 | 10/2006 | Huang |
| 2006/0250524 A1 | 11/2006 | Roche |
| 2006/0274908 A1 | 12/2006 | Choi |
| 2007/0016440 A1 | 1/2007 | Stroup |
| 2007/0032733 A1 | 2/2007 | Burton |
| 2007/0033069 A1 | 2/2007 | Rao et al. |
| 2007/0056727 A1 | 3/2007 | Newman |
| 2007/0071256 A1 | 3/2007 | Ito |
| 2007/0143433 A1 | 6/2007 | Daigle |
| 2007/0169614 A1 | 7/2007 | Sasaki et al. |
| 2007/0179434 A1 | 8/2007 | Weinert et al. |
| 2007/0249949 A1 | 10/2007 | Hadley |
| 2007/0250505 A1 | 10/2007 | Yang et al. |
| 2007/0250613 A1 | 10/2007 | Gulledge |
| 2007/0274531 A1 | 11/2007 | Camp |
| 2008/0012701 A1 | 1/2008 | Kass et al. |
| 2008/0020803 A1 | 1/2008 | Rios et al. |
| 2008/0027673 A1 | 1/2008 | Trumm |
| 2008/0051919 A1 | 2/2008 | Sakai et al. |
| 2008/0052945 A1 | 3/2008 | Matas et al. |
| 2008/0058626 A1 | 3/2008 | Miyata et al. |
| 2008/0077073 A1 | 3/2008 | Keenan et al. |
| 2008/0082145 A1 | 4/2008 | Skwarek et al. |
| 2008/0096726 A1 | 4/2008 | Riley et al. |
| 2008/0133742 A1 | 6/2008 | Southiere et al. |
| 2008/0146892 A1 | 6/2008 | Leboeuf et al. |
| 2008/0159547 A1 | 7/2008 | Schuler et al. |
| 2008/0161161 A1 | 7/2008 | Pipinich et al. |
| 2008/0161707 A1 | 7/2008 | Farringdon et al. |
| 2008/0200312 A1 | 8/2008 | Tagliabue |
| 2008/0205660 A1 | 8/2008 | Goldstein |
| 2008/0228045 A1 | 9/2008 | Gao et al. |
| 2008/0229226 A1 | 9/2008 | Rowbottom et al. |
| 2008/0240519 A1 | 10/2008 | Nagamitsu |
| 2008/0254767 A1 | 10/2008 | Jin |
| 2008/0300110 A1 | 12/2008 | Smith et al. |
| 2009/0007017 A1 | 1/2009 | Anzures et al. |
| 2009/0007596 A1 | 1/2009 | Goldstein et al. |
| 2009/0012988 A1 | 1/2009 | Brown |
| 2009/0052677 A1 | 2/2009 | Smith |
| 2009/0065578 A1 | 3/2009 | Peterson et al. |
| 2009/0118100 A1 | 5/2009 | Oliver et al. |
| 2009/0170532 A1 | 7/2009 | Lee et al. |
| 2009/0180631 A1 | 7/2009 | Michael et al. |
| 2009/0210078 A1 | 8/2009 | Crowley |
| 2009/0216556 A1 | 8/2009 | Martin et al. |
| 2009/0222056 A1 | 9/2009 | Lindh et al. |
| 2009/0235253 A1 | 9/2009 | Hope |
| 2009/0245537 A1 | 10/2009 | Morin |
| 2009/0259134 A1 | 10/2009 | Levine |
| 2009/0262088 A1 | 10/2009 | Moll-carrillo et al. |
| 2009/0267776 A1 | 10/2009 | Glenn et al. |
| 2009/0287103 A1 | 11/2009 | Pillai |
| 2009/0287327 A1 | 11/2009 | Hsu et al. |
| 2009/0290721 A1 | 11/2009 | Goldstein et al. |
| 2010/0003951 A1 | 1/2010 | Ray et al. |
| 2010/0010832 A1 | 1/2010 | Boute et al. |
| 2010/0017489 A1 | 1/2010 | Birnbaum et al. |
| 2010/0027807 A1 | 2/2010 | Jeon |
| 2010/0046767 A1 | 2/2010 | Bayley et al. |
| 2010/0060586 A1 | 3/2010 | Pisula et al. |
| 2010/0062905 A1 | 3/2010 | Rottler et al. |
| 2010/0064255 A1 | 3/2010 | Rottler et al. |
| 2010/0073162 A1 | 3/2010 | Johnson et al. |
| 2010/0076331 A1 | 3/2010 | Chan et al. |
| 2010/0099539 A1 | 4/2010 | Haataja |
| 2010/0119093 A1 | 5/2010 | Uzuanis et al. |
| 2010/0121700 A1 | 5/2010 | Wigder et al. |
| 2010/0125306 A1 | 5/2010 | Mccabe et al. |
| 2010/0137106 A1 | 6/2010 | Oshima et al. |
| 2010/0145209 A1 | 6/2010 | Lee et al. |
| 2010/0145220 A1 | 6/2010 | Van |
| 2010/0150378 A1 | 6/2010 | Lee et al. |
| 2010/0222645 A1 | 9/2010 | Nadler et al. |
| 2010/0264097 A1 | 10/2010 | Sun et al. |
| 2010/0292600 A1 | 11/2010 | Dibenedetto et al. |
| 2010/0298899 A1 | 11/2010 | Donnelly et al. |
| 2010/0312138 A1 | 12/2010 | Regas |
| 2011/0032105 A1 | 2/2011 | Hoffman et al. |
| 2011/0057799 A1 | 3/2011 | Taneff |
| 2011/0066051 A1 | 3/2011 | Moon et al. |
| 2011/0071765 A1 | 3/2011 | Yodfat et al. |
| 2011/0071869 A1 | 3/2011 | Obrien et al. |
| 2011/0093481 A1 | 4/2011 | Hussam |
| 2011/0098928 A1 | 4/2011 | Hoffman et al. |
| 2011/0106553 A1 | 5/2011 | Tanaka et al. |
| 2011/0112418 A1 | 5/2011 | Feild et al. |
| 2011/0125041 A1 | 5/2011 | Fischell et al. |
| 2011/0137678 A1 | 6/2011 | Williams |
| 2011/0152656 A1 | 6/2011 | Weinert et al. |
| 2011/0159469 A1 | 6/2011 | Hwang et al. |
| 2011/0166631 A1 | 7/2011 | Breining |
| 2011/0167369 A1 | 7/2011 | Van |
| 2011/0195383 A1 | 8/2011 | Weiss |
| 2011/0214162 A1 | 9/2011 | Brakensiek et al. |
| 2011/0218407 A1 | 9/2011 | Haberman et al. |
| 2011/0230169 A1 | 9/2011 | Ohki |
| 2011/0245623 A1 | 10/2011 | Chutani et al. |
| 2011/0261079 A1 | 10/2011 | Ingrassia et al. |
| 2011/0275940 A1 | 11/2011 | Nims et al. |
| 2011/0306389 A1 | 12/2011 | Nagayama |
| 2011/0307821 A1 | 12/2011 | Martens |
| 2012/0002510 A1 | 1/2012 | Berman, Jr. |
| 2012/0015778 A1 | 1/2012 | Lee et al. |
| 2012/0015779 A1 | 1/2012 | Powch et al. |
| 2012/0029303 A1 | 2/2012 | Shaya |
| 2012/0034897 A1 | 2/2012 | Kreitzer et al. |
| 2012/0038651 A1 | 2/2012 | Case et al. |
| 2012/0041767 A1 | 2/2012 | Hoffman et al. |
| 2012/0042039 A1 | 2/2012 | Mark |
| 2012/0059664 A1 | 3/2012 | Georgiev et al. |
| 2012/0065480 A1 | 3/2012 | Badilini et al. |
| 2012/0071770 A1 | 3/2012 | Grey et al. |
| 2012/0112908 A1 | 5/2012 | Prykaeri et al. |
| 2012/0116550 A1 | 5/2012 | Hoffman et al. |
| 2012/0150759 A1 | 6/2012 | Tarjan |
| 2012/0159380 A1 | 6/2012 | Kocienda et al. |
| 2012/0179319 A1 | 7/2012 | Gilman et al. |
| 2012/0203124 A1 | 8/2012 | Lim |
| 2012/0215115 A1 | 8/2012 | Takahashi |
| 2012/0232414 A1 | 9/2012 | Mollicone et al. |
| 2012/0245447 A1 | 9/2012 | Karan et al. |
| 2012/0283524 A1 | 11/2012 | Kiani et al. |
| 2012/0283587 A1 | 11/2012 | Gosh et al. |
| 2012/0283855 A1 | 11/2012 | Hoffman et al. |
| 2012/0290109 A1 | 11/2012 | Engelberg et al. |
| 2012/0302843 A1 | 11/2012 | Otsubo et al. |
| 2012/0311585 A1 | 12/2012 | Gruber et al. |
| 2012/0316455 A1 | 12/2012 | Rahman et al. |
| 2012/0317167 A1 | 12/2012 | Rahman et al. |
| 2012/0321094 A1 | 12/2012 | Schiller et al. |
| 2013/0002425 A1 | 1/2013 | Hatch et al. |
| 2013/0011819 A1 | 1/2013 | Horseman |
| 2013/0012788 A1 | 1/2013 | Horseman |
| 2013/0013331 A1 | 1/2013 | Horseman |
| 2013/0033376 A1 | 2/2013 | Seyed et al. |
| 2013/0054150 A1 | 2/2013 | Sacks et al. |
| 2013/0054720 A1 | 2/2013 | Kang et al. |
| 2013/0065569 A1 | 3/2013 | Leipzig et al. |
| 2013/0067050 A1 | 3/2013 | Kotteri et al. |
| 2013/0072765 A1 | 3/2013 | Kahn et al. |
| 2013/0073933 A1 | 3/2013 | Eppolito |
| 2013/0073960 A1 | 3/2013 | Eppolito et al. |
| 2013/0095459 A1 | 4/2013 | Tran |
| 2013/0110264 A1 | 5/2013 | Weast et al. |
| 2013/0114100 A1 | 5/2013 | Torii et al. |

(56) References Cited

U.S. PATENT DOCUMENTS

| | | |
|---|---|---|
| 2013/0115583 A1 | 5/2013 | Gordon et al. |
| 2013/0138734 A1 | 5/2013 | Crivello et al. |
| 2013/0144653 A1 | 6/2013 | Poe et al. |
| 2013/0151285 A1 | 6/2013 | Mclaren et al. |
| 2013/0158367 A1 | 6/2013 | Pacione et al. |
| 2013/0158416 A1 | 6/2013 | Hatlestad et al. |
| 2013/0185097 A1 | 7/2013 | Saria et al. |
| 2013/0197679 A1 | 8/2013 | Balakrishnan et al. |
| 2013/0202121 A1 | 8/2013 | Georgiou et al. |
| 2013/0215042 A1 | 8/2013 | Messerschmidt et al. |
| 2013/0215119 A1 | 8/2013 | Vanhoecke |
| 2013/0231575 A1 | 9/2013 | Erkkila et al. |
| 2013/0231711 A1 | 9/2013 | Kaib |
| 2013/0231947 A1 | 9/2013 | Shusterman |
| 2013/0263719 A1 | 10/2013 | Watterson et al. |
| 2013/0268398 A1 | 10/2013 | Agami et al. |
| 2013/0274628 A1 | 10/2013 | Fausti et al. |
| 2013/0304616 A1 | 11/2013 | Raleigh et al. |
| 2013/0317380 A1 | 11/2013 | Liley et al. |
| 2013/0324210 A1 | 12/2013 | Doig et al. |
| 2013/0325358 A1 | 12/2013 | Oshima et al. |
| 2013/0325396 A1 | 12/2013 | Yuen et al. |
| 2013/0330694 A1 | 12/2013 | Watterson |
| 2013/0332286 A1 | 12/2013 | Medelius et al. |
| 2014/0005947 A1 | 1/2014 | Jeon et al. |
| 2014/0037107 A1 | 2/2014 | Marino et al. |
| 2014/0038781 A1 | 2/2014 | Foley et al. |
| 2014/0039840 A1 | 2/2014 | Yuen et al. |
| 2014/0073486 A1 | 3/2014 | Ahmed et al. |
| 2014/0081118 A1 | 3/2014 | Reinhold et al. |
| 2014/0088995 A1 | 3/2014 | Damani |
| 2014/0089836 A1 | 3/2014 | Damani et al. |
| 2014/0108998 A1 | 4/2014 | Chaudhri et al. |
| 2014/0127996 A1 | 5/2014 | Park et al. |
| 2014/0129007 A1 | 5/2014 | Utter |
| 2014/0129243 A1 | 5/2014 | Utter, II |
| 2014/0135592 A1 | 5/2014 | Ohnemus et al. |
| 2014/0142403 A1 | 5/2014 | Brumback et al. |
| 2014/0143678 A1 | 5/2014 | Mistry et al. |
| 2014/0164611 A1 | 6/2014 | Molettiere et al. |
| 2014/0173521 A1 | 6/2014 | Mayor |
| 2014/0176335 A1 | 6/2014 | Brumback et al. |
| 2014/0176475 A1 | 6/2014 | Myers et al. |
| 2014/0180595 A1 | 6/2014 | Brumback et al. |
| 2014/0180786 A1 | 6/2014 | Sullivan |
| 2014/0184422 A1 | 7/2014 | Mensinger et al. |
| 2014/0189510 A1 | 7/2014 | Ozcan |
| 2014/0197946 A1 | 7/2014 | Park et al. |
| 2014/0200426 A1 | 7/2014 | Taub et al. |
| 2014/0200691 A1 | 7/2014 | Lee et al. |
| 2014/0240122 A1 | 8/2014 | Roberts et al. |
| 2014/0240349 A1 | 8/2014 | Tuukkanen |
| 2014/0266776 A1 | 9/2014 | Miller et al. |
| 2014/0274413 A1 | 9/2014 | Chelst |
| 2014/0275852 A1 | 9/2014 | Hong et al. |
| 2014/0275854 A1 | 9/2014 | Venkatraman et al. |
| 2014/0275856 A1 | 9/2014 | Kohlrausch et al. |
| 2014/0278220 A1 | 9/2014 | Yuen |
| 2014/0288390 A1 | 9/2014 | Hong et al. |
| 2014/0297217 A1 | 10/2014 | Yuen |
| 2014/0310598 A1 | 10/2014 | Sprague et al. |
| 2014/0310643 A1 | 10/2014 | Karmanenko et al. |
| 2014/0327527 A1 | 11/2014 | Goldstein et al. |
| 2014/0331314 A1 | 11/2014 | Fujioka |
| 2014/0336796 A1 | 11/2014 | Agnew |
| 2014/0337041 A1 | 11/2014 | Madden et al. |
| 2014/0344687 A1 | 11/2014 | Durham et al. |
| 2014/0354494 A1 | 12/2014 | Katz |
| 2014/0358012 A1 | 12/2014 | Richards et al. |
| 2014/0358473 A1 | 12/2014 | Goel et al. |
| 2014/0358584 A1 | 12/2014 | Worden et al. |
| 2014/0371887 A1 | 12/2014 | Hoffman et al. |
| 2015/0004578 A1 | 1/2015 | Gilley et al. |
| 2015/0018632 A1 | 1/2015 | Khair |
| 2015/0046814 A1 | 2/2015 | Haughay et al. |
| 2015/0057942 A1 | 2/2015 | Self et al. |
| 2015/0058263 A1 | 2/2015 | Landers |
| 2015/0065095 A1 | 3/2015 | Seo et al. |
| 2015/0067513 A1 | 3/2015 | Zambetti et al. |
| 2015/0073285 A1 | 3/2015 | Albert et al. |
| 2015/0081060 A1 | 3/2015 | Hwang et al. |
| 2015/0081210 A1 | 3/2015 | Yeh et al. |
| 2015/0081529 A1 | 3/2015 | Lee et al. |
| 2015/0089536 A1 | 3/2015 | Byerley |
| 2015/0099991 A1 | 4/2015 | Yamaguchi et al. |
| 2015/0100348 A1 | 4/2015 | Connery et al. |
| 2015/0106025 A1 | 4/2015 | Keller et al. |
| 2015/0110277 A1 | 4/2015 | Pidgeon et al. |
| 2015/0110279 A1 | 4/2015 | Tejerina |
| 2015/0113553 A1 | 4/2015 | Pan |
| 2015/0120633 A1 | 4/2015 | Norlander et al. |
| 2015/0124067 A1 | 5/2015 | Bala et al. |
| 2015/0125832 A1 | 5/2015 | Tran |
| 2015/0127365 A1 | 5/2015 | Rizvi et al. |
| 2015/0130830 A1 | 5/2015 | Nagasaki et al. |
| 2015/0142689 A1 | 5/2015 | Squires |
| 2015/0164349 A1 | 6/2015 | Gopalakrishnan et al. |
| 2015/0173686 A1 | 6/2015 | Furuta et al. |
| 2015/0179186 A1 | 6/2015 | Swierk et al. |
| 2015/0180746 A1 | 6/2015 | Day et al. |
| 2015/0181314 A1 | 6/2015 | Swanson |
| 2015/0182843 A1 | 7/2015 | Esposito et al. |
| 2015/0185967 A1 | 7/2015 | Ly et al. |
| 2015/0193217 A1 | 7/2015 | Xiang et al. |
| 2015/0196804 A1 | 7/2015 | Koduri et al. |
| 2015/0205930 A1 | 7/2015 | Shaanan et al. |
| 2015/0205947 A1 | 7/2015 | Berman et al. |
| 2015/0216448 A1 | 8/2015 | Lotan et al. |
| 2015/0217163 A1 | 8/2015 | Amis et al. |
| 2015/0220883 A1 | 8/2015 | Bfar et al. |
| 2015/0230717 A1 | 8/2015 | Wan |
| 2015/0251053 A1 | 9/2015 | Hoffman et al. |
| 2015/0261918 A1 | 9/2015 | Thornbury, Jr. |
| 2015/0262499 A1 | 9/2015 | Wicka et al. |
| 2015/0269848 A1 | 9/2015 | Yuen et al. |
| 2015/0286800 A1 | 10/2015 | Kanagala et al. |
| 2015/0287421 A1 | 10/2015 | Benway et al. |
| 2015/0288797 A1 | 10/2015 | Vincent |
| 2015/0288944 A1 | 10/2015 | Nistico et al. |
| 2015/0289823 A1 | 10/2015 | Rack-gomer et al. |
| 2015/0297134 A1 | 10/2015 | Albert et al. |
| 2015/0324751 A1 | 11/2015 | Orenstein et al. |
| 2015/0343709 A1 | 12/2015 | Gerstle et al. |
| 2015/0347690 A1 | 12/2015 | Keen et al. |
| 2015/0347711 A1 | 12/2015 | Soli et al. |
| 2015/0350799 A1 | 12/2015 | Schnaare et al. |
| 2015/0350861 A1 | 12/2015 | Soli et al. |
| 2015/0351655 A1 | 12/2015 | Coleman |
| 2015/0374310 A1 | 12/2015 | Lee |
| 2016/0000379 A1 | 1/2016 | Pougatchev et al. |
| 2016/0004432 A1 | 1/2016 | Bernstein et al. |
| 2016/0015275 A1 | 1/2016 | Samadani et al. |
| 2016/0019360 A1 | 1/2016 | Pahwa et al. |
| 2016/0027282 A1 | 1/2016 | Lee |
| 2016/0055420 A1 | 2/2016 | Karanam et al. |
| 2016/0058313 A1 | 3/2016 | Sato |
| 2016/0058336 A1 | 3/2016 | Blahnik et al. |
| 2016/0058337 A1 | 3/2016 | Blahnik et al. |
| 2016/0062540 A1 | 3/2016 | Yang et al. |
| 2016/0062582 A1 | 3/2016 | Wilson et al. |
| 2016/0063215 A1 | 3/2016 | Zamer |
| 2016/0066842 A1 | 3/2016 | Kokkoneva et al. |
| 2016/0070275 A1 | 3/2016 | Anderson et al. |
| 2016/0072896 A1 | 3/2016 | Petersen et al. |
| 2016/0085937 A1 | 3/2016 | Dettinger et al. |
| 2016/0086500 A1 | 3/2016 | Kaleal, III |
| 2016/0098522 A1 | 4/2016 | Weinstein |
| 2016/0103985 A1 | 4/2016 | Shim et al. |
| 2016/0106398 A1 | 4/2016 | Kuppuswami |
| 2016/0107031 A1 | 4/2016 | Palatsi et al. |
| 2016/0109961 A1 | 4/2016 | Parshionikar |
| 2016/0132046 A1 | 5/2016 | Beoughter et al. |
| 2016/0135719 A1 | 5/2016 | Von Kraus et al. |
| 2016/0135731 A1 | 5/2016 | Drennan |

(56) References Cited

U.S. PATENT DOCUMENTS

| | | |
|---|---|---|
| 2016/0140828 A1 | 5/2016 | Deforest |
| 2016/0150978 A1 | 6/2016 | Yuen et al. |
| 2016/0156584 A1 | 6/2016 | Hum et al. |
| 2016/0166181 A1 | 6/2016 | Shennib |
| 2016/0166195 A1 | 6/2016 | Radecka et al. |
| 2016/0174857 A1 | 6/2016 | Eggers et al. |
| 2016/0180026 A1 | 6/2016 | Kim et al. |
| 2016/0189051 A1 | 6/2016 | Mahmood |
| 2016/0196635 A1 | 7/2016 | Cho et al. |
| 2016/0210099 A1 | 7/2016 | Hampapuram et al. |
| 2016/0220225 A1 | 8/2016 | Wang et al. |
| 2016/0235325 A1 | 8/2016 | Chou |
| 2016/0235374 A1 | 8/2016 | Miller et al. |
| 2016/0246880 A1 | 8/2016 | Battiah et al. |
| 2016/0249857 A1 | 9/2016 | Choi et al. |
| 2016/0249864 A1 | 9/2016 | Kang et al. |
| 2016/0250517 A1 | 9/2016 | Tilvis et al. |
| 2016/0256082 A1 | 9/2016 | Ely et al. |
| 2016/0256741 A1 | 9/2016 | Holma et al. |
| 2016/0263435 A1 | 9/2016 | Venkatraman et al. |
| 2016/0270717 A1 | 9/2016 | Luna et al. |
| 2016/0270740 A1 | 9/2016 | Raisoni et al. |
| 2016/0275990 A1 | 9/2016 | Vassort |
| 2016/0278659 A1 | 9/2016 | Kaib et al. |
| 2016/0278667 A1 | 9/2016 | Villard et al. |
| 2016/0279475 A1 | 9/2016 | Aragones et al. |
| 2016/0285985 A1 | 9/2016 | Molettiere et al. |
| 2016/0287177 A1 | 10/2016 | Huppert et al. |
| 2016/0292373 A1 | 10/2016 | Spors et al. |
| 2016/0299769 A1 | 10/2016 | Hunter et al. |
| 2016/0301761 A1 | 10/2016 | Sanchez-sandoval et al. |
| 2016/0301794 A1 | 10/2016 | Schlakman et al. |
| 2016/0302666 A1 | 10/2016 | Shaya |
| 2016/0302717 A1 | 10/2016 | Tawa et al. |
| 2016/0313869 A1 | 10/2016 | Jang et al. |
| 2016/0314670 A1 | 10/2016 | Roberts et al. |
| 2016/0314683 A1 | 10/2016 | Felch et al. |
| 2016/0317341 A1 | 11/2016 | Galvan |
| 2016/0324457 A1 | 11/2016 | Dagum |
| 2016/0324488 A1 | 11/2016 | Olsen |
| 2016/0328736 A1 | 11/2016 | Wang et al. |
| 2016/0328991 A1 | 11/2016 | Simpson et al. |
| 2016/0332025 A1 | 11/2016 | Repka |
| 2016/0346607 A1 | 12/2016 | Rapfogel |
| 2016/0357616 A1 | 12/2016 | Yu et al. |
| 2016/0360100 A1 | 12/2016 | Kim et al. |
| 2016/0360972 A1 | 12/2016 | Kusakabe et al. |
| 2016/0367138 A1 | 12/2016 | Kim et al. |
| 2016/0371464 A1 | 12/2016 | Bricker |
| 2016/0375306 A1 | 12/2016 | Gu et al. |
| 2017/0000348 A1 | 1/2017 | Karsten et al. |
| 2017/0000359 A1 | 1/2017 | Kohli et al. |
| 2017/0001073 A1 | 1/2017 | Krueger et al. |
| 2017/0007159 A1 | 1/2017 | Dieffenderfer et al. |
| 2017/0007167 A1 | 1/2017 | Kostic et al. |
| 2017/0014037 A1 | 1/2017 | Coppola et al. |
| 2017/0021184 A1 | 1/2017 | Pavel et al. |
| 2017/0024399 A1 | 1/2017 | Boyle et al. |
| 2017/0024539 A1 | 1/2017 | Webb et al. |
| 2017/0032168 A1 | 2/2017 | Kim |
| 2017/0039327 A1 | 2/2017 | Bitran et al. |
| 2017/0042485 A1 | 2/2017 | Chung et al. |
| 2017/0043214 A1 | 2/2017 | Higashi |
| 2017/0046024 A1 | 2/2017 | Dascola et al. |
| 2017/0046052 A1 | 2/2017 | Lee et al. |
| 2017/0053542 A1 | 2/2017 | Wilson et al. |
| 2017/0065224 A1 | 3/2017 | Rahko et al. |
| 2017/0070833 A1 | 3/2017 | Shennib |
| 2017/0071551 A1 | 3/2017 | Jain et al. |
| 2017/0075551 A1 | 3/2017 | Robinson et al. |
| 2017/0084196 A1 | 3/2017 | Nusbaum et al. |
| 2017/0086693 A1 | 3/2017 | Peterson et al. |
| 2017/0091567 A1 | 3/2017 | Wang et al. |
| 2017/0095695 A1 | 4/2017 | Mangusson et al. |
| 2017/0127997 A1 | 5/2017 | Hyde et al. |
| 2017/0132395 A1 | 5/2017 | Futch |
| 2017/0136297 A1 | 5/2017 | Penie |
| 2017/0143262 A1 | 5/2017 | Kurunmäki et al. |
| 2017/0147197 A1 | 5/2017 | Yang et al. |
| 2017/0150917 A1 | 6/2017 | Brief et al. |
| 2017/0156593 A1 | 6/2017 | Ferber et al. |
| 2017/0161014 A1 | 6/2017 | Kikugawa et al. |
| 2017/0172522 A1 | 6/2017 | Insler et al. |
| 2017/0177797 A1 | 6/2017 | Kumniawan et al. |
| 2017/0181645 A1 | 6/2017 | Mahalingam et al. |
| 2017/0181678 A1 | 6/2017 | Newberry |
| 2017/0188841 A1 | 7/2017 | Ma et al. |
| 2017/0188893 A1 | 7/2017 | Venkatraman et al. |
| 2017/0188979 A1 | 7/2017 | Volpe |
| 2017/0202496 A1 | 7/2017 | Ramanathan |
| 2017/0215811 A1 | 8/2017 | Newberry |
| 2017/0225034 A1 | 8/2017 | Kass et al. |
| 2017/0235443 A1 | 8/2017 | Suzuki |
| 2017/0237694 A1 | 8/2017 | Choudhary et al. |
| 2017/0239524 A1 | 8/2017 | Lee et al. |
| 2017/0243508 A1 | 8/2017 | Cheng et al. |
| 2017/0258455 A1 | 9/2017 | Qi |
| 2017/0266494 A1 | 9/2017 | Crankson et al. |
| 2017/0269792 A1 | 9/2017 | Xu et al. |
| 2017/0274149 A1 | 9/2017 | Aeschlimann |
| 2017/0274267 A1 | 9/2017 | Blahnik |
| 2017/0281026 A1 | 10/2017 | Nick et al. |
| 2017/0287313 A1 | 10/2017 | Park et al. |
| 2017/0293727 A1 | 10/2017 | Klaassen et al. |
| 2017/0294174 A1 | 10/2017 | Albadawi et al. |
| 2017/0300186 A1 | 10/2017 | Kuhar et al. |
| 2017/0301039 A1 | 10/2017 | Dyer et al. |
| 2017/0303844 A1 | 10/2017 | Baker et al. |
| 2017/0319184 A1 | 11/2017 | Sano |
| 2017/0319941 A1 | 11/2017 | Smith et al. |
| 2017/0329933 A1 | 11/2017 | Brust et al. |
| 2017/0330297 A1 | 11/2017 | Cronin et al. |
| 2017/0332980 A1 | 11/2017 | Fifield et al. |
| 2017/0337033 A1 | 11/2017 | Duyan et al. |
| 2017/0348562 A1 | 12/2017 | Jung et al. |
| 2017/0354845 A1 | 12/2017 | Williams et al. |
| 2017/0357329 A1 | 12/2017 | Park et al. |
| 2017/0357520 A1 | 12/2017 | De Vries et al. |
| 2017/0364637 A1 | 12/2017 | Kshepakaran et al. |
| 2018/0000426 A1 | 1/2018 | Li |
| 2018/0001184 A1 | 1/2018 | Tran et al. |
| 2018/0011686 A1 | 1/2018 | Zhao et al. |
| 2018/0032234 A1 | 2/2018 | Michalske |
| 2018/0039410 A1 | 2/2018 | Kim et al. |
| 2018/0042559 A1 | 2/2018 | Cabrera et al. |
| 2018/0047277 A1 | 2/2018 | Thyroff |
| 2018/0049659 A1 | 2/2018 | Briante et al. |
| 2018/0049696 A1 | 2/2018 | Eom et al. |
| 2018/0053200 A1 | 2/2018 | Cronin et al. |
| 2018/0055490 A1 | 3/2018 | Lee et al. |
| 2018/0056130 A1 | 3/2018 | Bitran et al. |
| 2018/0060522 A1 | 3/2018 | Petterson et al. |
| 2018/0064356 A1 | 3/2018 | Mendenhall et al. |
| 2018/0064388 A1 | 3/2018 | Heneghan et al. |
| 2018/0065025 A1 | 3/2018 | Toda et al. |
| 2018/0070861 A1 | 3/2018 | Eastman et al. |
| 2018/0074462 A1 | 3/2018 | Helder et al. |
| 2018/0074464 A1 | 3/2018 | Essery et al. |
| 2018/0078182 A1 | 3/2018 | Chen et al. |
| 2018/0081918 A1 | 3/2018 | Gravenites et al. |
| 2018/0096739 A1 | 4/2018 | Sano |
| 2018/0107962 A1 | 4/2018 | Lundin et al. |
| 2018/0117414 A1 | 5/2018 | Miyasaka et al. |
| 2018/0120985 A1 | 5/2018 | Wallace et al. |
| 2018/0122214 A1 | 5/2018 | Freedman et al. |
| 2018/0132768 A1 | 5/2018 | Sasahara et al. |
| 2018/0137937 A1 | 5/2018 | Gass et al. |
| 2018/0140211 A1 | 5/2018 | Nakazawa et al. |
| 2018/0140903 A1 | 5/2018 | Poure et al. |
| 2018/0140927 A1 | 5/2018 | Kito et al. |
| 2018/0154212 A1 | 6/2018 | Park et al. |
| 2018/0189077 A1 | 7/2018 | Gupta et al. |
| 2018/0189343 A1 | 7/2018 | Embiricos et al. |
| 2018/0206766 A1 | 7/2018 | Blahnik et al. |

(56) References Cited

U.S. PATENT DOCUMENTS

| | | |
|---|---|---|
| 2018/0211020 A1 | 7/2018 | Fukuda |
| 2018/0226150 A1 | 8/2018 | Hayter et al. |
| 2018/0239869 A1 | 8/2018 | Laing et al. |
| 2018/0255159 A1 | 9/2018 | Cohen et al. |
| 2018/0256036 A1 | 9/2018 | Kogure et al. |
| 2018/0256078 A1 | 9/2018 | Vaterlaus |
| 2018/0256095 A1 | 9/2018 | Arnold et al. |
| 2018/0263510 A1 | 9/2018 | Cronin et al. |
| 2018/0263517 A1 | 9/2018 | Kubo |
| 2018/0272190 A1 | 9/2018 | Miura et al. |
| 2018/0279885 A1 | 10/2018 | Bulut |
| 2018/0294053 A1 | 10/2018 | Runyon et al. |
| 2018/0318647 A1 | 11/2018 | Foley et al. |
| 2018/0329584 A1 | 11/2018 | Williams et al. |
| 2018/0336530 A1 | 11/2018 | Johnson et al. |
| 2018/0339195 A1 | 11/2018 | Bernotas |
| 2018/0345078 A1 | 12/2018 | Blahnik et al. |
| 2018/0350451 A1 | 12/2018 | Ohnemus et al. |
| 2018/0368814 A1 | 12/2018 | R. Kudtarkar |
| 2018/0376107 A1 | 12/2018 | Shibaev et al. |
| 2019/0008467 A1 | 1/2019 | Averina et al. |
| 2019/0012898 A1 | 1/2019 | Wittrup |
| 2019/0014205 A1 | 1/2019 | Miloseski et al. |
| 2019/0018588 A1 | 1/2019 | Debates et al. |
| 2019/0025995 A1 | 1/2019 | Williams |
| 2019/0034049 A1 | 1/2019 | Williams et al. |
| 2019/0034050 A1 | 1/2019 | Williams et al. |
| 2019/0034494 A1 | 1/2019 | Bradley et al. |
| 2019/0043337 A1 | 2/2019 | Liu et al. |
| 2019/0073618 A1 | 3/2019 | Kanukurthy et al. |
| 2019/0089701 A1 | 3/2019 | Mercury et al. |
| 2019/0090800 A1 | 3/2019 | Bosworth et al. |
| 2019/0090816 A1 | 3/2019 | Horseman |
| 2019/0104951 A1 | 4/2019 | Valys et al. |
| 2019/0108908 A1 | 4/2019 | Faulks et al. |
| 2019/0122523 A1 | 4/2019 | Roberts et al. |
| 2019/0138696 A1 | 5/2019 | Carpenter et al. |
| 2019/0150854 A1 | 5/2019 | Chung et al. |
| 2019/0184234 A1 | 6/2019 | Packles et al. |
| 2019/0192086 A1 | 6/2019 | Menon et al. |
| 2019/0206538 A1 | 7/2019 | Xing et al. |
| 2019/0209777 A1 | 7/2019 | O'connell et al. |
| 2019/0223843 A1 | 7/2019 | Vitti |
| 2019/0228179 A1 | 7/2019 | Rakshit et al. |
| 2019/0228640 A1 | 7/2019 | Freedman et al. |
| 2019/0232111 A1 | 8/2019 | Williams et al. |
| 2019/0240534 A1 | 8/2019 | Black |
| 2019/0252054 A1 | 8/2019 | Dirani et al. |
| 2019/0274562 A1 | 9/2019 | Soli et al. |
| 2019/0274563 A1 | 9/2019 | Soli et al. |
| 2019/0274564 A1 | 9/2019 | Soli et al. |
| 2019/0274565 A1 | 9/2019 | Soli et al. |
| 2019/0278556 A1 | 9/2019 | Usher et al. |
| 2019/0279520 A1 | 9/2019 | Wilson et al. |
| 2019/0298230 A1 | 10/2019 | Nicholson et al. |
| 2019/0302995 A1 | 10/2019 | Robinson et al. |
| 2019/0333614 A1 | 10/2019 | Burger et al. |
| 2019/0336044 A1 | 11/2019 | Williams et al. |
| 2019/0336045 A1 | 11/2019 | Williams et al. |
| 2019/0336827 A1 | 11/2019 | Intonato et al. |
| 2019/0339849 A1 | 11/2019 | Williams et al. |
| 2019/0342616 A1 | 11/2019 | Domm et al. |
| 2019/0365332 A1 | 12/2019 | Fedichev et al. |
| 2019/0380624 A1 | 12/2019 | Ota et al. |
| 2019/0385708 A1 | 12/2019 | Hong et al. |
| 2019/0387982 A1 | 12/2019 | Buller |
| 2020/0000441 A1 | 1/2020 | Lafon et al. |
| 2020/0014967 A1 | 1/2020 | Putnam |
| 2020/0054931 A1 | 2/2020 | Martin et al. |
| 2020/0069258 A1 | 3/2020 | Grinberg |
| 2020/0098278 A1 | 3/2020 | Doti et al. |
| 2020/0100693 A1 | 4/2020 | Velo |
| 2020/0101365 A1 | 4/2020 | Wilson et al. |
| 2020/0126673 A1 | 4/2020 | Tanabe et al. |
| 2020/0203012 A1 | 6/2020 | Kamath et al. |
| 2020/0214650 A1 | 7/2020 | Lee et al. |
| 2020/0245928 A1 | 8/2020 | Kang et al. |
| 2020/0261011 A1 | 8/2020 | Seppänen et al. |
| 2020/0273566 A1 | 8/2020 | Bhowmik et al. |
| 2020/0297249 A1 | 9/2020 | Williams et al. |
| 2020/0315544 A1 | 10/2020 | Levine |
| 2020/0323441 A1 | 10/2020 | Deno et al. |
| 2020/0350052 A1 | 11/2020 | Saint et al. |
| 2020/0356242 A1 | 11/2020 | Wilson et al. |
| 2020/0356687 A1 | 11/2020 | Salzman et al. |
| 2020/0374682 A1 | 11/2020 | Newman et al. |
| 2020/0379611 A1 | 12/2020 | Dryer et al. |
| 2020/0381099 A1 | 12/2020 | Crowley et al. |
| 2020/0381123 A1 | 12/2020 | Dryer et al. |
| 2020/0382866 A1 | 12/2020 | Felton |
| 2020/0382867 A1 | 12/2020 | Felton |
| 2020/0384314 A1 | 12/2020 | Lee et al. |
| 2021/0019713 A1 | 1/2021 | Vangala et al. |
| 2021/0068714 A1 | 3/2021 | Crowley et al. |
| 2021/0110908 A1 | 4/2021 | Blahnik et al. |
| 2021/0191584 A1 | 6/2021 | Williams et al. |
| 2021/0204815 A1 | 7/2021 | Koskela et al. |
| 2021/0225482 A1 | 7/2021 | Crowley et al. |
| 2021/0255826 A1 | 8/2021 | Devine et al. |
| 2021/0287520 A1 | 9/2021 | Maeda et al. |
| 2021/0369130 A1 | 12/2021 | Felton et al. |
| 2021/0373746 A1 | 12/2021 | Felton et al. |
| 2021/0373747 A1 | 12/2021 | Felton et al. |
| 2021/0373748 A1 | 12/2021 | Felton et al. |
| 2021/0375157 A1 | 12/2021 | Sundstrom et al. |
| 2021/0375450 A1 | 12/2021 | Felton et al. |
| 2022/0047250 A1 | 2/2022 | Clements et al. |
| 2022/0047918 A1 | 2/2022 | Williams et al. |
| 2022/0066902 A1 | 3/2022 | Narra et al. |
| 2022/0109932 A1 | 4/2022 | Felton et al. |
| 2022/0142515 A1 | 5/2022 | Crowley |
| 2022/0157143 A1 | 5/2022 | Selvam et al. |
| 2022/0160258 A1 | 5/2022 | Williams et al. |
| 2022/0273204 A1 | 9/2022 | Kamath et al. |
| 2023/0016144 A1 | 1/2023 | Dryer et al. |
| 2023/0020517 A1 | 1/2023 | Narra et al. |
| 2023/0101625 A1 | 3/2023 | Soli et al. |
| 2023/0114054 A1 | 4/2023 | Crowley et al. |
| 2023/0136700 A1 | 5/2023 | Williams et al. |
| 2023/0389806 A1 | 12/2023 | Felton et al. |

FOREIGN PATENT DOCUMENTS

| | | |
|---|---|---|
| CN | 102448555 A | 5/2012 |
| CN | 103191557 A | 7/2013 |
| CN | 103250158 A | 8/2013 |
| CN | 103403627 A | 11/2013 |
| CN | 103474080 A | 12/2013 |
| CN | 103561640 A | 2/2014 |
| CN | 103927175 A | 7/2014 |
| CN | 103986813 A | 8/2014 |
| CN | 104720765 A | 6/2015 |
| CN | 105260078 A | 1/2016 |
| CN | 105320454 A | 2/2016 |
| CN | 105388998 A | 3/2016 |
| CN | 105632508 A | 6/2016 |
| CN | 105721667 A | 6/2016 |
| CN | 105980008 A | 9/2016 |
| CN | 106164808 A | 11/2016 |
| CN | 106371816 A | 2/2017 |
| CN | 106415559 A | 2/2017 |
| CN | 106510719 A | 3/2017 |
| CN | 106537397 A | 3/2017 |
| CN | 106709235 A | 5/2017 |
| CN | 106725384 A | 5/2017 |
| CN | 106901720 A | 6/2017 |
| CN | 107278138 A | 10/2017 |
| CN | 107361755 A | 11/2017 |
| CN | 107454831 A | 12/2017 |
| CN | 107469327 A | 12/2017 |
| CN | 107508995 A | 12/2017 |
| CN | 107591211 A | 1/2018 |
| CN | 107713981 A | 2/2018 |
| CN | 108604327 A | 9/2018 |

(56) References Cited

FOREIGN PATENT DOCUMENTS

| | | |
|---|---|---|
| CN | 109287140 A | 1/2019 |
| CN | 111344796 A | 6/2020 |
| DE | 202017002874 U1 | 9/2017 |
| EP | 2391004 A1 | 11/2011 |
| EP | 2529663 A1 | 12/2012 |
| EP | 2568409 A1 | 3/2013 |
| EP | 2921899 A2 | 9/2015 |
| EP | 3042606 A1 | 7/2016 |
| EP | 3096235 A1 | 11/2016 |
| EP | 3101882 A2 | 12/2016 |
| EP | 3117767 A1 | 1/2017 |
| EP | 3557590 A1 | 10/2019 |
| JP | 5-288869 A | 11/1993 |
| JP | 2004-80496 A | 3/2004 |
| JP | 2004-174006 A | 6/2004 |
| JP | 2004-318503 A | 11/2004 |
| JP | 2005-79814 A | 3/2005 |
| JP | 3635663 B2 | 4/2005 |
| JP | 2007-330513 A | 12/2007 |
| JP | 2008-011865 A | 1/2008 |
| JP | 2009-78134 A | 4/2009 |
| JP | 2009-232301 A | 10/2009 |
| JP | 2009-538571 A | 11/2009 |
| JP | 2010-517725 A | 5/2010 |
| JP | 2010-122901 A | 6/2010 |
| JP | 2010-162297 A | 7/2010 |
| JP | 2010-181280 A | 8/2010 |
| JP | 2010-182287 A | 8/2010 |
| JP | 2011-197992 A | 10/2011 |
| JP | 2011-200575 A | 10/2011 |
| JP | 2012-502343 A | 1/2012 |
| JP | 2012-35071 A | 2/2012 |
| JP | 2012-45373 A | 3/2012 |
| JP | 2012-86088 A | 5/2012 |
| JP | 2012-524640 A | 10/2012 |
| JP | 2012-239808 A | 12/2012 |
| JP | 2013-17631 A | 1/2013 |
| JP | 2013-530776 A | 8/2013 |
| JP | 2013-192608 A | 9/2013 |
| JP | 2013-207323 A | 10/2013 |
| JP | 2013-544140 A | 12/2013 |
| JP | 2015-28686 A | 2/2015 |
| JP | 2015-73590 A | 4/2015 |
| JP | 2015-213686 A | 12/2015 |
| JP | 2016-502875 A | 2/2016 |
| JP | 2016-158867 A | 9/2016 |
| JP | 2016-528016 A | 9/2016 |
| JP | 2016-177151 A | 10/2016 |
| JP | 2016-185288 A | 10/2016 |
| JP | 2016-202751 A | 12/2016 |
| JP | 2016-538926 A | 12/2016 |
| JP | 2017-40981 A | 2/2017 |
| JP | 2017-117265 A | 6/2017 |
| JP | 2017-515520 A | 6/2017 |
| JP | 2017-134689 A | 8/2017 |
| JP | 2017-526073 A | 9/2017 |
| JP | 2017-182393 A | 10/2017 |
| JP | 2017-529880 A | 10/2017 |
| JP | 2017-211994 A | 11/2017 |
| JP | 2017-532069 A | 11/2017 |
| JP | 2018-504660 A | 2/2018 |
| JP | 6382433 B1 | 8/2018 |
| JP | 2018-191122 A | 11/2018 |
| JP | 2019-28806 A | 2/2019 |
| JP | 2019-32461 A | 2/2019 |
| JP | 2019-505035 A | 2/2019 |
| JP | 2019-36226 A | 3/2019 |
| JP | 2019-55076 A | 4/2019 |
| JP | 2019-207536 A | 12/2019 |
| JP | 2020-651 A | 1/2020 |
| JP | 2021-512429 A | 5/2021 |
| KR | 10-2002-0060421 A | 7/2002 |
| KR | 10-2008-0051460 A | 6/2008 |
| KR | 10-2012-0023657 A | 3/2012 |
| KR | 10-2012-0098854 A | 9/2012 |
| KR | 10-2012-0132732 A | 12/2012 |
| KR | 10-2013-0111569 A | 10/2013 |
| KR | 10-2013-0111570 A | 10/2013 |
| KR | 10-2015-0026635 A | 3/2015 |
| KR | 10-2015-0115385 A | 10/2015 |
| KR | 10-1594486 B1 | 2/2016 |
| KR | 10-2016-0027943 A | 3/2016 |
| KR | 10-2016-0028351 A | 3/2016 |
| KR | 10-2016-0076264 A | 6/2016 |
| KR | 10-2016-0077199 A | 7/2016 |
| KR | 10-2016-0105129 A | 9/2016 |
| KR | 10-2016-0142418 A | 12/2016 |
| KR | 10-2017-0003608 A | 1/2017 |
| KR | 10-2017-0019040 A | 2/2017 |
| KR | 10-2017-0019745 A | 2/2017 |
| KR | 10-2017-0029014 A | 3/2017 |
| KR | 10-2017-0032471 A | 3/2017 |
| KR | 10-2018-0129188 A | 12/2018 |
| KR | 10-2019-0094795 A | 8/2019 |
| WO | 97/38626 A1 | 10/1997 |
| WO | 2003/067202 A2 | 8/2003 |
| WO | 2005/029242 A2 | 3/2005 |
| WO | 2006/046648 A1 | 5/2006 |
| WO | 2008/073359 A2 | 6/2008 |
| WO | 2009/095908 A2 | 8/2009 |
| WO | 2010/028320 A1 | 3/2010 |
| WO | 2010/126825 A1 | 11/2010 |
| WO | 2011/072111 A2 | 6/2011 |
| WO | 2012/048832 A1 | 4/2012 |
| WO | 2012/060588 A1 | 5/2012 |
| WO | 2012/061438 A2 | 5/2012 |
| WO | 2012/061440 A2 | 5/2012 |
| WO | 2013/103570 A1 | 7/2013 |
| WO | 2013/109916 A1 | 7/2013 |
| WO | 2013/169870 A1 | 11/2013 |
| WO | 2014/015378 A1 | 1/2014 |
| WO | 2014/207875 A1 | 12/2014 |
| WO | 2015/027133 A1 | 2/2015 |
| WO | 2015/084353 A1 | 6/2015 |
| WO | 2015/089484 A1 | 6/2015 |
| WO | 2015/131065 A1 | 9/2015 |
| WO | 2015/153803 A1 | 10/2015 |
| WO | 2015/164845 A1 | 10/2015 |
| WO | 2015/183828 A1 | 12/2015 |
| WO | 2015/187799 A1 | 12/2015 |
| WO | 2015/198488 A1 | 12/2015 |
| WO | 2016/022203 A1 | 2/2016 |
| WO | 2016/036472 A1 | 3/2016 |
| WO | 2016/036582 A2 | 3/2016 |
| WO | 2016/151479 A1 | 9/2016 |
| WO | 2016/161152 A1 | 10/2016 |
| WO | 2016/164475 A1 | 10/2016 |
| WO | 2016/179559 A2 | 11/2016 |
| WO | 2016/207745 A1 | 12/2016 |
| WO | 2017/003045 A1 | 1/2017 |
| WO | 2017/037242 A1 | 3/2017 |
| WO | 2017/054277 A1 | 4/2017 |
| WO | 2017/062621 A1 | 4/2017 |
| WO | 2017/087642 A1 | 5/2017 |
| WO | 2017/090810 A1 | 6/2017 |
| WO | 2017/172046 A1 | 10/2017 |
| WO | 2017/215203 A1 | 12/2017 |
| WO | 2018/132507 A1 | 7/2018 |
| WO | 2018/148356 A1 | 8/2018 |
| WO | 2018/213401 A1 | 11/2018 |
| WO | 2019/020977 A1 | 1/2019 |
| WO | 2019/099553 A1 | 5/2019 |
| WO | 2019/168956 A1 | 9/2019 |
| WO | 2019/177769 A1 | 9/2019 |
| WO | 2019/240513 A1 | 12/2019 |
| WO | 2022/010573 A1 | 1/2022 |

OTHER PUBLICATIONS

Notice of Allowance received for Korean Patent Application No. 10-2022-7031866, dated May 1, 2023, 7 pages (2 pages of English Translation and 5 pages of Official Copy).

(56) References Cited

OTHER PUBLICATIONS

Notice of Allowance received for U.S. Appl. No. 18/078,444, dated May 12, 2023, 9 pages.
Office Action received for Australian Patent Application No. 2021261861, dated May 3, 2023, 4 pages.
Office Action received for German Patent Application No. 112020002566.7, dated Mar. 24, 2023, 32 pages (14 pages of English Translation and 18 pages of official copy).
Levy et al., "A good little tool to get to know yourself a bit better", a qualitative study on users' experiences of app-supported menstrual tracking in Europe., In: BMC Public Health, vol. 19, 2019, pp. 1-11.
Applicant-Initiated Interview Summary received for U.S. Appl. No. 17/031,723, dated Jan. 23, 2023, 4 pages.
Non-Final Office Action received for U.S. Appl. No. 17/952,053, dated Jan. 12, 2023, 12 pages.
Notice of Allowance received for U.S. Appl. No. 17/317,084, dated Jan. 6, 2023, 6 pages.
Office Action received for Australian Patent Application No. 2021261861, dated Jan. 12, 2023, 4 pages.
Office Action received for Australian Patent Application No. 2022202459, dated Jan. 6, 2023, 3 pages.
Supplemental Notice of Allowance received for U.S. Appl. No. 17/317,084, dated Jan. 19, 2023, 2 pages.
Applicant-Initiated interview Summary received for U.S. Appl. No. 16/851,451, dated Nov. 29, 2022, 4 pages.
Extended European Search Report received for European Patent Application No. 22190169.7, dated Nov. 23. 2022, 11 pages.
Final Office Action received for U.S. Appl. No. 16/888,780, dated Nov. 25, 2022, 10 pages.
Invitation to Pay Search Fees received for European Patent Application No. 20746438.9, dated Dec. 2, 2022, 4 pages.
Non-Final Office Action received for U.S. Appl. No. 17/031,723, dated Dec. 5, 2022, 27 pages.
Office Action received for Japanese Patent Application No. 2021-153558, dated Nov. 21, 2022, 8 pages (4 pages of English Translation and 4 pages of Official Copy).
Office Action received for Korean Patent Application No. 10-2022-7031866, dated Nov. 18, 2022, 11 pages (5 pages of English Translation and 6 pages of Official Copy).
Brief Communication Regarding Oral Proceedings received for European Patent Application No. 20182116.2, mailed on Apr. 13, 2022, 3 pages.
Corrected Notice of Allowance received for U.S. Appl. No. 17/031,717, dated Apr. 15, 2022, 3 pages.
Decision to Refuse received for European Patent Application No. 20180581.9, dated Apr. 13, 2022, 16 pages.
Minutes of the Oral Proceedings received for European Patent Application No. 20180581.9, mailed on Apr. 13, 2022, 10 pages.
Minutes of the Oral Proceedings received for European Patent Application No. 20180592.6, mailed on Apr. 7, 2022, 10 pages.
Non-Final Office Action received for U.S. Appl. No. 16/888,780, dated Apr. 20, 2022, 22 pages.
Notice of Acceptance received for Australian Patent Application No. 2020239692, dated Apr. 6, 2022, 3 pages.
Notice of Allowance received for Japanese Patent Application No. 2020-160023, dated Apr. 11, 2022, 4 pages (1 page of English Translation and 3 pages of Official Copy).
Notice of Allowance received for Japanese Patent Application No. 2021571467, dated Apr. 11, 2022, 4 pages (1 page of English Translation and 3 pages of Official Copy).
Notice of Allowance received for Korean Patent Application No. 10-2021-7031939, dated Apr. 5, 2022, 4 pages (1 page of English Translation and 3 pages of Official Copy).
Supplemental Notice of Allowance received for U.S. Appl. No. 16/894,309, dated Apr. 8, 2022, 3 pages.
Brief Communication Regarding Oral Proceedings received for European Patent Application No. 20746438.9, mailed on Nov. 7, 2022, 1 page.
Invitation to Pay Search Fees received for European Patent Application No. 20760607.0, dated Nov. 21, 2022, 3 pages.
Notice of Acceptance received for Australian Patent Application No. 2020288147, dated Dec. 22, 2021, 3 pages.
Notice of Allowance received for Chinese Patent Application No. 202010618569.X, dated Jan. 7, 2022, 2 pages (1 page of English Translation and 1 page of Official Copy).
Notice of Allowance received for U.S. Appl. No. 16/990,846, dated Jan. 20, 2022, 6 pages.
Office Action received for Chinese Patent Application No. 202011220489.5, dated Dec. 1, 2021, 19 pages (11 pages of English Translation and 8 pages of Official Copy).
Office Action received for Japanese Patent Application No. 2020-551585, dated Jan. 6, 2022, 11 pages (5 pages of English Translation and 6 pages of Official Copy).
Corrected Notice of Allowance received for U.S. Appl. No. 17/197,628, dated Apr. 27, 2022, 3 pages.
Intention to Grant received for European Patent Application No. 20180592.6, dated Apr. 20, 2022, 21 pages.
Extended European Search Report received for European Patent Application No. 20203526.7, dated Jan. 29, 2021, 13 pages.
Final Office Action received for U.S. Appl. No. 16/143,997, dated Feb. 9, 2021, 16 pages.
Notice of Allowance received for U.S. Appl. No. 16/144,753, dated Feb. 10, 2021, 8 pages.
Notice of Allowance received for U.S. Appl. No. 16/144,864, dated Feb. 9, 2021, 13 pages.
Office Action received for Korean Patent Application No. 10-2019-7033834, dated Jan. 22, 2021, 13 pages (6 pages of English Translation and 7 pages of Official Copy).
Office Action received for Korean Patent Application No. 10-2020-7026391, dated Jan. 27, 2021, 5 pages (2 pages of English Translation and 3 pages of Official Copy).
Office Action received for Korean Patent Application No. 10-2020-7026453, dated Jan. 27, 2021, 5 pages (2 pages of English Translation and 3 pages of Official Copy).
Corrected Notice of Allowance received for U.S. Appl. No. 17/031,717, dated May 19, 2022, 3 pages.
Non-Final Office Action received for U.S. Appl. No. 16/851,451, dated May 9, 2022, 26 pages.
Applicant-Initiated Interview Summary received for U.S. Appl. No. 16/907,261, dated Jul. 16, 2021, 10 pages.
Notice of Allowance received for Korean Patent Application No. 10-2019-7033834, dated Jul. 3, 2021, 4 pages (2 pages of English Translation and 2 pages of Official Copy).
Notice of Allowance received for U.S. Appl. No. 16/138,809, dated Jul. 20, 2021, 6 pages.
Office Action received for Chinese Patent Application No. 201910858933.7, dated Jun. 29, 2021, 8 pages (3 pages of English Translation and 5 pages of Official Copy).
Applicant-Initiated Interview Summary received for U.S. Appl. No. 16/143,997, dated May 3, 2021, 4 pages.
Non-Final Office Action received for U.S. Appl. No. 16/990,846, dated May 10, 2021, 16 pages.
Notice of Allowance received for U.S. Appl. No. 16/143,997, dated May 13, 2021, 10 pages.
Notice of Allowance received for U.S. Appl. No. 16/880,552, dated May 12, 2021, 7 pages.
Office Action received for Chinese Patent Application No. 202010618240.3, dated Mar. 29, 2021, 21 pages (11 pages of English Translation and 10 pages of Official Copy).
Office Action received for Danish Patent Application No. PA202070620, dated May 10, 2021, 5 pages.
Office Action received for Japanese Patent Application No. 2020-547369, dated Apr. 9, 2021, 4 pages (2 pages of English Translation and 2 pages of Official Copy).
Brief Communication Regarding Oral Proceedings received for European Patent Application No. 20203526.7, mailed on Dec. 23, 2022, 4 pages.
International Preliminary Report on Patentability received for PCT Patent Application No. PCT/US2021/035227, dated Dec. 15, 2022, 10 pages.

(56) References Cited

OTHER PUBLICATIONS

International Preliminary Report on Patentability received for PCT Patent Application No. PCT/US2021/035504, dated Dec. 15, 2022, 8 pages.
Office Action received for Australian Patent Application No. 2020313970, dated Dec. 22, 2022, 3 pages.
Office Action received for Chinese Patent Application No. 201880032190.1, dated Nov. 14, 2022, 23 pages (12 pages of English Translation and 11 pages of Official Copy).
Applicant-Initiated Interview Summary received for U.S. Appl. No. 16/907,261, dated Mar. 25, 2021, 2 pages.
Decision on Appeal received for Korean Patent Application No. 10-2019-7025538, dated Feb. 24, 2021, 20 pages (4 pages of English Translation and 16 pages of Official Copy).
Final Office Action received for U.S. Appl. No. 16/907,261, dated Mar. 18, 2021, 20 pages.
Notice of Allowance received for Korean Patent Application No. 10-2019-7025538, dated Mar. 10, 2021, 5 pages (2 pages of English Translation and 3 pages of Official Copy).
Notice of Allowance received for U.S. Appl. No. 16/144,864, dated Mar. 30, 2021, 2 pages.
Notice of Allowance received for U.S. Appl. No. 16/880,714, dated Mar. 19, 2021, 7 pages.
Office Action received for Australian Patent Application No. 2019234289, dated Mar. 16, 2021, 8 pages.
Office Action received for European Patent Application No. 18727543.3, dated Mar. 26, 2021, 7 pages.
Result of Consultation received for European Patent Application No. 19726205.8, dated Mar. 15, 2021, 19 pages.
Advisory Action received for U.S. Appl. No. 17/031,779, dated Oct. 20, 2022, 5 pages.
Final Office Action received for U.S. Appl. No. 16/851,451, dated Oct. 20, 2022, 31 pages.
Office Action received for Australian Patent Application No. 2021261861, dated Oct. 14, 2022, 5 pages.
Office Action received for Chinese Patent Application No. 202010618240.3, dated Sep. 21, 2022, 16 pages (9 pages of English Translation and 7 pages of Official Copy).
Office Action received for Chinese Patent Application No. 202210004176.9, dated Sep. 28, 2022, 12 pages (6 pages of English Translation and 6 pages of Official Copy).
Office Action received for Danish Patent Application No. PA202070395, dated Oct. 7, 2022, 4 pages.
Supplemental Notice of Allowance received for U.S. Appl. No. 17/041,415, dated Oct. 13, 2022, 2 pages.
Applicant-Initiated Interview Summary received for U.S. Appl. No. 16/586,154, dated Sep. 3, 2021, 4 pages.
Applicant-Initiated Interview Summary received for U.S. Appl. No. 17/031,704, dated Feb. 9, 2021, 3 pages.
Applicant-Initiated Interview Summary received for U.S. Appl. No. 17/031,704, dated Jun. 25, 2021, 3 pages.
Applicant-Initiated Interview Summary received for U.S. Appl. No. 17/031,717, dated Jan. 29, 2021, 5 pages.
Applicant-Initiated Interview Summary received for U.S. Appl. No. 17/031,717, dated May 17, 2021, 5 pages.
Final Office Action received for U.S. Appl. No. 17/031,704, dated Apr. 1, 2021, 31 pages.
Final Office Action received for U.S. Appl. No. 17/031,717, dated Feb. 24, 2021, 23 pages.
Non-Final Office Action received for U.S. Appl. No. 17/031,704, dated Dec. 10, 2020, 30 pages.
Non-Final Office Action received for U.S. Appl. No. 17/031,717, dated Nov. 19, 2020, 22 pages.
Notice of Allowance received for Japanese Patent Application No. 2019-563407, dated Aug. 20, 2021, 4 pages (1 page of English Translation and 3 pages of Official Copy).
Notice of Allowance received for Korean Patent Application No. 10-2020-7026035, dated Aug. 23, 2021, 4 pages (2 page of English Translation and 2 pages of Official Copy).
Notice of Allowance received for U.S. Appl. No. 17/031,704, dated Jul. 21, 2021, 10 pages.
Notice of Allowance received for U.S. Appl. No. 17/031,727, dated Dec. 24, 2020, 12 pages.
Notice of Allowance received for U.S. Appl. No. 17/031,727, dated Jun. 25, 2021, 6 pages.
Notice of Allowance received for U.S. Appl. No. 17/031,727, dated Mar. 12, 2021, 7 pages.
Office Action received for Australian Patent Application No. 2020239740, dated Jul. 9, 2021, 4 pages.
Office Action received for Danish Patent Application No. PA202070619, dated Aug. 27, 2021, 12 pages.
Search Report and Opinion received for Danish Patent Application No. PA202070619, dated Dec. 2, 2020, 11 pages.
Supplemental Notice of Allowance received for U.S. Appl. No. 17/031,727, dated Jan. 15, 2021, 2 pages.
Applicant-Initiated Interview Summary received for U.S. Appl. No. 16/880,714, dated Feb. 26, 2021, 5 pages.
Final Office Action received for U.S. Appl. No. 16/894,309, dated Feb. 24, 2021, 30 pages.
International Search Report and Written Opinion received for PCT Patent Application No. PCT/US2020/035164, dated Feb. 8, 2021, 26 pages.
Non-Final Office Action received for U.S. Appl. No. 16/880,552, dated Feb. 19, 2021, 11 pages.
Office Action received for Danish Patent Application No. PA201970534, dated Feb. 16, 2021, 2 pages.
Office Action received for Korean Patent Application No. 10-2020-7026035, dated Feb. 19, 2021, 13 pages (6 pages of English Translation and 7 pages of Official Copy).
Applicant-Initiated Interview Summary received for U.S. Appl. No. 17/031,723, dated Aug. 30, 2022, 4 pages.
Applicant-Initiated Interview Summary received for U.S. Appl. No. 17/031,779, dated Aug. 29, 2022, 2 pages.
Decision to Grant received for European Patent Application No. 20180592.6, dated Sep. 1, 2022, 3 pages.
Notice of Allowance received for U.S. Appl. No. 17/041,415, dated Aug. 31, 2022, 7 pages.
Notice of Allowance received for U.S. Appl. No. 17/317,084, dated Aug. 29, 2022, 10 pages.
Office Action received for Korean Patent Application No. 10-2020-7033395, dated Aug. 29, 2022, 11 pages (4 pages of English Translation and 7 pages of Official Copy).
Applicant-Initiated Interview Summary received for U.S. Appl. No. 17/041,415, dated Jun. 29, 2022, 2 pages.
Final Office Action received for U.S. Appl. No. 17/031,723, dated Jul. 12, 2022, 25 pages.
Final Office Action received for U.S. Appl. No. 17/031,779, dated Jul. 14, 2022, 19 pages.
Notice of Allowance received for U.S. Appl. No. 17/031,717, dated Jul. 7, 2022, 12 pages.
Notice of Allowance received for U.S. Appl. No. 17/197,628, dated Jun. 24, 2022, 8 pages.
Summons to Attend Oral Proceedings received for European Patent Application No. 20203526.7, mailed on Jun. 23, 2022, 9 pages.
Notice of Allowance received for Japanese Patent Application No. 2020-547369, dated Jul. 16, 2021, 4 pages (1 page of English Translation and 3 pages of Official Copy).
Notice of Allowance received for U.S. Appl. No. 16/880,552, dated Jul. 23, 2021, 5 pages.
Office Action received for Australian Patent Application No. 2019234289, dated Jul. 20, 2021, 4 pages.
Office Action received for Australian Patent Application No. 2020239692, dated Jul. 20, 2021, 5 pages.
Notice of Acceptance received for Australian Patent Application No. 2021200787, dated Mar. 19, 2021, 3 pages.
Notice of Allowance received for U.S. Appl. No. 16/144,030, dated Apr. 5, 2021, 8 pages.
Office Action received for European Patent Application No. 20180581.9, dated Apr. 1, 2021, 11 pages.
Office Action received for European Patent Application No. 20180592.6, dated Apr. 1, 2021, 11 pages.

(56) References Cited

OTHER PUBLICATIONS

Office Action received for Japanese Patent Application No. 2018-184532, dated Mar. 1, 2021, 11 pages (6 pages of English Translation and 5 pages of Official Copy).
Corrected Notice of Allowance received for U.S. Appl. No. 16/143,997, dated Jun. 4, 2021, 2 pages.
Notice of Allowance received for U.S. Appl. No. 16/880,714, dated Jun. 9, 2021, 6 pages.
Office Action received for Australian Patent Application No. 2020256383, dated Jun. 4, 2021, 3 pages.
Office Action received for Danish Patent Application No. PA202070335, dated Jun. 11, 2021, 4 pages.
Office Action received for European Patent Application No. 19721883.7, dated Jun. 15, 2021, 9 pages.
Notice of Allowance received for Korean Patent Application No. 10-2022-7017918, dated Jun. 13, 2022, 6 pages (2 pages of English Translation and 4 pages of Official Copy).
Office Action received for Chinese Patent Application No. 202010618240.3, dated May 25, 2022, 20 pages (11 pages of English Translation and 9 pages of Official Copy).
Office Action received for Chinese Patent Application No. 202111611270.2, dated May 10, 2022, 16 pages (8 pages of English Translation and 8 pages of Official Copy).
Applicant-Initiated Interview Summary received for U.S. Appl. No. 16/586,154, dated Mar. 11, 2020, 4 pages.
Applicant-Initiated Interview Summary received for U.S. Appl. No. 16/138,809, dated Dec. 16, 2020, 7 pages.
Applicant-Initiated Interview Summary received for U.S. Appl. No. 16/586,154, dated Dec. 11, 2020, 5 pages.
Applicant-Initiated Interview Summary received for U.S. Appl. No. 16/880,552, dated Dec. 16, 2020, 6 pages.
Applicant-Initiated Interview Summary received for U.S. Appl. No. 16/894,309, dated Jan. 26, 2021, 3 pages.
Applicant-Initiated Interview Summary received for U.S. Appl. No. 16/907,261, dated Dec. 16, 2020, 6 pages.
Final Office Action received for U.S. Appl. No. 16/586,154, dated Jul. 6, 2020, 27 pages.
Gupta, Rajat, "Disable High vol. Warning (No Root) in Samsung S7, S8 / Android 7.0", Online available at: https://www.youtube.com/watch?v=9fKwRBtk-x8, Retrieved on Nov. 26, 2020; esp. 2:04, Aug. 6, 2017, 1 page.
International Search Report and Written Opinion received for PCT Patent Application No. PCT/US2020/035462, dated Sep. 11, 2020, 17 pages.
International Search Report and Written Opinion received for PCT Patent Application No. PCT/US2020/035474, dated Nov. 26, 2020, 16 pages.
International Search Report and Written Opinion received for PCT Patent Application No. PCT/US2020/042439, dated Oct. 9, 2020, 14 pages.
Invitation to Pay Additional Fees and Partial International Search Report received for PCT Patent Application No. PCT/US2020/035164, dated Oct. 16, 2020, 14 pages.
Lovejoy, Ben, "Apple Watch blood sugar measurement coming in Series 7, claims report", Available Online at: https://9to5mac.com/2021/01/25/apple-watch-blood-sugar-measurement/, Jan. 25, 2021, 6 pages.
Non-Final Office Action received for U.S. Appl. No. 16/586,154, dated Dec. 9, 2019, 23 pages.
Non-Final Office Action received for U.S. Appl. No. 16/880,714, dated Oct. 28, 2020, 11 pages.
Notice of Acceptance received for Australian Patent Application No. 2018268972, dated Dec. 18, 2020, 3 pages.
Notice of Allowance received for Japanese Patent Application No. 2020-104679, dated Jan. 4, 2021, 4 pages (1 page of English Translation and 3 pages of Official Copy).
Notice of Allowance received for U.S. Appl. No. 16/144,753, dated Dec. 4, 2020, 22 pages.
Notice of Allowance received for U.S. Appl. No. 16/880,552, dated Dec. 1, 2020, 7 pages.
Search Report and Opinion received for Danish Patent Application No. PA202070335, dated Nov. 27, 2020, 10 pages.
Search Report and Opinion received for Danish Patent Application No. PA202070395, dated Nov. 24, 2020, 10 pages.
Tech, Kalyani,"I See Some problems in Honor Band 5", Retrieved from: https://www.youtube.com/watch?v=5XPnYJFqajl, May 19, 2020, 1 page.
Ticks, Smartwatch,"Senbono S10 IP67 Waterproof Multi-Function Blood Pressure Sports Smartwatch: One Minute Overview", Retrieved from: https://www.youtube.com/watch?v=rMxLJvKIVBs, Oct. 30, 2019, 1 page.
Applicant-Initiated Interview Summary received for U.S. Appl. No. 16/851,451, dated Apr. 20, 2023, 4 pages.
Applicant-Initiated Interview Summary received for U.S. Appl. No. 17/952,053, dated Apr. 5, 2023, 6 pages.
Intention to Grant received for European Patent Application No. 18727543.3, dated Apr. 12, 2023, 9 pages.
Notice of Allowance received for U.S. Appl. No. 17/952,053, dated Apr. 17, 2023, 6 pages.
Office Action received for Chinese Patent Application No. 202210004176.9, dated Feb. 19, 2023, 23 pages (14 pages of English Translation and 9 pages of Official Copy).
Office Action received for Korean Patent Application No. 10-2020-0124134, dated Mar. 28, 2023, 9 pages (4 pages of English Translation and 5 pages of Official Copy).
Brief Communication Regarding Oral Proceedings received for European Patent Application No. 20180581.9, mailed on Nov. 30, 2021, 1 page.
Corrected Notice of Allowance received for U.S. Appl. No. 16/880,552, dated Dec. 22, 2021, 2 pages.
Corrected Notice of Allowance received for U.S. Appl. No. 16/921,312, dated Dec. 7, 2021, 2 pages.
International Preliminary Report on Patentability received for PCT Patent Application No. PCT/US2020/035164, dated Dec. 16, 2021, 19 pages.
International Preliminary Report on Patentability received for PCT Patent Application No. PCT/US2020/035462, dated Dec. 16, 2021, 16 pages.
International Preliminary Report on Patentability received for PCT Patent Application No. PCT/US2020/025768, dated Dec. 16, 2021, 8 pages.
International Preliminary Report on Patentability received for PCT Patent Application No. PCT/US2020/035474, dated Dec. 16, 2021, 11 pages.
Office Action received for Danish Patent Application No. PA202070395, dated Dec. 15, 2021, 5 pages.
Office Action received for Indian Patent Application No. 202014041484, dated Dec. 8, 2021, 8 pages.
Brief Communication Regarding Oral Proceedings received for European Patent Application No. 18727543.3, mailed on Mar. 23, 2023, 1 page.
Corrected Notice of Allowance received for U.S. Appl. No. 16/953,781, dated Mar. 30, 2023, 2 pages.
Non-Final Office Action received for U.S. Appl. No. 17/952,182, dated Mar. 28, 2023, 9 pages.
Office Action received for Australian Patent Application No. 2020313970, dated Mar. 22, 2023, 4 pages.
Office Action received for Australian Patent Application No. 2022202459, dated Mar. 27, 2023, 5 pages.
Office Action received for Danish Patent Application No. PA202070395, dated Mar. 31, 2023, 3 pages.
Office Action received for Japanese Patent Application No. 2022-502594, dated Mar. 20, 2023, 10 pages (5 pages of English Translation and 5 pages of Official Copy).
Result of Consultation received for European Patent Application No. 18727543.3, dated Mar. 15, 2023, 6 pages.
Applicant-Initiated Interview Summary received for U.S. Appl. No. 16/953,781, dated Oct. 31, 2022, 12 pages.
Notice of Allowance received for U.S. Appl. No. 16/953,781, dated Nov. 9, 2022, 7 pages.
Office Action received for European Patent Application No. 20746438.9, dated Oct. 31, 2022, 7 pages.

(56) References Cited

OTHER PUBLICATIONS

Summons to Attend Oral Proceedings received for European Patent Application No. 18727543.3, mailed on Oct. 25, 2022, 8 pages.
International Search Report and Written Opinion received for PCT Patent Application No. PCT/US2020/070280, dated Nov. 30, 2020, 20 pages.
Invitation to Pay Additional Fees received for PCT Patent Application No. PCT/US2020/070280, dated Oct. 7, 2020, 12 pages.
Notice of Allowance received for U.S. Appl. No. 16/144,864, dated Mar. 12, 2021, 2 pages.
Office Action received for Australian Patent Application No. 2020230340, dated Mar. 2, 2021, 6 pages.
Office Action received for Chinese Patent Application No. 202010606407.4, dated Jan. 27, 2021, 16 pages (7 pages of English Translation and 9 pages of Official Copy).
Office Action received for Japanese Patent Application No. 2019-563407, dated Feb. 5, 2021, 5 pages (2 pages of English Translation and 3 pages of Official Copy).
Cook James, "German Period Tracking App Clue Has Over 2.5 Million Active Users—But It's Still Not Sure How It's Going to Make Money", Available online at: https://www.businessinsider.in/tech/german-period-tracking-app-clue-has-over-2-5-million-active-users-but-its-still-not-sure-how-its-going-to-make-money/articleshow/50511307.cms, Jan. 9, 2016, 9 pages.
Final Office Action received for U.S. Appl. No. 16/586,154, dated May 24, 2021, 29 pages.
Notice of Allowance received for Korean Patent Application No. 10-2020-7026391, dated May 11, 2021, 3 pages (1 page of English Translation and 2 pages of Official Copy).
Notice of Allowance received for Korean Patent Application No. 10-2020-7026453, dated May 11, 2021, 3 pages (1 page of English Translation and 2 pages of Official Copy).
Office Action received for European Patent Application No. 20182116.2, dated May 25, 2021, 9 pages.
Applicant-Initiated Interview Summary received for U.S. Appl. No. 16/894,309, dated Jun. 25, 2021, 4 pages.
Corrected Notice of Allowance received for U.S. Appl. No. 16/143,997, dated Jul. 2, 2021, 2 pages.
Corrected Notice of Allowance received for U.S. Appl. No. 16/880,552, dated Jul. 7, 2021, 2 pages.
Office Action received for Australian Patent Application No. 2020230340, dated May 27, 2021, 5 pages.
Office Action received for Chinese Patent Application No. 202010606407.4, dated Jun. 2, 2021, 12 pages (5 pages of English Translation and 7 pages of Official Copy).
Office Action received for Chinese Patent Application No. 202011220489.5, dated Jun. 1, 2021, 12 pages (6 pages of English Translation and 6 pages of Official Copy).
Office Action received for Japanese Patent Application No. 2020-153166, dated May 31, 2021, 6 pages (3 pages of English Translation and 3 pages of Official Copy).
Applicant-Initiated Interview Summary received for U.S. Appl. No. 17/031,717, dated Nov. 4, 2021, 5 pages.
Corrected Notice of Allowance received for U.S. Appl. No. 16/143,997, dated Nov. 16, 2021, 2 pages.
Corrected Notice of Allowance received for U.S. Appl. No. 17/031,704, dated Nov. 2, 2021, 7 pages.
Notice of Allowance received for U.S. Appl. No. 16/894,309, dated Nov. 5, 2021, 12 pages.
Office Action received for Australian Patent Application No. 2019234289, dated Nov. 1, 2021, 4 pages.
Notice of Acceptance received for Australian Patent Application No. 2020256383, dated Aug. 3, 2021, 3 pages.
Notice of Allowance received for U.S. Appl. No. 16/907,261, dated Aug. 13, 2021, 8 pages.
Summons to Attend Oral Proceedings received for European Patent Application No. 20180581.9, mailed on Aug. 18, 2021, 15 pages.
Summons to Attend Oral Proceedings received for European Patent Application No. 20180592.6, mailed on Aug. 11, 2021, 16 pages.
Brief Communication Regarding Oral Proceedings received for European Patent Application No. 20180581.9, mailed on Jan. 26, 2022, 1 page.
Brief Communication regarding Oral Proceedings received for European Patent Application No. 20180592.6, mailed on Jan. 26, 2022, 2 pages.
Intention to Grant received for Danish Patent Application No. PA202070619, dated Jan. 17, 2022, 2 pages.
International Preliminary Report on Patentability received for PCT Patent Application No. PCT/US2020/042439, dated Jan. 27, 2022, 10 pages.
Non-Final Office Action received for U.S. Appl. No. 17/031,723, dated Jan. 24, 2022, 17 pages.
Notice of Allowance received for Chinese Patent Application No. 202010606407.4, dated Jan. 24, 2022, 2 pages (1 page of English Translation and 1 page of Official Copy).
Notice of Allowance received for Japanese Patent Application No. 2018-184532, dated Jan. 17, 2022, 4 pages (1 page of English Translation and 3 pages of Official Copy).
Notice of Allowance received for Korean Patent Application No. 10-2021-7042504, dated Jan. 17, 2022, 6 pages (1 page of English Translation and 5 pages of Official Copy).
Office Action received for Japanese Patent Application No. 2020-160023, dated Jan. 17, 2022, 11 pages (06 pages of English Translation and 05 pages of Official Copy).
Result of Consultation received for European Patent Application No. 20180581.9, dated Jan. 21, 2022, 14 pages.
Result of Consultation received for European Patent Application No. 20180592.6, dated Jan. 26, 2022, 18 pages.
Supplemental Notice of Allowance received for U.S. Appl. No. 16/894,309, dated Jan. 25, 2022, 2 pages.
Applicant-Initiated Interview Summary received for U.S. Appl. No. 16/586,154, dated Apr. 14, 2021, 4 pages.
Applicant-Initiated Interview Summary received for U.S. Appl. No. 16/880,552, dated Apr. 21, 2021, 3 pages.
Notice of Allowance received for Japanese Patent Application No. 2019-162293, dated Apr. 9, 2021, 4 pages (1 page of English Translation and 3 pages of Official Copy).
Notice of Allowance received for U.S. Appl. No. 16/138,809, dated Apr. 16, 2021, 11 pages.
Office Action received for Chinese Patent Application No. 202010618569.X, dated Mar. 12, 2021, 14 pages (7 pages of English Translation and 7 pages of Official Copy).
Corrected Notice of Allowance received for U.S. Appl. No. 16/921,312, dated Sep. 24, 2021, 2 pages.
Non-Final Office Action received for U.S. Appl. No. 17/031,717, dated Sep. 14, 2021, 35 pages.
Notice of Allowance received for Japanese Patent Application No. 2020-153166, dated Sep. 13, 2021, 4 pages (1 page of English Translation and 3 pages of Official Copy).
Notice of Allowance received for U.S. Appl. No. 16/907,261, dated Sep. 28, 2021, 6 pages.
Notice of Allowance received for U.S. Appl. No. 16/921,312, dated Sep. 14, 2021, 9 pages.
Notice of Allowance received for U.S. Appl. No. 16/990,846, dated Sep. 22, 2021, 9 pages.
Office Action received for Chinese Patent Application No. 202010618569.X, dated Sep. 7, 2021, 7 pages (4 pages of English Translation and 3 pages of Official Copy).
Supplemental Notice of Allowance received for U.S. Appl. No. 16/880,714, dated Sep. 16, 2021, 2 pages.
Applicant-Initiated Interview Summary received for U.S. Appl. No. 17/031,723, dated Mar. 21, 2021, 5 pages.
International Preliminary Report on Patentability received for PCT Patent Application No. PCT/US2020/070280, dated Mar. 17, 2022, 15 pages.
Non-Final Office Action received for U.S. Appl. No. 17/041,415, dated Mar. 29, 2022, 11 pages.
Notice of Allowance received for U.S. Appl. No. 17/031,717, dated Mar. 16, 2022, 12 pages.
Notice of Allowance received for U.S. Appl. No. 17/197,628, dated Mar. 23, 2022, 35 pages.

(56) References Cited

OTHER PUBLICATIONS

Applicant-Initiated Interview Summary received for U.S. Appl. No. 17/031,779, dated Mar. 10, 2022, 2 pages.
International Search Report and Written Opinion received for PCT Patent Application No. PCT/US2021/048568, dated Jan. 7, 2022, 14 pages.
Notice of Acceptance received for Australian Patent Application No. 2020239740, dated Feb. 22, 2022., 3 pages.
Notice of Allowance received for U.S. Appl. No. 16/894,309, dated Feb. 25, 2022, 9 pages.
Corrected Notice of Allowance received for U.S. Appl. No. 17/031,779, dated Jun. 14, 2023, 2 pages.
Non-Final Office Action received for U.S. Appl. No. 17/031,723, dated Jun. 2, 2023, 23 pages.
Notice of Allowance received for Japanese Patent Application No. 2021-153558, dated Jun. 9, 2023, 4 pages (1 page of English Translation and 3 pages of Official Copy).
Office Action received for Chinese Patent Application No. 201880032190.1, dated May 31, 2023, 20 pages (12 pages of English Translation and 8 pages of Official Copy).
Office Action received for Chinese Patent Application No. 202210004176.9, dated Apr. 28, 2023, 12 pages (6 pages of English Translation and 6 pages of Official Copy).
Office Action received for Indian Patent Application No. 202215032692, dated Jun. 15, 2023, 3 pages.
Office Action received for Japanese Patent Application No. 2022-078277, dated Jun. 9, 2023, 11 pages (6 pages of English Translation and 5 pages of Official Copy).
Supplemental Notice of Allowance received for U.S. Appl. No. 18/078,444, dated Jun. 15, 2023, 2 pages.
Brief Communication regarding Oral Proceedings received for European Patent Application No. 20180592.6, mailed on Dec. 21, 2021, 1 page.
Notice of Allowance received for Korean Patent Application No. 10-2021-7038005, dated Dec. 14, 2021, 4 pages (2 pages of English Translation and 2 pages of Official Copy).
Office Action received for Chinese Patent Application No. 202010606407.4, dated Nov. 18, 2021, 6 pages (3 pages of English Translation and 3 pages of Official Copy).
Office Action received for Chinese Patent Application No. 202010618240.3, dated Dec. 3, 2021, 23 pages (14 pages of English Translation and 9 pages of Official Copy).
Summons to Attend Oral Proceedings received for European Patent Application No. 20182116.2, mailed on Dec. 21, 2021, 7 pages.
Supplemental Notice of Allowance received for U.S. Appl. No. 16/894,309, dated Dec. 24, 2021, 2 pages.
Brief Communication Regarding Oral Proceedings received for European Patent Application No. 20203526.7, mailed on Jan. 18, 2023, 1 page.
Intention to Grant received for European Patent Application No. 20203526.7, dated Feb. 10, 2023, 9 pages.
Notice of Allowance received for Chinese Patent Application No. 202210238202.4, dated Jan. 13, 2023, 7 pages (3 pages of English Translation and 4 pages of Official Copy).
Notice of Allowance received for Japanese Patent Application No. 2021-167557, dated Jan. 27, 2023, 4 pages (1 page of English Translation and 3 pages of Official Copy).
Notice of Allowance received for U.S. Appl. No. 17/031,779, dated Feb. 1, 2023, 11 pages.
Office Action received for European Patent Application No. 20746438.9, dated Feb. 1, 2023, 9 pages.
Office Action received for European Patent Application No. 20760607.0, dated Feb. 1, 2023, 13 pages.
Result of Consultation received for European Patent Application No. 20203526.7, dated Jan. 13, 2023, 3 pages.
Notice of Allowance received for U.S. Appl. No. 16/143,997, dated Sep. 30, 2021, 8 pages.
Office Action received for Australian Patent Application No. 2020239740, dated Sep. 28, 2021, 5 pages.
Notice of Allowance received for U.S. Appl. No. 16/586,154, dated Oct. 15, 2021, 8 pages.
Office Action received for Australian Patent Application No. 2020230340, dated Oct. 11, 2021, 4 pages.
Intention to Grant received for European Patent Application No. 20182116.2, dated Jun. 2, 2022, 8 pages.
Minutes of the Oral Proceedings received for European Patent Application No. 20182116.2, mailed on May 24, 2022, 7 pages.
Notice of Allowance received for Korean Patent Application No. 10-2022-7008569, dated May 19, 2022, 5 pages (2 pages of English Translation and 3 pages of Official Copy).
Office Action received for Australian Patent Application No. 2021204422, dated May 31, 2022, 2 pages.
Office Action received for Chinese Patent Application No. 202011220489.5, dated Apr. 25, 2022, 15 pages (9 pages of English Translation and 6 pages of Official Copy).
Applicant-Initiated Interview Summary received for U.S. Appl. No. 17/031,723, dated Jun. 22, 2023, 2 pages.
Notice of Acceptance received for Australian Patent Application No. 2020313970, dated Jun. 22, 2023, 3 pages.
Notice of Acceptance received for Australian Patent Application No. 2022203508, dated Jun. 27, 2023, 3 pages.
Office Action received for Korean Patent Application No. 10-2020-0124134, dated Jun. 23, 2023, 8 pages (4 pages of English Translation and 4 pages of Official Copy).
Final Office Action received for U.S. Appl. No. 16/851,451, dated Jun. 1, 2023, 35 pages.
Notice of Allowance received for U.S. Appl. No. 17/031,779, dated May 26, 2023, 9 pages.
Office Action received for Australian Patent Application No. 2022203508, dated May 19, 2023, 2 pages.
Office Action received for Australian Patent Application No. 2022204568, dated May 22, 2023, 4 pages.
Office Action received for Australian Patent Application No. 2022235614, dated May 9, 2023, 2 pages.
International Search Report and Written Opinion received for PCT Patent Application No. PCT/US2021/035504, dated Sep. 16, 2021, 12 pages.
Notice of Allowance received for U.S. Appl. No. 16/880,552, dated Nov. 24, 2021, 5 pages.
Notice of Allowance received for U.S. Appl. No. 16/921,312, dated Nov. 29, 2021, 5 pages.
Office Action received for Danish Patent Application No. PA202070335, dated Nov. 17, 2021, 6 pages.
Office Action received for Danish Patent Application No. PA202070620, dated Nov. 19, 2021, 2 pages.
Office Action received for European Patent Application No. 20203526.7, dated Nov. 23, 2021, 9 pages.
Corrected Notice of Allowance received for U.S. Appl. No. 16/990,846, dated Feb. 9, 2022, 3 pages.
Non-Final Office Action received for U.S. Appl. No. 17/031,779, dated Feb. 16, 2022, 17 pages.
Office Action received for Australian Patent Application No. 2020239692, dated Jan. 27, 2022, 3 pages.
Office Action received for Chinese Patent Application No. 201910858933.7, dated Dec. 30, 2021, 9 pages (4 pages of English Translation and 5 pages of Official Copy).
Advisory Action received for U.S. Appl. No. 16/144,864, dated Jul. 29, 2019, 6 pages.
Advisory Action received for U.S. Appl. No. 16/143,909, dated Nov. 7, 2019, 5 pages.
Advisory Action received for U.S. Appl. No. 16/143,997, dated Dec. 26, 2019, 7 pages.
Advisory Action received for U.S. Appl. No. 16/144,849, dated Aug. 12, 2019, 5 pages.
Advisory Action received for U.S. Appl. No. 16/144,864, dated Jul. 6, 2020, 6 pages.
Applicant Initiated Interview Summary received for U.S. Appl. No. 16/143,997, dated Aug. 13, 2020, 3 pages.
Applicant Initiated Interview Summary received for U.S. Appl. No. 16/144,735, dated Jun. 18, 2020, 3 pages.
Applicant Initiated Interview Summary received for U.S. Appl. No. 16/144,753, dated Jun. 18, 2020, 3 pages.

(56) References Cited

OTHER PUBLICATIONS

Applicant Initiated Interview Summary received for U.S. Appl. No. 16/144,849, dated Jan. 21, 2020, 6 pages.
Applicant Initiated Interview Summary received for U.S. Appl. No. 16/144,864, dated Apr. 29, 2020, 4 pages.
Applicant-Initiated Interview Summary received for U.S. Appl. No. 15/705,849, dated Feb. 14, 2020, 3 pages.
Applicant-Initiated Interview Summary received for U.S. Appl. No. 15/705,849, dated Jun. 29, 2020, 3 pages.
Applicant-Initiated Interview Summary received for U.S. Appl. No. 16/138,809, dated Jun. 9, 2020, 4 pages.
Applicant-Initiated Interview Summary received for U.S. Appl. No. 16/144,753, dated Nov. 4, 2020, 3 pages.
Applicant-Initiated Interview Summary received for U.S. Appl. No. 16/144,864, dated Jun. 22, 2020, 3 pages.
Applicant-Initiated Interview Summary received for U.S. Appl. No. 16/584,186, dated Feb. 3, 2020, 4 pages.
Applicant-Initiated Interview Summary received for U.S. Appl. No. 16/880,552, dated Oct. 20, 2020, 6 pages.
Certificate of Examination received for Australian Patent Application No. 2019100222, dated Aug. 29, 2019, 2 pages.
Corrected Notice of Allowance received for U.S. Appl. No. 16/143,909, dated Feb. 20, 2020, 3 pages.
Corrected Notice of Allowance received for U.S. Appl. No. 16/143,909, dated Mar. 18, 2020, 3 pages.
Corrected Notice of Allowance received for U.S. Appl. No. 16/143,959, dated Dec. 13, 2019, 2 pages.
Corrected Notice of Allowance received for U.S. Appl. No. 16/584,186, dated Jul. 31, 2020, 2 pages.
Corrected Notice of Allowance received for U.S. Appl. No. 16/880,552, dated Dec. 23, 2020, 2 pages.
Decision to Grant received for Danish Patent Application No. PA201870379, dated Jul. 5, 2019, 2 pages.
Decision to Grant received for Danish Patent Application No. PA201870600, dated Oct. 17, 2019, 2 pages.
Decision to Grant received for Danish Patent Application No. PA201870601, dated Aug. 17, 2020, 2 pages.
Decision to Grant received for Danish Patent Application No. PA201870602, dated Aug. 18, 2020, 2 pages.
European Search Report received for European Patent Application No. 20182116.2, dated Oct. 21, 2020, 4 pages.
Extended European Search Report received for European Patent Application No. 20180581.9, dated Aug. 12, 2020, 9 pages.
Extended European Search Report received for European Patent Application No. 20180592.6, dated Aug. 11, 2020, 10 pages.
Final Office Action received for U.S. Appl. No. 15/705,849, dated May 1, 2020, 17 pages.
Final Office Action received for U.S. Appl. No. 16/138,809, dated Aug. 27, 2020, 24 pages.
Final Office Action received for U.S. Appl. No. 16/143,909, dated Aug. 28, 2019, 20 pages.
Final Office Action received for U.S. Appl. No. 16/143,997, dated Sep. 30, 2019, 16 pages.
Final Office Action received for U.S. Appl. No. 16/144,030, dated Feb. 13, 2020, 11 pages.
Final Office Action received for U.S. Appl. No. 16/144,030, dated Oct. 1, 2019, 13 pages.
Final Office Action received for U.S. Appl. No. 16/144,735, dated May 4, 2020, 12 pages.
Final Office Action received for U.S. Appl. No. 16/144,753, dated Sep. 22, 2020, 9 pages.
Final Office Action received for U.S. Appl. No. 16/144,849, dated Jun. 7, 2019, 29 pages.
Final Office Action received for U.S. Appl. No. 16/144,864, dated May 17, 2019, 24 pages.
Final Office Action received for U.S. Appl. No. 16/144,864, dated May 28, 2020, 29 pages.
Fitbit App, Available online at: <http://web.archive.org/web/20180114083150/https://www.fitbit.com/au/app>, Jan. 14, 2018, 8 pages.
Graphs and Charts, Online available at: <https://www.teachervision.com/lesson-planning/graph-chart-teacher-resources, retrieved on Dec. 12, 2018, 4 pages.
Intention to Grant received for Danish Patent Application No. PA201870379, dated May 2, 2019, 2 pages.
Intention to Grant received for Danish Patent Application No. PA201870600, dated Jul. 10, 2019, 2 pages.
Intention to Grant received for Danish Patent Application No. PA201870601, dated Apr. 24, 2020, 2 pages.
Intention to Grant received for Danish Patent Application No. PA201870602, dated Apr. 24, 2020, 2 pages.
International Preliminary Report on Patentability received for PCT Patent Application No. PCT/US2018/031662, dated Nov. 28, 2019, 12 pages.
International Preliminary Report on Patentability received for PCT Patent Application No. PCT/US2019/019694, dated Sep. 24, 2020, 12 pages.
International Preliminary Report on Patentability received for PCT Patent Application No. PCT/US2019/024570, dated Nov. 19, 2020, 10 pages.
International Search Report and Written Opinion received for PCT Patent Application No. PCT/US2018/031662, dated Sep. 27, 2018, 17 pages.
International Search Report and Written Opinion received for PCT Patent Application No. PCT/US2019/019694, dated Sep. 2, 2019, 17 pages.
International Search Report and Written Opinion received for PCT Patent Application No. PCT/US2019/024570, dated Aug. 8, 2019, 18 pages.
International Search Report and written Opinion received for PCT Patent Application No. PCT/US2020/025768, dated Aug. 10, 2020, 11 pages.
Invitation to Pay Addition Fees and Partial International Search Report received for PCT Patent Application No. PCT/US2018/031662, dated Jul. 16, 2018, 13 pages.
Invitation to Pay Addition Fees received for PCT Patent Application No. PCT/US2020/035474, dated Oct. 2, 2020, 11 pages.
Invitation to Pay Additional Fees received for PCT Patent Application No. PCT/US2019/019694, dated Jul. 10, 2019, 12 pages.
Invitation to Pay Search Fees received for European Patent Application No. 19726205.8, dated Feb. 14, 2020, 5 pages.
Multi-Set Bar Chart, The Data Visualization Catalogue, Available Online at: https://datavizcatalogue.com/methods/multiset_barchart.html, Feb. 8, 2014, 3 pages.
Non-Final Office Action Received for U.S. Appl. No. 16/144,864, dated Dec. 18, 2018, 19 pages.
Non-Final Office Action received for U.S. Appl. No. 15/705,849, dated Nov. 12, 2019, 15 pages.
Non-Final Office Action received for U.S. Appl. No. 16/138,809, dated Feb. 28, 2020, 22 pages.
Non-Final Office Action received for U.S. Appl. No. 16/143,909, dated Apr. 19, 2019, 16 pages.
Non-Final Office Action received for U.S. Appl. No. 16/143,959, dated Apr. 17, 2019, 15 pages.
Non-Final Office Action received for U.S. Appl. No. 16/143,997, dated Jul. 27, 2020, 15 pages.
Non-Final Office Action received for U.S. Appl. No. 16/143,997, dated May 21, 2019, 15 pages.
Non-Final Office Action received for U.S. Appl. No. 16/144,030, dated Apr. 12, 2019, 8 pages.
Non-Final Office Action received for U.S. Appl. No. 16/144,030, dated Nov. 5, 2020, 5 pages.
Non-Final Office Action received for U.S. Appl. No. 16/144,735, dated Feb. 19, 2020, 10 pages.
Non-Final Office Action received for U.S. Appl. No. 16/144,753, dated Mar. 5, 2020, 9 pages.
Non-Final Office Action received for U.S. Appl. No. 16/144,849, dated Dec. 31, 2018, 28 pages.
Non-Final Office Action received for U.S. Appl. No. 16/144,849, dated Sep. 17, 2019, 9 pages.
Non-Final Office Action received for U.S. Appl. No. 16/144,864, dated Jan. 31, 2020, 29 pages.

(56) References Cited

OTHER PUBLICATIONS

Non-Final Office Action received for U.S. Appl. No. 16/584,186, dated Dec. 6, 2019, 13 pages.
Non-Final Office Action received for U.S. Appl. No. 16/586,154, dated Dec. 28, 2020, 26 pages.
Non-Final Office Action received for U.S. Appl. No. 16/880,552, dated Jul. 23, 2020, 19 pages.
Non-Final Office Action received for U.S. Appl. No. 16/894,309, dated Oct. 15, 2020, 24 pages.
Non-Final Office Action received for U.S. Appl. No. 16/907,261, dated Sep. 30, 2020, 22 pages.
Notice of Acceptance received for Australian Patent Application No. 2019222943, dated May 5, 2020, 3 pages.
Notice of Acceptance received for Australian Patent Application No. 2020204153, dated Jul. 6, 2020, 3 pages.
Notice of Allowance received for Chinese Patent Application No. 201910972529.2, dated Sep. 14, 2020, 6 pages.
Notice of Allowance received for U.S. Appl. No. 15/705,849, dated Jul. 28, 2020, 10 pages.
Notice of Allowance received for U.S. Appl. No. 15/705,849, dated Oct. 16, 2020, 14 pages.
Notice of Allowance received for U.S. Appl. No. 16/143,909, dated Jan. 21, 2020, 9 pages.
Notice of Allowance received for U.S. Appl. No. 16/143,959, dated Oct. 31, 2019, 10 pages.
Notice of Allowance received for U.S. Appl. No. 16/144,671, dated Feb. 10, 2020, 17 pages.
Notice of Allowance received for U.S. Appl. No. 16/144,735, dated Jul. 21, 2020, 13 pages.
Notice of Allowance received for U.S. Appl. No. 16/144,735, dated Oct. 28, 2020, 13 pages.
Notice of Allowance received for U.S. Appl. No. 16/144,849, dated Apr. 17, 2020, 2 pages.
Notice of Allowance received for U.S. Appl. No. 16/144,849, dated Mar. 6, 2020, 9 pages.
Notice of Allowance received for U.S. Appl. No. 16/144,864, dated Jul. 28, 2020, 27 pages.
Notice of Allowance received for U.S. Appl. No. 16/144,864, dated Sep. 10, 2020, 3 pages.
Notice of Allowance received for U.S. Appl. No. 16/144,864, dated Sep. 16, 2020, 2 pages.
Notice of Allowance received for U.S. Appl. No. 16/144,864, dated Sep. 29, 2020, 2 pages.
Notice of Allowance received for U.S. Appl. No. 16/584,186, dated Mar. 24, 2020, 10 pages.
Office Action received for Australian Patent Application No. 2018268972, dated Jul. 9, 2020, 4 pages.
Office Action received for Australian Patent Application No. 2019100222, dated May 24, 2019, 6 pages.
Office Action received for Australian Patent Application No. 2019100495, dated Mar. 6, 2020, 3 pages.
Office Action received for Australian Patent Application No. 2019100495, dated Mar. 16, 2020, 3 pages.
Office Action received for Australian Patent Application No. 2019100495, dated Sep. 17, 2019, 7 pages.
Office Action received for Australian Patent Application No. 2019222943, dated Oct. 3, 2019, 3 pages.
Office Action received for Australian Patent Application No. 2019234289, dated Nov. 2, 2020, 6 pages.
Office Action received for Australian Patent Application No. 2020230340, dated Nov. 2, 2020, 5 pages.
Office Action received for Chinese Patent Application No. 201910858933.7, dated Aug. 18, 2020, 14 pages.
Office Action received for Chinese Patent Application No. 201910972529.2, dated Jun. 28, 2020, 8 pages.
Office Action received for Danish Patent Application No. PA201870378, dated Feb. 25, 2019, 3 pages.
Office Action received for Danish Patent Application No. PA201870378, dated Jan. 6, 2020, 3 pages.
Office Action received for Danish Patent Application No. PA201870379, dated Feb. 28, 2019, 3 pages.
Office Action received for Danish Patent Application No. PA201870380, dated Mar. 5, 2020, 2 pages.
Office Action received for Danish Patent Application No. PA201870380, dated Mar. 27, 2019, 4 pages.
Office Action received for Danish Patent Application No. PA201870380, dated Sep. 11, 2018, 9 pages.
Office Action received for Danish Patent Application No. PA201870599, dated Dec. 20, 2019, 5 pages.
Office Action received for Danish Patent Application No. PA201870600, dated May 8, 2019, 3 pages.
Office Action received for Danish Patent Application No. PA201870601, dated Dec. 13, 2018, 8 pages.
Office Action received for Danish Patent Application No. PA201870601, dated Jan. 14, 2020, 3 pages.
Office Action received for Danish Patent Application No. PA201870601, dated Jun. 25, 2019, 3 pages.
Office Action received for Danish Patent Application No. PA201870602, dated Feb. 5, 2020, 3 pages.
Office Action received for Danish Patent Application No. PA201870602, dated Jun. 26, 2019, 3 Pages.
Office Action received for Danish Patent Application No. PA201970534, dated Jun. 29, 2020, 2 pages.
Office Action received for European Patent Application No. 19721883.7, dated Jan. 10, 2020, 4 pages.
Office Action received for European Patent Application No. 19721883.7, dated May 28, 2020, 11 pages.
Office Action received for European Patent Application No. 19726205.8, dated Jun. 26, 2020, 9 pages.
Office Action received for European Patent Application No. 20182116.2, dated Nov. 6, 2020, 9 pages.
Office Action received for Japanese Patent Application No. 2019-162293, dated Jan. 31, 2020, 8 pages.
Office Action received for Japanese Patent Application No. 2019-162293, dated Jul. 27, 2020, 9 pages.
Office Action received for Japanese Patent Application No. 2020-104679, dated Sep. 18, 2020, 13 pages.
Office Action received for Korean Patent Application No. 10-2019-7025538, dated Aug. 15, 2020, 8 pages.
Office Action received for Korean Patent Application No. 10-2019-7025538, dated Feb. 17, 2020, 12 pages.
Result of Consultation received for European Patent Application No. 19721883.7, dated Oct. 7, 2020, 3 pages.
Search Report and Opinion received for Danish Patent Application No. PA201870378, dated Sep. 10, 2018, 9 pages.
Search Report and Opinion received for Danish Patent Application No. PA201870379, dated Sep. 14, 2018, 9 pages.
Search Report and Opinion received for Danish Patent Application No. PA201870599, dated Dec. 21, 2018, 9 pages.
Search Report and Opinion received for Danish Patent Application No. PA201870600, dated Jan. 31, 2019, 8 pages.
Search Report and Opinion received for Danish Patent Application No. PA201870602, dated Dec. 19, 2018, 8 pages.
Search Report and Opinion received for Danish Patent Application No. PA201970534, dated Sep. 23, 2019, 6 pages.
Search Report and Opinion received for Danish Patent Application No. PA202070620, dated Dec. 11, 2020, 9 pages.
Summons to Attend Oral Proceedings received for European Patent Application No. 19726205.8, dated Oct. 29, 2020, 13 pages.
Supplemental Notice of Allowance received for U.S. Appl. No. 16/144,849, dated Mar. 31, 2020, 2 pages.
Suunto Spartan Trainer Wrist HR 1.12, Online Available at:—https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
Visual Pace Alarm app, Available Online at: https://apps.garmin.com/en-US/apps/3940f3a2-4847-4078-a911-d77422966c82, Oct. 19, 2016, 1 page.
Casella Cel Casella, "The Casella dBadge2—World's First Truly Wireless Noise Dosimeter and Airwave App!", Retrieved from URL: <https://www.youtube.com/watch?v=Xvy2fl3cgYo>, May 27, 2015, 3 pages.

(56) References Cited

OTHER PUBLICATIONS

Chatrzarrin Hanieh, "Feature Extraction for the Differentiation of Dry and Wet Cough Sounds", Carleton University, Sep. 2011, 144 pages.
CNET, "Google Fit's automatic activity tracking is getting smarter on Android Wear", Available online at: https://www.youtube.com/watch?v=IttzlCid_d8, May 18, 2016, 1 page.
DC Rainmaker, "Garmin Fenix3 New Auto Climb Functionality", Available online at: https://www.youtube.com/watch?v=iuavOSNpVRc, Feb. 19, 2015, 1 page.
Evergreen et al., "Bar Chart", Better Evaluation, Available Online at: https://www.betterevaluation.org/en/evaluation-options/BarChart, Oct. 31, 2014, 8 pages.
Epstein et al., "Examining Menstrual Tracking to Inform the Design of Personal Informatics Tools", Proceedings of the 2017 CHI Conference on Human Factors in Computing Systems, CHI '17, ACM Press, Denver, CO, USA, May 6-11, 2017.
Garmin, "Fenix 5x Owner's Manual", Online Available at:—https://web.archive.org/web/20180127170640/https://static.garmin.com/pumac/fenix5x_OM_EN.pdf, Jan. 27, 2018, 42 pages.
Haslam Oliver, "Stop Coronavirus in its Tracks by Using This Apple Watch App to Time Hand Washes", Available Online at: <https://www.imore.com/stop-coronavirus-its-tracks-using-apple-watch-app-time-hand-washes>, Mar. 12, 2020, 12 pages.
Liaqat et al., "Challenges with Real-World Smartwatch based Audio Monitoring", WearSys'18, Munich, Germany, Available Online at: <https://doi.org/10.1145/3211960.3211977>, Jun. 10, 2018, 6 pages.
Lyles Taylor, "Wear OS Smartwatches are Now Sending Reminders to Wash Your Hands", Available Online at: <https://www.theverge.com/2020/4/14/21221294/google-wear-os-smartwatches-reminders-wash-your-hands>, Apr. 14, 2020, 2 pages.
Megadepot, "Casella dBadge2 Noise Dosimeter", Retrieved from URL: <https://www.youtube.com/watch?v=pHiHLiYCD08>, Jun. 12, 2018, 3 pages.
Moglia et al., "Evaluation of Smartphone Menstrual Cycle Tracking Applications Using an Adapted Applications Scoring System", Obstetrics and Gynecology, vol. 127. No. 6, Jun. 2016, pp. 1153-1160.
Myflo App, "Functional Medicine Period Tracker and Hormone Balancing App", Available online at <https://web.archive.org/web/20170127104125/https://myflotracker.com/>, Jan. 2017, 14 pages.
Myflo Tutorial, "How to change the start date of your current period", Available online at <https://www.youtube.com/watch?v=uQQ-odIBJB4>, Jan. 23, 2017, 3 pages.
Myflo Tutorial, "Setting and changing the end date of your period", Available online at <https://www.youtube.com/watch?v=UvAA4OgqL3E>, Jan. 23, 2017, 3 pages.
Peters Jay, "Samsung's Smartwatches Get a Hand-Washing Reminder and Timer App", Available Online at: < https://www.theverge.com/2020/4/17/21225205/samsung-smartwatch-galaxy-active-hand-washing-timer-reminder-app>, Apr. 17, 2020, 2 pages.
Rizknows, "TomTom Multisport Cardio Review", Online available at:—https://www.youtube.com/watch?v=WoVCzLrSN9A, Sep. 4, 2015, 1 page.
Schoon Ben, "Wear OS Now Sends a Reminder to Wash Your Hands Every Few Hours", Available Online at: <https://9to5google.com/2020/04/14/wear-os-wash-hands-reminder-coronavirus/>, Apr. 14, 2020, 7 pages.
Smith, "Garmin Fenix 5 Activity/Smart Watch Review", Online Available at:—https://www.youtube.com/watch?v=6PkQxXQxpoU, Sep. 2, 2017, 1 page.
Sportstechguides, "Garmin Fenix 5: How to Add Power Data Fields", Online Available at:—https://www.youtube.com/watch?v=ZkPptnnXEiQ, Apr. 29, 2017, 2 pages.
Sportstechguides, "Garmin Fenix 5: How to Set Up Run Alerts", Online Available at:—https://www.youtube.com/watch?v=gSMwv8vlhB4, May 13, 2017, 2 pages.
Studiosixdigital, "Dosimeter", Retrieved from URL: <https://studiosixdigital.com/audiotools-modules-2/spl-modules/dosimeter.html>, Mar. 3, 2017, 6 pages.

Suunto, "Suunto Spartan—Heart Rate Zones", Online Available at:—https://www.youtube.com/watch?v=aixfoCnSOOU, Mar. 19, 2018, 2 pages.
Teunmo, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.
TomTom, "TomTom Runner & Multi-Sport Reference Guide", Online available at:—https://web.archive.org/web/20150908075934/http://download.tomtom.com/open/manuals/Runner_Multi-Sport/refman/TomTom-Runner-Multi-Sport-RG-en-GB.pdf, Sep. 8, 2015, 44 pages.
Wesley, "Apple Watch Series 1", online available at:—http://toolbox.info/blog/archives/1737-unknown.html, May 28, 2015, 5 pages.
Youtube, "Apple Watch Series 3", Online available at:—https://www.youtube.com/watch?v=iBPr9gEfkK8, Nov. 21, 2017, 15 pages.
Zlelik, "Garmin Fenix 5 Open Water Swimming Activity Demo", "Online Available at:—https://www.youtube.com/watch?v=iSVhdvw2dcs", Jun. 9, 2017, 1 page.
Decision to Grant received for Danish Patent Application No. PA202070619, dated Aug. 11, 2022, 2 pages.
Notice of Acceptance received for Australian Patent Application No. 2021204422, dated Aug. 15, 2022, 3 pages.
Office Action received for Japanese Patent Application No. 2021-167557, dated Aug. 15, 2022, 5 pages (3 pages of English Translation and 2 pages of Official Copy).
Applicant-Initiated Interview Summary received for U.S. Appl. No. 16/851,451, dated Aug. 5, 2022, 3 pages.
Applicant-Initiated Interview Summary received for U.S. Appl. No. 16/888,780, dated Aug. 2, 2022, 4 pages.
Corrected Notice of Allowance received for U.S. Appl. No. 17/197,628, dated Jul. 29, 2022, 2 pages.
Non-Final Office Action received for U.S. Appl. No. 16/953,781, dated Jul. 26, 2022, 9 pages.
Notice of Allowance received for Japanese Patent Application No. 2020-551585, dated Jul. 22, 2022, 4 pages (1 page of English Translation and 3 pages of Official Copy).
Office Action received for Korean Patent Application No. 10-2020-0124134, dated Jul. 28, 2022, 22 pages (11 pages of English Translation and 11 pages of Official Copy).
International Preliminary Report on Patentability received for PCT Patent Application No. PCT/US2021/048568, dated Mar. 9, 2023, 11 pages.
Non-Final Office Action received for U.S. Appl. No. 16/851,451, dated Feb. 24, 2023, 28 pages.
Non-Final Office Action received for U.S. Appl. No. 17/337,147, dated Feb. 21, 2023, 15 pages.
Notice of Allowance received for U.S. Appl. No. 16/953,781, dated Feb. 27, 2023, 5 pages.
Office Action received for Australian Patent Application No. 2022204568, dated Mar. 11, 2023, 4 pages.
Notice of Allowance received for Chinese Patent Application No. 202111611270.2, dated Sep. 21, 2022, 4 pages (1 page of English Translation and 3 pages of Official Copy).
Supplemental Notice of Allowance received for U.S. Appl. No. 17/041,415, dated Sep. 20, 2022, 2 pages.
Supplemental Notice of Allowance received for U.S. Appl. No. 17/317,084, dated Sep. 20, 2022, 2 pages.
Corrected Notice of Allowance received for U.S. Appl. No. 16/143,997, dated Oct. 21, 2021, 2 pages.
Corrected Notice of Allowance received for U.S. Appl. No. 16/586,154, dated Oct. 27, 2021, 2 pages.
International Search Report and Written Opinion received for PCT Patent Application No. PCT/US2021/035227, dated Oct. 6, 2021, 17 pages.
Office Action received for Danish Patent Application No. PA202070619, dated Oct. 14, 2021, 3 pages.
Office Action received for Korean Patent Application No. 10-2021-7031939, dated Oct. 19, 2021. 11 pages (5 pages of English Translation and 6 pages of Official Copy).
Notice of Acceptance received for Australian Patent Application No. 2022235614, dated Jul. 6, 2023, 3 pages.

(56) References Cited

OTHER PUBLICATIONS

Notice of Allowance received for Japanese Patent Application No. 2022-502594, dated Jul. 7, 2023, 4 pages (1 page of English Translation and 3 pages of Official Copy).
Office Action received for Danish Patent Application No. PA202070395, dated Jul. 5, 2023, 6 pages.
Office Action received for European Patent Application No. 20746438.9, dated Jul. 4, 2023, 7 pages.
Applicant-Initiated Interview Summary received for U.S. Appl. No. 17/896,791, dated Oct. 12, 2023, 2 pages.
Non-Final Office Action received for U.S. Appl. No. 17/584,190, dated Oct. 5, 2023, 17 pages.
Notice of Acceptance received for Australian Patent Application No. 2023212604, dated Oct. 12, 2023, 3 pages.
Notice of Allowance received for Chinese Patent Application No. 201880032190.1, dated Oct. 7, 2023, 4 pages (1 page of English Translation and 3 pages of Official Copy).
Office Action received for Australian Patent Application No. 2021283914, dated Sep. 25, 2023, 5 pages.
Supplemental Notice of Allowance received for U.S. Appl. No. 18/078,444, dated Oct. 16, 2023, 4 pages.
Decision to Grant received for European Patent Application No. 18727543.3, dated Aug. 18, 2023, 2 pages.
Examiner-Initiated Interview received for U.S. Appl. No. 17/896,791, dated Sep. 1, 2023, 2 pages.
Final Office Action received for U.S. Appl. No. 17/031,723, dated Oct. 4, 2023, 13 pages.
Non-Final Office Action received for U.S. Appl. No. 16/888,780, dated Aug. 17, 2023, 12 pages.
Non-Final Office Action received for U.S. Appl. No. 17/896,791, dated Aug. 30, 2023, 11 pages.
Notice of Acceptance received for Australian Patent Application No. 2022204568, dated Jul. 27, 2023, 3 pages.
Notice of Allowance received for Japanese Patent Application No. 2022-078280, dated Sep. 4, 2023, 4 pages (1 page of English Translation and 3 pages of Official Copy).
Notice of Allowance received for U.S. Appl. No. 18/078,444, dated Aug. 31, 2023, 6 pages.
Office Action received for Australian Patent Application No. 2021261861, dated Sep. 22, 2023, 5 pages.
Office Action received for Australian Patent Application No. 2023212604, dated Sep. 4, 2023, 3 pages.
Office Action received for European Patent Application No. 20760607.0, dated Aug. 17, 2023, 7 pages.
Office Action received for Japanese Patent Application No. 2022-078280, dated Jul. 24, 2023, 8 pages (4 pages of English Translation and 4 pages of Official Copy).
Office Action received for Japanese Patent Application No. 2022-131993, dated Sep. 15, 2023, 6 pages (3 pages of English Translation and 3 pages of Official Copy).
Luo et al., "Detection and Prediction of Ovulation From Body Temperature Measured by an In-Ear Wearable Thermometer", IEEE Transactions on Biomedical Engineering, Available online at: 10.1109/TBME.2019.2916823, vol. 67, No. 2, May 15, 2019, pp. 512-522.
Alivecor Kardia By, "How to Record a Clean EKG With Kardiaband", Available Online at: https://www.youtube.com/watch?v=_VIc9VE6VO4&t=2s, Nov. 30, 2017, 2 pages.
Applicant-Initiated Interview Summary received for U.S. Appl. No. 17/031,723, dated Oct. 31, 2023, 4 pages.
Applicant-Initiated Interview Summary received for U.S. Appl. No. 17/584,190, dated Dec. 4, 2023, 5 pages.
Decision on Appeal received for Korean Patent Application No. 10-2020-0124134, dated Oct. 20, 2023, 24 pages (4 pages of English Translation and 20 pages of Official Copy).
Extended European Search Report received for European Patent Application No. 23189089.8, dated Nov. 23, 2023, 11 pages.
Final Office Action received for U.S. Appl. No. 17/337,147, dated Oct. 31, 2023, 17 pages.
Hardwick Tim, "AliveCor 'Kardia Band' Medical Grade EKG Analyzer for Apple Watch Receives FDA Approval", MacRumors, Available online at: https://www.macrumors.com/2017/11/30/alivecor-kardia-ekg-band-medical-fda-apple-watch/, Nov. 30, 2017, 3 pages.
Notice of Allowance received for Japanese Patent Application No. 2022-078277, dated Oct. 27, 2023, 4 pages (1 page of English Translation and 3 pages of Official Copy).
Notice of Allowance received for Korean Patent Application No. 10-2020-0124134, dated Nov. 21, 2023, 8 pages (2 pages of English Translation and 6 pages of Official Copy).
Office Action received for Chinese Patent Application No. 202180053264.1, dated Sep. 23, 2023, 17 pages (9 pages of English Translation and 8 pages of Official Copy).
Office Action received for Danish Patent Application No. PA202070395, dated Nov. 3, 2023, 3 pages.
Office Action received for European Patent Application No. 20746438.9, dated Oct. 31, 2023, 9 pages.
Office Action received for European Patent Application No. 20751022.3, dated Oct. 19, 2023, 8 pages.
Office Action received for European Patent Application No. 20753659.0, dated Oct. 26, 2023, 9 pages.
Office Action received for Japanese Patent Application No. 2023-110196, dated Nov. 6, 2023, 4 pages (2 pages of English Translation and 2 pages of Official Copy).
Prasad et al., "Understanding Sharing Preferences and Behavior for Mhealth Devices", Proceedings of the 2012 ACM workshop on Privacy in the electronic society, Available online at: https://dl.acm.org/doi/10.1145/2381966.2381983, Oct. 15, 2012, pp. 117-128.
Corrected Notice of Allowance received for U.S. Appl. No. 17/896,791, dated Jan. 2, 2024, 2 pages.
Final Office Action received for U.S. Appl. No. 17/952,182, dated Jan. 4, 2024, 9 pages.
Office Action received for European Patent Application No. 20760607.0, dated Jan. 3, 2024, 7 pages.
Office Action received for Japanese Patent Application No. 2022-573764, dated Dec. 25, 2023, 8 pages (4 pages of English Translation and 4 pages of Official Copy).
Applicant-Initiated Interview Summary received for U.S. Appl. No. 16/888,780, dated Dec. 14, 2023, 3 pages.
International Search Report and Written Opinion received for PCT Patent Application No. PCT/US2023/022549, dated Aug. 1, 2023, 13 pages.
Notice of Allowance received for Japanese Patent Application No. 2022-131993, dated Dec. 18, 2023, 4 pages (1 page of English Translation and 3 pages of Official Copy).
Notice of Allowance received for U.S. Appl. No. 17/896,791, dated Dec. 15, 2023, 9 pages.
Office Action received for Korean Patent Application No. 10-2022-7012608, dated Dec. 5, 2023, 12 pages (5 pages of English Translation and 7 pages of Official Copy).

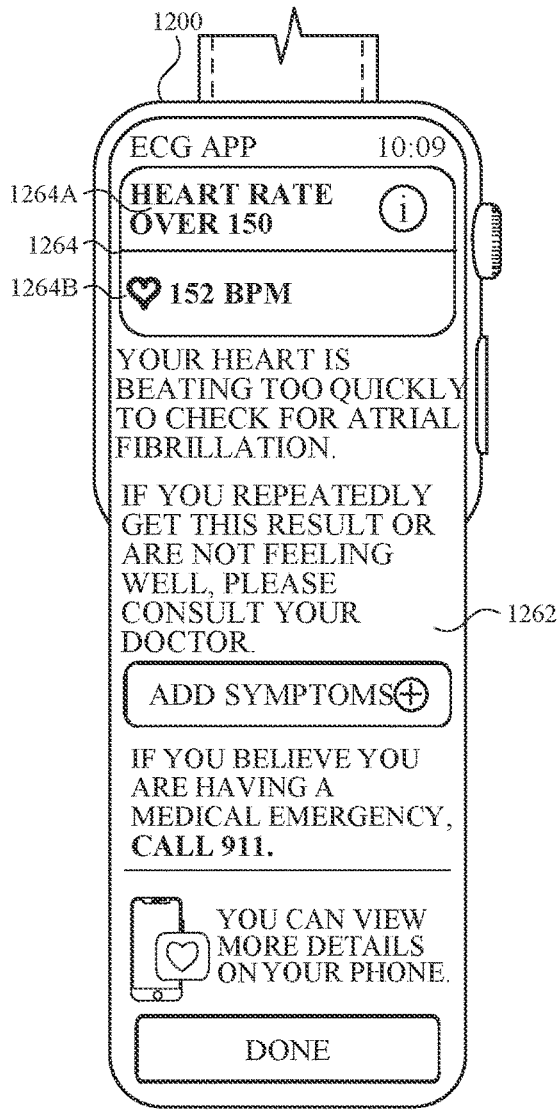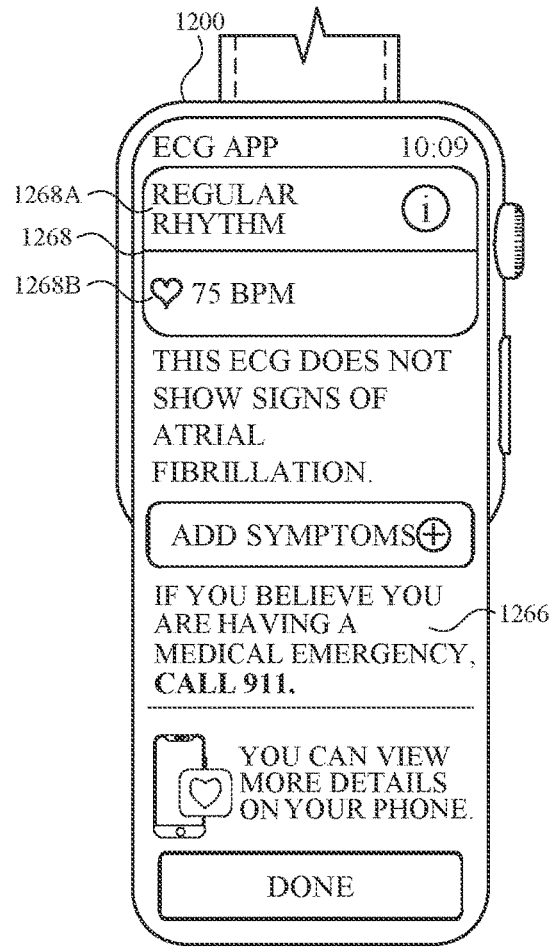
*FIG. 12Q*
*FIG. 12R*

USER INTERFACES FOR HEALTH MONITORING

CROSS-REFERENCE TO RELATED APPLICATIONS

This application is a continuation of U.S. patent application Ser. No. 16/144,030, entitled "USER INTERFACES FOR HEALTH MONITORING," filed Sep. 27, 2018, which claims priority to: U.S. Provisional Patent Application Ser. No. 62/657,881, entitled "USER INTERFACES FOR HEALTH MONITORING," filed Apr. 15, 2018; U.S. Provisional Patent Application Ser. No. 62/657,870, entitled "USER INTERFACES FOR HEALTH MONITORING," filed Apr. 15, 2018; U.S. Provisional Patent Application Ser. No. 62/643,699, entitled "USER INTERFACES FOR HEALTH MONITORING," filed Mar. 15, 2018; and U.S. Provisional Patent Application Ser. No. 62/641,994, entitled "USER INTERFACES FOR HEALTH MONITORING," filed Mar. 12, 2018. The contents of each of these applications are hereby incorporated by reference in their entireties.

This application relates to U.S. Provisional Patent Application Ser. No. 62/554,196, entitled "WEARABLE DEVICE WITH ELECTRODES FOR SENSING BIOLOGICAL PARAMETERS," filed Sep. 5, 2017, the contents of which are hereby incorporated by reference in their entirety and are also included in their entirety as Appendix A.

FIELD

The present disclosure relates generally to computer user interfaces, and more specifically to techniques for managing health monitoring.

BACKGROUND

Monitoring health, such as heart health using heart rhythm and heart rate information, using electronic devices is a convenient and effective method of providing and maintaining awareness of one's health. Using electronic devices enable a user to quickly and easily capture biometric information used to monitor the user's health.

BRIEF SUMMARY

Some techniques for managing health monitoring using electronic devices, however, are generally cumbersome and inefficient. For example, some existing techniques use a complex and time-consuming user interface, which may include multiple key presses or keystrokes. Existing techniques require more time than necessary, wasting user time and device energy. This latter consideration is particularly important in battery-operated devices.

Accordingly, the present technique provides electronic devices with faster, more efficient methods and interfaces for managing health monitoring. Such methods and interfaces optionally complement or replace other methods for managing health monitoring. Such methods and interfaces reduce the cognitive burden on a user and produce a more efficient human-machine interface. For battery-operated computing devices, such methods and interfaces conserve power and increase the time between battery charges. Such methods and interfaces enable a user to quickly and easily capture health information (thereby also incentivizing the user to frequently monitor his or her health) and to conveniently view and manage recorded health information (thereby raising awareness of the user's current health status to the user).

In accordance with some embodiments, a method performed at a first electronic device with a display and one or more input devices, wherein the first electronic device is paired with a second electronic device, is described. The method comprises: displaying, on the display, a first portion of a tutorial for using a function of the second electronic device; detecting, via the one or more input devices, a request to proceed with the tutorial; in response to detecting the request to proceed with the tutorial, displaying, on the display, instructions to perform an operation on the second electronic device that involves the function of the second electronic device; receiving, from the second electronic device, an indication that the instructions have been carried out; and in response to receiving the indication that the instructions have been carried out, displaying, on the display, a second portion of the tutorial that is different from the first portion.

In accordance with some embodiments, a non-transitory computer-readable storage medium is described. The non-transitory computer-readable storage medium storing one or more programs configured to be executed by one or more processors of a first electronic device with a display and one or more input devices, wherein the first electronic device is paired with a second electronic device, the one or more programs including instructions for: displaying, on the display, a first portion of a tutorial for using a function of the second electronic device; detecting, via the one or more input devices, a request to proceed with the tutorial; in response to detecting the request to proceed with the tutorial, displaying, on the display, instructions to perform an operation on the second electronic device that involves the function of the second electronic device; receiving, from the second electronic device, an indication that the instructions have been carried out; and in response to receiving the indication that the instructions have been carried out, displaying, on the display, a second portion of the tutorial that is different from the first portion.

In accordance with some embodiments, a transitory computer-readable storage medium is described. The transitory computer-readable storage medium storing one or more programs configured to be executed by one or more processors of a first electronic device with a display and one or more input devices, wherein the first electronic device is paired with a second electronic device, the one or more programs including instructions for: displaying, on the display, a first portion of a tutorial for using a function of the second electronic device; detecting, via the one or more input devices, a request to proceed with the tutorial; in response to detecting the request to proceed with the tutorial, displaying, on the display, instructions to perform an operation on the second electronic device that involves the function of the second electronic device; receiving, from the second electronic device, an indication that the instructions have been carried out; and in response to receiving the indication that the instructions have been carried out, displaying, on the display, a second portion of the tutorial that is different from the first portion.

In accordance with some embodiments, a first electronic device is described. The first electronic device, wherein the first electronic device is paired with a second electronic device, comprises: a display, one or more input devices; one or more processors; and memory storing one or more programs configured to be executed by the one or more processors, the one or more programs including instructions for: displaying, on the display, a first portion of a tutorial for using a function of the second electronic device; detecting, via the one or more input devices, a request to proceed with the tutorial; in response to detecting the request to proceed with the tutorial, displaying, on the display, instructions to perform an operation on the second electronic device that involves the function of the second electronic device; receiving, from the second electronic device, an indication that the instructions have been carried out; and in response to receiving the indication that the instructions have been carried out, displaying, on the display, a second portion of the tutorial that is different from the first portion.

In accordance with some embodiments, a first electronic device is described. The first electronic device, wherein the first electronic device is paired with a second electronic device, comprises: a display, one or more input devices; means for displaying, on the display, a first portion of a tutorial for using a function of the second electronic device; means for detecting, via the one or more input devices, a request to proceed with the tutorial; means, in response to detecting the request to proceed with the tutorial, for displaying, on the display, instructions to perform an operation on the second electronic device that involves the function of the second electronic device; means for receiving, from the second electronic device, an indication that the instructions have been carried out; and means, in response to receiving the indication that the instructions have been carried out, for displaying, on the display, a second portion of the tutorial that is different from the first portion.

In accordance with some embodiments, a method performed at a first electronic device with a display and one or more input devices including a biometric sensor is described. The method comprises: displaying, on the display, a first user interface indicating that the first electronic device is ready to detect biometric information; detecting a first input with the biometric sensor that satisfies first criteria; in response to detecting the first input with the biometric sensor: starting to record biometric information detected by the biometric sensor; and displaying, on the display, a second user interface that is different from the first user interface, wherein the second user interface includes an indication of progress in recording the biometric information; after recording at least a portion of the biometric information, detecting, via the one or more input devices, that the first criteria are no longer met; in response to detecting that the first criteria are no longer met for a first period of time, resetting the indication of progress in recording the biometric information and maintaining display of the second user interface; and in response to detecting that the first criteria are no longer met for a second period of time that is longer than the first period of time, replacing display of the second user interface with the first user interface.

In accordance with some embodiments, a non-transitory computer-readable storage medium is described. The non-transitory computer-readable storage medium storing one or more programs configured to be executed by one or more processors of a first electronic device with a display and one or more input devices including a biometric sensor, the one or more programs including instructions for: displaying, on the display, a first user interface indicating that the first electronic device is ready to detect biometric information; detecting a first input with the biometric sensor that satisfies first criteria; in response to detecting the first input with the biometric sensor: starting to record biometric information detected by the biometric sensor; and displaying, on the display, a second user interface that is different from the first user interface, wherein the second user interface includes an indication of progress in recording the biometric information; after recording at least a portion of the biometric information, detecting, via the one or more input devices, that the first criteria are no longer met; in response to detecting that the first criteria are no longer met for a first period of time, resetting the indication of progress in recording the biometric information and maintaining display of the second user interface; and in response to detecting that the first criteria are no longer met for a second period of time that is longer than the first period of time, replacing display of the second user interface with the first user interface.

In accordance with some embodiments, a transitory computer-readable storage medium is described. The transitory computer-readable storage medium storing one or more programs configured to be executed by one or more processors of a first electronic device with a display and one or more input devices including a biometric sensor, the one or more programs including instructions for: displaying, on the display, a first user interface indicating that the first electronic device is ready to detect biometric information; detecting a first input with the biometric sensor that satisfies first criteria; in response to detecting the first input with the biometric sensor: starting to record biometric information detected by the biometric sensor; and displaying, on the display, a second user interface that is different from the first user interface, wherein the second user interface includes an indication of progress in recording the biometric information; after recording at least a portion of the biometric information, detecting, via the one or more input devices, that the first criteria are no longer met; in response to detecting that the first criteria are no longer met for a first period of time, resetting the indication of progress in recording the biometric information and maintaining display of the second user interface; and in response to detecting that the first criteria are no longer met for a second period of time that is longer than the first period of time, replacing display of the second user interface with the first user interface.

In accordance with some embodiments, a first electronic device is described. The first electronic device comprises: a display; one or more input devices including a biometric sensor; one or more processors; and memory storing one or more programs configured to be executed by the one or more processors, the one or more programs including instructions for: displaying, on the display, a first user interface indicating that the first electronic device is ready to detect biometric information; detecting a first input with the biometric sensor that satisfies first criteria; in response to detecting the first input with the biometric sensor: starting to record biometric information detected by the biometric sensor; and displaying, on the display, a second user interface that is different from the first user interface, wherein the second user interface includes an indication of progress in recording the biometric information; after recording at least a portion of the biometric information, detecting, via the one or more input devices, that the first criteria are no longer met; in response to detecting that the first criteria are no longer met for a first period of time, resetting the indication of progress in recording the biometric information and maintaining display of the second user interface; and in response to detecting that the first criteria are no longer met for a second period of time that is longer than the first period of time, replacing display of the second user interface with the first user interface.

In accordance with some embodiments, a first electronic device is described. The first electronic device comprises: a display; one or more input devices including a biometric sensor; means for displaying, on the display, a first user interface indicating that the first electronic device is ready to detect biometric information; means for detecting a first input with the biometric sensor that satisfies first criteria; means, in response to detecting the first input with the biometric sensor, for: starting to record biometric information detected by the biometric sensor; and displaying, on the display, a second user interface that is different from the first user interface, wherein the second user interface includes an indication of progress in recording the biometric information; means, after recording at least a portion of the biometric information, for detecting, via the one or more input devices, that the first criteria are no longer met; means, in response to detecting that the first criteria are no longer met for a first period of time, for resetting the indication of progress in recording the biometric information and maintaining display of the second user interface; and means, in response to detecting that the first criteria are no longer met for a second period of time that is longer than the first period of time, for replacing display of the second user interface with the first user interface.

In accordance with some embodiments, a method performed at a first electronic device with a display and one or more input devices including a first input device with an integrated biometric sensor is described. The method comprises: displaying, on the display, a user interface of an application for capturing biometric information from the biometric sensor; while displaying the user interface of the application for capturing biometric information from the biometric sensor, detecting a first activation of the first input device; in response to detecting the first activation of the first input device and while capturing biometric information from the biometric sensor: in accordance with a determination that the first activation of the first input device was detected when first criteria are met, wherein the first criteria are based on progress toward capturing biometric information with the biometric sensor, performing a predefined operation associated with the first input device that interrupts capture of the biometric information; and in accordance with a determination that the first activation of the first input device was detected when the first criteria are not met, continuing to capture the biometric information without performing the predefined operation associated with the first input device.

In accordance with some embodiments, a non-transitory computer-readable storage medium is described. The non-transitory computer-readable storage medium storing one or more programs configured to be executed by one or more processors of a first electronic device with a display and one or more input devices including a first input device with an integrated biometric sensor, the one or more programs including instructions for: displaying, on the display, a user interface of an application for capturing biometric information from the biometric sensor; while displaying the user interface of the application for capturing biometric information from the biometric sensor, detecting a first activation of the first input device; in response to detecting the first activation of the first input device and while capturing biometric information from the biometric sensor: in accordance with a determination that the first activation of the first input device was detected when first criteria are met, wherein the first criteria are based on progress toward capturing biometric information with the biometric sensor, performing a predefined operation associated with the first input device that interrupts capture of the biometric information; and in accordance with a determination that the first activation of the first input device was detected when the first criteria are not met, continuing to capture the biometric information without performing the predefined operation associated with the first input device.

In accordance with some embodiments, a transitory computer-readable storage medium is described. The transitory computer-readable storage medium storing one or more programs configured to be executed by one or more processors of a first electronic device with a display and one or more input devices including a first input device with an integrated biometric sensor, the one or more programs including instructions for: displaying, on the display, a user interface of an application for capturing biometric information from the biometric sensor; while displaying the user interface of the application for capturing biometric information from the biometric sensor, detecting a first activation of the first input device; in response to detecting the first activation of the first input device and while capturing biometric information from the biometric sensor: in accordance with a determination that the first activation of the first input device was detected when first criteria are met, wherein the first criteria are based on progress toward capturing biometric information with the biometric sensor, performing a predefined operation associated with the first input device that interrupts capture of the biometric information; and in accordance with a determination that the first activation of the first input device was detected when the first criteria are not met, continuing to capture the biometric information without performing the predefined operation associated with the first input device.

In accordance with some embodiments, a first electronic device is described. The first electronic device comprises: a display; one or more input devices including a first input device with an integrated biometric sensor; one or more processors; and memory storing one or more programs configured to be executed by the one or more processors, the one or more programs including instructions for: displaying, on the display, a user interface of an application for capturing biometric information from the biometric sensor; while displaying the user interface of the application for capturing biometric information from the biometric sensor, detecting a first activation of the first input device; in response to detecting the first activation of the first input device and while capturing biometric information from the biometric sensor: in accordance with a determination that the first activation of the first input device was detected when first criteria are met, wherein the first criteria are based on progress toward capturing biometric information with the biometric sensor, performing a predefined operation associated with the first input device that interrupts capture of the biometric information; and in accordance with a determination that the first activation of the first input device was detected when the first criteria are not met, continuing to capture the biometric information without performing the predefined operation associated with the first input device.

In accordance with some embodiments, a first electronic device is described. The first electronic device comprises: a display; one or more input devices including a first input device with an integrated biometric sensor; means for displaying, on the display, a user interface of an application for capturing biometric information from the biometric sensor; means, while displaying the user interface of the application for capturing biometric information from the biometric sensor, for detecting a first activation of the first input device; means, in response to detecting the first activation of the first input device and while capturing biometric information from the biometric sensor, for: in accordance with a determination that the first activation of the first input device was detected when first criteria are met, wherein the first criteria are based on progress toward capturing biometric information with the biometric sensor, performing a predefined operation associated with the first input device that interrupts capture of the biometric information; and in accordance with a determination that the first activation of the first input device was detected when the first criteria are not met, continuing to capture the biometric information without performing the predefined operation associated with the first input device.

In accordance with some embodiments, a method performed at a first electronic device with a display and one or more input devices is described. The method comprises: capturing biometric information with a biometric sensor that is in communication with the first electronic device; displaying, on the display, a representation of an evaluation of a medical characteristic determined based on the biometric information captured by the biometric sensor; while displaying the representation of the evaluation of the medical characteristic, detecting, via the one or more input devices, a sequence of one or more inputs to add user-specified symptoms to the evaluation of the medical characteristic; in response to detecting the sequence of one or more inputs: in accordance with a determination that at least one of the user-specified symptoms meet respective criteria, displaying, on the display, a first user interface that includes an affordance that, when activated, initiates a process for seeking immediate medical attention; and in accordance with a determination that the user-specified symptoms do not meet the respective criteria, displaying, on the display, the representation of the evaluation of the medical characteristic and one or more representations of user-specified symptoms without displaying the first user interface.

In accordance with some embodiments, a non-transitory computer-readable storage medium is described. The non-transitory computer-readable storage medium storing one or more programs configured to be executed by one or more processors of a first electronic device with a display and one or more input devices, the one or more programs including instructions for: capturing biometric information with a biometric sensor that is in communication with the first electronic device; displaying, on the display, a representation of an evaluation of a medical characteristic determined based on the biometric information captured by the biometric sensor; while displaying the representation of the evaluation of the medical characteristic, detecting, via the one or more input devices, a sequence of one or more inputs to add user-specified symptoms to the evaluation of the medical characteristic; in response to detecting the sequence of one or more inputs: in accordance with a determination that at least one of the user-specified symptoms meet respective criteria, displaying, on the display, a first user interface that includes an affordance that, when activated, initiates a process for seeking immediate medical attention; and in accordance with a determination that the user-specified symptoms do not meet the respective criteria, displaying, on the display, the representation of the evaluation of the medical characteristic and one or more representations of user-specified symptoms without displaying the first user interface.

In accordance with some embodiments, a transitory computer-readable storage medium is described. The transitory computer-readable storage medium storing one or more programs configured to be executed by one or more processors of a first electronic device with a display and one or more input devices, the one or more programs including instructions for: capturing biometric information with a biometric sensor that is in communication with the first electronic device; displaying, on the display, a representation of an evaluation of a medical characteristic determined based on the biometric information captured by the biometric sensor; while displaying the representation of the evaluation of the medical characteristic, detecting, via the one or more input devices, a sequence of one or more inputs to add user-specified symptoms to the evaluation of the medical characteristic; in response to detecting the sequence of one or more inputs: in accordance with a determination that at least one of the user-specified symptoms meet respective criteria, displaying, on the display, a first user interface that includes an affordance that, when activated, initiates a process for seeking immediate medical attention; and in accordance with a determination that the user-specified symptoms do not meet the respective criteria, displaying, on the display, the representation of the evaluation of the medical characteristic and one or more representations of user-specified symptoms without displaying the first user interface.

In accordance with some embodiments, a first electronic device is described. The first electronic device comprises: a display; one or more input devices; one or more processors; and memory storing one or more programs configured to be executed by the one or more processors, the one or more programs including instructions for: capturing biometric information with a biometric sensor that is in communication with the first electronic device; displaying, on the display, a representation of an evaluation of a medical characteristic determined based on the biometric information captured by the biometric sensor; while displaying the representation of the evaluation of the medical characteristic, detecting, via the one or more input devices, a sequence of one or more inputs to add user-specified symptoms to the evaluation of the medical characteristic; in response to detecting the sequence of one or more inputs: in accordance with a determination that at least one of the user-specified symptoms meet respective criteria, displaying, on the display, a first user interface that includes an affordance that, when activated, initiates a process for seeking immediate medical attention; and in accordance with a determination that the user-specified symptoms do not meet the respective criteria, displaying, on the display, the representation of the evaluation of the medical characteristic and one or more representations of user-specified symptoms without displaying the first user interface.

In accordance with some embodiments, a first electronic device is described. The first electronic device comprises: a display; one or more input devices; means for capturing biometric information with a biometric sensor that is in communication with the first electronic device; means for displaying, on the display, a representation of an evaluation of a medical characteristic determined based on the biometric information captured by the biometric sensor; means, while displaying the representation of the evaluation of the medical characteristic, for detecting, via the one or more input devices, a sequence of one or more inputs to add user-specified symptoms to the evaluation of the medical characteristic; means, in response to detecting the sequence of one or more inputs, for: in accordance with a determination that at least one of the user-specified symptoms meet respective criteria, displaying, on the display, a first user interface that includes an affordance that, when activated, initiates a process for seeking immediate medical attention; and in accordance with a determination that the user-specified symptoms do not meet the respective criteria, displaying, on the display, the representation of the evaluation of the medical characteristic and one or more representations of user-specified symptoms without displaying the first user interface.

In accordance with some embodiments, a method performed at an electronic device with a display and one or more input devices, the electronic device operably connected to a plurality of biometric sensors, is described. The method comprises: receiving first biometric information from a first biometric sensor of the plurality of biometric sensors; in response to receiving the first biometric information and in accordance with a determination that the first biometric information satisfies first criteria, displaying, on the display, an alert including a first affordance for detecting additional biometric information; receiving, via the one or more input devices, user activation of the first affordance; and subsequent to receiving the user activation of the first affordance, receiving second biometric information associated with the first biometric information from a second biometric sensor of the plurality of biometric sensors that is different from the first biometric sensor.

In accordance with some embodiments, a non-transitory computer-readable storage medium is described. The non-transitory computer-readable storage medium storing one or more programs configured to be executed by one or more processors of an electronic device with a display and one or more input devices, the electronic device operably connected to a plurality of biometric sensors, the one or more programs including instructions for: receiving first biometric information from a first biometric sensor of the plurality of biometric sensors; in response to receiving the first biometric information and in accordance with a determination that the first biometric information satisfies first criteria, displaying, on the display, an alert including a first affordance for detecting additional biometric information; receiving, via the one or more input devices, user activation of the first affordance; and subsequent to receiving the user activation of the first affordance, receiving second biometric information associated with the first biometric information from a second biometric sensor of the plurality of biometric sensors that is different from the first biometric sensor.

In accordance with some embodiments, a transitory computer-readable storage medium is described. The transitory computer-readable storage medium storing one or more programs configured to be executed by one or more processors of an electronic device with a display and one or more input devices, the electronic device operably connected to a plurality of biometric sensors, the one or more programs including instructions for: receiving first biometric information from a first biometric sensor of the plurality of biometric sensors; in response to receiving the first biometric information and in accordance with a determination that the first biometric information satisfies first criteria, displaying, on the display, an alert including a first affordance for detecting additional biometric information; receiving, via the one or more input devices, user activation of the first affordance; and subsequent to receiving the user activation of the first affordance, receiving second biometric information associated with the first biometric information from a second biometric sensor of the plurality of biometric sensors that is different from the first biometric sensor.

In accordance with some embodiments, an electronic device is described. The electronic device comprises: a display; one or more input devices; is operably connected to a plurality of biometric sensors; memory storing one or more programs configured to be executed by the one or more processors, the one or more programs including instructions for: receiving first biometric information from a first biometric sensor of the plurality of biometric sensors; in response to receiving the first biometric information and in accordance with a determination that the first biometric information satisfies first criteria, displaying, on the display, an alert including a first affordance for detecting additional biometric information; receiving, via the one or more input devices, user activation of the first affordance; and subsequent to receiving the user activation of the first affordance, receiving second biometric information associated with the first biometric information from a second biometric sensor of the plurality of biometric sensors that is different from the first biometric sensor.

In accordance with some embodiments, an electronic device is described. The electronic device comprises: a display; one or more input devices; is operably connected to a plurality of biometric sensors; means for receiving first biometric information from a first biometric sensor of the plurality of biometric sensors; means, in response to receiving the first biometric information and in accordance with a determination that the first biometric information satisfies first criteria, for displaying, on the display, an alert including a first affordance for detecting additional biometric information; means for receiving, via the one or more input devices, user activation of the first affordance; and means, subsequent to receiving the user activation of the first affordance, for receiving second biometric information associated with the first biometric information from a second biometric sensor of the plurality of biometric sensors that is different from the first biometric sensor.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for managing health monitoring, thereby increasing the effectiveness, efficiency, and user satisfaction with such devices. Such methods and interfaces may complement or replace other methods for managing health monitoring.

DESCRIPTION OF THE FIGURES

For a better understanding of the various described embodiments, reference should be made to the Description of Embodiments below, in conjunction with the following drawings in which like reference numerals refer to corresponding parts throughout the figures.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for managing health monitoring. For example, there is a need for electronic devices that quickly and conveniently capture biometric information from a user to enable the user to easily monitor his or her health. For another example, there is a need for electronic devices that manage captured biometric information from the user such that the user can easily and conveniently access and view monitoring and evaluation results. For another example, there is a need for electronic devices that efficiently present evaluation results to the user to enable the user to easily understand and properly respond to the results. Such techniques can reduce the cognitive burden on a user who accesses health monitoring features, thereby enhancing productivity. Further, such techniques can reduce processor and battery power otherwise wasted on redundant user inputs.

Figure 6A:
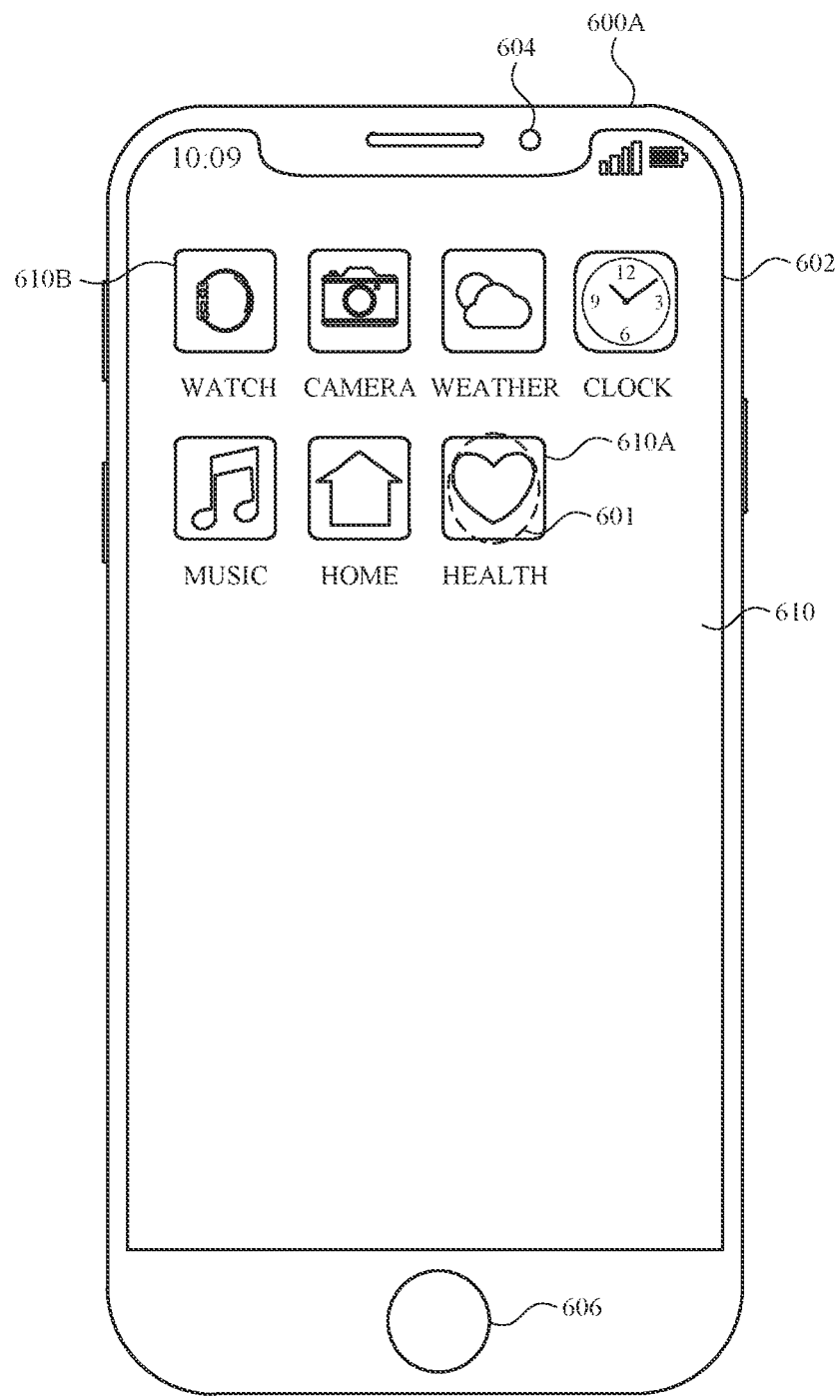
FIGS. 6A-6AE illustrate exemplary user interfaces for initial setup of health monitoring.
Figure 7A:
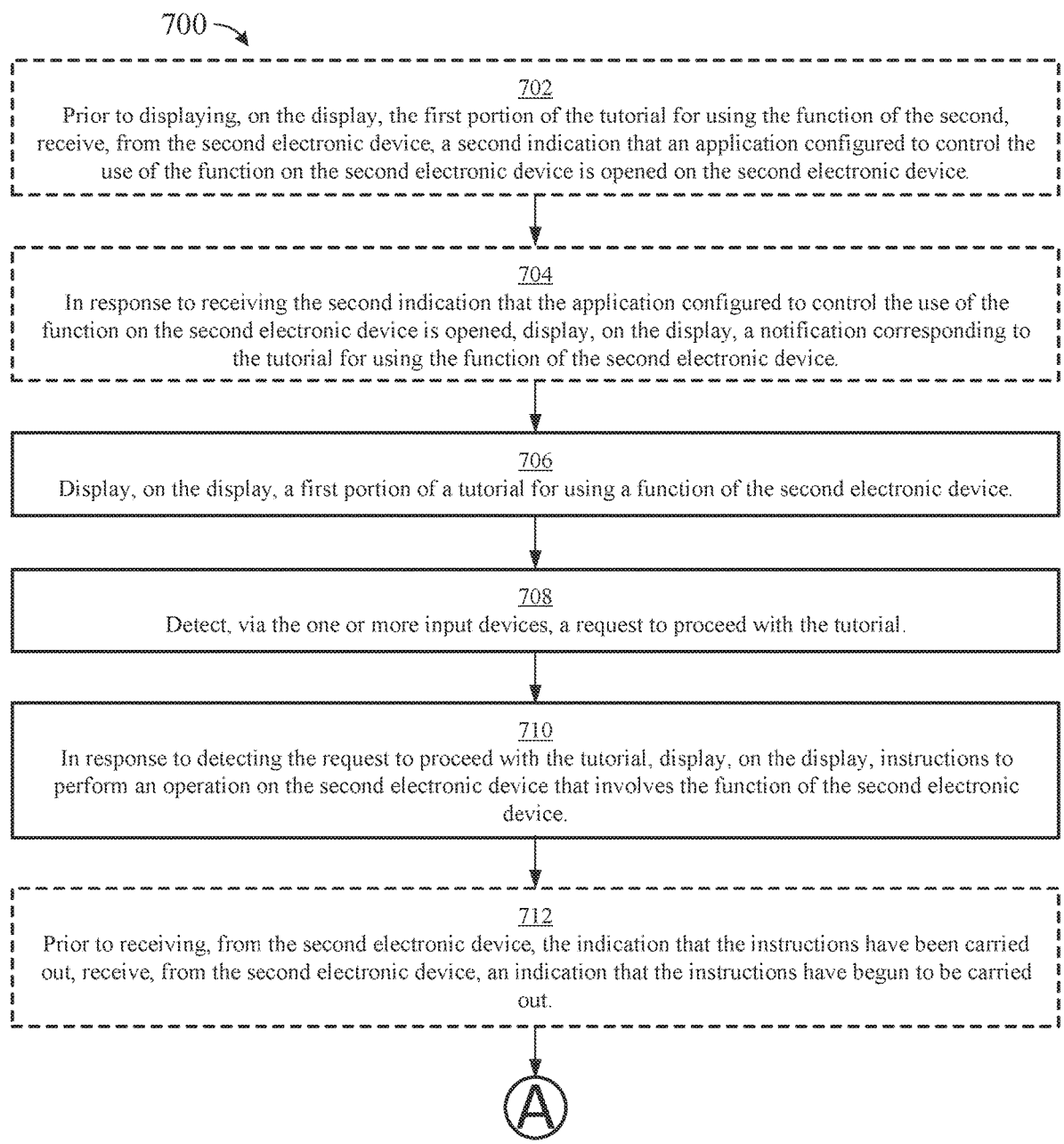
FIGS. 7A-7C illustrate a flow diagram for initial setup of heath monitoring, in accordance with some embodiments.
Figure 7B:
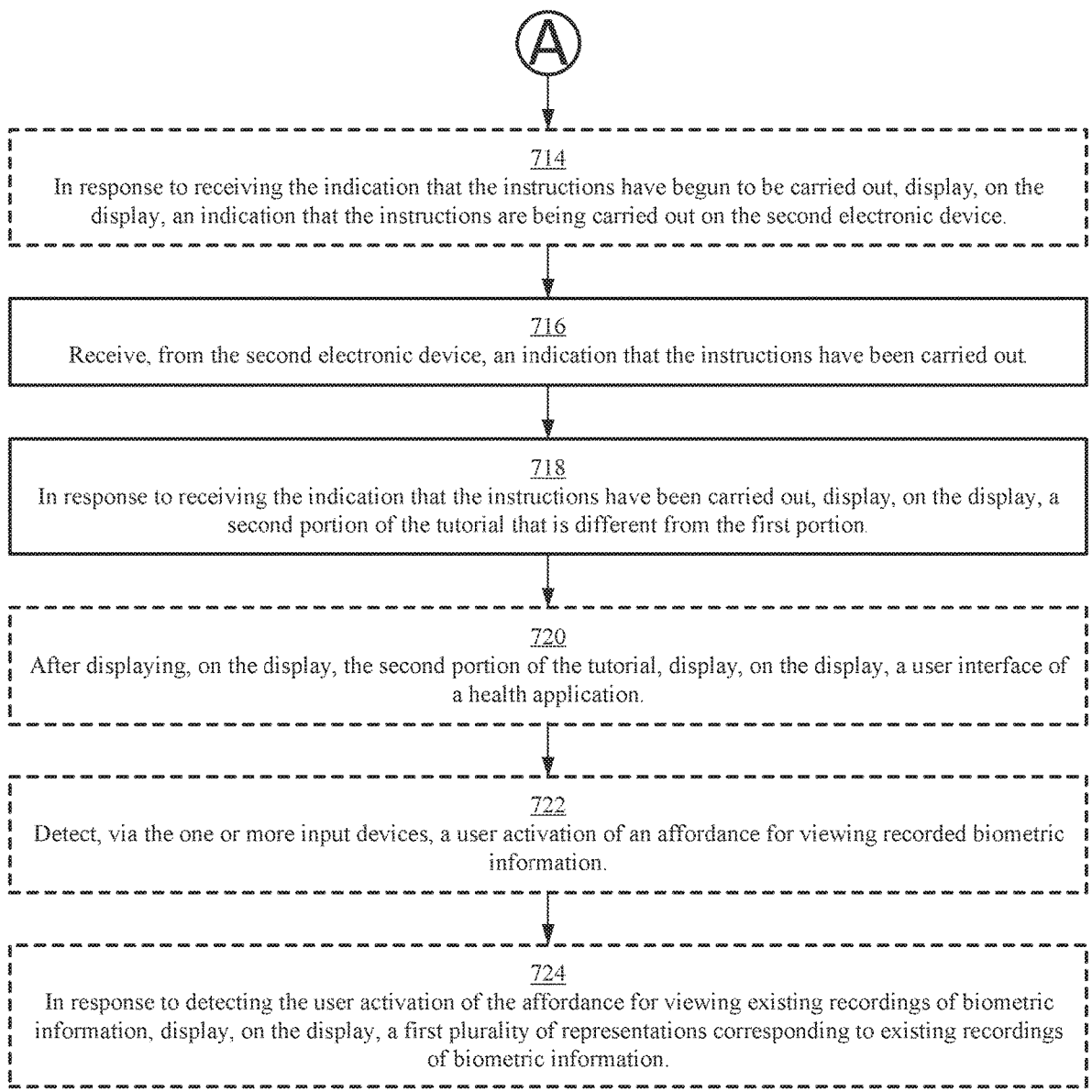
Figure 7C:
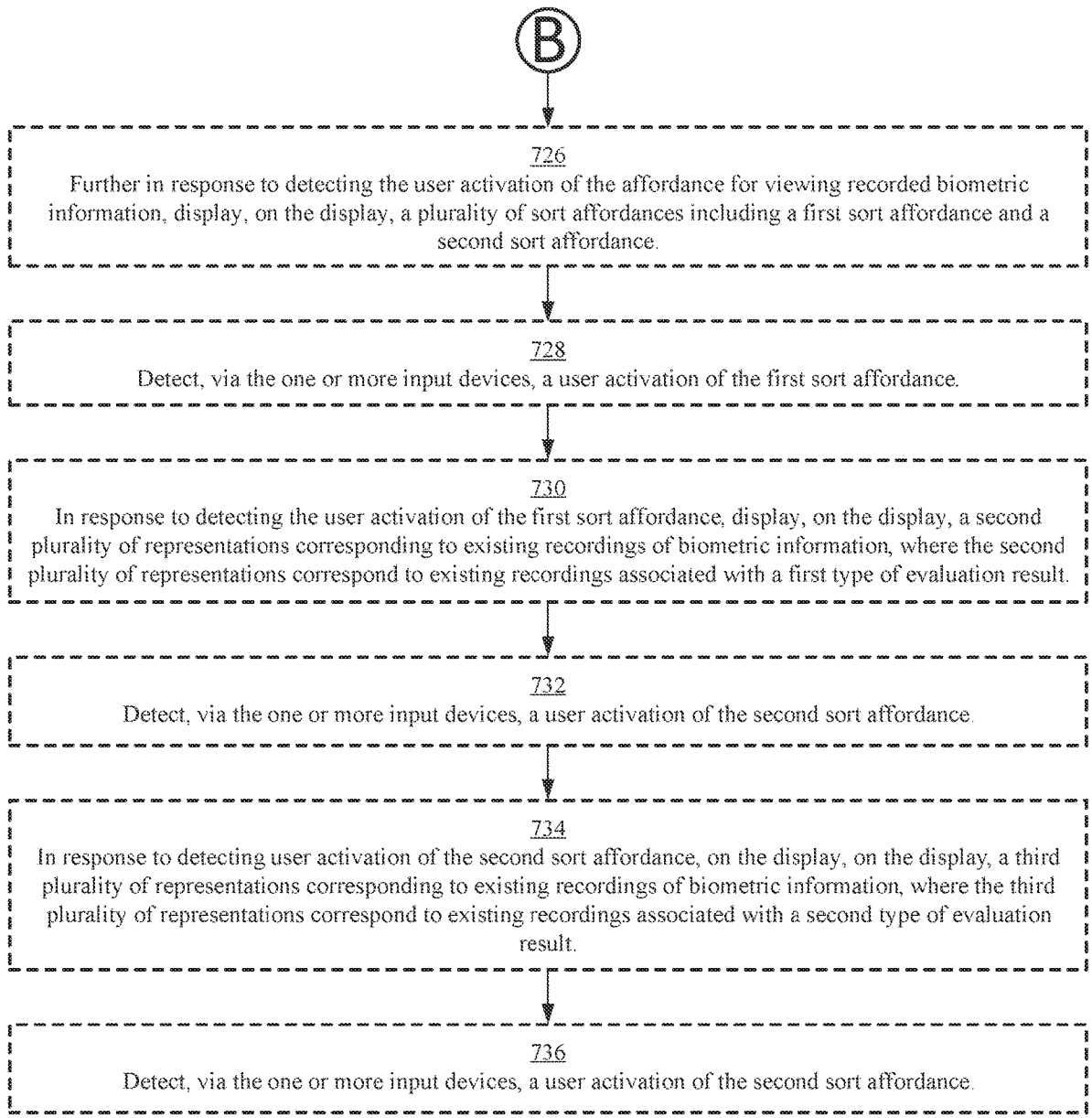
Figure 8A:
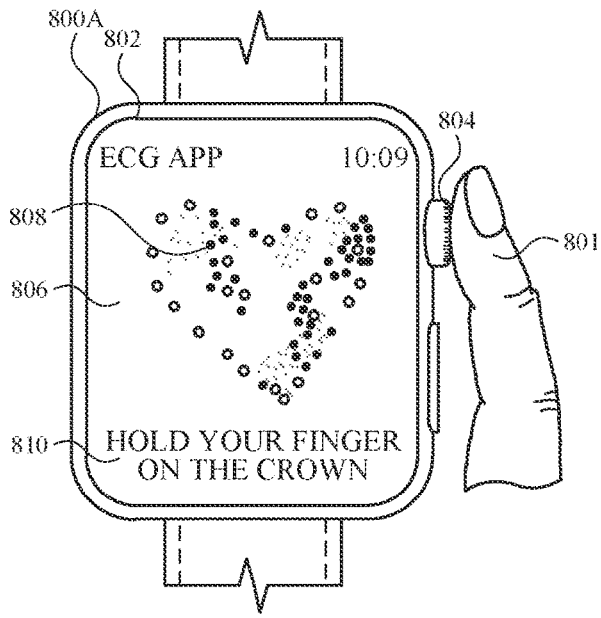
FIGS. 8A-8S illustrate exemplary user interfaces for recording biometric information for use in health monitoring.
Figure 8S:
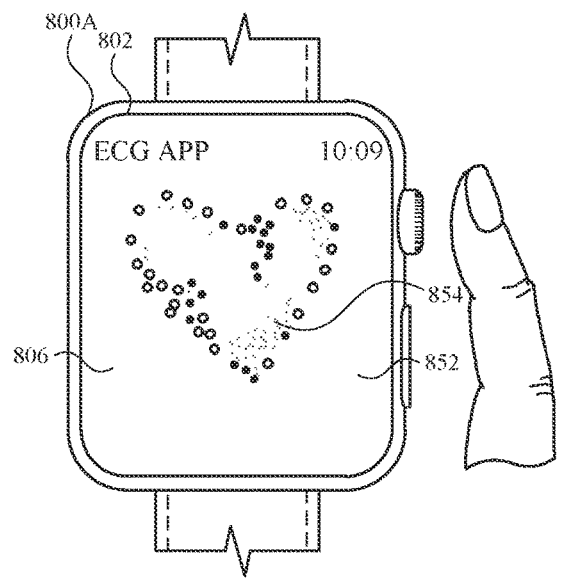
Figure 9A:
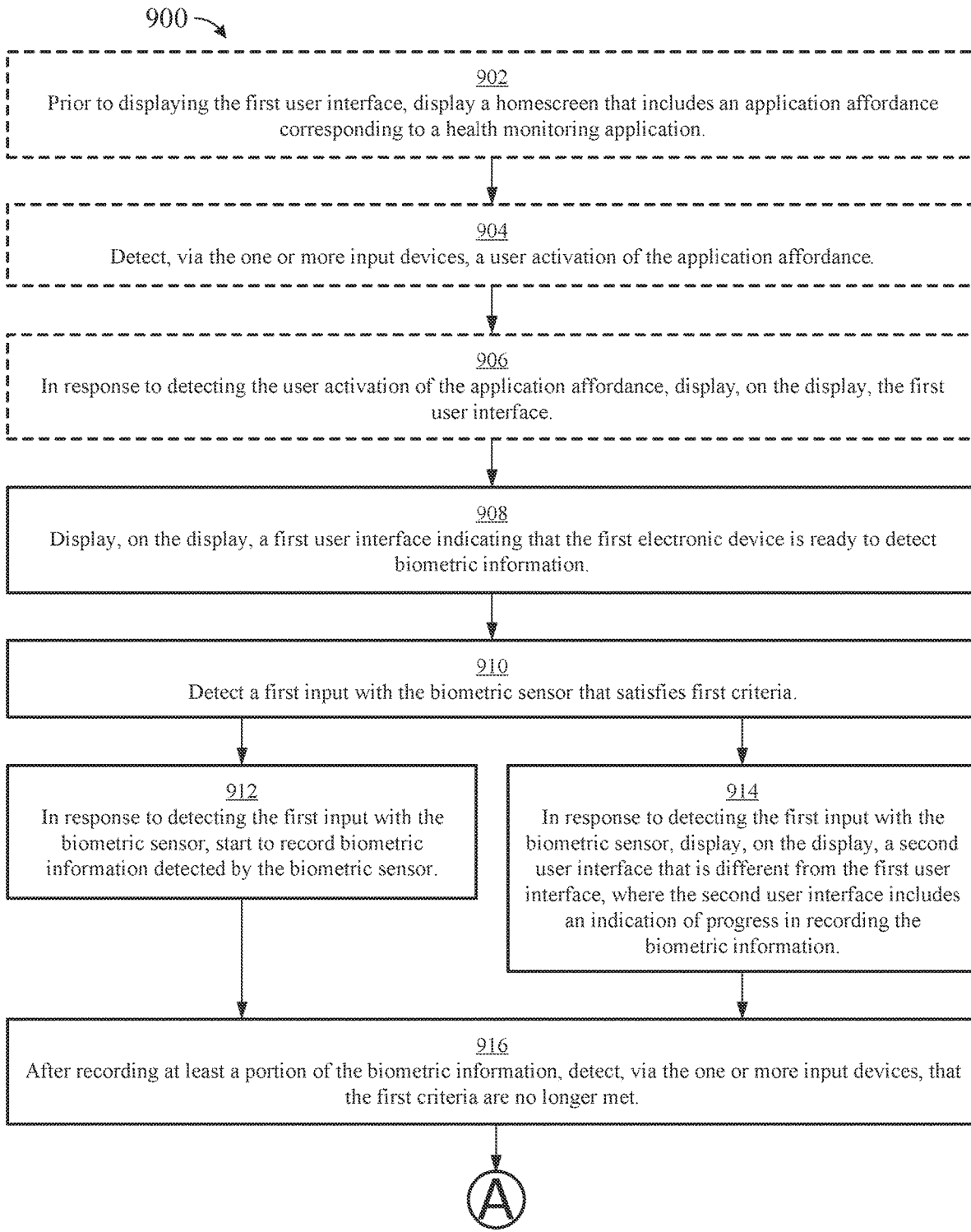
FIGS. 9A-9B illustrate a flow diagram for recording biometric information for health monitoring, in accordance with some embodiments.
Figure 9B:
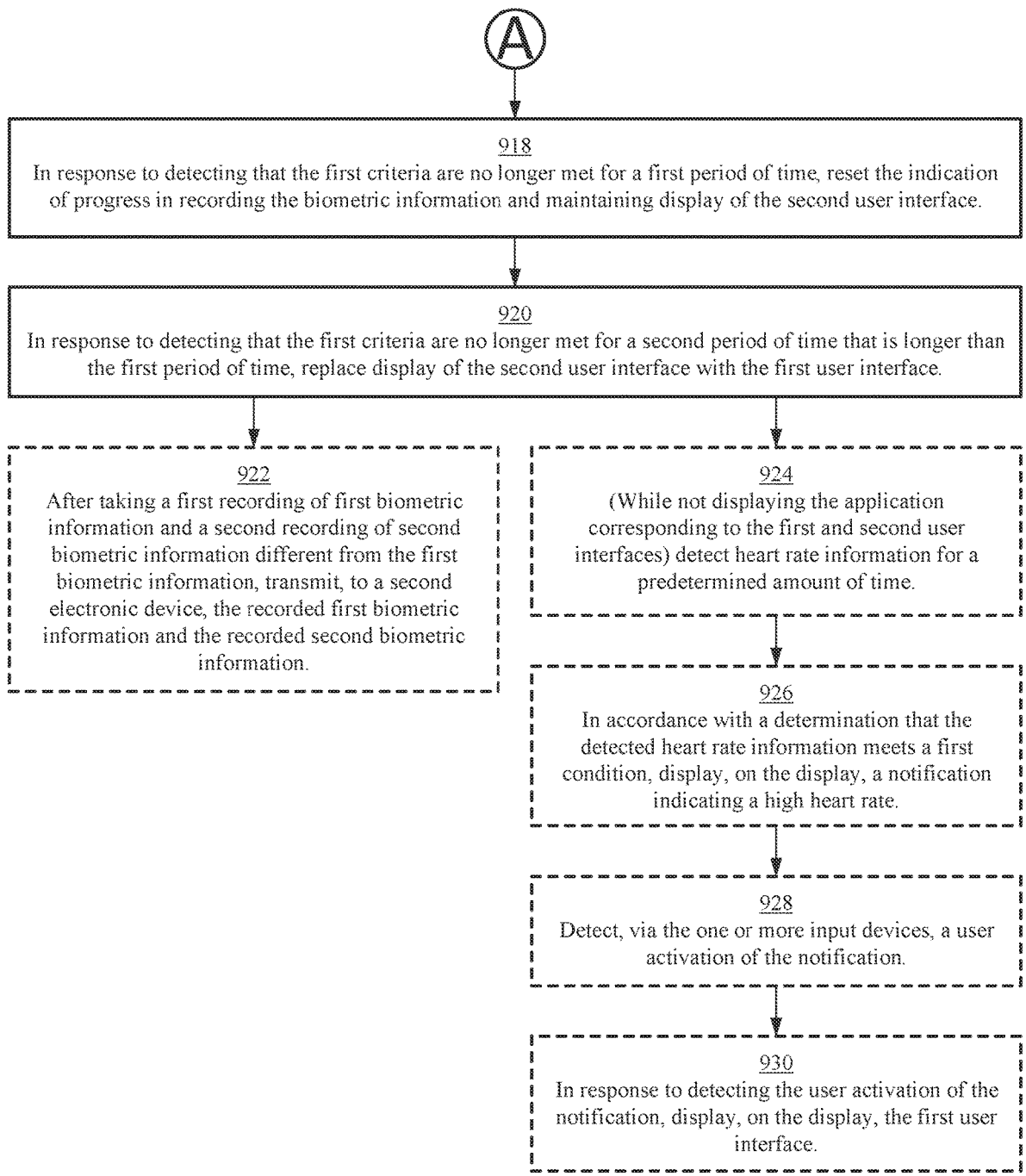
Figure 11:
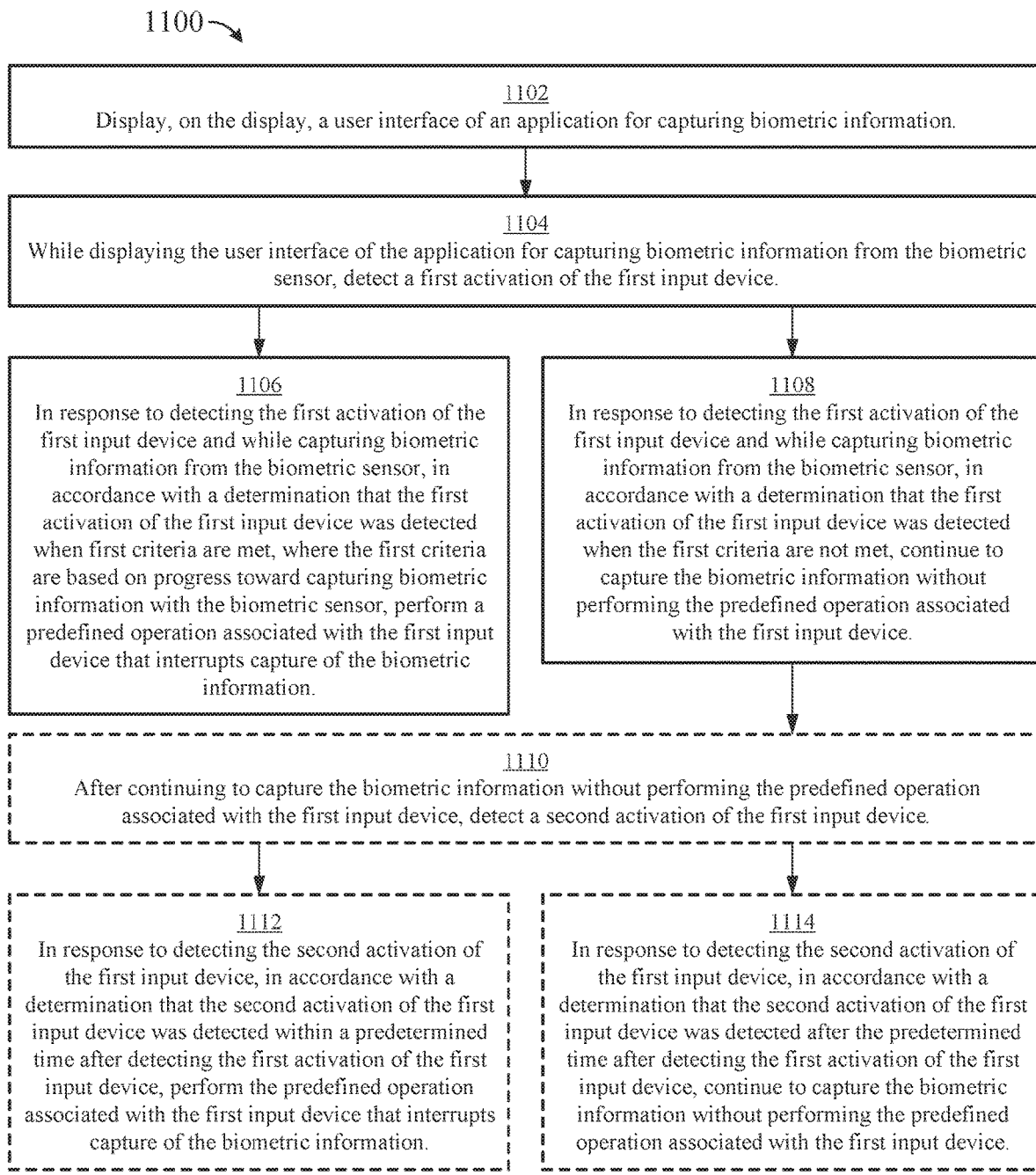
FIG. 11 illustrates a flow diagram for using an input device for health monitoring, in accordance with some embodiments.
Figure 12A:
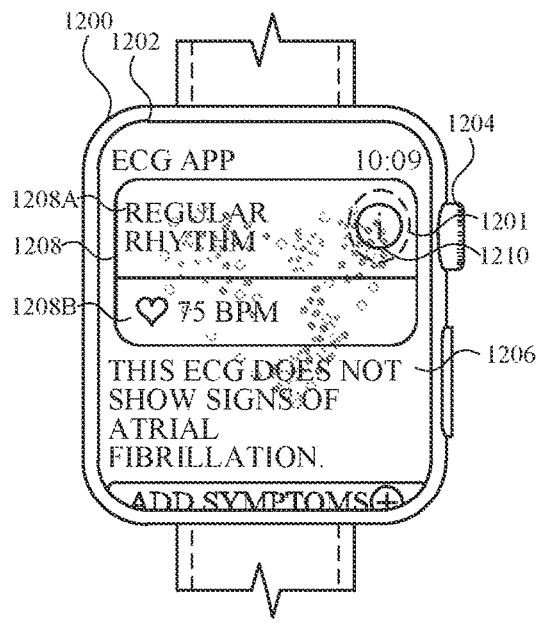
FIGS. 12A-12S illustrate exemplary user interfaces for managing aspects of health monitoring.
Figure 12S:
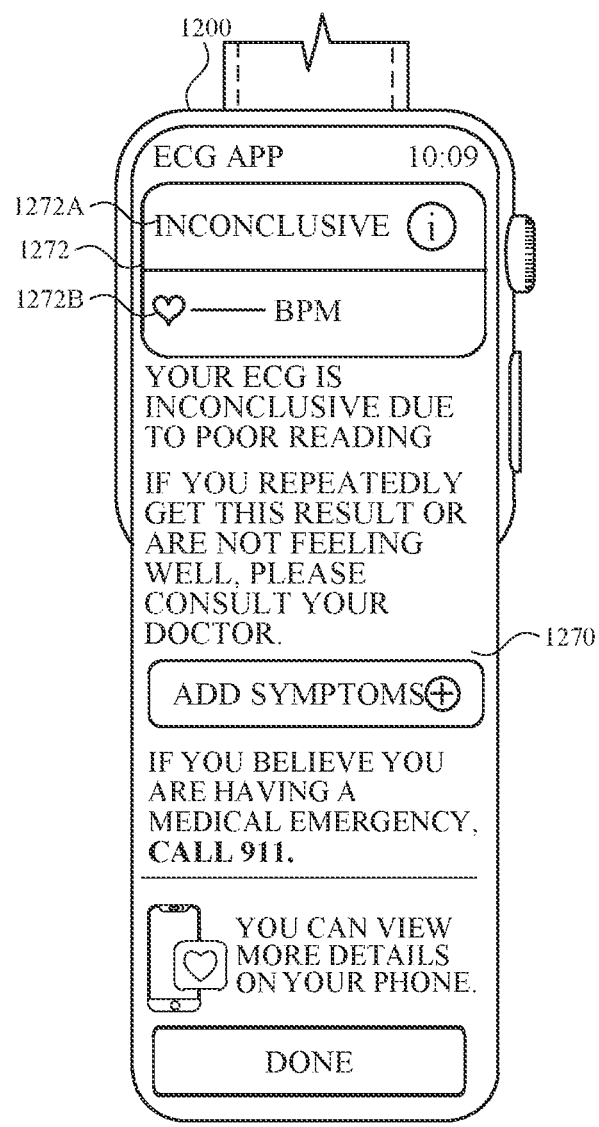
Figure 13A:
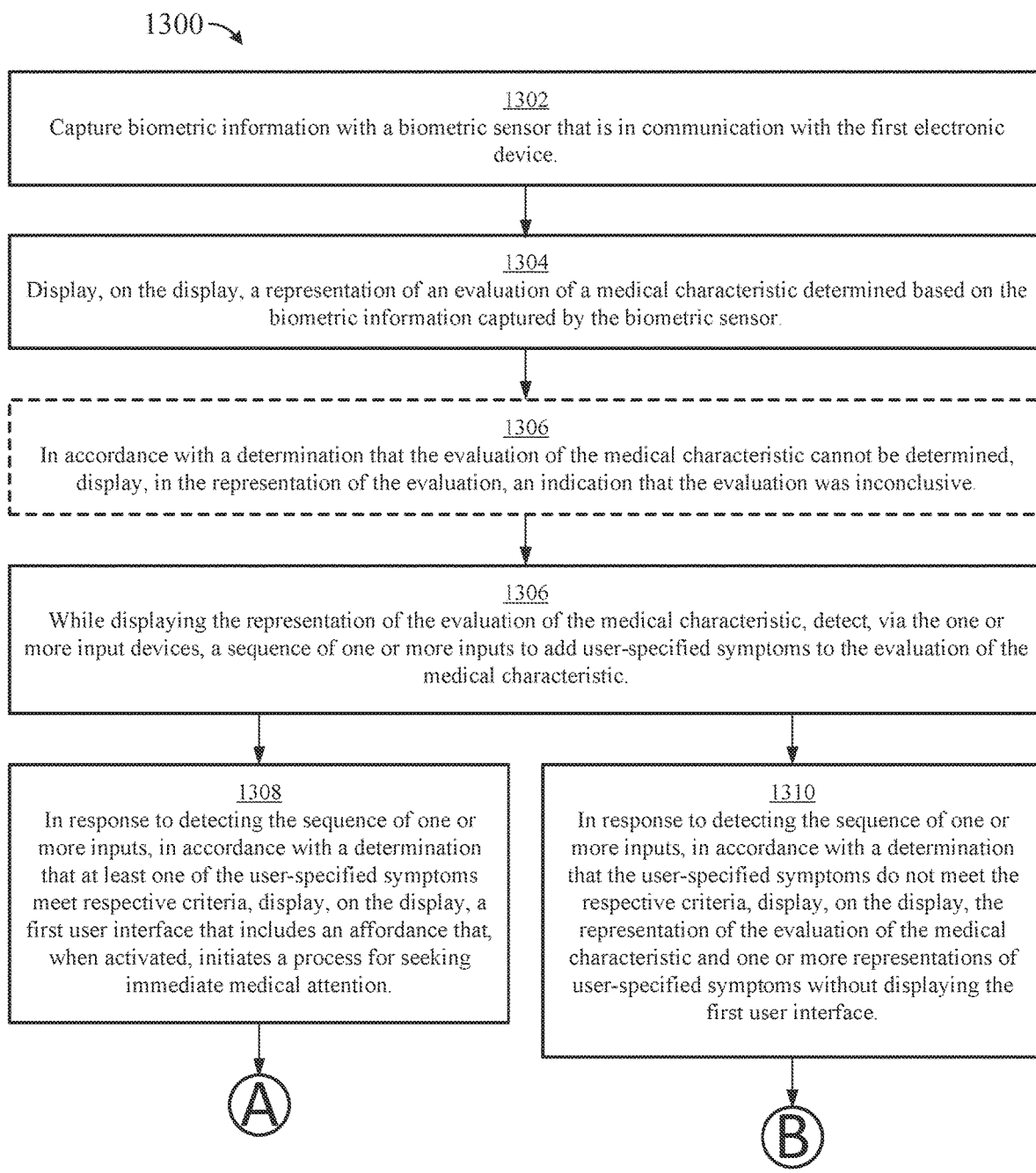
FIGS. 13A-13B illustrate a flow diagram for managing aspects of health monitoring, in accordance with some embodiments.
Figure 13B:
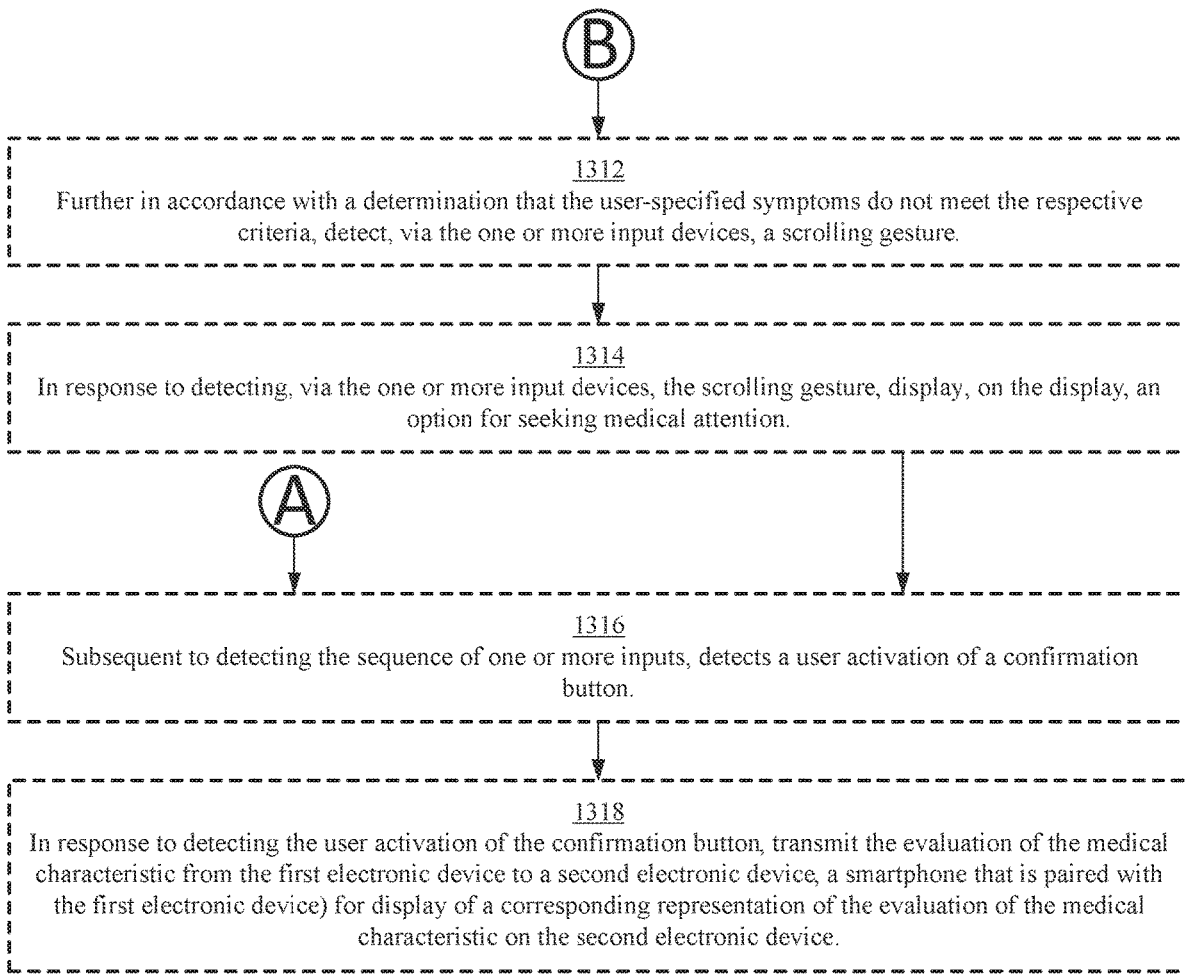

Below, FIGS. 1A-1B, 2, 3, 4A-4B, and 5A-5H provide a description of exemplary devices for performing the techniques for managing event notifications. FIGS. 6A-6AE illustrate exemplary user interfaces for initial setup of health monitoring. FIGS. 7A-7C illustrate a flow diagram for initial setup of heath monitoring. The user interfaces in FIGS. 6A-6AE are used to illustrate the processes described below, including the processes in FIGS. 7A-7C. FIGS. 8A-8S illustrate exemplary user interfaces for recording biometric information for use in health monitoring. FIGS. 9A-9B illustrate a flow diagram for recording biometric information for health monitoring, in accordance with some embodiments. The user interfaces in FIGS. 8A-8S are used to illustrate the processes described below, including the processes in FIGS. 9A-9B. FIGS. 10A-10J illustrate exemplary user interfaces for using an input device for health monitoring. FIG. 11 illustrates a flow diagram for using an input device for health monitoring, in accordance with some embodiments. The user interfaces in FIGS. 10A-10J are used to illustrate the processes described below, including the processes in FIG. 11. FIGS. 12A-12S illustrate exemplary user interfaces for managing aspects of health monitoring. FIGS. 13A-13B illustrate a flow diagram for managing aspects of health monitoring, in accordance with some embodiments. The user interfaces in FIGS. 12A-12S are used to illustrate the processes described below, including the processes in FIGS. 13A-13B. FIGS. 14A-14I illustrate exemplary user interfaces for providing a health condition alert. FIG. 15 illustrates a flow diagram for providing a health condition alert, in accordance with some embodiments. The user interfaces in FIGS. 14A-14I are used to illustrate the processes described below, including the processes in FIG. 15.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, California Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
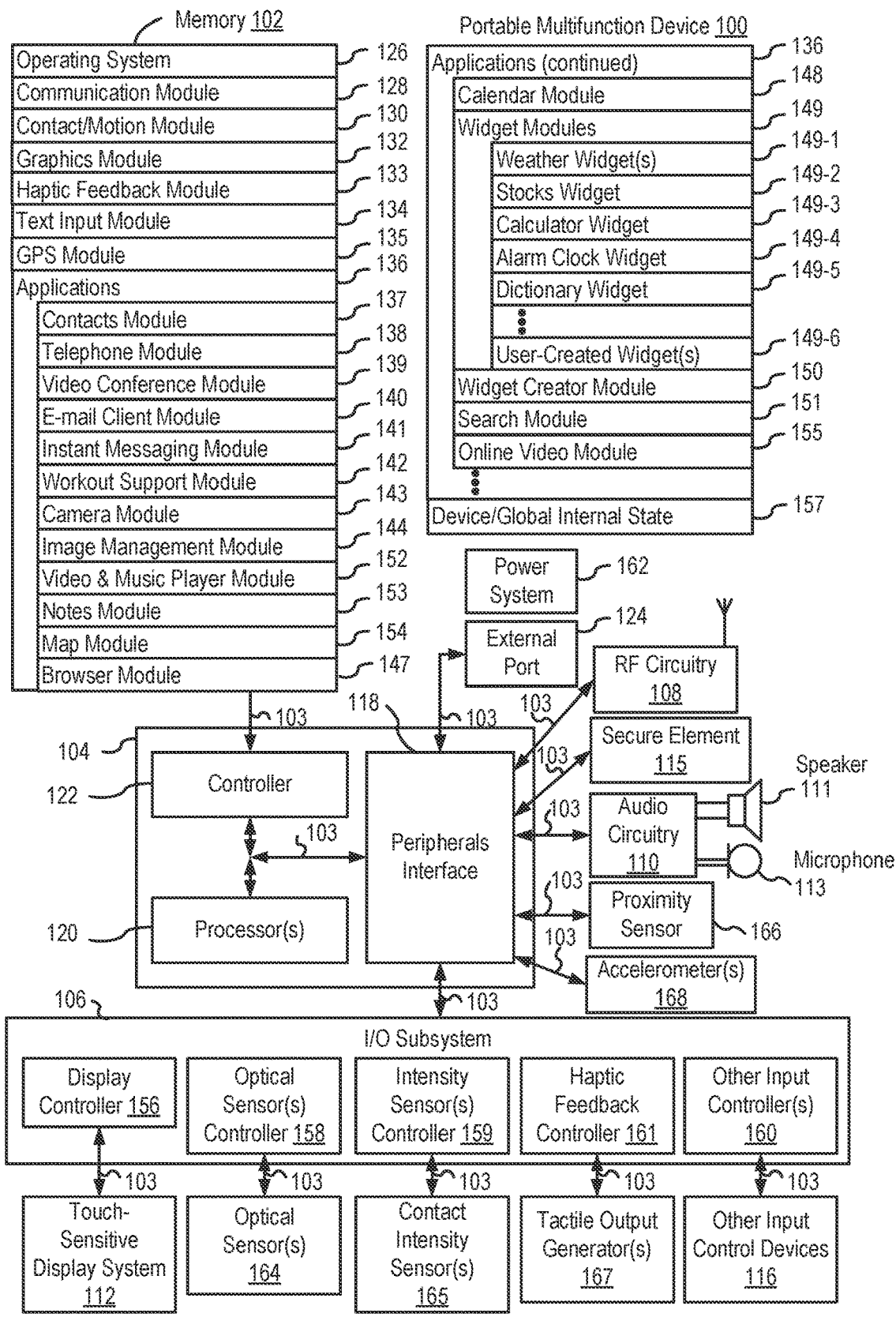
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, California.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad (not shown) for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer (not shown) and a GPS (or GLONASS or other global navigation system) receiver (not shown) for obtaining information concerning the location and orientation (e.g., portrait or landscape) of device 100.

Figure 3:
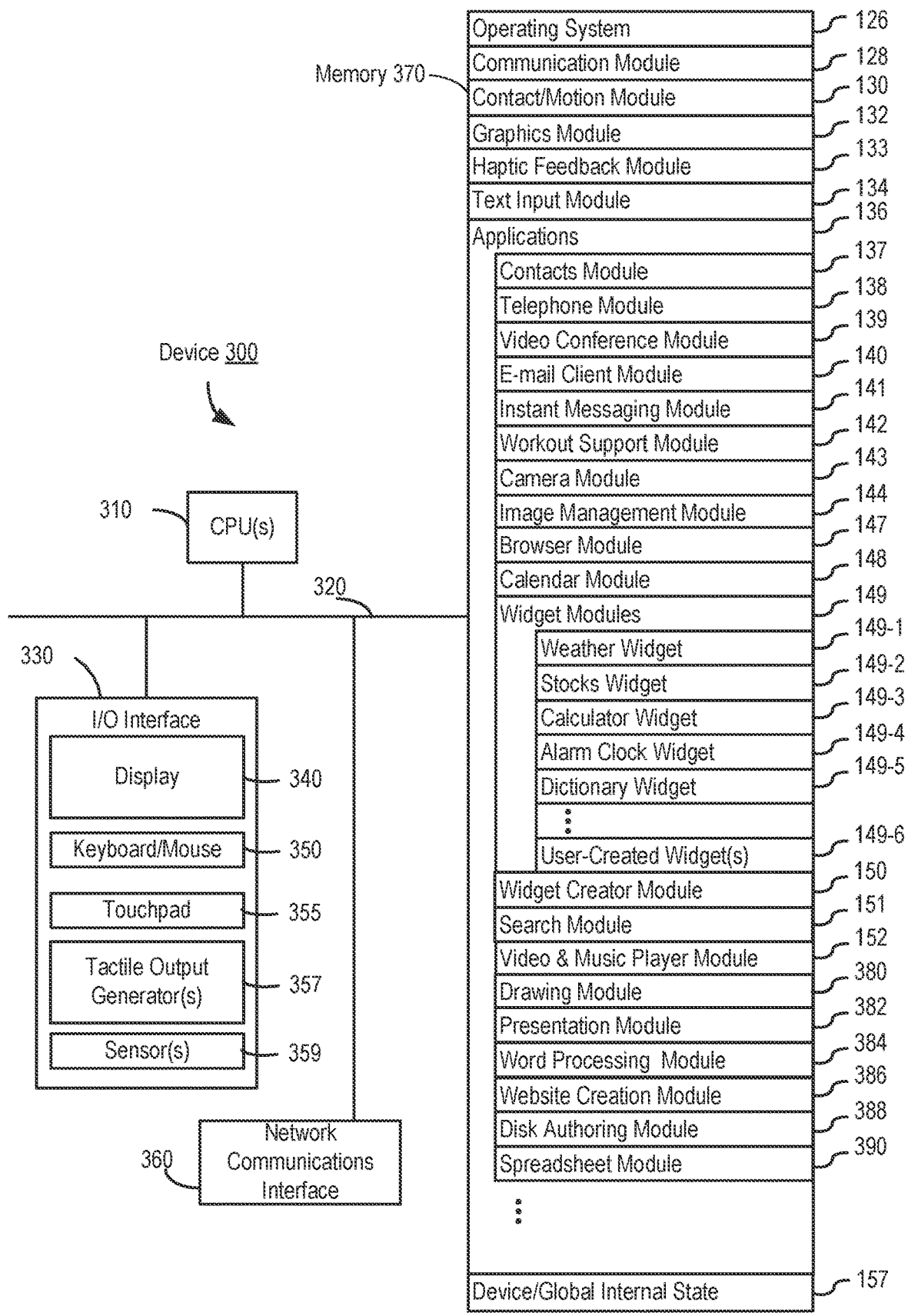
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
  Contacts module 137 (sometimes called an address book or contact list);
  Telephone module 138;
  Video conference module 139;
  E-mail client module 140;
  Instant messaging (IM) module 141;
  Workout support module 142;
  Camera module 143 for still and/or video images;
  Image management module 144;
  Video player module;
  Music player module;
  Browser module 147;
  Calendar module 148;
  Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
  Widget creator module 150 for making user-created widgets 149-6;
  Search module 151;
  Video and music player module 152, which merges video player module and music player module;
  Notes module 153;
  Map module 154; and/or
  Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors (e.g., heart rate or heart rhythm sensors) used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
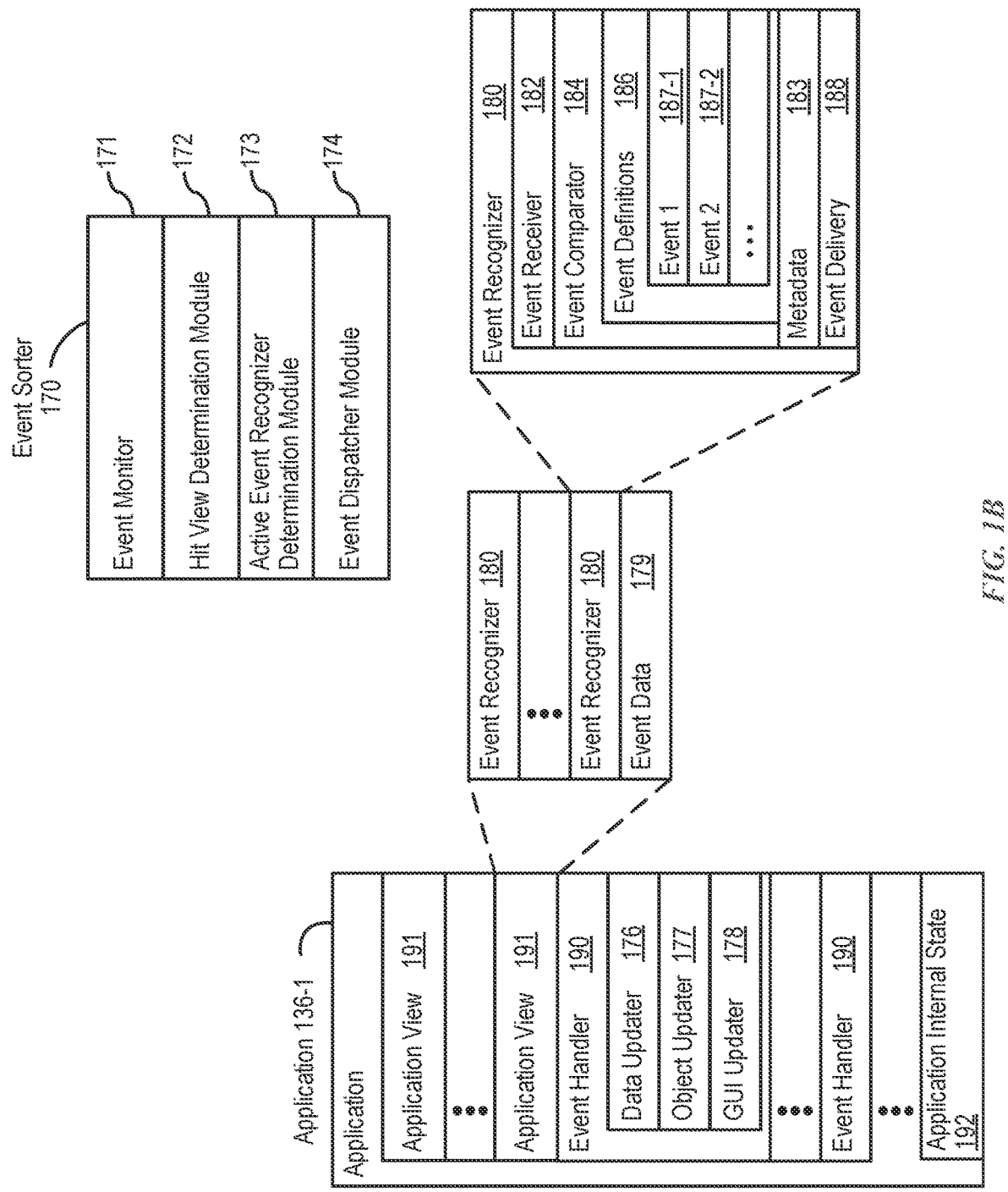
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit (not shown) or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
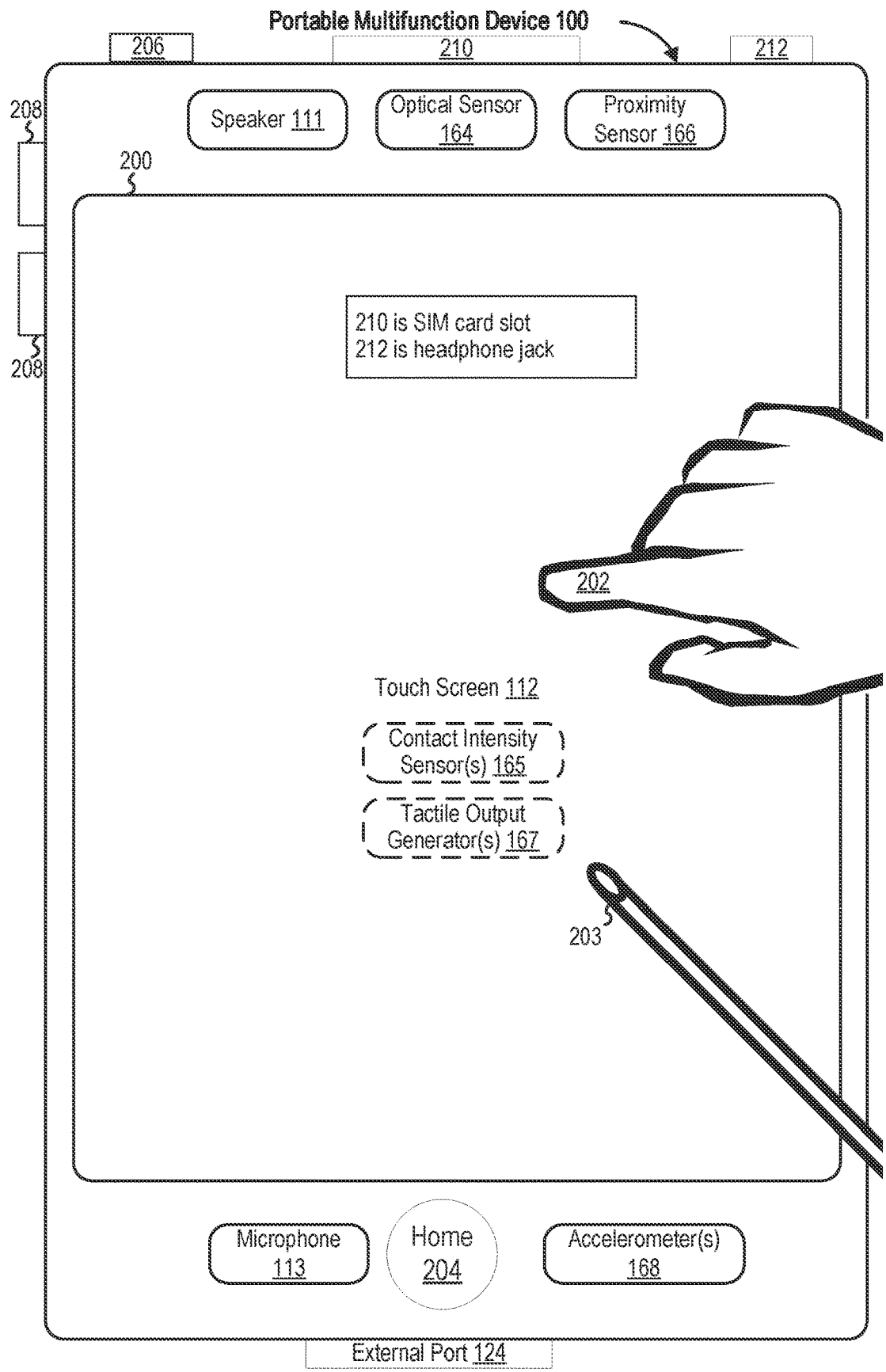
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
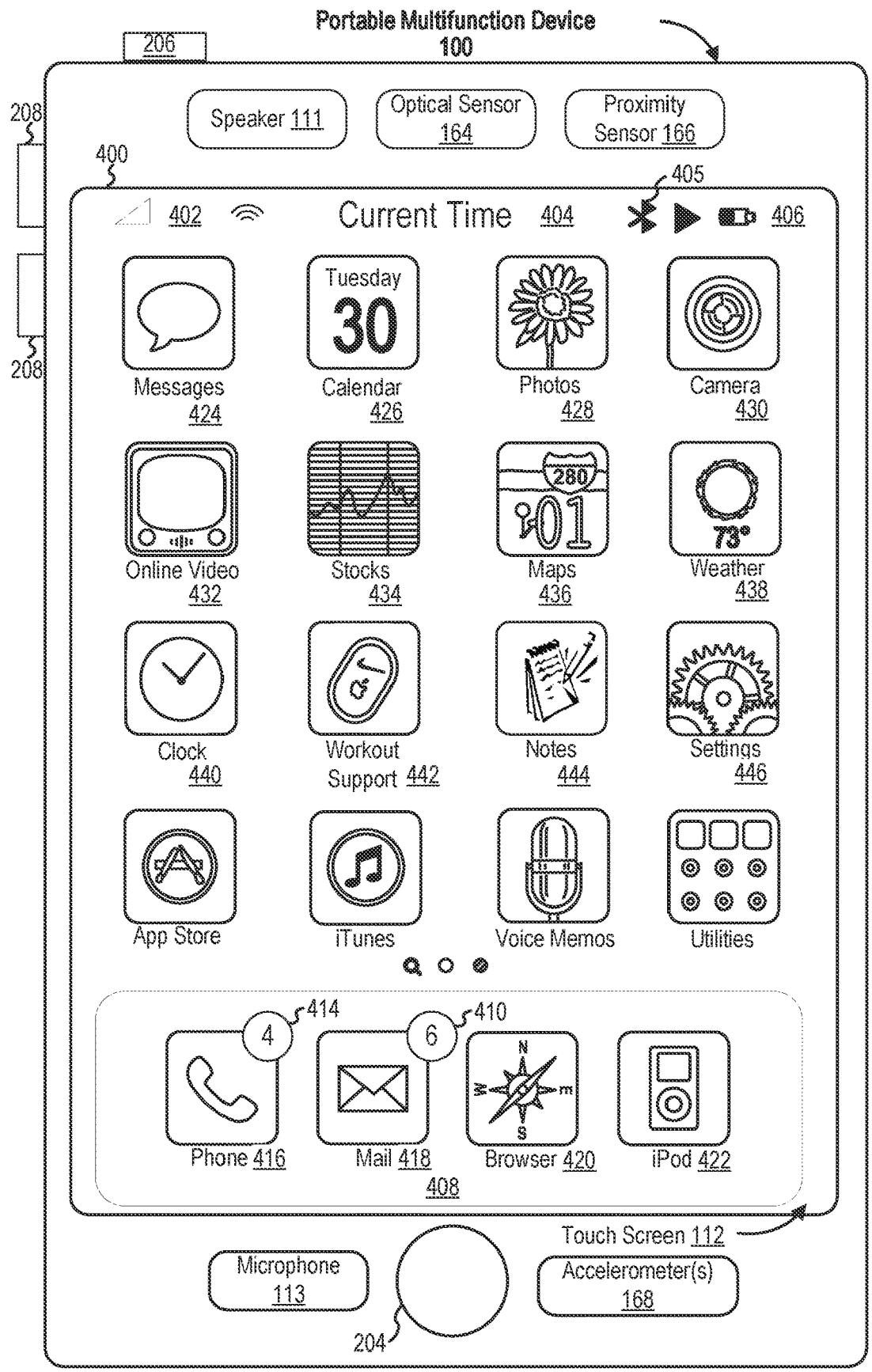
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

- Signal strength indicator(s) 402 for wireless communication(s), such as cellular and Wi-Fi signals;
- Time 404;
- Bluetooth indicator 405;
- Battery status indicator 406;
- Tray 408 with icons for frequently used applications, such as:
    - Icon 416 for telephone module 138, labeled "Phone," which optionally includes an indicator 414 of the number of missed calls or voicemail messages;
    - Icon 418 for e-mail client module 140, labeled "Mail," which optionally includes an indicator 410 of the number of unread e-mails;
    - Icon 420 for browser module 147, labeled "Browser;" and
    - Icon 422 for video and music player module 152, also referred to as iPod (trademark of Apple Inc.) module 152, labeled "iPod;" and
- Icons for other applications, such as:
    - Icon 424 for IM module 141, labeled "Messages;"
    - Icon 426 for calendar module 148, labeled "Calendar;"
    - Icon 428 for image management module 144, labeled "Photos;"
    - Icon 430 for camera module 143, labeled "Camera;"
    - Icon 432 for online video module 155, labeled "Online Video;"
    - Icon 434 for stocks widget 149-2, labeled "Stocks;"
    - Icon 436 for map module 154, labeled "Maps;"
    - Icon 438 for weather widget 149-1, labeled "Weather;"
    - Icon 440 for alarm clock widget 149-4, labeled "Clock;"
    - Icon 442 for workout support module 142, labeled "Workout Support;"
    - Icon 444 for notes module 153, labeled "Notes;" and
    - Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

Figure 4B:
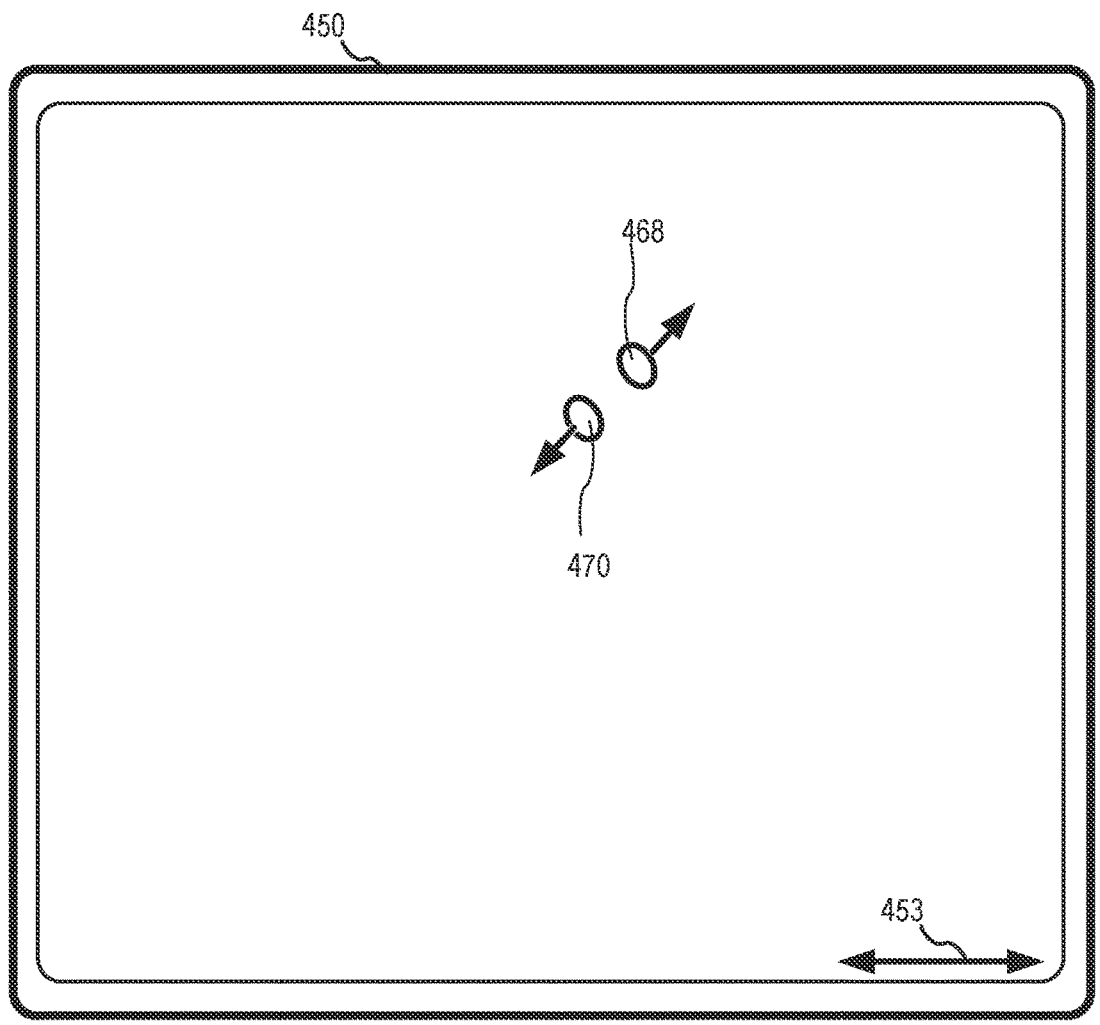
FIG. 4B illustrates an exemplary user interface for a multifunction device with a touch-sensitive surface that is separate from the display in accordance with some embodiments.
Figure 4B:
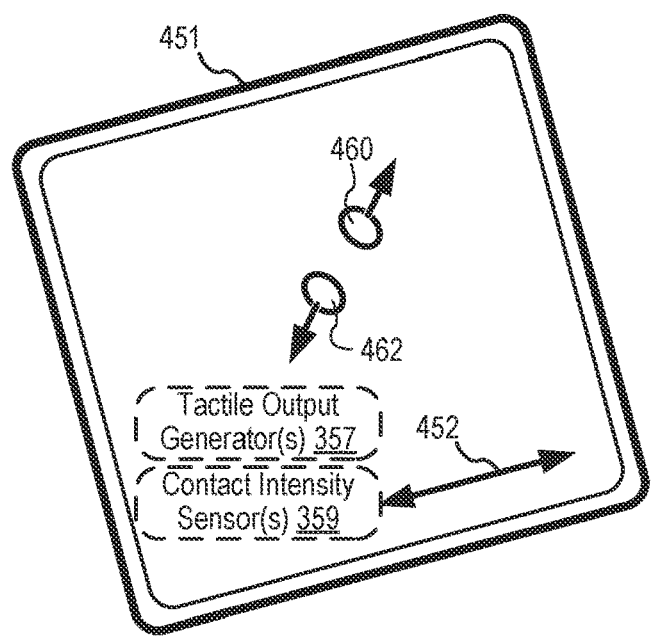

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
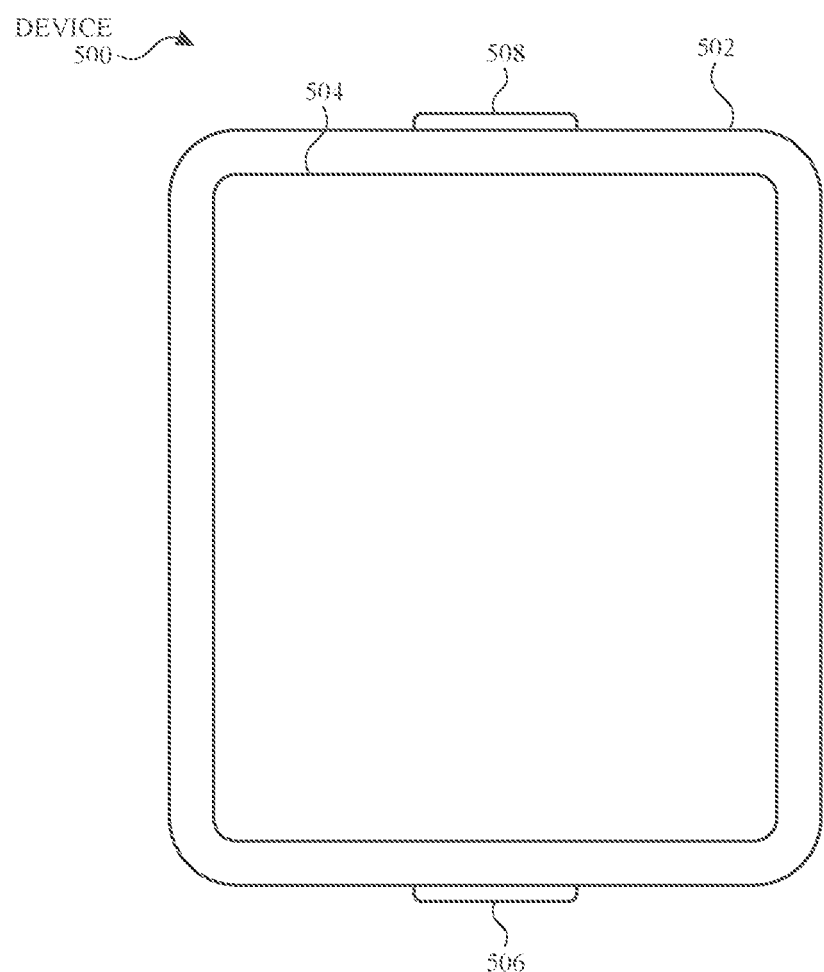
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
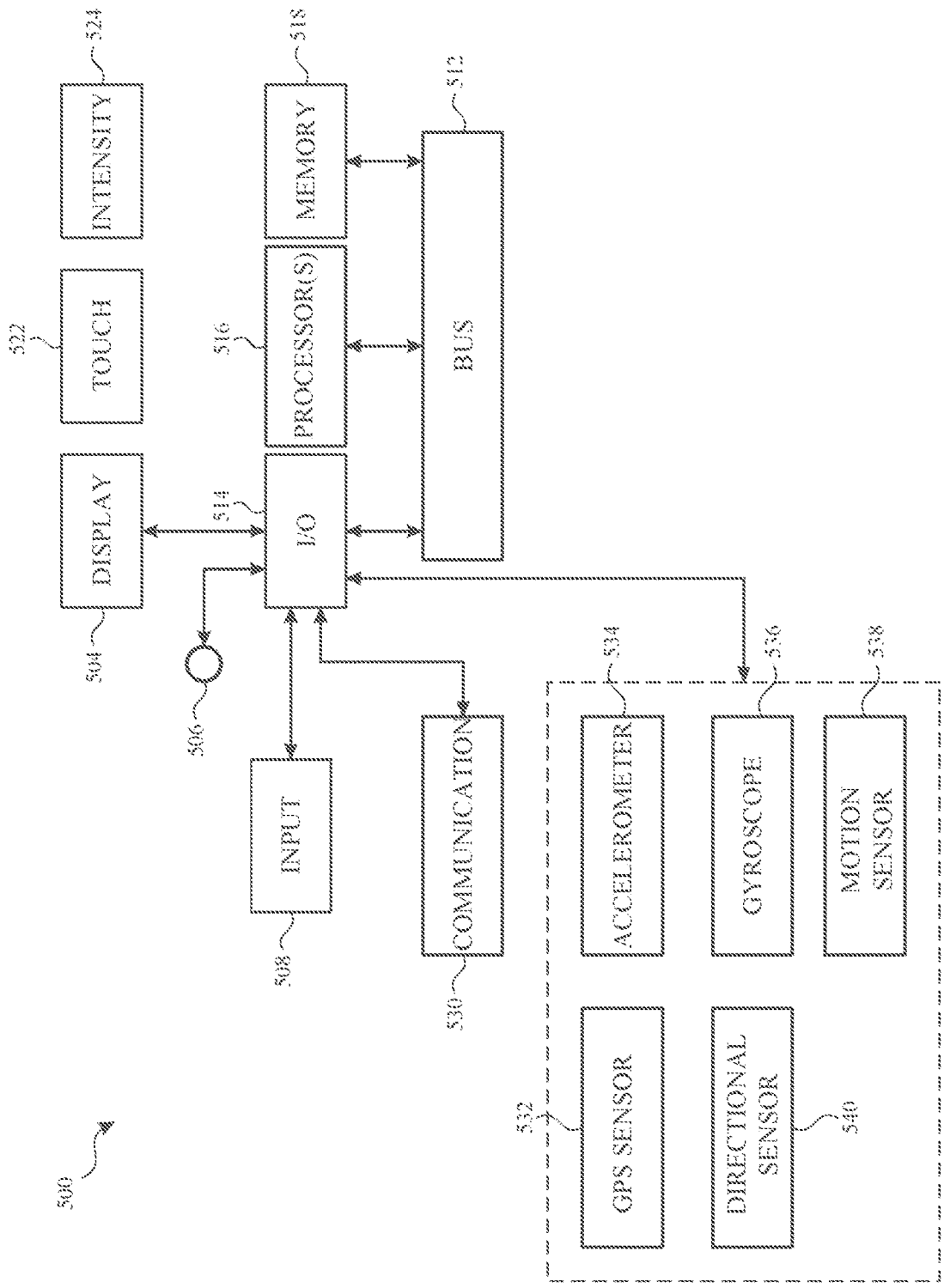
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device (e.g., a rotating crown), for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700 (FIGS. 7A-7C), 900 (FIGS. 9A-9B), 1100 (FIG. 11), and 1300 (FIGS. 13A-13B). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

Figure 5C:
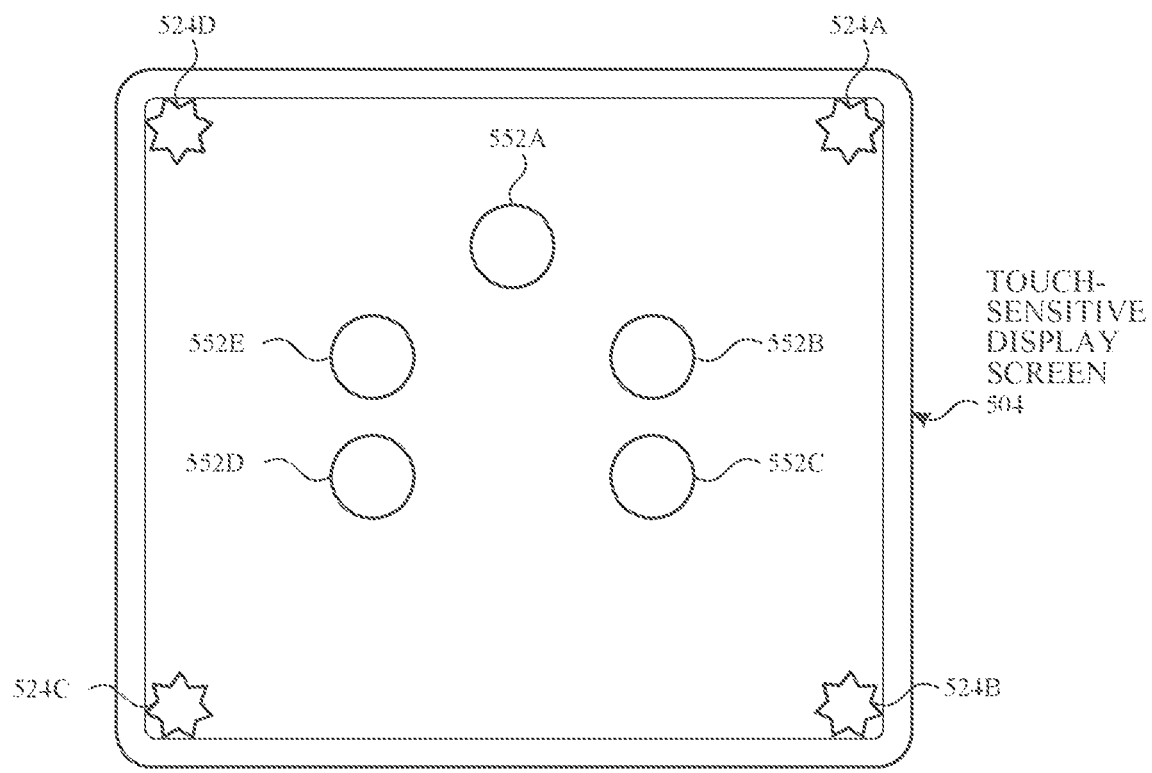
FIGS. 5C-5D illustrate exemplary components of a personal electronic device having a touch-sensitive display and intensity sensors in accordance with some embodiments.
Figure 5C:
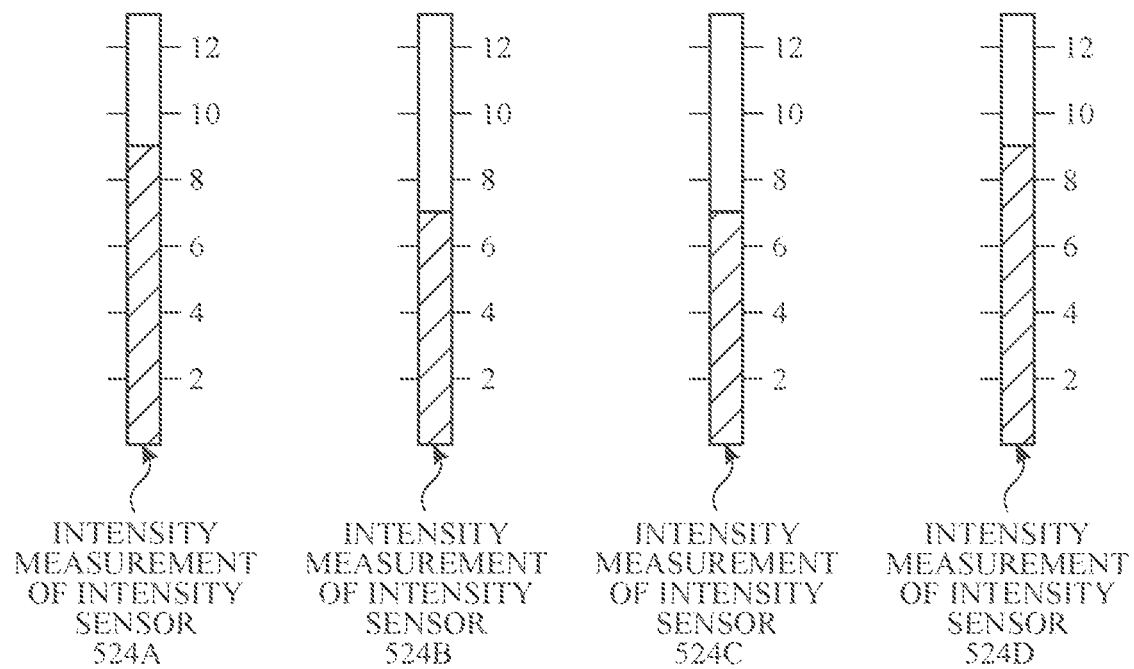
Figure 5D:
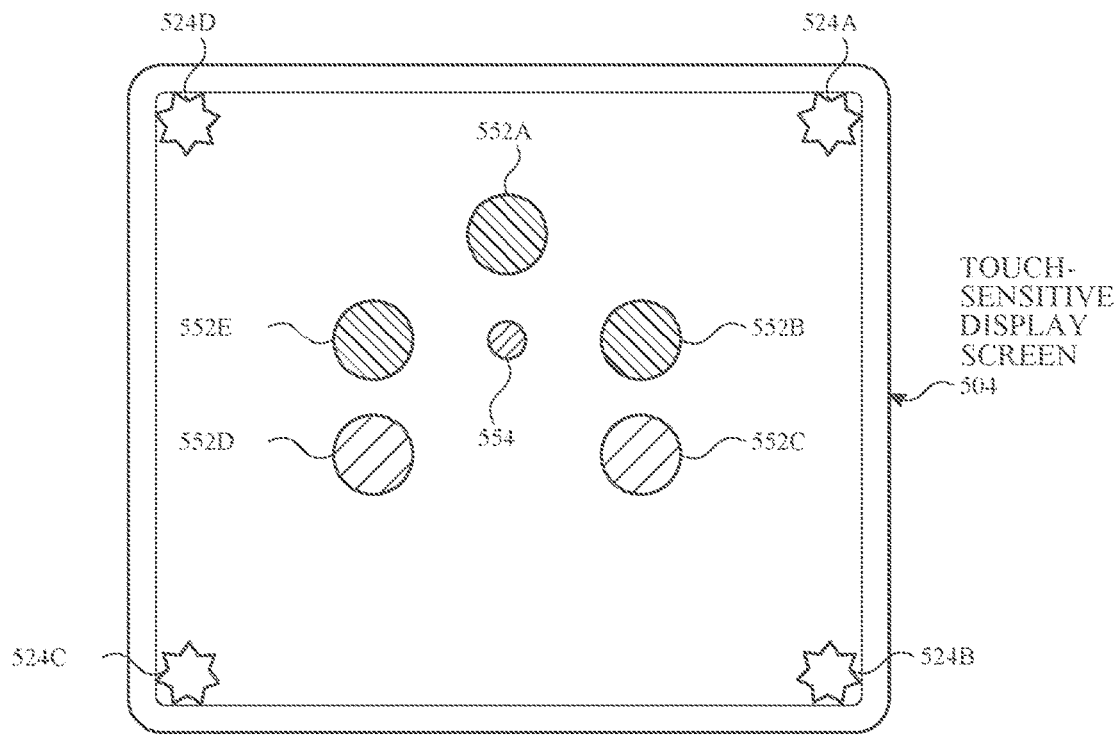
Figure 5D:
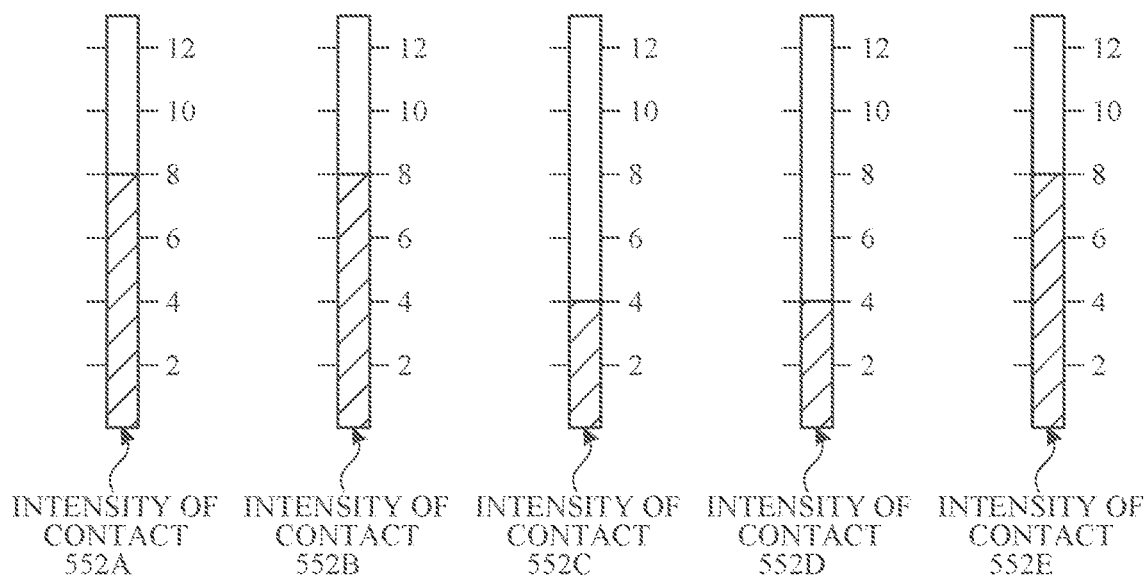

FIG. 5C illustrates detecting a plurality of contacts 552A-552E on touch-sensitive display screen 504 with a plurality of intensity sensors 524A-524D. FIG. 5C additionally includes intensity diagrams that show the current intensity measurements of the intensity sensors 524A-524D relative to units of intensity. In this example, the intensity measurements of intensity sensors 524A and 524D are each 9 units of intensity, and the intensity measurements of intensity sensors 524B and 524C are each 7 units of intensity. In some implementations, an aggregate intensity is the sum of the intensity measurements of the plurality of intensity sensors 524A-524D, which in this example is 32 intensity units. In some embodiments, each contact is assigned a respective intensity that is a portion of the aggregate intensity. FIG. 5D illustrates assigning the aggregate intensity to contacts 552A-552E based on their distance from the center of force 554. In this example, each of contacts 552A, 552B, and 552E are assigned an intensity of contact of 8 intensity units of the aggregate intensity, and each of contacts 552C and 552D are assigned an intensity of contact of 4 intensity units of the aggregate intensity. More generally, in some implementations, each contact j is assigned a respective intensity $I_j$ that is a portion of the aggregate intensity, A, in accordance with a predefined mathematical function, $I_j = A \cdot (D_j / \Sigma D_i)$, where $D_j$ is the distance of the respective contact j to the center of force, and/$D_i$ is the sum of the distances of all the respective contacts (e.g., i=1 to last) to the center of force. The operations described with reference to FIGS. 5C-5D can be performed using an electronic device similar or identical to device 100, 300, or 500. In some embodiments, a characteristic intensity of a contact is based on one or more intensities of the contact. In some embodiments, the intensity sensors are used to determine a single characteristic intensity (e.g., a single characteristic intensity of a single contact). It should be noted that the intensity diagrams are not part of a displayed user interface, but are included in FIGS. 5C-5D to aid the reader.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

Figure 5E:
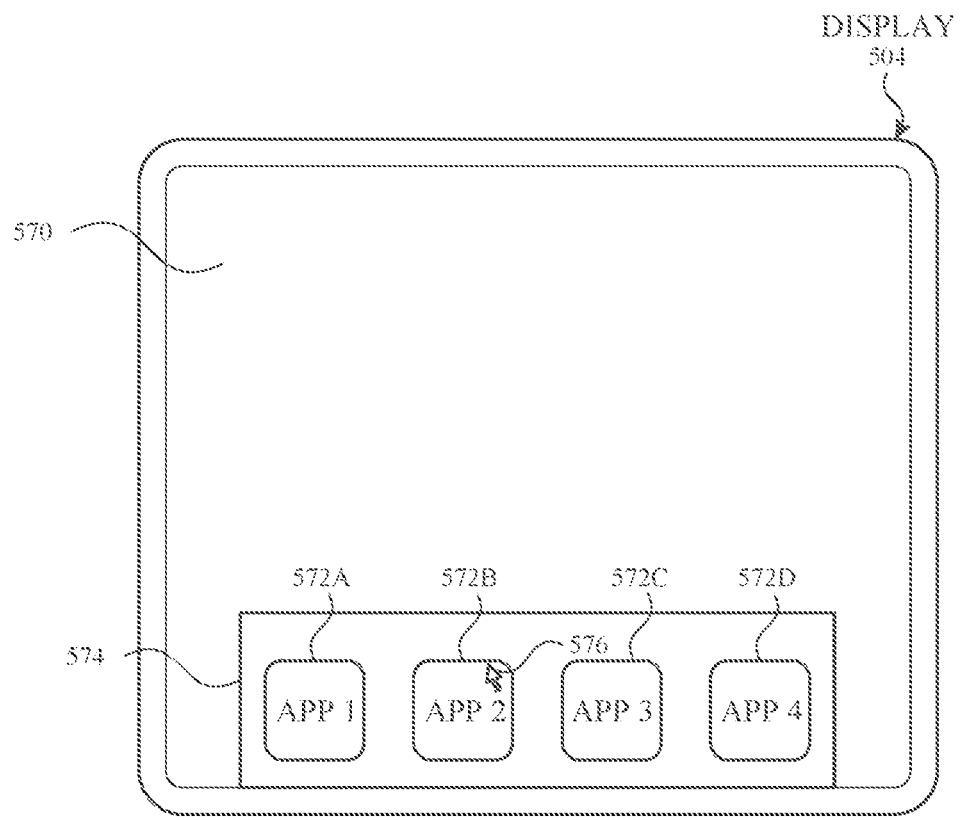
FIGS. 5E-5H illustrate exemplary components and user interfaces of a personal electronic device in accordance with some embodiments.
Figure 5E:
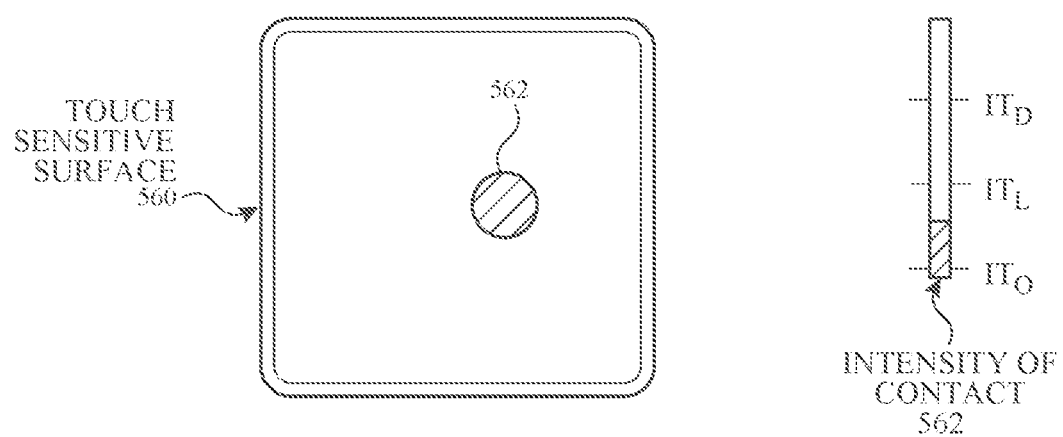
Figure 5F:
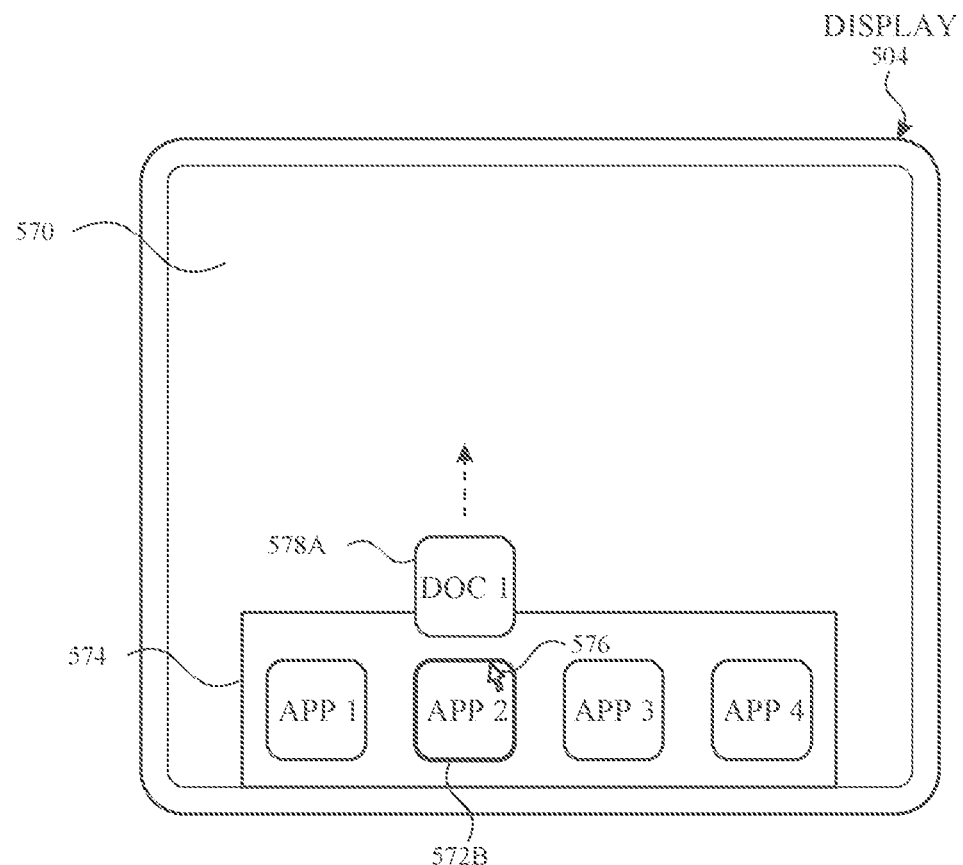
Figure 5F:
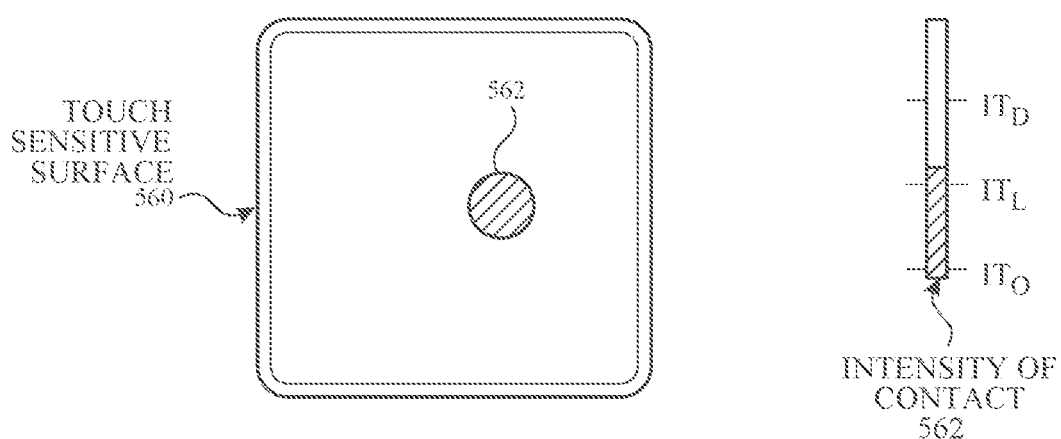
Figure 5G:
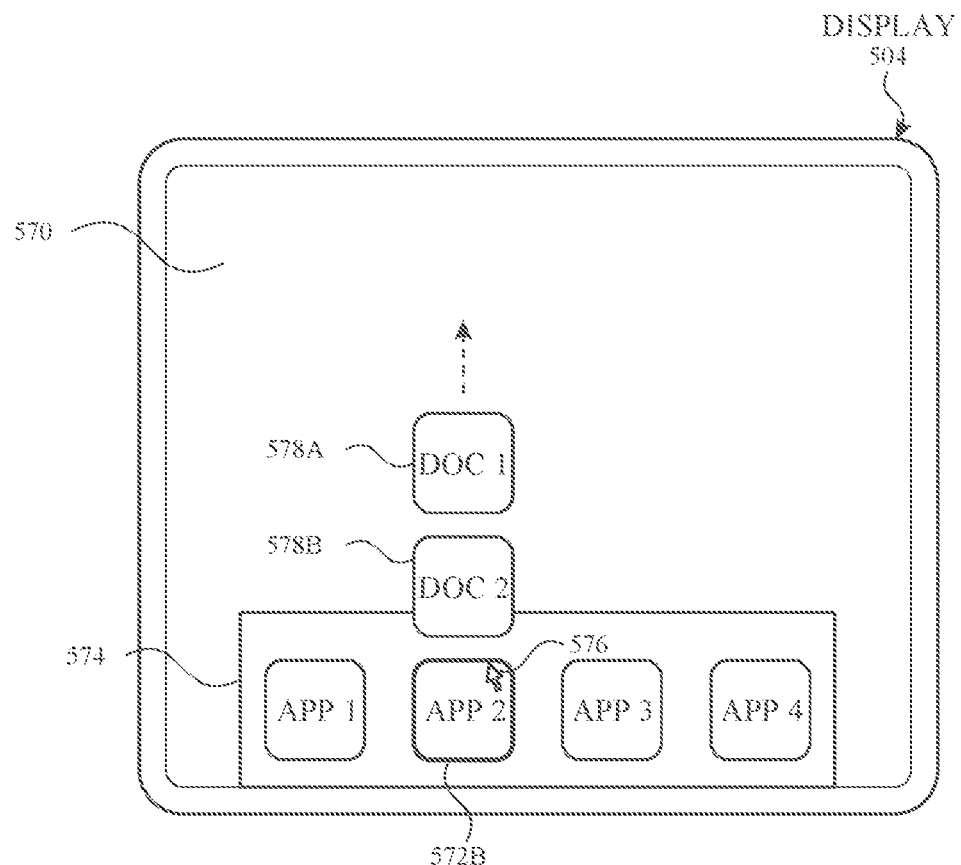
Figure 5G:
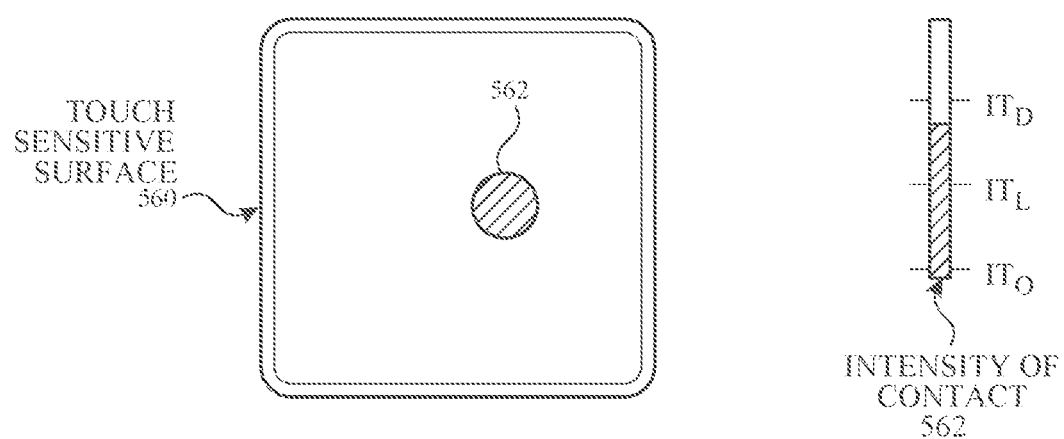
Figure 5H:
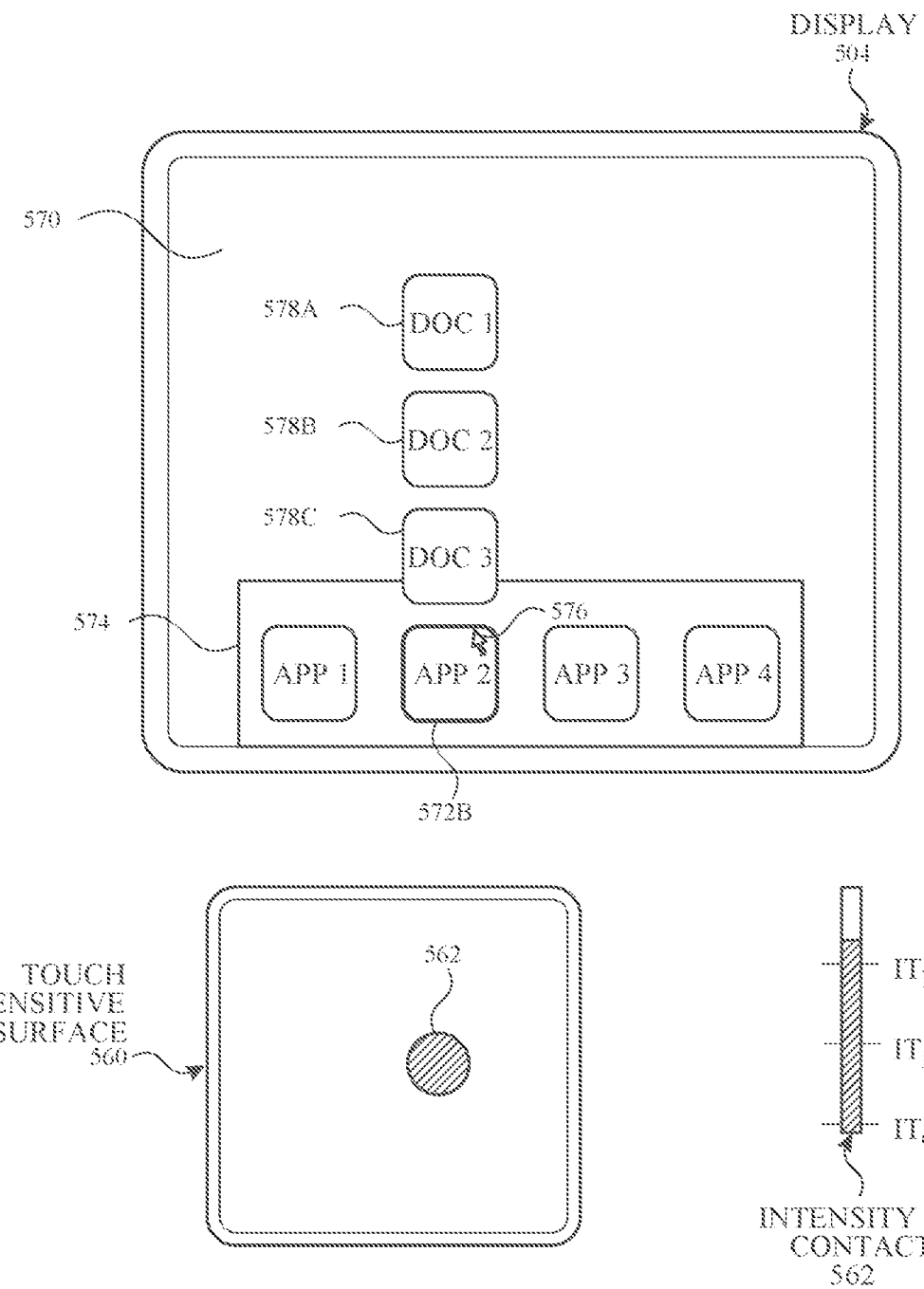

FIGS. 5E-5H illustrate detection of a gesture that includes a press input that corresponds to an increase in intensity of a contact 562 from an intensity below a light press intensity threshold (e.g., "$IT_L$") in FIG. 5E, to an intensity above a deep press intensity threshold (e.g., "$IT_D$") in FIG. 5H. The gesture performed with contact 562 is detected on touch-sensitive surface 560 while cursor 576 is displayed over application icon 572B corresponding to App 2, on a displayed user interface 570 that includes application icons 572A-572D displayed in predefined region 574. In some embodiments, the gesture is detected on touch-sensitive display 504. The intensity sensors detect the intensity of contacts on touch-sensitive surface 560. The device determines that the intensity of contact 562 peaked above the deep press intensity threshold (e.g., "$IT_D$"). Contact 562 is maintained on touch-sensitive surface 560. In response to the detection of the gesture, and in accordance with contact 562 having an intensity that goes above the deep press intensity threshold (e.g., "$IT_D$") during the gesture, reduced-scale representations 578A-578C (e.g., thumbnails) of recently opened documents for App 2 are displayed, as shown in FIGS. 5F-5H. In some embodiments, the intensity, which is compared to the one or more intensity thresholds, is the characteristic intensity of a contact. It should be noted that the intensity diagram for contact 562 is not part of a displayed user interface, but is included in FIGS. 5E-5H to aid the reader.

In some embodiments, the display of representations 578A-578C includes an animation. For example, representation 578A is initially displayed in proximity of application icon 572B, as shown in FIG. 5F. As the animation proceeds, representation 578A moves upward and representation 578B is displayed in proximity of application icon 572B, as shown in FIG. 5G. Then, representations 578A moves upward, 578B moves upward toward representation 578A, and representation 578C is displayed in proximity of application icon 572B, as shown in FIG. 5H. Representations 578A-578C form an array above icon 572B. In some embodiments, the animation progresses in accordance with an intensity of contact 562, as shown in FIGS. 5F-5G, where the representations 578A-578C appear and move upwards as the intensity of contact 562 increases toward the deep press intensity threshold (e.g., "$IT_D$"). In some embodiments, the intensity, on which the progress of the animation is based, is the characteristic intensity of the contact. The operations described with reference to FIGS. 5E-5H can be performed using an electronic device similar or identical to device 100, 300, or 500.

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

As used herein, the terms "open application" or "executing application" refer to a software application with retained state information (e.g., as part of device/global internal state 157 and/or application internal state 192). An open or executing application is, optionally, any one of the following types of applications:

an active application, which is currently displayed on a display screen of the device that the application is being used on;

a background application (or background processes), which is not currently displayed, but one or more processes for the application are being processed by one or more processors; and a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

Attention is now directed towards embodiments of user interfaces ("UI") and associated processes that are implemented on one or more electronic device(s), such as portable multifunction device 100, device 300, or device 500.

FIGS. 6A-6AE illustrate exemplary user interfaces for initial setup of health monitoring, in accordance with some embodiments. The user interfaces in these figures are used to illustrate the processes described below, including the processes in FIGS. 7A-7C. The exemplary user interfaces in these figures relate generally to monitoring health using recorded biometric information, and are not limited to a specific type of biometric information. Only for the sake of convenience, the exemplary user interfaces in these figures are described with reference to a type of biometric information-electrocardiogram (hereinafter "ECG") information.

FIG. 6A illustrates a first electronic device 600A (e.g., a smartphone) with a display 602 and one or more input devices. In some embodiments, the one or more input devices include a touch layer of display 602 for detecting touch input, one or more image sensors 604 (e.g., a camera, a depth sensor), a first mechanical button 606 configured to perform one or more operations (e.g., and including an integrated biometric sensor, such as a fingerprint sensor), and a second mechanical button 608 configured to perform one or more operations. In some embodiments, first electronic device 600A includes a wireless communication radio (e.g., for LTE, Bluetooth, WiFi connections). In some embodiments, first electronic device 600A is paired with a second electronic device (e.g., a smartwatch). In some embodiments, the second electronic device corresponds to second electronic device 600B described below with reference to FIGS. 6S-6X.

In FIG. 6A, first electronic device 600A is displaying, on display 602, a homescreen user interface 610 corresponding to a homescreen of the operating system running on the device. In some embodiments, homescreen user interface 610 includes a plurality of icons corresponding to different applications that are installed on the device, including a health application corresponding to icon 610A. In some embodiments, the health application can be used to manage a user's biometric information, such as heart rhythm information and/or heart rate information (e.g., using recorded ECG information).

In some embodiments, first electronic device 600A detects (e.g., via a touch input) a user activation 601 of icon 610A corresponding to a health application, which includes features concerning management of recordings of biometric information, including ECG information. In response to detecting user activation 601, first electronic device 600A launches the health application (e.g., by replacing display of homescreen user interface 610 with a user interface of the health application).

In some embodiments, the health application includes an ECG affordance for viewing and managing existing ECG recordings on the device, where the ECG information is recorded using a related ECG application on a second electronic device (e.g., second electronic device 600B described with reference to FIGS. 6S-6X), where the ECG application on the second electronic device (e.g., second electronic device 600B) is associated with the ECG management features of the health application on first electronic device 600A. In some embodiments, if the ECG management features have not yet been setup on first electronic device 600A (e.g., the user has not yet used the ECG recording feature), launching of the ECG management features on the health application (e.g., in response to detecting a user selection of the ECG affordance) causes display of a first page of a tutorial for performing initial setup of the ECG management features of the health application (e.g., as described with reference to FIG. 6F).

Figure 6B:
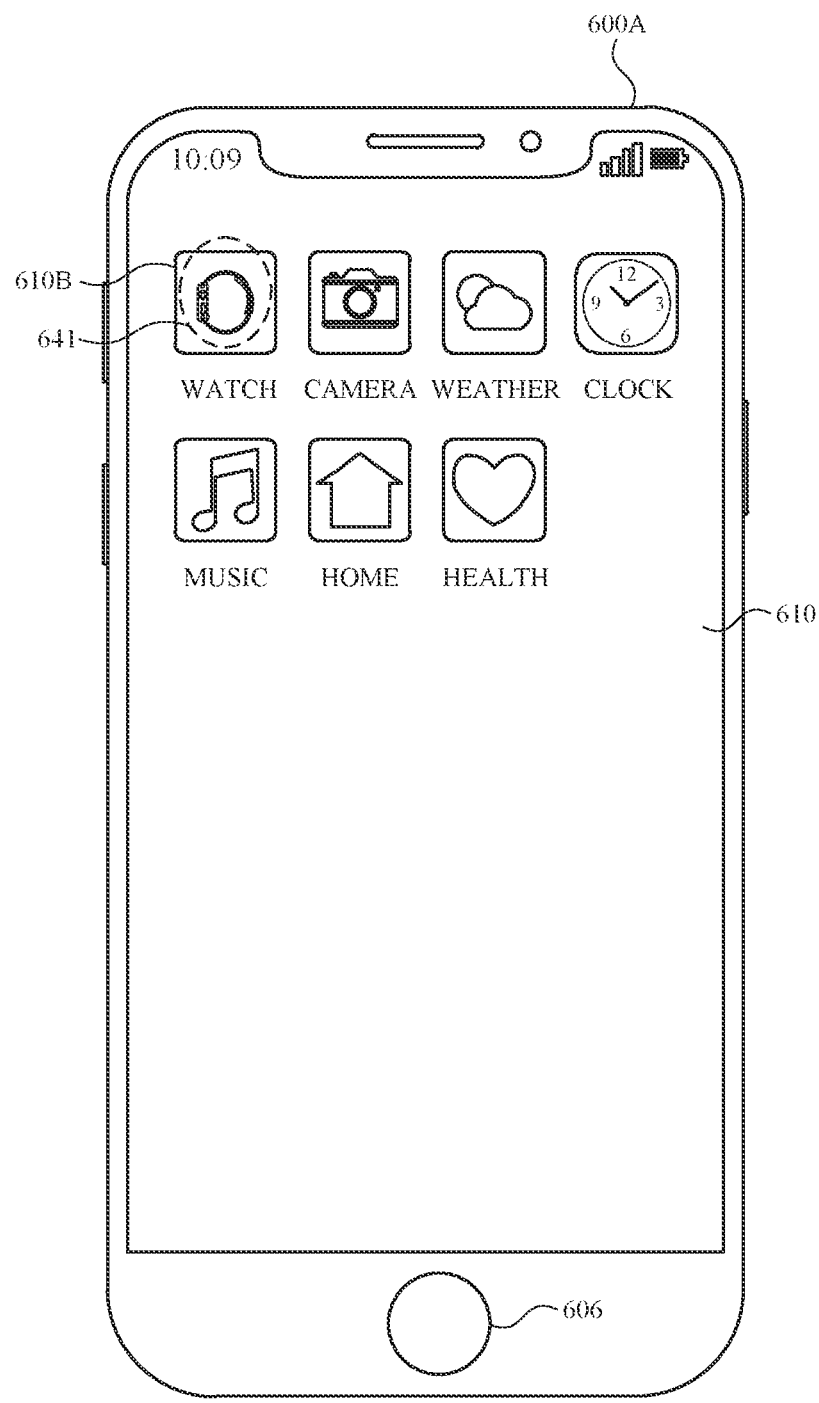

In some embodiments, homescreen user interface 610 includes a paired device application corresponding to icon 610B and associated with a device paired with first electronic device 600A (e.g., second electronic device 600B). In some embodiments, while displaying homescreen user interface 610, first electronic device 600A detects (e.g., via a tap input) a user activation 641 of icon 610B, as shown in FIG. 6B.

Figure 6C:
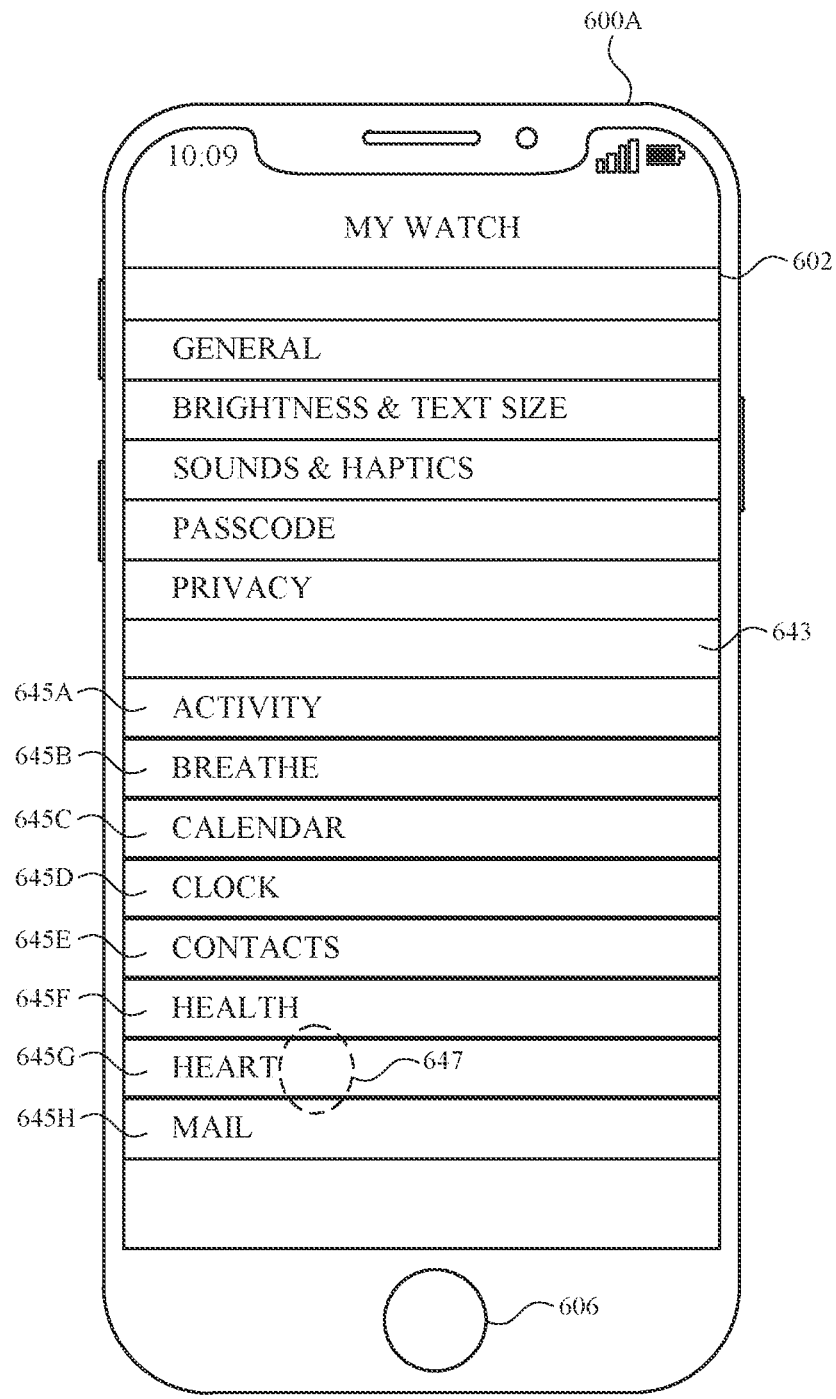

In some embodiments, in response to detecting user activation 641, first electronic device 600A displays, on display 602, a main user interface 643 of the paired device application, as shown in FIG. 6C. In some embodiments, the paired device application includes a plurality of application setting affordances 645A-645H corresponding to various applications installed on the paired device (e.g., second electronic device 600B), including a heart application setting affordance 645G corresponding to a heart application (e.g., the ECG application) installed on the paired device. In some embodiments, while displaying main user interface 643 of the paired device application, the device detects (e.g., via a tap input) a user activation 647 of heart application setting affordance 645G.

Figure 6D:
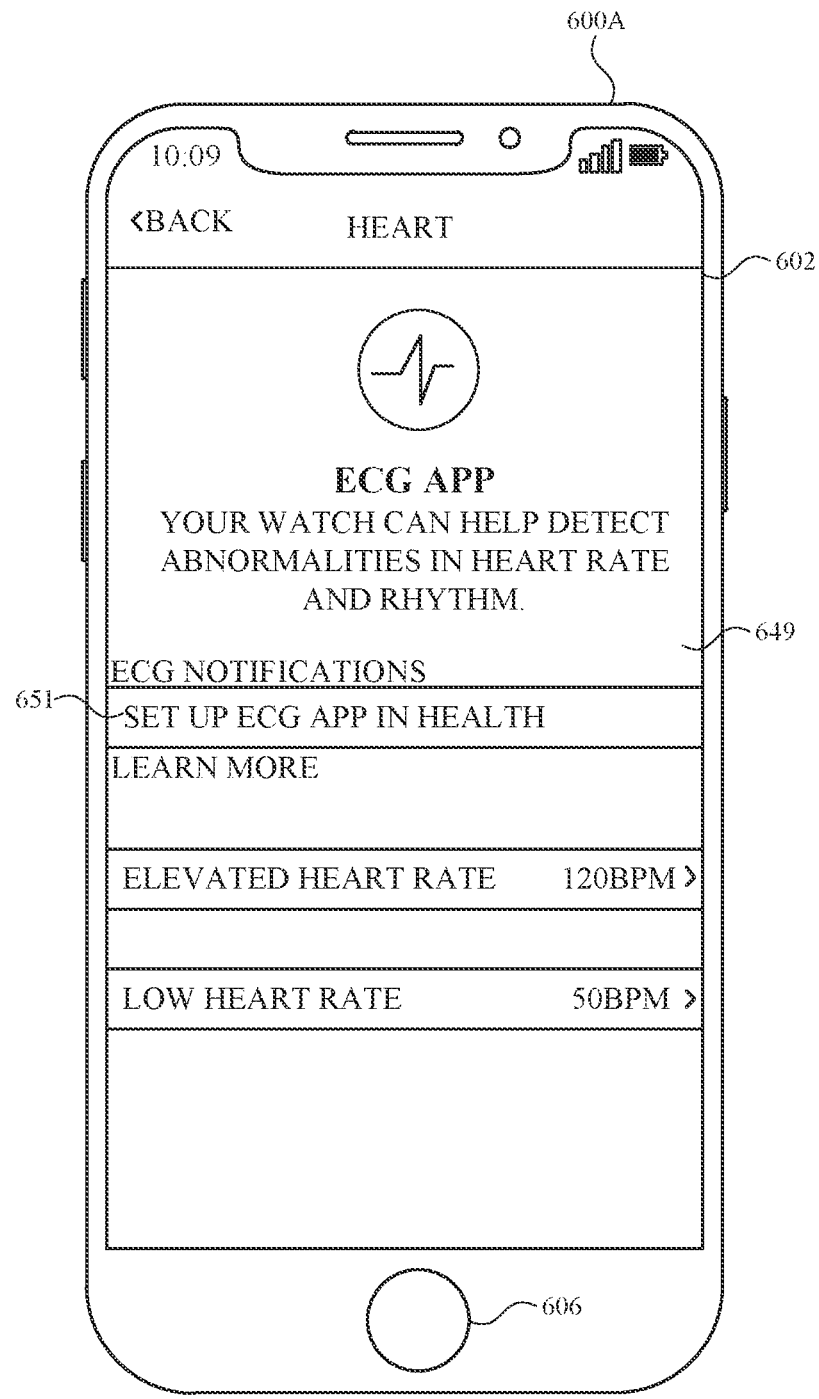

In some embodiments, in response to detecting user activation 647 of heart application setting affordance 645G, first electronic device 600A displays, on display 602, an application settings page 649 for changing and/or configuring application settings of the corresponding heart application (e.g., the ECG application) on second electronic device 600B, as shown in FIG. 6D. In some embodiments, if ECG management features have not yet been setup on first electronic device 600A, application settings page 649 includes an affordance 651 (e.g., an affordance labelled "Set up ECG functionality" or "Set up ECG application in Health") for performing initial setup of the ECG management features. In some embodiments, first electronic device 600A launches the first page of the tutorial (e.g., as described with reference to FIG. 6F) in response to detecting a user activation of affordance 651.

Figure 6E:
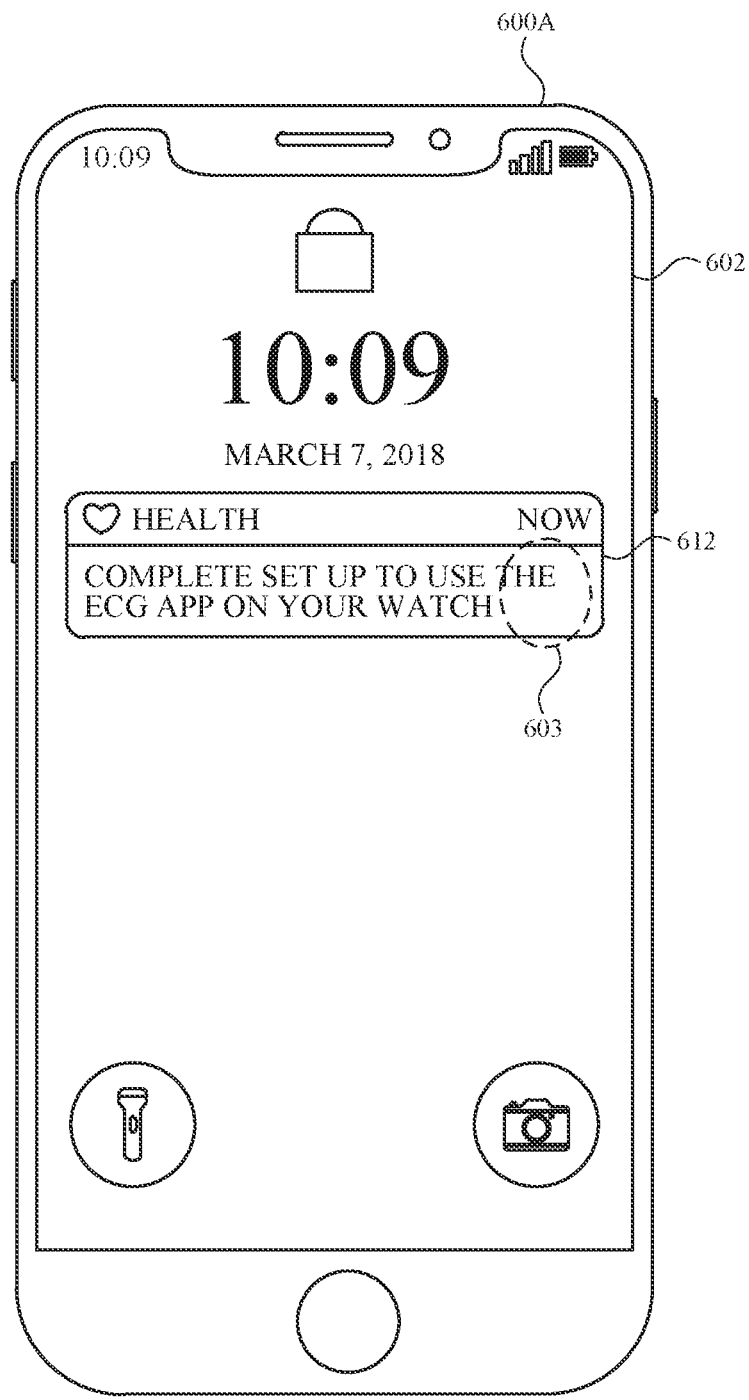

FIG. 6E illustrates first electronic device 600A displaying, on display 602, a (selectable) notification 612 indicating (to the user of the device) that an ECG application, which is associated with the health application on first electronic device 600A, has launched (or is active) on a second electronic device (e.g., second electronic device 600B). In some embodiments, notification 612 is displayed on a lockscreen user interface of the first electronic device. In some embodiments, notification 612 is displayed in homescreen user interface 610 of the device (e.g., at a top portion of the display). In some embodiments, notification 612 is displayed over a user interface of an application (e.g., email application, web browser application) running on the device (e.g., at a top portion of the display).

In some embodiments, notification 612 indicates that initial setup (e.g., onboarding) of the ECG management features of the health application need to be performed in order to utilize ECG features of the application. In some embodiments, while displaying notification 612, first electronic device 600A detects (e.g., via a touch input) a user selection 603 of notification 612. In response to detecting user selection 603, first electronic device 600A launches a first page of a tutorial for performing initial setup of the ECG management features and associated ECG application.

Figure 6F:
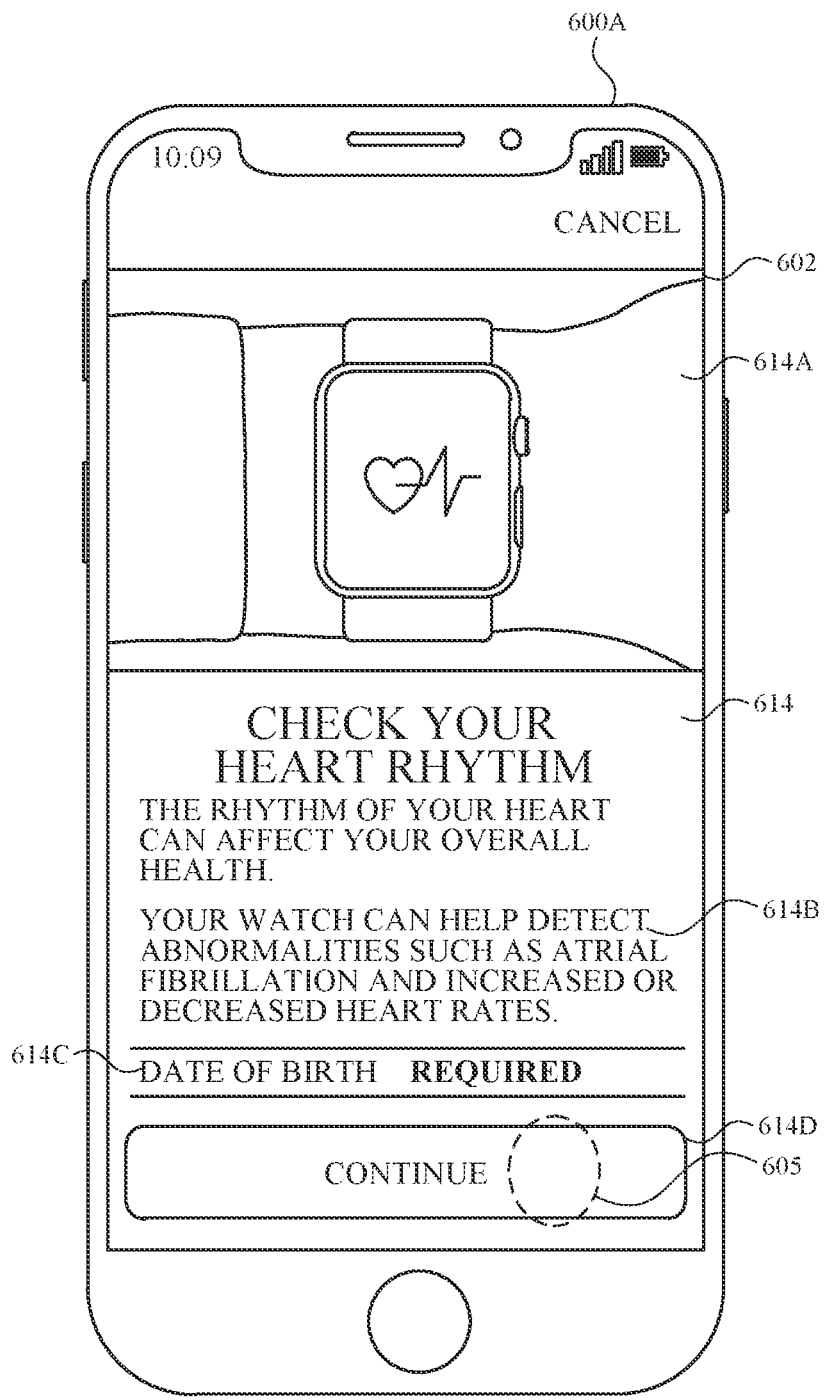

FIG. 6F illustrates first electronic device 600A displaying, on display 602, a first page 614 of the tutorial for performing initial setup of the ECG management features and associated ECG application. In some embodiments, first page 614 of the tutorial includes a graphical indication region 614A that graphically indicates (e.g., via a static image, via an animation) a function of the ECG management features and associated ECG application (e.g., recording heart rhythm information and/or heart rate information) and instructions on how to perform the function (e.g., using the associated ECG application on a smartwatch paired to the device). In some embodiments, first page 614 of the tutorial includes a text description region 614B describing a use of the ECG management features and associated ECG application (e.g., stating "Check your heart rhythm") and background information relevant to the use of the ECG management features and associated ECG application.

In some embodiments, first page 614 of the tutorial includes a date of birth entry field 614C for receiving a user input corresponding to the user's date of birth, where the user's date of birth is used to determine whether the user meets a minimum age requirement (e.g., 22 years of age) to use the features of the ECG application. In some embodiments, date of birth entry field 614C includes scrollable month, day, and year fields. In some embodiments, first page 614 of the tutorial does not include date of birth entry field 614C. In some embodiments, first page 614 of the tutorial includes (e.g., in addition to or alternatively to date of birth entry field 614C) an age restriction message (e.g., stating "You must be 22 years or older") indicating to the user that the user must meet the minimum age requirement.

In some embodiments, first page 614 of the tutorial includes an affordance 614D for proceeding with the tutorial. In FIG. 6F, while displaying first page 614 of the tutorial for performing initial setup of the ECG management features and associated ECG application, first electronic device 600A detects (e.g., via a touch input) a user activation 605 of affordance 614D for proceeding with the tutorial. In some embodiments, in accordance with a determination that the minimum age requirement is not met (e.g., a determination made in response to detecting user activation 605), first electronic device 600A displays, on display 602, an error notification (e.g., stating "The ECG application is not intended for use by people under 22") indicating that the user does not meet the requisite minimum age requirement. In some embodiments, the error notification is overlaid on first page 614 of the tutorial. In some embodiments, while displaying the error notification, the background of the display (displaying first page 614) is dimmed (thereby emphasizing the displayed error notification).

Figure 6G:
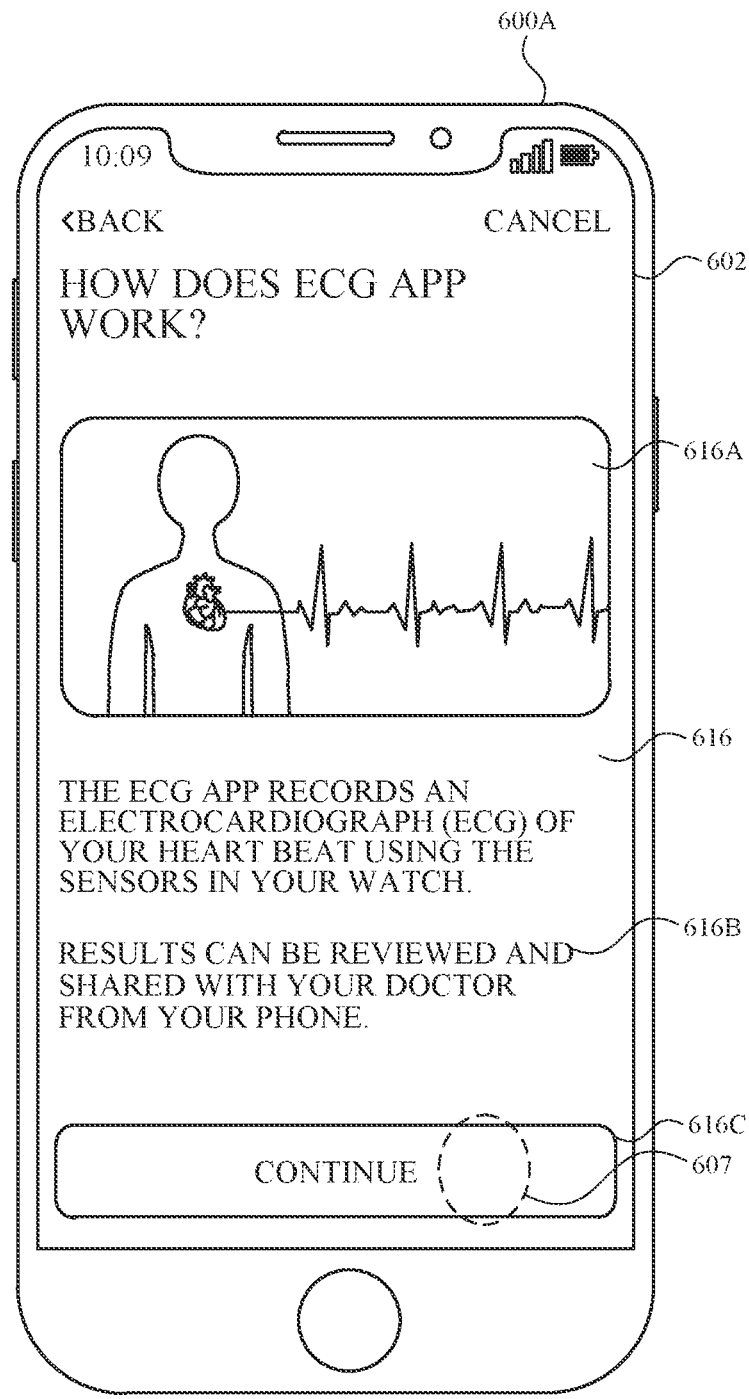

In some embodiments, in response to detecting user activation 605 (and in accordance with a determination that the minimum age requirement is met), first electronic device 600A displays, on display 602 (e.g., replaces display of first page 614 with), a second page 616 of the tutorial, as shown in FIG. 6G.

FIG. 6G illustrates first electronic device 600A displaying, on display 602, second page 616 of the tutorial for performing initial setup of the ECG management features and the associated ECG application (e.g., where the associated ECG application is running on or can be launched on a second electronic device, such as second electronic device 600B). In some embodiments, second page 616 of the tutorial includes an animation region 616A that graphically indicates (e.g., via a static image, via an animation) example ECG information captured using the application. In some examples, animation region 616A includes an example tachogram-animation. In some examples, the example tachogram-animation includes one or more objects that continuously move across the animation by tracking the tachogram-like portion of the animation. In some embodiments, second page 616 of the tutorial includes a text description region 616B that summarizes how the ECG information is captured from the user and how the recorded biometric information can be viewed by the user. In some embodiments, second page 616 of the tutorial includes an affordance 616C for proceeding with the tutorial.

In FIG. 6G, while displaying second page 616 of the tutorial for performing initial setup of the ECG management features and associated ECG application, first electronic device 600A detects (e.g., via a touch input) a user activation 607 of affordance 616C for proceeding with the tutorial. In some embodiments, in response to detecting user activation 607, the device displays, on display 602 (e.g., replaces display of first page 616 with), a possible results page 618 of the tutorial, as shown in FIG. 6H.

Figure 6H:
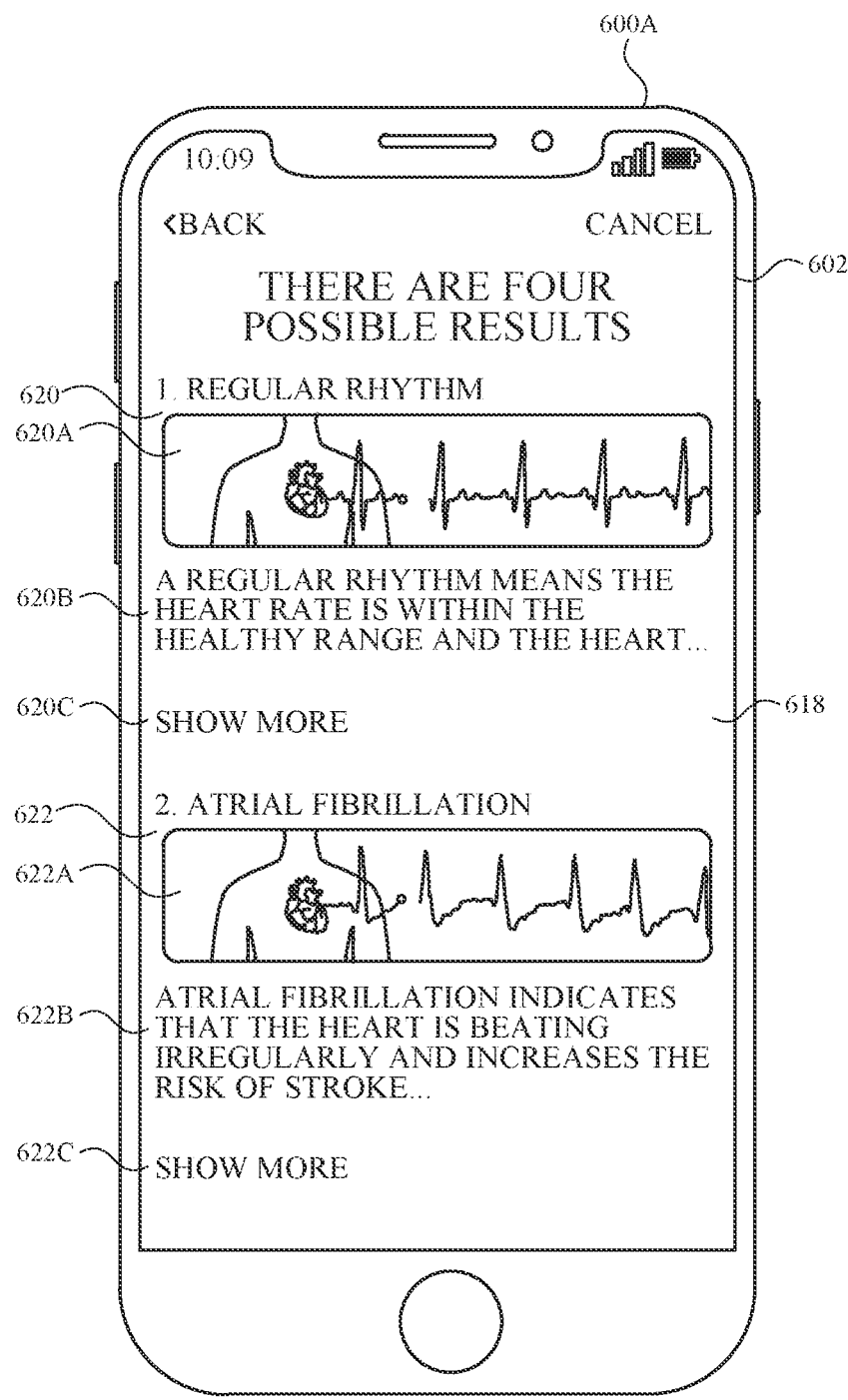

FIG. 6H illustrates first electronic device 600A displaying, on display 602, possible results page 618 of the tutorial for performing initial setup of the ECG management features and associated ECG application. In some embodiments, possible results page 618 includes a plurality of representations of possible evaluation results that can be made based on ECG information recorded using the associated ECG application on a second electronic device (e.g., second electronic device 600B).

In some embodiments, the plurality of representations of possible evaluation results shown in possible results page 618 of the tutorial include possible evaluation results corresponding to heart rhythm and heart rate that are captured from an ECG recording. In some embodiments, a first possible evaluation result is a "regular rhythm" result (or a "normal result"), which corresponds to a result where no abnormal signs were determined from the ECG recording of the user. In some embodiments, a second possible evaluation result is an "abnormal heart rhythm" result (e.g., an "Atrial Fibrillation" result) that corresponds to a result where abnormal heart rhythm signs (and, in some cases, high/low heart rate signs) were determined from the ECG recording of the user. In some embodiments, a third possible evaluation result is an "abnormal heart rate" result (e.g., a "high or low heart rate" result), which corresponds to a result where an unusually (or abnormally) high or low heart rate was determined from the ECG recording of the user (e.g., above 150 BPM or below 50 BPM). In some embodiments, a fourth possible evaluation result is an "inconclusive" result, which corresponds to a result where no evaluation result could be determined from the ECG recording of the user (e.g., because of a poor reading).

In some embodiments, as shown in FIG. 6H, possible results page 618 shows a plurality of representations of possible evaluation results, where not all of the representations are concurrently visible on the display. In FIG. 6H, a representation 620 of the first evaluation result (a "regular" result) and (a portion of) a representation of 622 of the second evacuation result (a "Atrial Fibrillation" result) is visible on the display.

In some embodiments, as shown in FIG. 6H, each representation of a possible evaluation result shown on possible results page 618 includes an animation region that includes a graphical animation (e.g., a tachogram-like animation, a beating heart animation, one or more objects that continuously/repeatedly move across the tachogram-like animation in a particular frequency) that represents its respective evaluation result and a text region that shows a portion of a text description explaining (medical) characteristics of its respective evaluation result.

In FIG. 6H, representation 620 of a "regular" result includes an animation region 620A that includes an example animation of a "regular" result and a text region 620B that shows a portion of a text description explaining characteristics of a "regular" result, and representation 622 of an "Atrial Fibrillation" result includes an animation region 622A that includes an example animation of an "Atrial Fibrillation" result and a text region 622B that shows a portion of a text description explaining medical characteristics of an "Atrial Fibrillation" result. In some embodiments, the animations include a beating heart animation and a tachogram-like animation that in combination illustrate a rhythm and rate of heartbeats.

In some embodiments, a representation of a possible evaluation result also includes an expand affordance (e.g., a "show more" affordance) for displaying the full text description of the respective evaluation result (e.g., by expanding the text region). In FIG. 6H, representation 620 of a "regular" result includes an expand affordance 620C which, when selected (e.g., via a touch input), causes display of the full text description (e.g., which includes additional text information not shown in text region 620B) about a "regular" result, and representation 622 of an "Atrial Fibrillation" result includes an expand affordance 622C which, when selected (e.g., via a touch input), causes display of the full text description (e.g., which includes additional text information not shown in text region 622B) about an "Atrial Fibrillation" result.

Figure 6I:
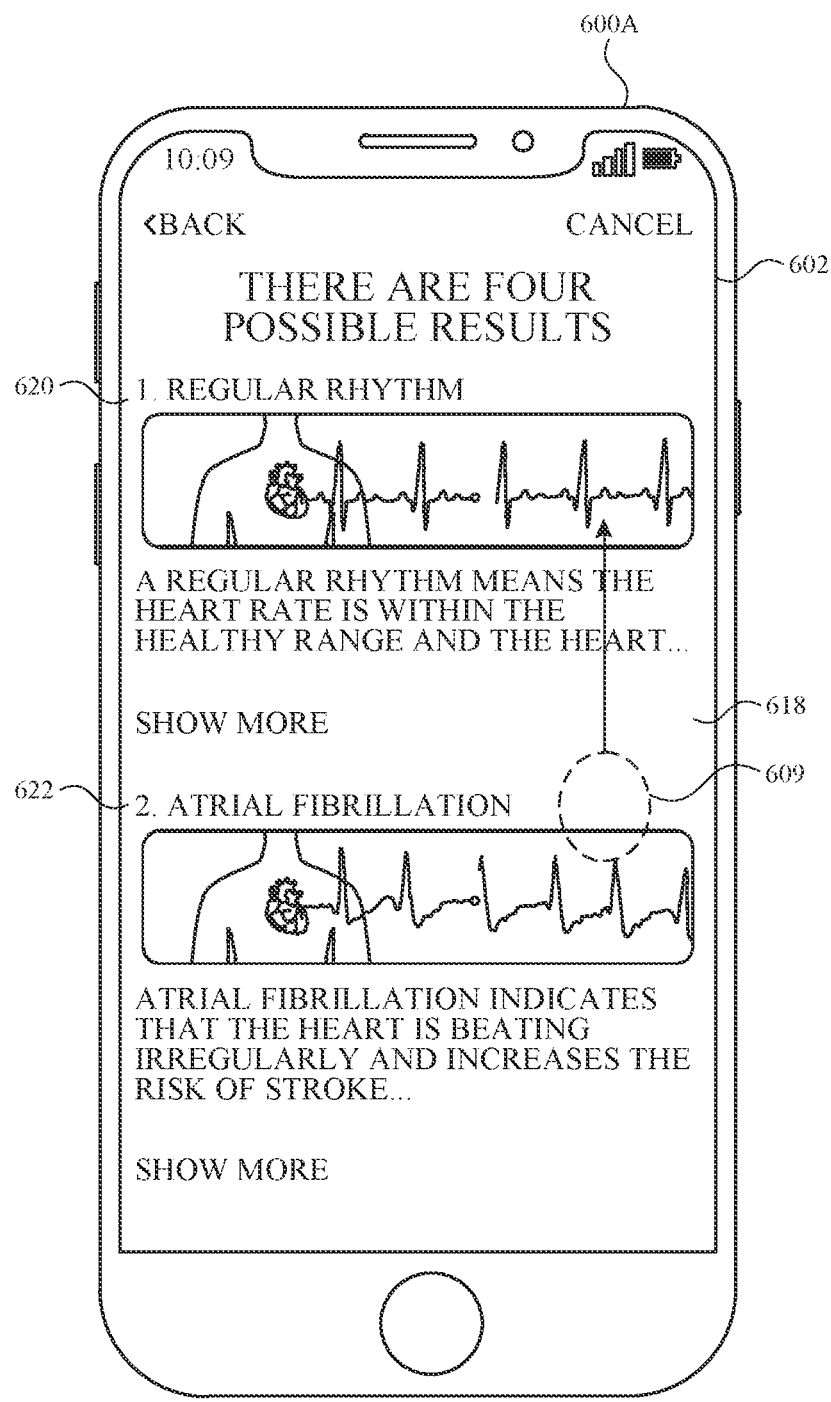

In FIG. 6I, while displaying possible results page 618 with representation 620 and representation 622 visible on display 602, first electronic device 600A detects a scrolling input 609 (e.g., a scrolling touch gesture on the display). In response to detecting scrolling input 609, the device scrolls possible results page 618 such that one or more other representations of other possible evaluation results become visible on display 602, as shown in FIG. 6J.

Figure 6J:
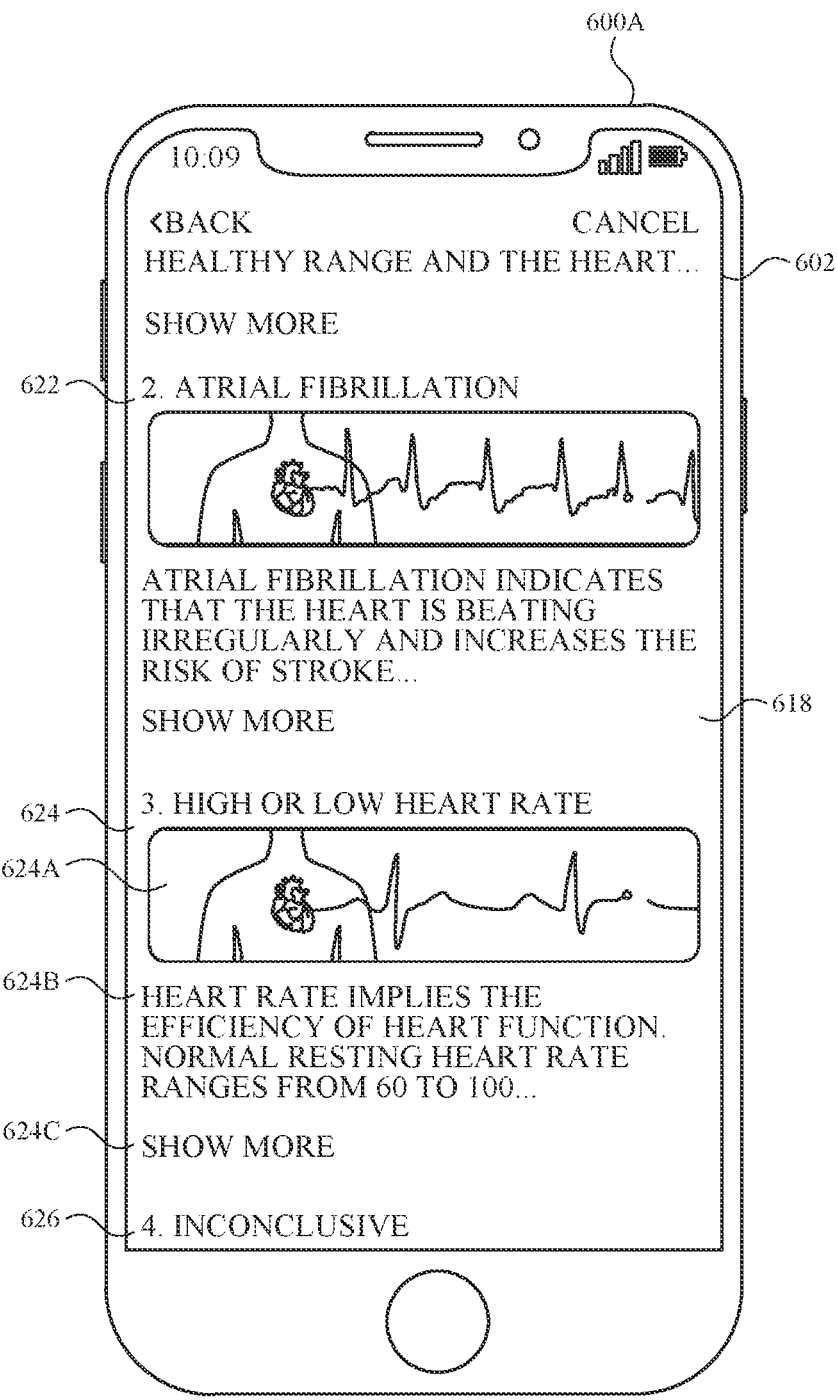

In FIG. 6J, representation 624 of a "high or low heart rate" result is fully visible on display 602. As with the other representations of possible evaluation results, representation 624 includes an animation region 624A that includes an example graphical animation of a "high or low heart rate" result, a text region 624B showing a portion of a text description explaining medical characteristics of a "high or low heart rate" result, and an expand affordance 624C for expanding text region 624C to fully show all of the text of the text description. Also in FIG. 6J, representation 622 of an "Atrial Fibrillation" remains fully visible on the display while only a portion of representation 626 of an "inconclusive" result is visible on the display.

Figure 6K:
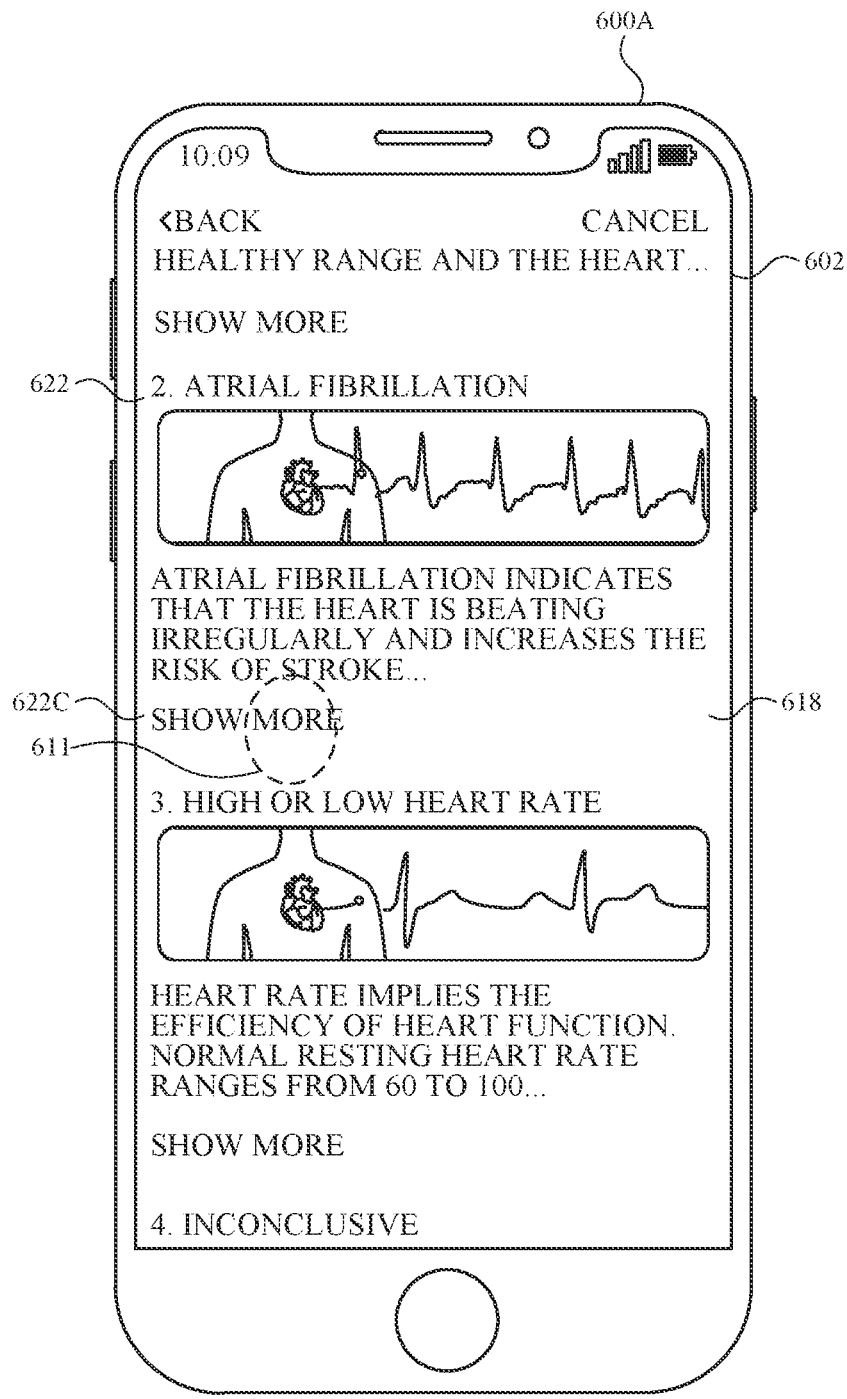
Figure 6L:
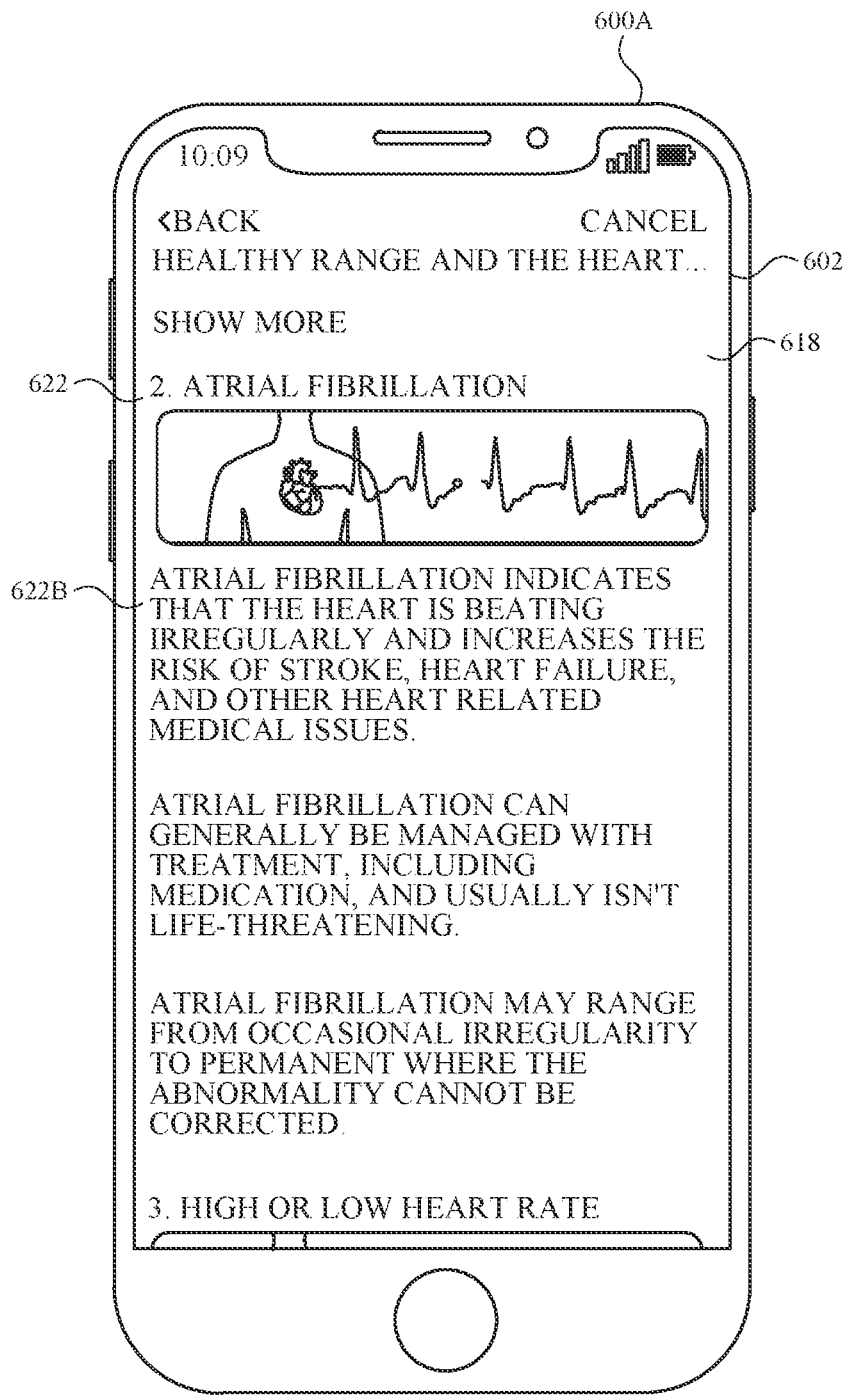

In FIG. 6K, while displaying possible results page 618 with representation 620 of a "Atrial Fibrillation" result visible on display 602, first electronic device 600A detects (e.g., via a touch input) a user activation 611 of expand affordance 622C (e.g., because the user wants to view all of the text of the text description describing the "Atrial Fibrillation" result). As shown in FIG. 6L, in response to detecting user activation 622C of expand affordance 622C, first electronic device 600A expands text region 622B of representation 622 of the "Atrial Fibrillation" result to display the full text of the text description. In some embodiments, upon expanding the text region, the expand affordance is removed from the representation. In some embodiments, upon expanding the text region, the expand affordance is replaced with a contract affordance (e.g., a "show less" affordance).

Figure 6M:
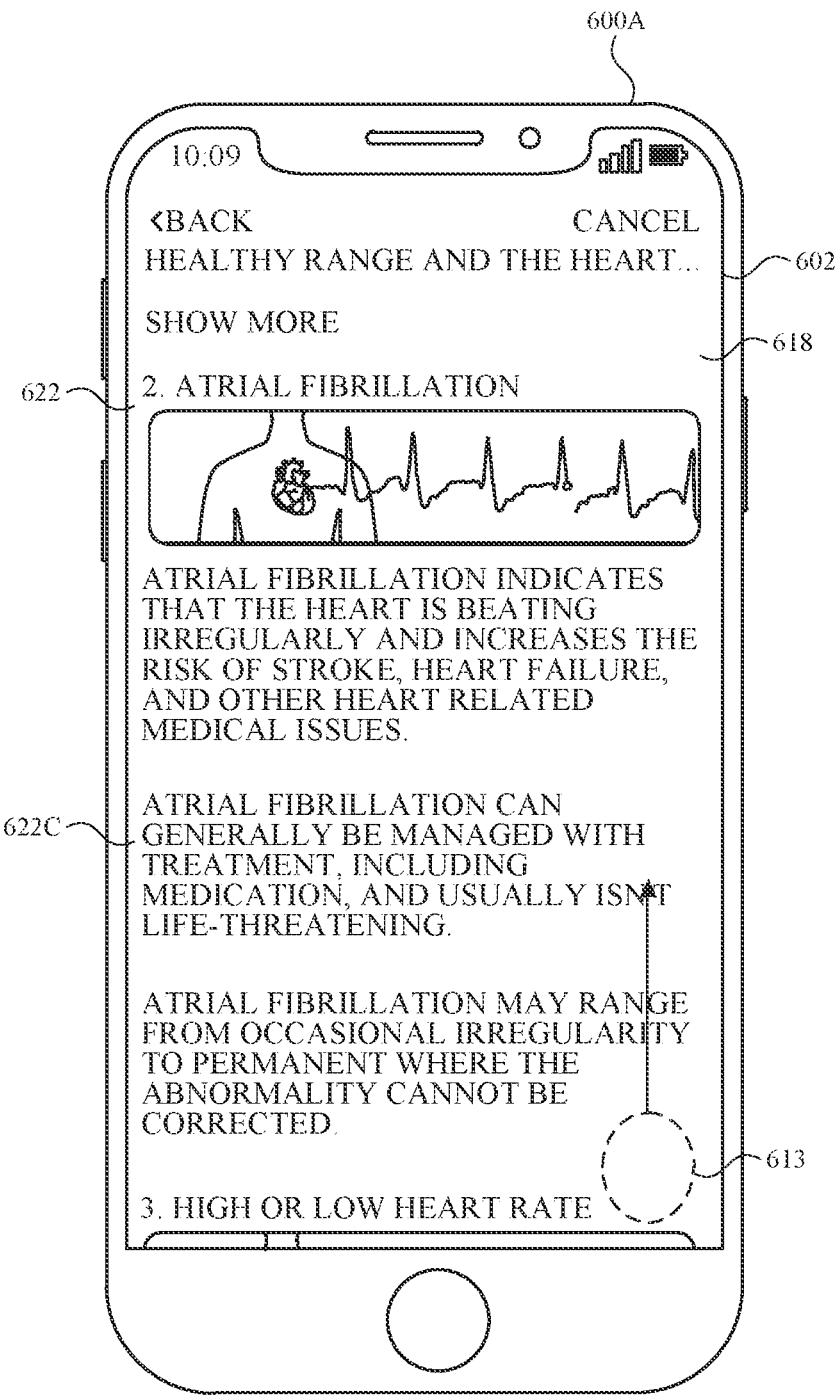

In FIG. 6M, while displaying, on display 602, possible results page 618 with an expanded text region 622C of representation 622 of an "Atrial Fibrillation" result, first electronic device detects (e.g., via a touch layer of the display) a scrolling input 613 (e.g., a scrolling touch gesture). In response to detecting scrolling input 613, the device scrolls possible results page 618 such that all of representation 626 of an "inconclusive" result is visible on the display, as shown in FIG. 6N.

Figure 6N:
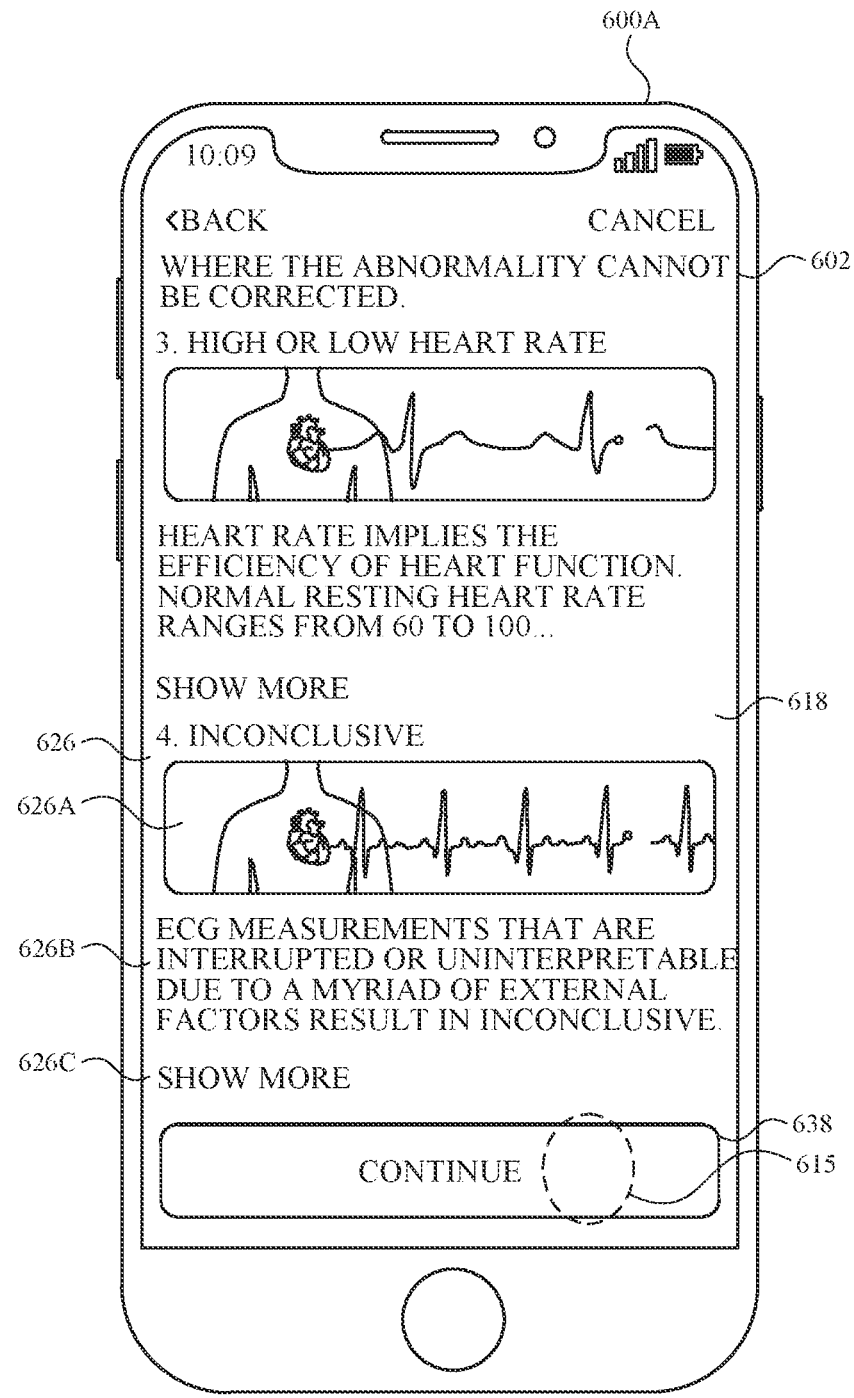

In FIG. 6N, representation 626 of an "inconclusive" result is fully visible on display 602. As with the other representations of possible evaluation results, representation 626 includes an animation region 626A that includes an example graphical animation of an "inconclusive" result, a text region 626B showing a portion of a text description explaining medical characteristics of an "inconclusive" result, and an expand affordance 626C for expanding text region 626C to fully show all of the text of the text description. In some embodiments, possible results page 618 includes (e.g., at the bottom of the page), an affordance 628 for proceeding with the tutorial.

In some embodiments, as mentioned, the animations (of animations regions 620A-626A) of the plurality of representations 620-626 of possible evaluation results on possible results page 618 comprise a beating heart animation and a tachogram-like animation that in combination illustrate a rhythm and rate of heartbeats. In some embodiments, the animations are synchronized. In some examples, each animation comprises repeating loops, where each loop consists of an object (e.g., a circular object) leaving the beating heart animation and moving across the screen while tracking the tachogram-like animation. The repeating loops of the plurality of animations (of representations 620-626) are synchronized to begin and end at the on synched time intervals.

In FIG. 6N, while displaying, on display 602, affordance 628 possible results page 618 for proceeding with the tutorial, first electronic device 600A detects (e.g., via a touch input) a user activation 615 of affordance 628 for proceeding with the tutorial. In response to detecting user activation 615, first electronic device 600A displays, on display 602 (e.g., replaces display of possible results page 618 with), a limitations page 630, as shown in FIG. 6O.

In some embodiments, limitations page 630 indicates to the user (e.g., via a text description) some limitations of evaluation results determined from ECG recordings taken on the second electronic device (e.g., second electronic device 600B). In some examples, limitations page 630 includes a list 630A of one or more medical characteristics that cannot be determined from recorded ECG information (e.g., heart attack, blood clots/stroke). In some embodiments, limitations page 630 includes (e.g., at the bottom of the page), an affordance 630B for proceeding with the tutorial.

Figure 6O:
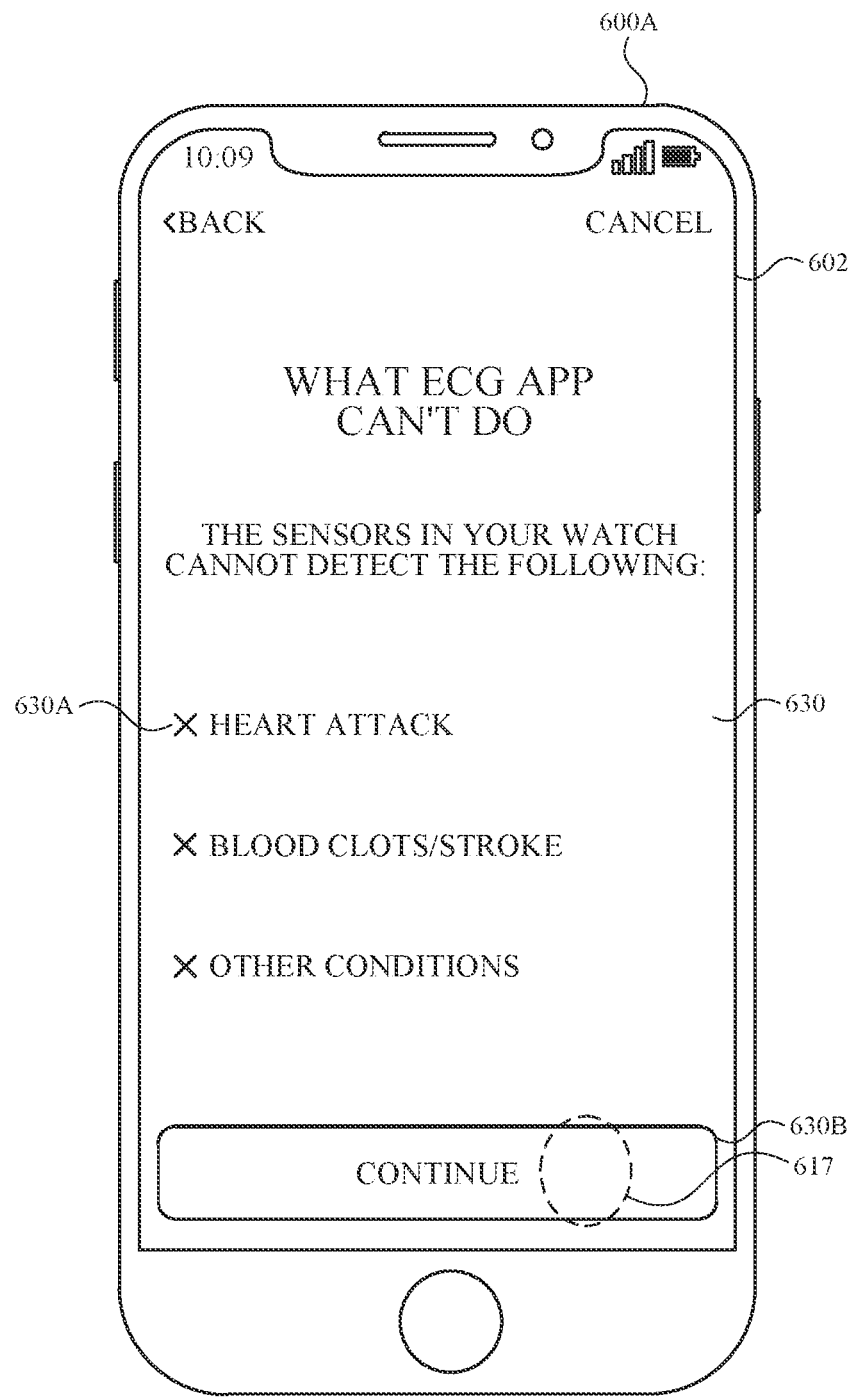

In FIG. 6O, while displaying, on display 602, limitations page 630, first electronic device 600A detects (e.g., via a touch input) a user activation 617 of affordance 630B for proceeding with the tutorial. In some embodiments, in response to detecting user activation 617 of affordance 630B, the device displays, on display 602, an instructions page 632, as shown in FIG. 6P.

In some embodiments, one or more of pages 614, 616, 618, and/or 632 of the tutorial (as shown in FIGS. 6F, 6G, 6H, and 6O, respectively) include a cancel affordance. In some embodiments, upon detecting user selection of a cancel affordance (e.g., in any one of pages 614, 616, 618, and/or 632 of the tutorial), first electronic device 600A displays, on display 602, a notification 653, as shown in FIG. 6Q. In some embodiments, notification 653 includes an indication 653A (e.g., stating "If you cancel now, you will go through the setup again before you can take an ECG recording") informing the user that the current progress through the tutorial will be lost and the initial setup process will need to be re-initiated in order for the user to begin taking ECG recordings on second electronic device 600B. In some embodiments, notification 653 includes a confirmation affordance 653B (e.g., stating "Set up later") for confirming the cancellation of the setup process and thus exit the tutorial. In some embodiments, while displaying notification 653, the background of the display is dimmed (thereby emphasizing notification 653).

Figure 6P:
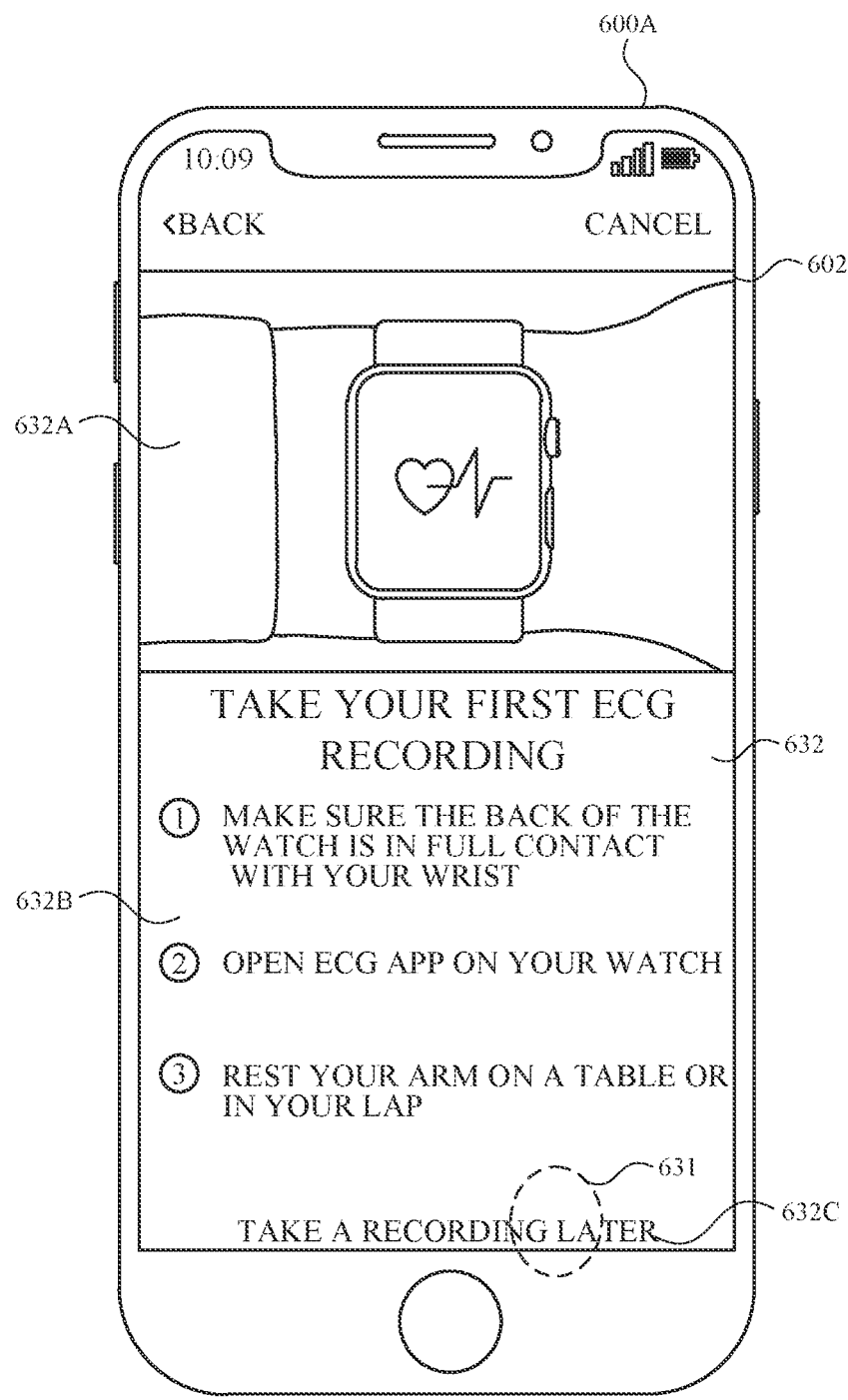
Figure 6Q:
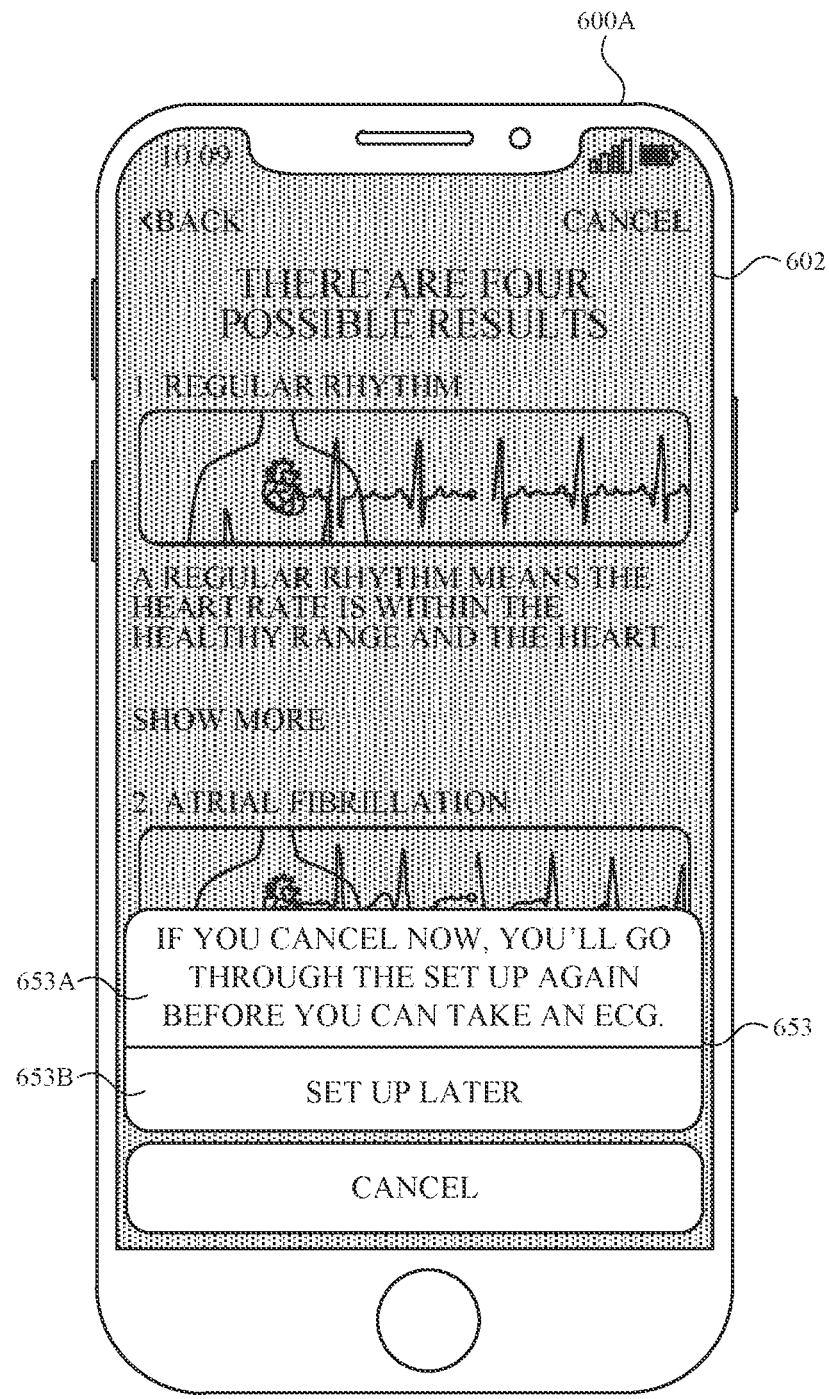

FIG. 6P shows first electronic device 600A displaying, on display 602, instructions page 632. In some embodiments, instructions page 632 includes a graphical indication region 632A and a text indication region 632B that provides instructions for how to proceed with an ECG recording using the second electronic device (e.g., second electronic device 600B). In some examples, graphical indication region 632A corresponds to graphical indication region 614A of first page 614 of the tutorial, and graphically indicates (e.g., via a static image, via an animation) a user taking an ECG recording using the second electronic device (e.g., second electronic device 600B). In some examples, text indication region 632B includes a list of instructions including required steps to perform the ECG recording on the second electronic device which can be, for example, a smartwatch with one or more biometric sensors that is paired to first electronic device 600A (e.g., second electronic device 600B).

In some embodiments, instructions page 632 includes a postpone affordance 632C (e.g., showing "Take a recording later") that enables a user to postpone taking the first ECG recording to a later time (and thus allows the user to complete the initial setup process without performing a first ECG recording). In some embodiments, while displaying instructions page 632, first electronic device 600A detects (e.g., via a touch input) a user activation 631 of postpone affordance 632C.

Figure 6R:
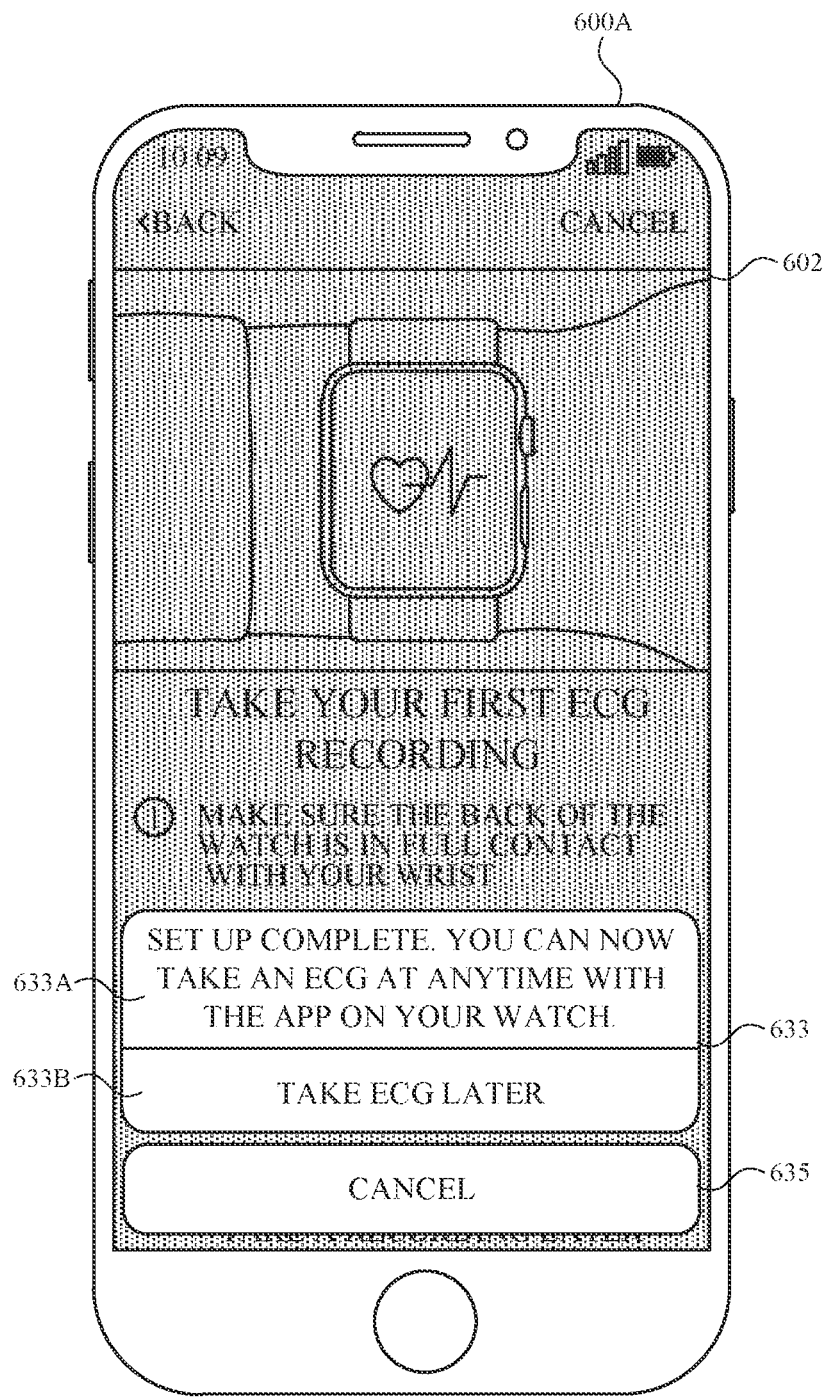

In some embodiments, in response to detecting user activation 631 of postpone affordance 632C, first electronic device 600A displays, on display 602, a confirmation notification 633, as shown in FIG. 6R In some embodiments, confirmation notification 633 is overlaid on instructions page 632. In some embodiments, confirmation notification 633 includes a text indication 633A indicating to the user that the initial setup process is complete and that the second electronic device (e.g., second electronic device 600B) is now enabled to perform ECG recordings. In some embodiments, confirmation notification 633 includes a confirm affordance 633B for acknowledging the completion of the ECG initial setup process (without taking a first ECG recording) and exiting the setup process. In some embodiments, in addition to confirmation notification 633, the device displays a cancel affordance 635 for exiting dismissing confirmation notification 633 and returning to instructions page 632. In some embodiments, while displaying confirmation notification 633 (and cancel affordance 635), the background of the display (displaying instructions page 632) is dimmed (thereby emphasizing the displayed confirmation notification).

Figure 6S:
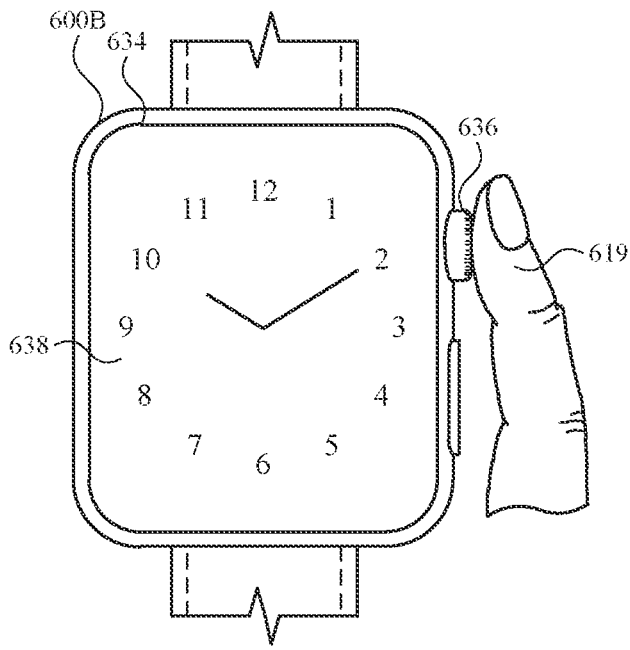

FIGS. 6S-6X illustrate second electronic device 600B (e.g., a smartwatch) having a display 634 and one or more input devices (e.g., including a touch layer of display 634 and one or more mechanical buttons, such as a depressible, rotating crown). In some embodiments, second electronic device 600B includes one or more biometric sensors (e.g., for recording ECG information, for detecting heart rhythm and heart rate of the user) comprising one or more electrodes integrated in an input device 636 (e.g., a mechanical input device, such as a depressible, rotating crown) of second electronic device 600B. In some embodiments, the one or more biometric sensors of second electronic device 600B further comprise one or more electrodes of (e.g., integrated in) a housing portion (e.g., the backplate) of second electronic device 600B, where the one or more electrodes integrated in the input device operate in conjunction with the one or more electrodes of the housing portion to capture biometric information (e.g., ECG information). Features concerning the one or more biometric sensors of second electronic device 600B used to capture biometric information (e.g., ECG information) is described in greater detail in Appendix A. In FIG. 6S, second electronic device 600B is displaying a watch face user interface 638 (e.g., a time screen of the device).

Figure 6T:
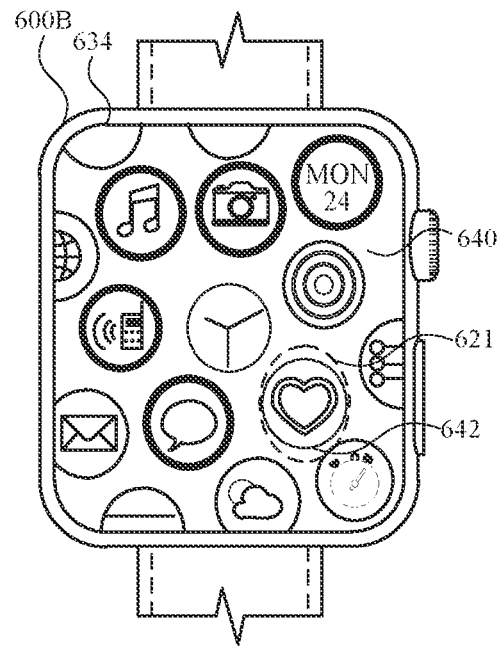

In FIG. 6S, while displaying lock user interface 638, second electronic device 600B detects a user input 619 on input device 636. In some embodiments, user input 619 is a single press of input device 636 (e.g., such that the force of the press is past a threshold amount to cause a "click" of input device 636). In some embodiments, in response to detecting user input 619 on input device 636, the second electronic device displays, on display 634 (e.g., replaces display of lock user interface 638 with), a home user interface 640 (e.g., corresponding to a home screen of the device, a screen that includes a plurality of icons corresponding to applications installed on the device and can be launched on the device), as shown in FIG. 6T. Home user interface 640 includes an icon 642 (e.g., an icon graphically depicted with a heart) corresponding to an ECG application installed on the device, where the ECG application on second electronic device 600B is associated with ECG management features of the health application installed on first electronic device 600A.

Figure 6U:
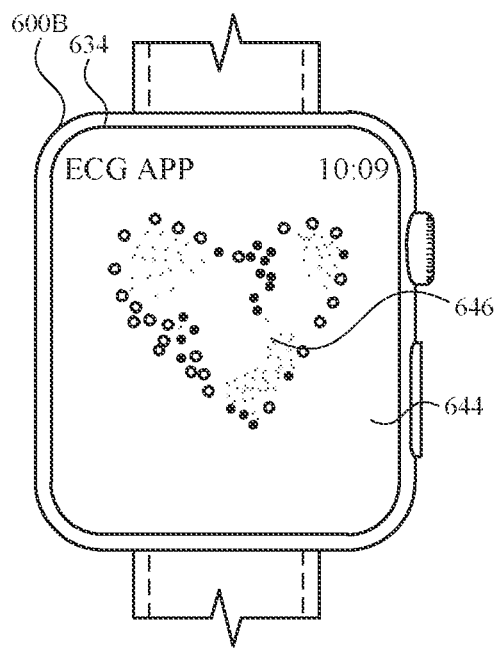

In FIG. 6T, while displaying, on display 634, icon 642 corresponding to the ECG application, second electronic device 600B detects (e.g., via a touch input) a user activation 621 of icon 642. In response to detecting user activation of icon 642, the device launches and displays the ECG application and displays, on display 634 (e.g., replaces home user interface 640 with), a user interface 644 of the ECG application, as shown in FIG. 6U.

In some embodiments, user interface 644 of the ECG application includes an animation 646 (e.g., a fluid animation) that depicts a particular shape (e.g., a heart). In some examples, as shown in FIG. 6U, animation 646 comprises a plurality of dynamic objects (e.g., circular objects) that form the particular shape (e.g., a heart), where the shape appears three-dimensional and is visually fluid as the plurality of dynamic objects constantly move while maintaining the structure of the shape.

Figure 6V:
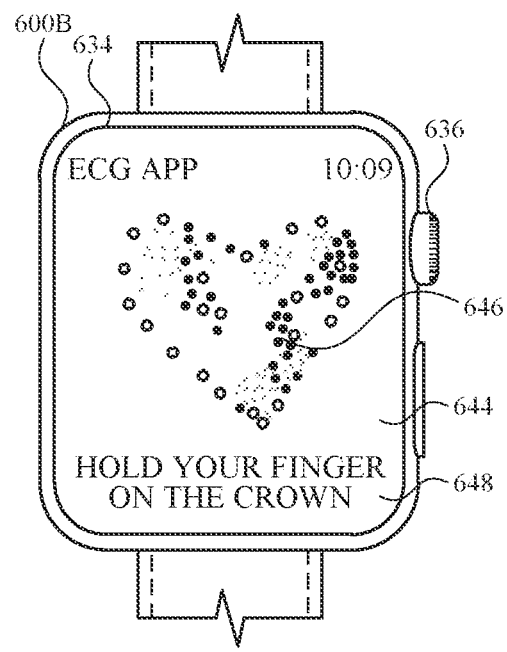

In some embodiments, after a predetermined amount of time (e.g., 5 seconds) has passed from the launch and display of the ECG application on second electronic device 600B (but the device has not detected any additional inputs from the user), second electronic device 600B displays, on user interface 644 (and while maintaining display of animation 646), a notification message 648 indicating to the user that an action must be performed (by the user) to proceed with recording ECG information using the device (e.g., "Hold your finger on the crown"), as shown in FIG. 6V. In some embodiments, the user provides a user input (e.g., a contact or touch of a finger) on first input device 636 (e.g., which includes one or more integrated electrodes operating in conjunction with one or more electrodes in a housing portion (e.g., backplate) of second electronic device 600B) to proceed with the recording of the ECG information, as instructed by notification message 648.

Figure 6W:
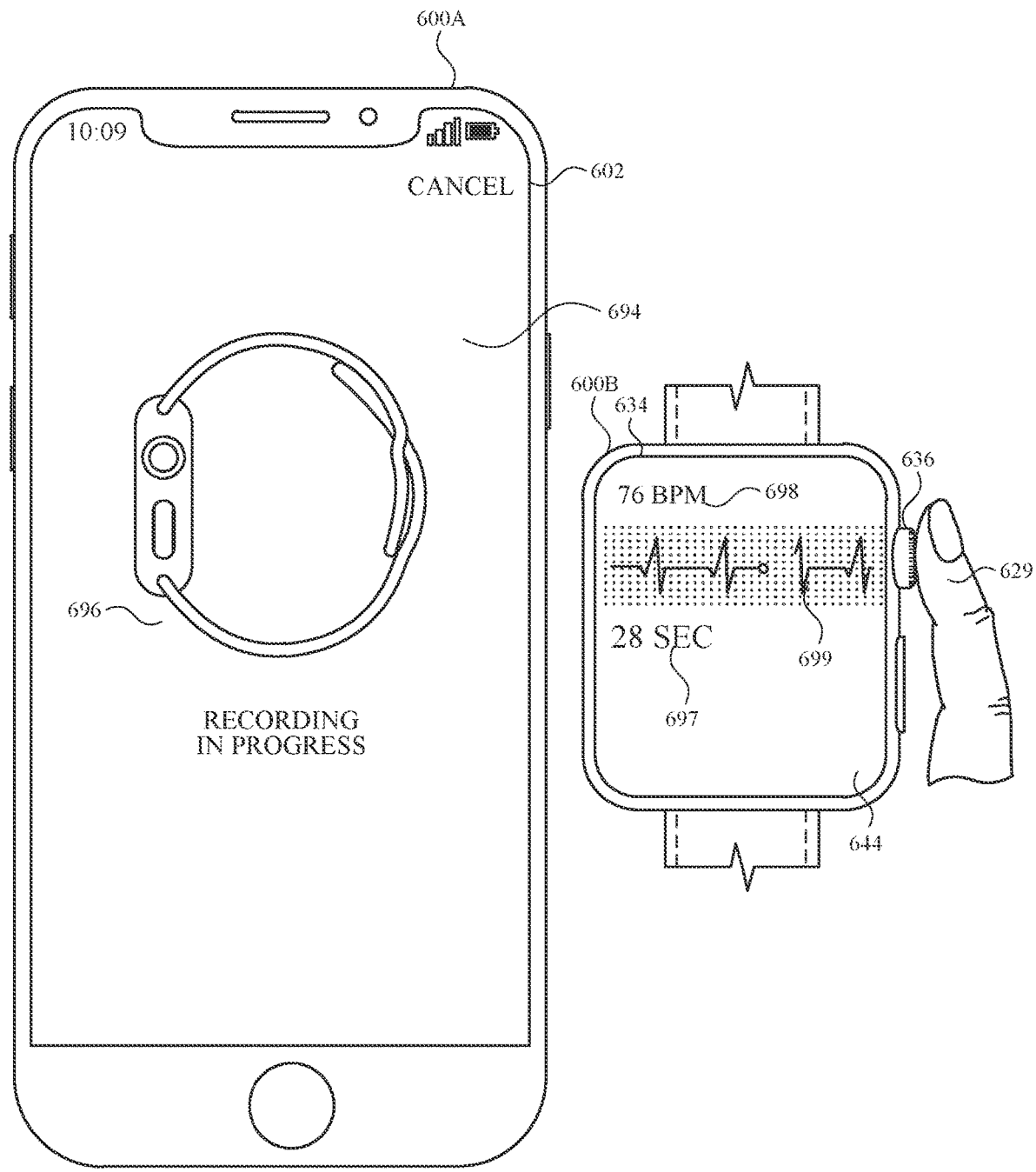

FIG. 6W illustrates first electronic device 600A displaying, on display 602, a recording-in-progress page 694 of the tutorial. In some embodiments, while recording ECG information on second electronic device 600B, first electronic device 600A displays, in recording-in-progress page 694 of the health application associated with the ECG application, an indication 696 that the ECG recording is being carried out on second electronic device 600B. In some examples, indication 696 includes a graphical indication portion (e.g., illustrating an image corresponding to the device being used to perform the recording) and a text indication portion (e.g., stating "Recording in Progress").

FIG. 6W also illustrates second electronic device 600B displaying, on display 634, user interface 644 of the ECG application while the ECG recording (e.g., corresponding to a user input 629 on input device 636) is being carried out. In some embodiments, while recording the ECG information, second electronic device 600B displays a BPM indicator 698 showing the heart rate being detected by the recording. In some embodiments, while recording the ECG information, second electronic device 600B further displays, over animation 646 (e.g., which, upon recording, transitions form its initial shape, such as a heart, to a grid-like pattern), a tachogram 699 that graphically depicts the ongoing recording. In some embodiments, while recording ECG information, a timer 697 continuously reflects (e.g., by counting down) the remaining time to successfully complete the recording. Features concerning aspects of performing an ECG recording (e.g., on a device such as second electronic device 600B) is described in greater detail below in FIGS. 8A-8S, 10A-10J, and 12A-12S.

Figure 6X:
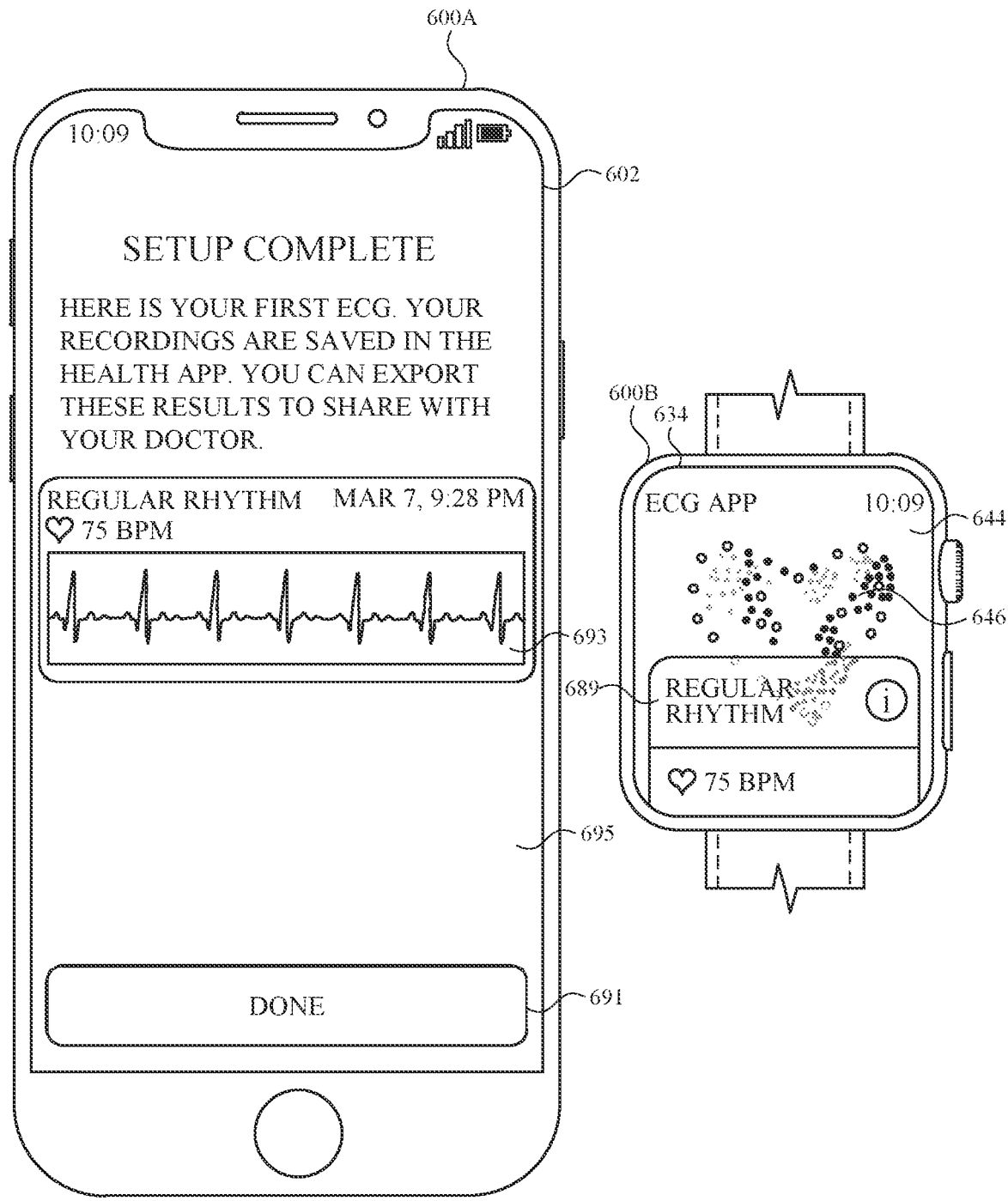

FIG. 6X illustrates first electronic device 600A and second electronic device 600B (immediately) after completing the ECG recording form FIG. 6W. In some embodiments, upon completing the ECG recording, second electronic device 600B transmits (e.g., via a Bluetooth connection) data of the ECG recording to first electronic device 600A. In some embodiments, upon completing the ECG recording, second electronic device 600B transmits (e.g., via a LTE or WiFi connection) data of the ECG recording to an external server, where the external server is also accessible by first electronic device 600A. In some embodiments, second electronic device 600B can record and locally store a plurality of ECG recordings and transmit the plurality of ECG recordings to first electronic device 600A.

In some embodiments, (immediately) after completing the ECG recording, first electronic device 600A displays a summary page 695 of the tutorial, where summary page 695 includes a representation 693 of the completed recording. In some embodiments, representation 693 includes the evaluation result (e.g., "Regular Rhythm"), the heart rate reading (e.g., in BPM), and a graphical depiction (e.g., a tachogram) of the recording. In some embodiments, summary page 695 of the tutorial includes an affordance 693 for leaving the summary page. In some embodiments, summary page 695 of first electronic device 600A includes a completion button 691 for exiting the tutorial (after having completed the tutorial). In some embodiments, when the tutorial is completed without the user having taken a first ECG recording, as described with reference to FIG. 6R, representation 639 of summary page 695 is displayed without an indication of an evaluation result, a heart rate reading, and a graphical depiction of a recording (e.g., the evaluation result, heart rate reading, and graphical depiction fields are blank).

In some embodiments, (immediately) after completing the ECG recording, second electronic device 600B displays at least a portion of a corresponding summary page 689 (e.g., over user interface 644 of the ECG application with animation 646 in its initial pattern (e.g., a fluid heart-shaped pattern, as shown in FIG. 6V)). In some embodiments, summary page 689 includes the evaluation result (e.g., "Regular Result") and other related information about the completed recording. In some embodiments, summary page 689 slides onto the display from an edge of the display (e.g., a bottom edge of the display). Features concerning aspects of an ECG recording being performed on a device (e.g., second electronic device 600B) is described in greater detail below in FIGS. 12A-12S.

In some embodiments, the user can perform a plurality of ECG recordings using the ECG application on second electronic device 600B. In some embodiments, the plurality of ECG recordings are transmitted from second electronic device 600B to first electronic device 600A (or to an external server accessible by first electronic device 600A) for viewing and management via the ECG management features of the health application on first electronic device 600A.

Figure 6Y:
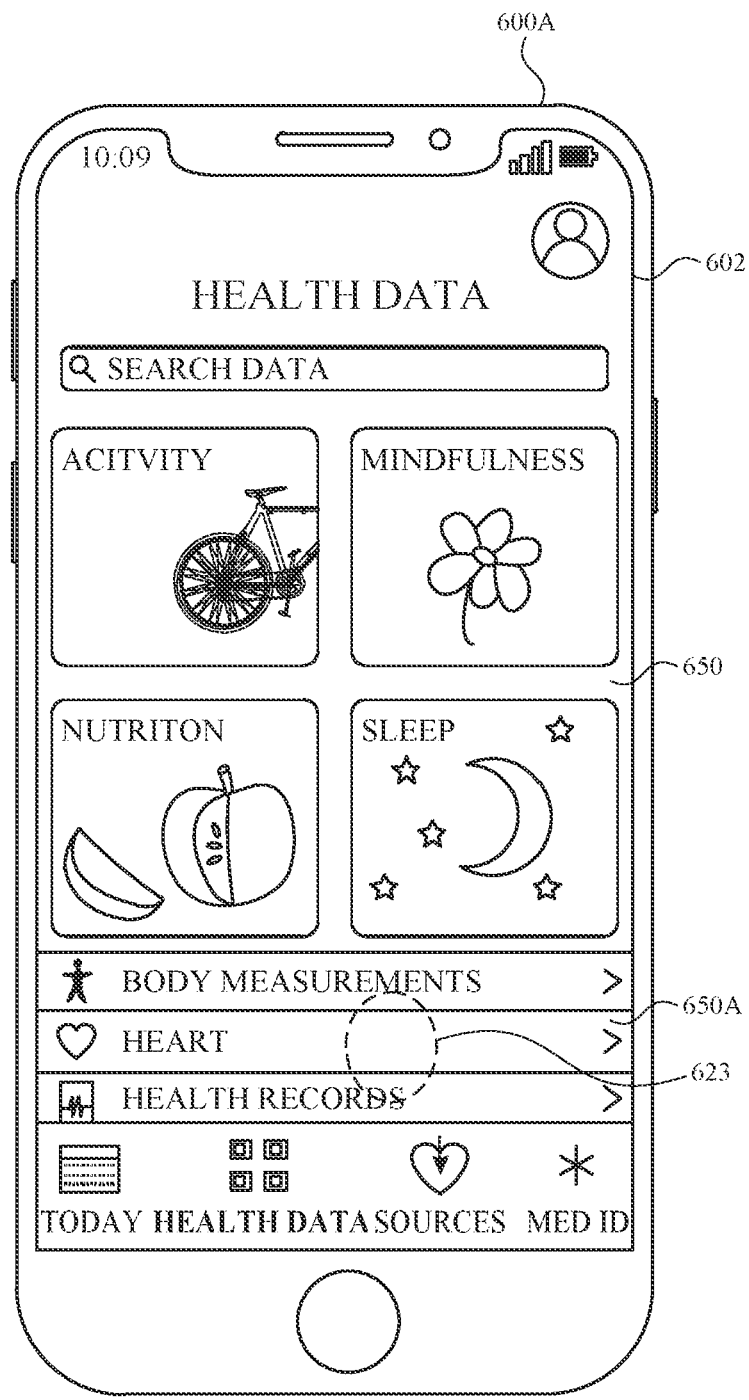

FIG. 6Y illustrates first electronic device 600A displaying, on display 602, a health data user interface 650 of the health application (e.g., that is associated with the ECG application on second electronic device 600B) after having performed several ECG readings using second device 600B. In some embodiments, the health application is accessible via a corresponding icon on a home user interface of the operating system of first electronic device 600A.

In some embodiments, health data user interface 650 of the health application includes an affordance 650A (e.g., stating "Heart") for viewing and managing heart health information. In FIG. 6Y, while displaying health data user interface 650, first electronic device 600A detects (e.g., via a touch input) a user activation 623 of affordance 650A. In response to detecting user activation 623, the device displays, on display 602, a heart data user interface 652 corresponding to heart-specific features of the health application.

In some embodiments, heart data user interface 652 of the health application on first electronic device 600A includes a heart rate affordance 654. In some embodiments, heart rate affordance 654 includes an indication of a range of the user's heart rate measured (e.g., via second electronic device 600B) during a certain period of time (e.g., today). In some embodiments, in response to detecting a user selection on heart rate affordance 654, heart data user interface 652 displays a graphical depiction of the heart rate information summarized by heart rate affordance 654 within a graphical depiction region 656 of the user interface (and further highlights the affordance with a particular visual characteristic, such as a different color, to indicate to the user that the heart rate affordance is currently selected by the user).

In some embodiments, heart data user interface 652 of the health application on first electronic device 600A includes an ECG affordance 658. In some embodiments, ECG affordance 658 includes a summary of a heart health evaluation result (e.g., a "regular" result, a "Atrial Fibrillation" result, a "high or low heart rate" result, an "inconclusive" result) determined from one or more ECG recordings performed during a certain time period (e.g., today), and a number of recordings taken during the time period (e.g., "2 readings"). In some embodiments, ECG affordance 658 includes an information affordance 658A for viewing and managing information about existing ECG recordings (e.g., previously performed by the user on second electronic device 600B).

Figure 6Z:
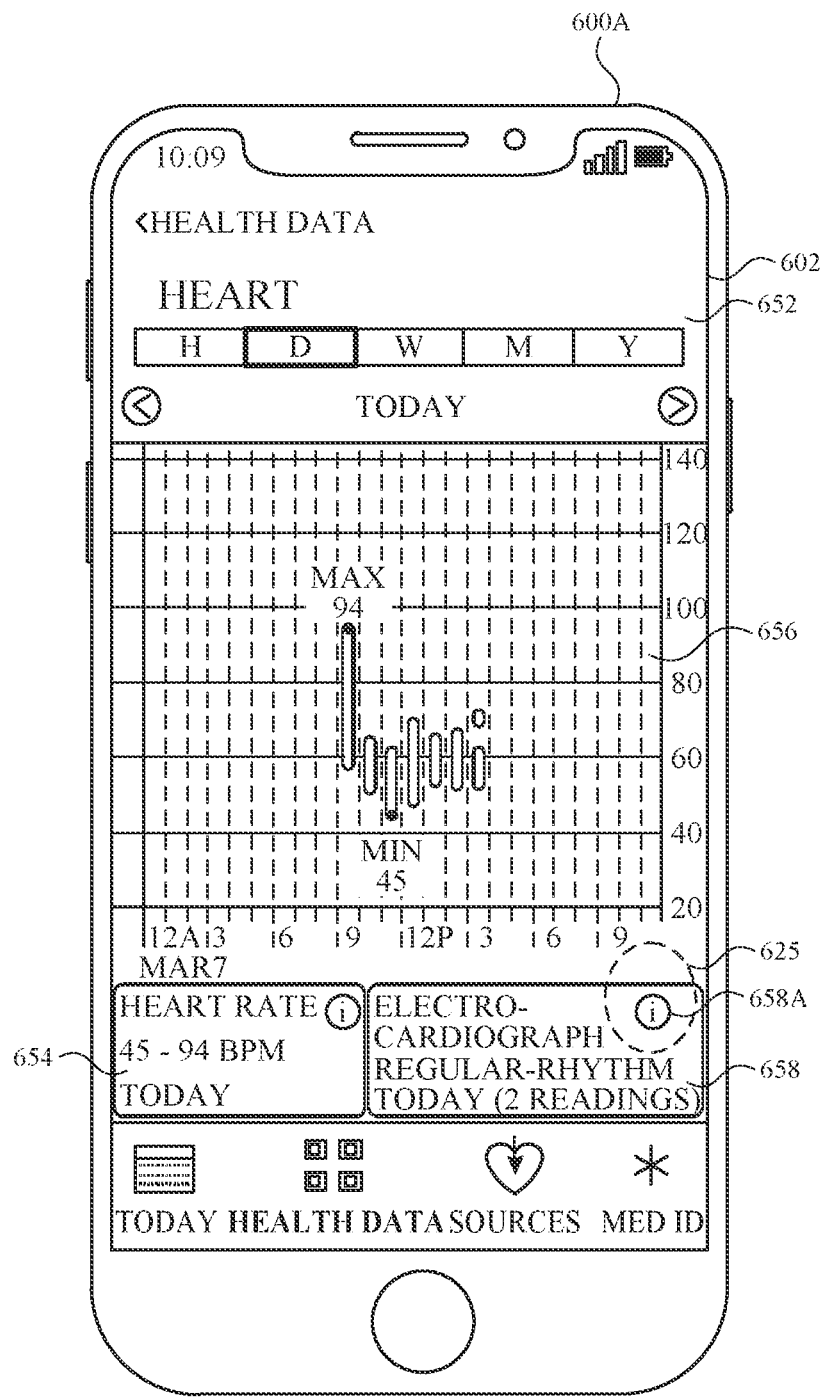
Figure 6A:
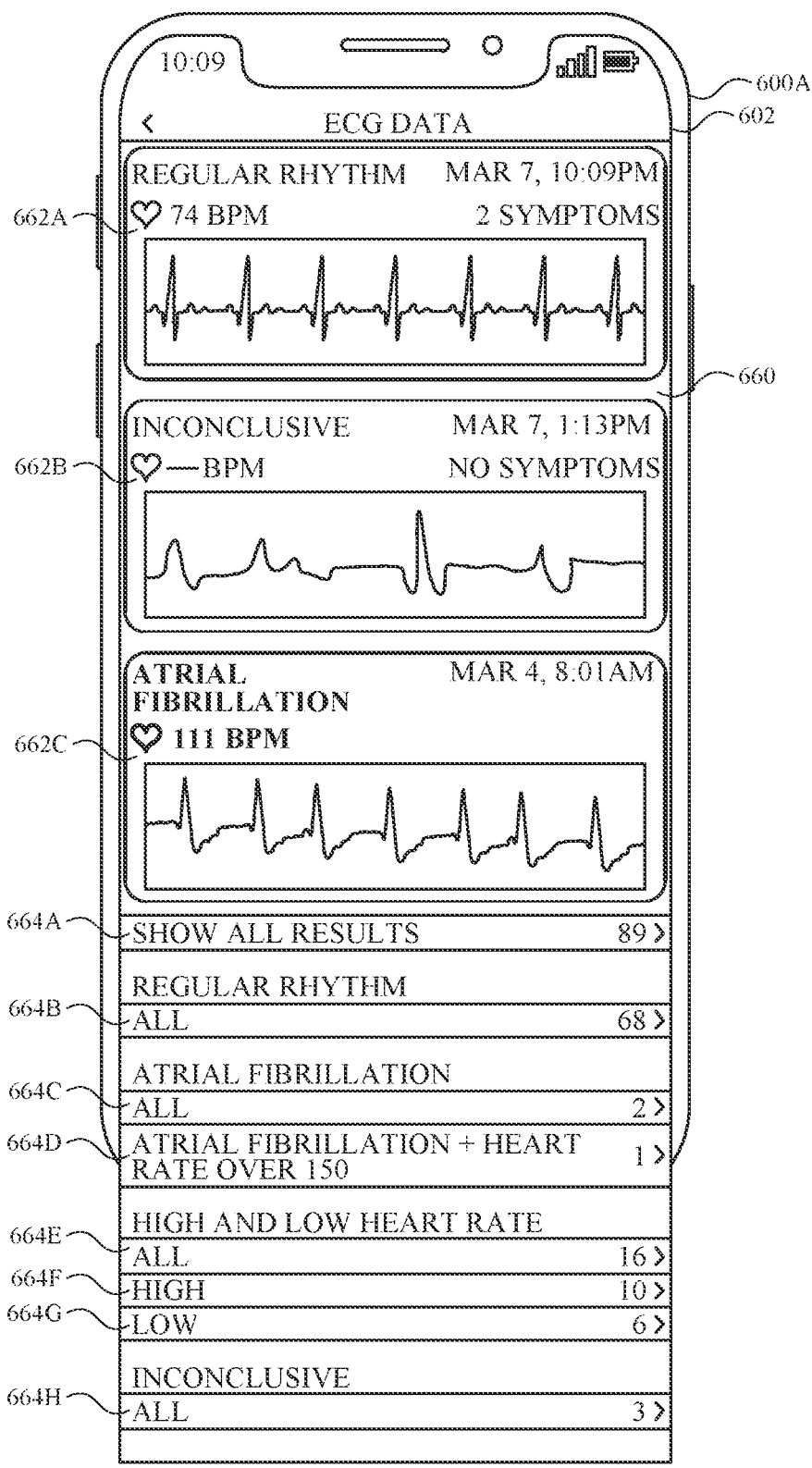
Figure 6A:
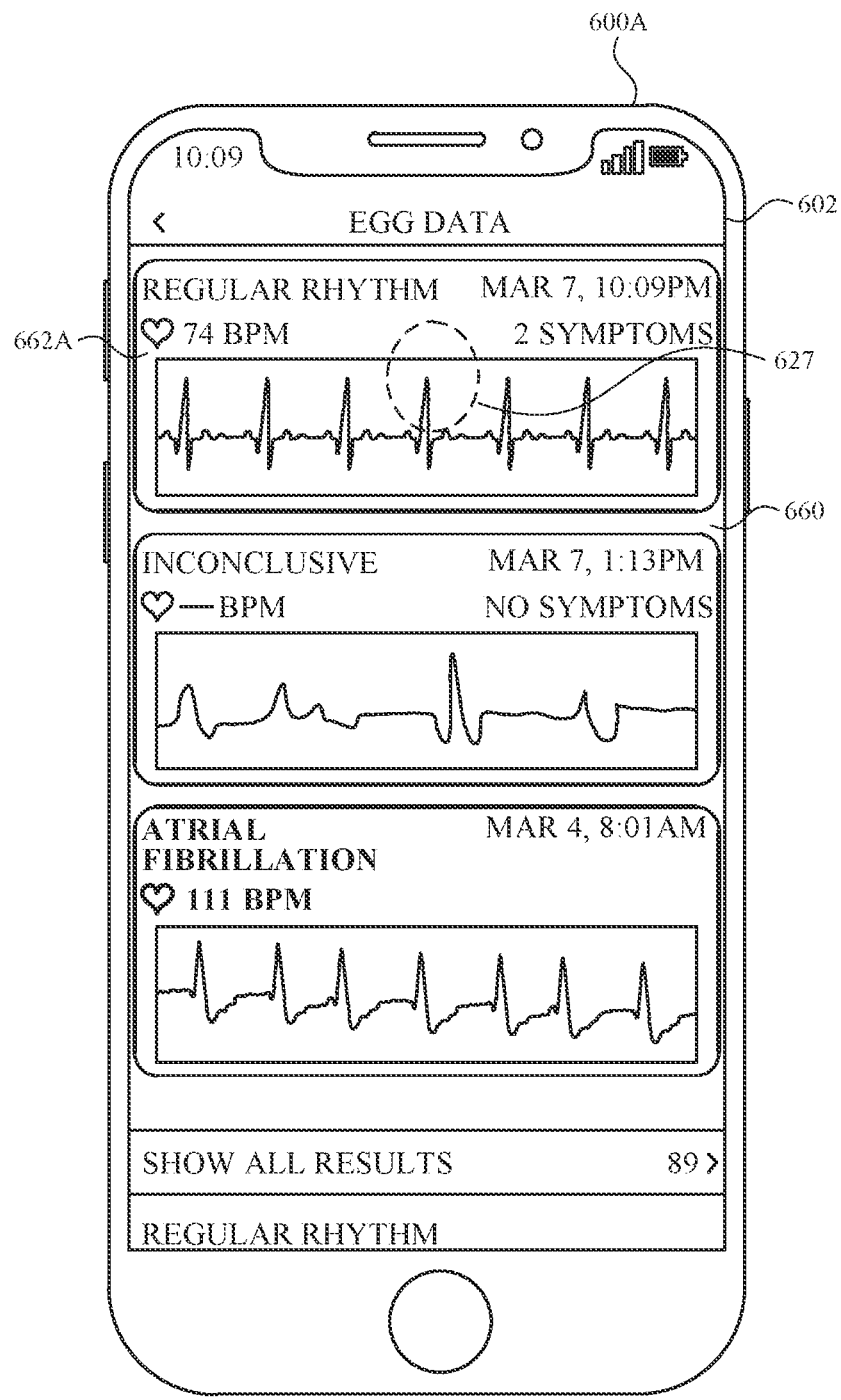
Figure 6A:
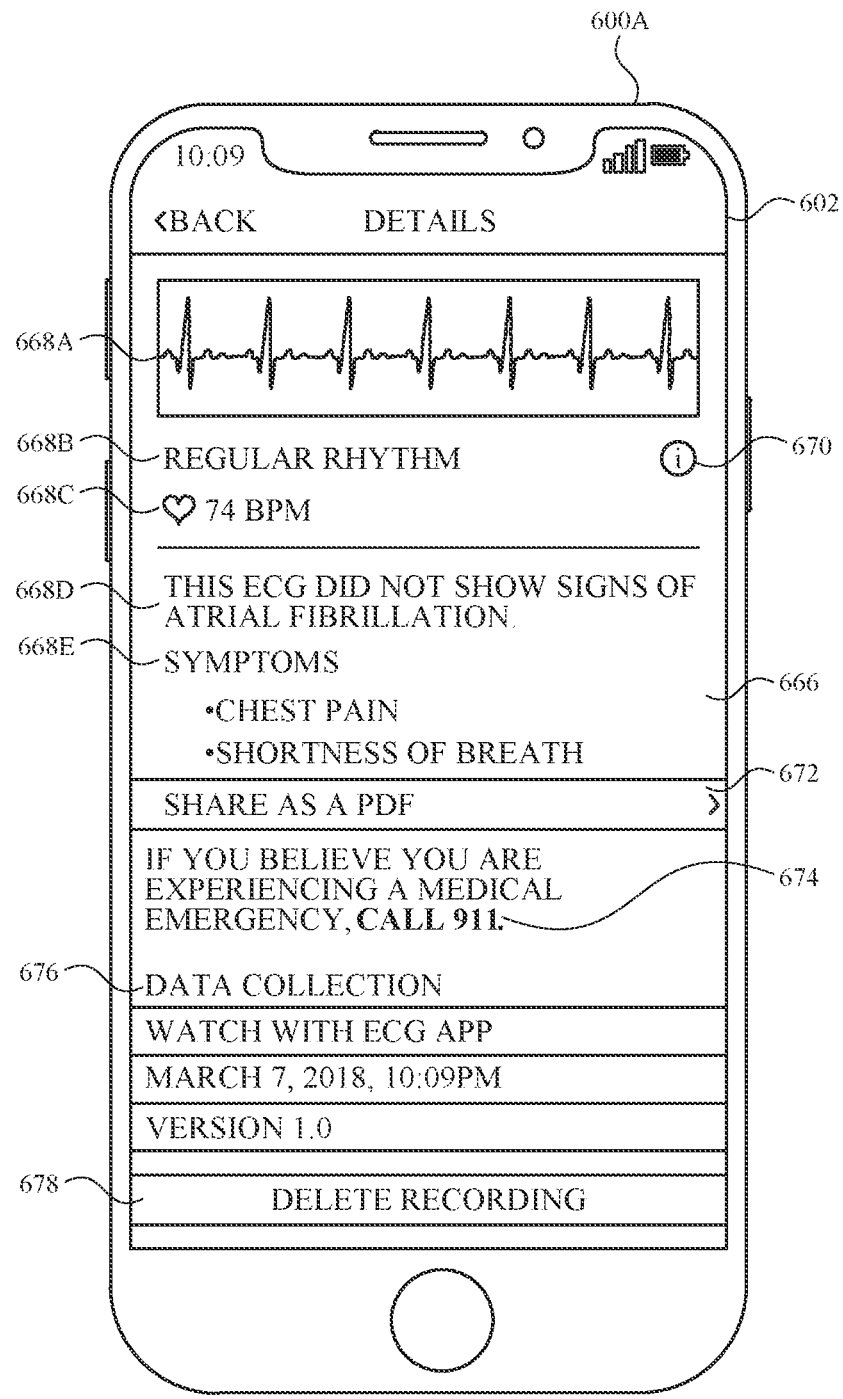
Figure 6A:
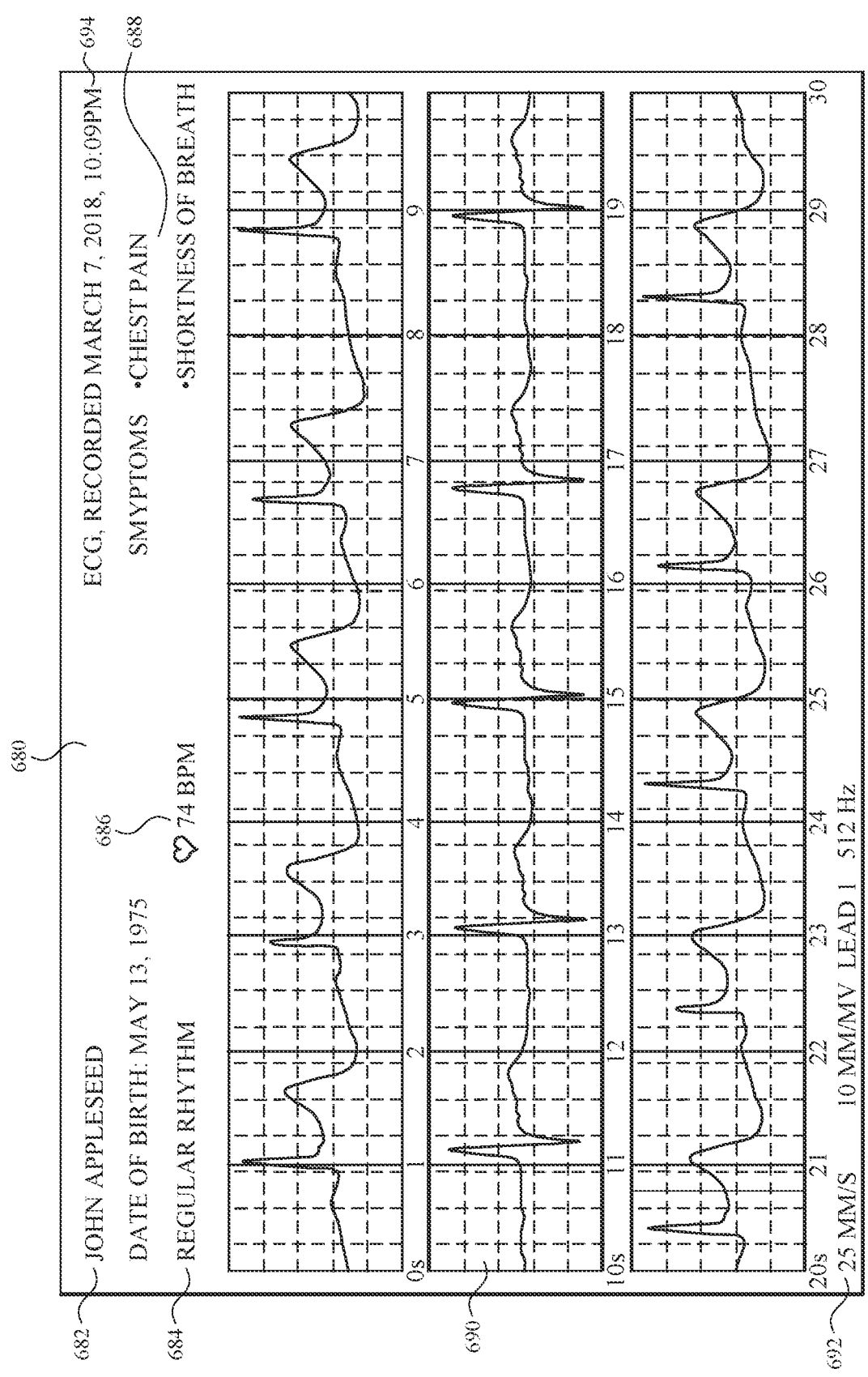
Figure 6A:
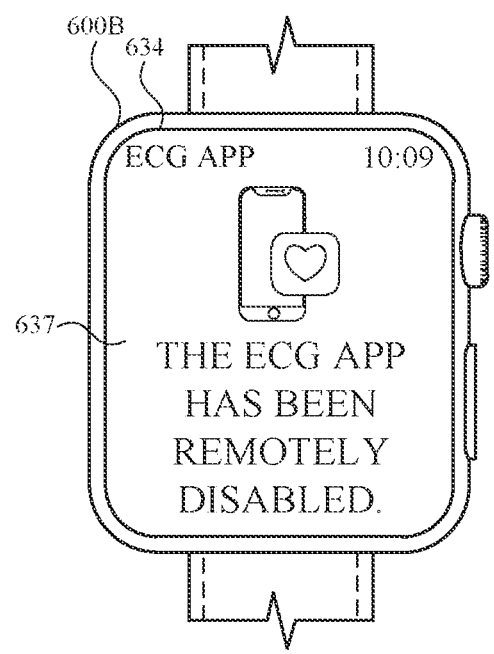

In FIG. 6Z, while displaying heart data user interface 652 with ECG affordance 658 visible on display 602, first electronic device 600A detects (e.g., via a touch input) a user activation 625 of information affordance 658A of ECG affordance 658. In response to detecting user activation 625 of information affordance 658A, first electronic device 600A displays, on display 602, an ECG management user interface 660, as shown in FIG. 6AA.

In some embodiments, ECG management user interface 660 (initially) displays a predetermined number (e.g., three) of representations of the most-recent evaluation result determined from corresponding most-recent ECG recordings performed on second electronic device 600B. In some embodiments, the representations of the most-recent evaluation results include a graphical portion (e.g., a tachogram) that graphically depicts the recording and a text portion that indicates the type of evaluation result (e.g., a "regular" result, an "Atrial Fibrillation" result, a "high or low heart rate" result, an "inconclusive" result) and a measured heart rate (e.g., in BPM). In some embodiments, the representations of the most-recent evaluation results include an indication of one or more user-specified symptoms associated with the result and/or the number of user-specified symptoms associated with the result. In some embodiments, if the user specified that there are no symptoms to be associated with a result, then a "no symptoms" indication is showed in the corresponding representation of the result. In some embodiments, if the user did not specify any symptoms for a result (or indicate that there are no symptoms for the result), then a symptoms indication is not shown in the corresponding representation of the result. Features related to user selection of symptoms for a respective evaluation result is described in greater detail with reference to FIGS. 12A-12S.

In some embodiments, first electronic device 600A detects a user activation of ECG affordance 658 at a location on the affordance that does not correspond to information affordance 658A. In some embodiments, in response to the user activation, first electronic device 600A replaces display of the heart rate information shown in graphical depiction region 656 of FIG. 6Z with heart rhythm information, in a graphical form.

In FIG. 6AA, heart rhythm data user interface 660 shows a representation 662A corresponding to a most-recent ECG recording, a representation 662B corresponding to a second-most-recent ECG recording, and a representation 662C corresponding to a third-most-recent ECG recording. In some examples, representation 662A corresponds to a "regular" result, with a heart rate measurement of 74 BPM and an indication of 2 symptoms selected for the result. In some examples, representation 662B corresponds to an "inconclusive" result with no heart rate measurement determined for the result and a "no symptoms" specifically indicated by the user for the result. In some examples, representation 662C corresponds to an "Atrial Fibrillation" result, with a heart rate measurement of 111 BPM, and no indication or 0 or more selected symptoms because the user did not specify any symptoms or whether there were no symptoms for the result. Further, in some examples, because "Atrial Fibrillation" result is an abnormal result, at least a portion of representation 662C is highlighted with a particular visual characteristic (e.g., a warning color, such as yellow) that is different from a default visual characteristic.

In some embodiments, ECG management user interface 660 also includes a plurality of affordances for viewing additional/different representations of additional/different past evaluation results and sorting/filtering the existing evaluation results. In some examples, ECG management user interface 660 includes a "show all results" affordance 664A (e.g., which also indicates the number of associated existing recordings) for displaying representations of all past ECG recordings performed by the user. In some examples, ECG management user interface 660 includes a first filter affordance 664B for displaying (e.g., filtering the existing recordings to show) representations of all of the existing ECG recordings corresponding to a "regular" result (e.g., representation 662A). In some examples, ECG management user interface 660 includes a second filter affordance 664C for displaying (e.g., filtering the existing recordings to show) representations of all of the existing ECG recordings corresponding to a "Atrial Fibrillation" result (e.g., representation 662C). In some examples, ECG management user interface 660 includes a second filter affordance 664C for displaying (e.g., filtering the existing recordings to show) representations of all of the existing ECG recordings corresponding to a "Atrial Fibrillation" result (e.g., representation 662C). In some examples, ECG management user interface 660 includes a third filter affordance 664D for displaying (e.g., filtering the existing recordings to show) representations of all of the existing ECG recordings corresponding to both a "Atrial Fibrillation" result and a "high heart rate" (e.g., a heart rate over 150 BPM) result. In some examples, ECG management user interface 660 includes a fourth filter affordance 664E for displaying (e.g., filtering the existing recordings to show) representations of all of the existing ECG recordings corresponding to both a "high heart rate" (e.g., a heart rate over 150 BPM) result and a "low heart rate" (e.g., a heart rate below 50 BPM) result. In some examples, ECG management user interface 660 includes a fifth filter affordance 664F for displaying (e.g., filtering the existing recordings to show) representations of all of the existing ECG recordings corresponding to a "high heart rate" (e.g., a heart rate over 150 BPM) result. In some examples, ECG management user interface 660 includes a sixth filter affordance 664G for displaying (e.g., filtering the existing recordings to show) representations of all of the existing ECG recordings corresponding to a "low heart rate" (e.g., a heart rate below 50 BPM) result. In some examples, ECG management user interface 660 includes a seventh filter affordance 664H for displaying (e.g., filtering the existing recordings to show) representations of all of the existing ECG recordings corresponding to an "inconclusive" result (e.g., because the measured heart rate was too high or too low to determine an evaluation result, because the captured ECG information was incomplete and/or unreadable to determine an evaluation result).

In FIG. 6AB, while displaying ECG management user interface 660 on display 602, first electronic device 600A detects (e.g., via a touch input) a user selection 627 of representation 662A (corresponding to a "regular" result, with a heart rate measurement of 74 BPM and an indication of 2 symptoms selected for the result). In response to detecting user selection 627, first electronic device 600A displays, on display 602 (e.g., replaces display of ECG management user interface 660 with), a details page 666 corresponding to the selected evaluation result, as shown in FIG. 6AC.

In some embodiments, a details page includes one or more descriptive items (e.g., a tachogram, a type of evaluation result, a measured BPM of the result, a presence of lack of presence of Atrial Fibrillation, one or more selected symptoms) associated with the selected evaluation result. Details page 666 corresponds to the evaluation result of representation 662A (from FIG. 6AB), which is a "regular" result. In some examples, details page 666 includes an animation 668A that graphically depicts the recording of this regular result (e.g. a tachogram representing the measured heart rhythm and heart rate data), an indication 668B that indicates the determined evaluation result of the recording (a "regular" result), an indication 668C that indicates whether one or more specific medical characteristics (e.g., Atrial Fibrillation) was determined from the ECG recording (e.g., "This recording did not show signs of Atrial Fibrillation"), and an indication 668D that indicates (or lists) the user-specified symptoms associated with the ECG recording (e.g., "chest pain" and "shortness of breath").

In some embodiments, a details page (e.g., details page 666) includes an information affordance 670 which causes display of a text description explaining general medical characteristics of the corresponding evaluation result. In some examples, the text description corresponds to the full text description displayed in an expanded text region of possible results page 618 of the tutorial, as described above with reference to FIGS. 6H-6N.

In some embodiments, a details page (e.g., details page 666) includes a share affordance 672 for sharing a document (e.g., a PDF document) summarizing the corresponding ECG recording with an indicated external source (e.g., transmitting the document to an email account). An exemplary document generated for transmittal to the indicated external source is shown in FIG. 6AD. In some embodiments, in response to detecting a user selection of share affordance 672, first electronic device 600A generates the document and enables the user to input an intended recipient (e.g., an email account) for (automatic) transmittal of the generated document to the intended recipient.

In some embodiments, a details page (e.g., details page 666) includes an emergency contact affordance 674 (e.g., for seeking immediate medical care, for contacting 911). In some embodiments, in response to detecting a user selection of emergency contact affordance 674, first electronic device 600A initiates a phone call to an emergency contact (e.g., 911).

In some embodiments, a details page (e.g., details page 666) includes a metadata list 676 indicating one or more information items related to the ECG recording (e.g., the device used to perform the recording, the time of the recording, an operating system of the device used to perform the recording).

In some embodiments, a details page (e.g., details page 666) includes a delete affordance 678 for deleting the ECG recording (e.g., from local storage on first electronic device 600A, from local storage on the second electronic device used to perform the recording, such as second electronic device 600B, from remote storage on an external server).

FIG. 6AD illustrates a document 680 (e.g., a PDF document) generated in response to detecting a user selection of share affordance 672 from details page 666. In some examples, document 680 includes basic user information 682 (e.g., name of the user, date of birth of the user). In some examples, document 680 includes an evaluation result 684 of the ECG recording (e.g., a "regular" result, an "Atrial Fibrillation" result, a "high or low heart rate" result, an "inconclusive" result). In some examples, document 680 includes a heart rate measurement 686 of the ECG recording (e.g., in BPM). In some examples, document 680 includes a time 694 of the ECG recording. In some examples, document 680 includes a list of symptoms 688 selected by the user for the ECG recording. In some examples, document 680 includes a tachogram 690 of the ECG recording (e.g., an unfiltered, full tachogram). In some examples, document 680 includes legend information 692 describing tachogram 690.

In some embodiments, first electronic device 600A can enable and disable (e.g., via the health application and/or the paired device application described with reference to FIG. 6A) ECG recording functionality on second electronic device 600B. In some embodiments, when the ECG application is launched on second electronic device 600B while ECG recording functionality is disabled (by first electronic device 600A), second electronic device 600B displays, on display 634, an error notification user interface 637 indicating to the user (e.g., via text stating "The ECG application has been remotely disabled") that an ECG recording cannot be performed because ECG recording functionality has been disabled (by first electronic device 600A), as shown in FIG. 6AE.

FIGS. 7A-7C are a flow diagram illustrating a method for initial setup of heath monitoring, in accordance with some embodiments. Method 700 is performed at a first electronic device (e.g., 100, 300, 500, 600A) with a display and one or more input devices (e.g., a biometric sensor, a touch layer of the display), where the first electronic device is paired with a second electronic device (e.g., 600B). Some operations in method 700 are, optionally, combined, the orders of some operations are, optionally, changed, and some operations are, optionally, omitted.

As described below, method 700 provides an intuitive way for managing health monitoring. The method reduces the cognitive burden on a user for managing health monitoring, thereby creating a more efficient human-machine interface. For battery-operated computing devices, enabling a user to manage health monitoring faster and more efficiently conserves power and increases the time between battery charges.

The first electronic device (e.g., 600A) displays (706), on the display (e.g., 602), a first portion of a tutorial (e.g., 614, 616, 618, 630, 632) for using a function (e.g., measuring heart rhythm information (an electrocardiogram) or heart rate information (BPM)) of the second electronic device (e.g., 600B) (e.g., a function performed using one or more biometric sensors of the second electronic device). Displaying the first portion of the tutorial for using the function of the second electronic device reduces the number of inputs needed by the user to initialize the first electronic device (e.g., 600A) and the second electronic device (e.g., 600B) for using the function by providing guidance on how to successfully complete the initialization process and providing important background information about using the function (e.g., without forcing the user to, without any guidance, test the function in order to learn how to use the function). Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, prior to displaying, on the display (e.g., 602), the first portion of the tutorial (e.g., 614, 616, 618, 630, 632) for using the function of the second electronic device (e.g., 600B), the first electronic device (e.g., 600A) receives (702) (e.g., via a wireless communication radio of the first electronic device), from the second electronic device (e.g., 600B), a second indication that an application configured to control the use of the function on the second electronic device (e.g., 600B) is opened (e.g., launched, initiated) on the second electronic device (e.g., 600B). Displaying the second indication that the application configured to control the use of the function on the second device (e.g., 600B) is opened provides the user with feedback about the current state of the second electronic device and visually indicates to the user that the second electronic device is ready for the operation that uses the function. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in response to receiving the second indication that the application configured to control the use of the function on the second electronic device (e.g., 600B) is opened, the first electronic device (e.g., 600A) displays (704), on the display (e.g., 602), a notification (e.g., 612) corresponding to the tutorial for using the function of the second electronic device. Displaying, on the display (e.g., 602), the notification corresponding to the tutorial for using the function of the second electronic device provides the user with feedback about the current state of the second electronic device and visually indicates to the user a tutorial is available on the first electronic device (e.g., 600A) to proceed with configuring the use of the function on the second electronic device. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the notification (e.g., 612) informs the user that the application has launched on the second electronic device (e.g., 600B) and that the user can view the tutorial for using the function of the second electronic device (e.g., 600B) that relates to the launched application. In some embodiments, the first electronic device (e.g., 600A) displays, on the display (e.g., 602), the tutorial in response to detecting user selection (e.g., a tap gesture) of the notification (e.g., 612). Displaying, on the display (e.g., 602), the tutorial in response to detecting the user selection of the notification (e.g., 612) improves visual feedback by indicating to the user that the tutorial corresponding to the displayed notification has launched on the first electronic device (e.g., 600A). Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first electronic device (e.g., 600A) displays the first portion of the tutorial (e.g., 614, 616, 618, 630, 632) in response to an input received while displaying a user interface (e.g., 643) configured to modify one or more settings of the second electronic device (e.g., 600B). Displaying the first portion of the tutorial in response to an input received while displaying a user interface configured to modify one or more settings of the second electronic device improves visual feedback by indicating to the user that the displayed tutorial is associated with an application that can be used on the second electronic device. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

The first electronic device (e.g., 600A) detects (708), via the one or more input devices, a request to proceed with the tutorial (e.g., a user's tap input on one or more "continue" buttons, 614C, 616C, 628, 630B).

In response to detecting the request to proceed with the tutorial, the first electronic device (e.g., 600A) displays (710), on the display (e.g., 602), instructions to perform an operation (e.g., capturing/recording biometric data) on the second electronic device (e.g., 600B) that involves the function of the second electronic device (e.g., 600B). Displaying, on the display (e.g., 602) of the first electronic device (e.g., 600A), instructions to perform the operation on the second electronic device (e.g., 600B) that involves the function of the second electronic device improves visual feedback to the user indicating that the operation corresponding to the tutorial needs to be performed on the second electronic device (e.g., and not on the first electronic device). Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the operation on the second electronic device (e.g., 600B) includes capturing biometric data (e.g., using a biometric sensor of the second electronic device). In some embodiments, the biometric data that is captured by the second electronic device (e.g., 600b) is heart-related data (e.g., ECG data, BPM data).

In some embodiments, the first portion of the tutorial includes a plurality of graphical indications of possible results (e.g., 620, 622, 624, 626, heart rhythm evaluation results, heart rate measurements) of the operation (e.g., an ECG recording operation, a BPM measurement operation) performed on the second electronic device (e.g., 600b).

In some embodiments, the operation is evaluating a medical characteristic (of the user) including a heart rhythm evaluation (e.g., an electrocardiogram reading) and a heart rate evaluation (e.g., a BPM reading), and the possible results are selected from the group consisting of: a normal result (e.g., for the heart rhythm evaluation and/or for the heart rate evaluation), an abnormal heart rhythm pattern result (e.g., signs of Atrial Fibrillation), an abnormal heart rate result (e.g., BPM above a high threshold or below a low threshold, such as BPM over 150 or BPM below 50), and an inconclusive result (e.g., based on a poor reading).

In some embodiments, while displaying at least a first possible result (e.g., 624) of the possible results, where the first possible result includes a portion of (the text of) a first result summary (e.g., 624B, text summarizing medical characteristics related to the respective result), the first electronics device (e.g., 600A) detects, via the one or more input devices, a user activation of an expand affordance (e.g., 624C) associated with the first result summary. Providing the expand affordance while displaying at least the first possible result of the possible results, where the first possible result includes the portion of the first result summary improves visual feedback by indicating to the user that only a portion of the first result summary is not currently displayed, and that the expand affordance can be selected to cause all of the first result summary to be displayed. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, in response to detecting the user activation of the expand affordance (e.g., 624C), the first electronic device (e.g., 600A) displays, on the display (e.g., 602), all of (the text of) the first result summary.

In some embodiments, the plurality of graphical indications of possible results (e.g., 620, 622, 624, 626) include a first graphical indication (e.g., 620) that includes display of a first animation (e.g., 620A) related to a first possible result and a second graphical indication (e.g., 622) that includes a second animation (e.g., 622A) related to a second possible result, and the first animation and the second animation are synchronized. In some embodiments, the first animation and the second animations are dynamic animations that include a beating heart animation and tachogram-like features that depict a rhythm and rate of a heartbeat.

In some embodiments, while displaying, on the display (e.g., 602), the plurality of graphical indications (e.g., 620, 622, 624, 626) of possible results, the first electronic device (e.g., 600A) detects, via the one or more input devices, a scrolling gesture (e.g., a scroll on the touch layer of the display). In some embodiments, in response to detecting the scrolling gesture, the first electronic device (e.g., 600A) scrolls the plurality of graphical indications (e.g., 620, 622, 624, 626). In some embodiments, the first electronic device (e.g., 600A) displays, on the display (e.g., 602), a third graphical indication (e.g., 624) that includes a third animation (e.g., 624A) related to a third possible result, where the third animation is synchronized with the first animation (e.g., 620A) and the second animation (e.g., 622A).

In some embodiments, the first animation (e.g., 620A) includes a first portion of the animation (e.g., beating heart) that is animated at a fixed location and a second portion of the animation (e.g., dot) that animatedly moves from the fixed location to a second location. In some embodiments, the object follows a tachogram-like pattern when leaving the heart-shaped animation. In some embodiments, a first object of the first dynamic animation and a second object of the second dynamic animation repeatedly (continuously) leave their respective heart-shaped animations synchronously. Providing an animation (e.g., first animation 620A) for a graphical indication (e.g., one of 620, 622, 624, 626) of possible results improves visual feedback by indicating to the user that the operation discussed by the tutorial relates to heart monitoring, as shown in the animation, and providing visual guidance as to how each possible result derived from the heart monitoring operation differ. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first portion of the tutorial (e.g., 614, 616, 618, 630, 632) includes a limitations indication (e.g., 630, explaining to the user the limits of the operation, showing a list of medical characteristics that cannot be determined by the operation) that includes one or more medical characteristics that cannot be derived from the operation. Providing the limitations indication (e.g., 630) in the first portion of the tutorial improves visual feedback by visually indicating to the user, during the setup process (such that the user is more likely to be made aware), the one or more medical characteristics that cannot be derived from the operation. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

The first electronic device 600A receives (716) (e.g., after the user has carried out the instructions on the second electronic device (e.g., 600B), via a wireless radio communication between the devices), from the second electronic device (e.g., 600B), an indication that the instructions have been carried out (on the second electronic device).

In some embodiments, prior to receiving (e.g., via a wireless radio communication between the devices), from the second electronic device (e.g., 600B), the indication that the instructions have been carried out, the first electronic device (e.g., 600A) receives (712), from the second electronic device (e.g., 600B) (e.g., via the wireless radio communication between the devices), an indication that the instructions have begun to be carried out (on the second electronic device). In some embodiments, in response to receiving the indication that the instructions have begun to be carried out, the first electronic device (e.g., 600A) displays (714), on the display (e.g., 602), an indication (e.g., 820, a "recording in progress" page of the tutorial) that the instructions are being carried out on the second electronic device. Displaying, on the display (e.g., 602), the indication that the instructions are being carried out on the second electronic device (e.g., 600B) in response to receiving the indication that the instructions have begun to be carried out enhances visual feedback by visually indicating to the user that the operation is being successfully carried out on the second electronic device (and thus that the setup process is proceeding along as intended). Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In response to receiving the indication that the instructions have been carried out, the first electronic device (e.g., 600A) displays (718), on the display (e.g., 602), a second portion of the tutorial (e.g., 828, a "completion" page) that is different from the first portion. Displaying, on the display (e.g., 602), the second portion of the tutorial that is different from the first portion in response to receiving the indication that the instructions have been carried out improves visual feedback by indicating to the user that the operation performed on the second electronic device has been completed (e.g., and thus that the setup process has been successfully completed and that the operation is available for future use). Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the second portion of the tutorial (e.g., 828, a "completion" page) includes a graphical animation (e.g., a tachogram-like animation) that represents (biometric) information obtained from the operation on the second electronic device.

In some embodiments, after displaying, on the display (e.g., 602), the second portion of the tutorial (e.g., 828), the first electronic device (e.g., 600A) displays (720), on the display (e.g., 602), a user interface of a health application (e.g., 650, 656, 660).

In some embodiments, the first electronic device (e.g., 600A) detects (722), via the one or more input devices, a user activation of an affordance (e.g., 658A, an ECG affordance) for viewing recorded biometric information (e.g., recorded ECG and BPM readings). In some embodiments, the affordance (e.g., 658A) for viewing existing recordings of biometric information includes an indication of a number of existing recordings of biometric information (e.g., a number of recorded ECG and/or BPM readings). Providing the indication of the number of existing recordings of biometric information in the affordance for viewing existing recordings of biometric information improves visual feedback by conveniently conveying to the user the number of existing recordings that can be viewed in the health application. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in response to detecting the user activation of the affordance (e.g., 658A) for viewing existing recordings of biometric information, the first electronic device (e.g., 600A) displays (724), on the display (e.g., 602), a first plurality of representations (e.g., 662A-662C) corresponding to existing recordings of biometric information. In some embodiments, a representation of an existing recording of biometric information (e.g., 662A-66C) includes a tachogram corresponding to the recording, an evaluation result of the recording, the number of symptoms (if any) associated with the recording, and a heart rate (BPM) recorded by the recording. Displaying, on the display (e.g., 602), the first plurality of representations (e.g., 662A-662C) corresponding to existing recordings of biometric information in response to detecting the user activation of the affordance for viewing existing recordings of biometric information improves visual feedback by conveniently providing to the user representations of some existing recordings (e.g., some of the most recent recordings) that may be of most relevance to the user. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first plurality of representations of existing recordings of biometric information (e.g., 662A-66C) include a first representation (e.g., 662C) corresponding to a first existing recording with an abnormal evaluation result (e.g., an abnormal heart rhythm, such as a Atrial Fibrillation condition), where the first representation (e.g., 662C) includes an indication of the abnormal evaluation result that is displayed with a first visual characteristic (e.g., highlighted with a warning color, such as yellow). In some embodiments, the plurality of representations of existing recordings of biometric information (e.g., 662A-66C) include a fourth representation (e.g., 662A) corresponding to a fourth existing recording with a normal evaluation result, and the fourth representation includes an indication of the normal evaluation result that is displayed with a second visual characteristic (e.g., a default color) different from the first visual characteristic.

In some embodiments, the first plurality of representations of existing recordings of biometric information (e.g., 662A-66C) include a second representation (e.g., 662A, 662B) corresponding to a second existing recording associated with user-specified symptoms, where the second representation includes an indication of the number of user-specified symptoms associated with the second existing recording (e.g., "2 Symptoms," "No Symptoms"). In some embodiments, the first plurality of representations of existing recordings of biometric information (e.g., 662A-66C) include a third representation (e.g., 662C) corresponding to a third existing recording not associated with any user-specified symptoms (e.g., because the user did not specify any symptoms for the recording), where the third representation does not include an indication of user-specified symptoms associated with the third existing recording. Providing the second representation (e.g., 662A, 662B) corresponding to the second existing recording associated with user-specified symptoms improves visual feedback by conveniently indicating to the user whether or not (and if yes, how many) symptoms were previously selected by the user for the recording (e.g., thereby allowing the user to quickly recognize whether a particular recording by correspond to a more serious reading, if there are many user-specified symptoms associated with the recording). Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the user-specified symptoms cannot be modified after the symptoms have been specified and saved (by the user on the second electronic device).

In some embodiments, further in response to detecting the user activation of the affordance (e.g., 658A) for viewing recorded biometric information, the first electronic device (e.g., 600A) displays (726), on the display (e.g., 602), a plurality of sort affordances (e.g., 664A-664H, to filter visible recordings by the type of evaluation results, such as normal results, abnormal heart rhythm results, or abnormal heart rate results) including a first sort affordance and a second sort affordance. In some embodiments, the first sort affordance includes an indication of a number of existing recordings of biometric information associated with the first type of evaluation result, and the second sort affordance includes an indication of a number of existing recordings of biometric information associated with the second type of evaluation result. In some embodiments, the first electronic device (e.g., 600A) detects (728), via the one or more input devices, a user activation of the first sort affordance.

In some embodiments, in response to detecting the user activation of the first sort affordance, the first electronic device (e.g., 600A) displays (730), on the display (e.g., 602), a second plurality of representations (e.g., by replacing the first plurality of representations) corresponding to existing recordings of biometric information, where the second plurality of representations correspond to existing recordings associated with a first type of evaluation result (e.g., a normal result, an abnormal heart rhythm result, an abnormal heart rate result, an inconclusive result). In some embodiments, the first electronic device (e.g., 600A) detects (732), via the one or more input devices, a user activation of the second sort affordance.

In some embodiments, in response to detecting user activation of the second sort affordance, the first electronic device (e.g., 600A) displays (734), on the display (e.g., 602), a third plurality of representations (e.g., by replacing the first plurality of representations) corresponding to existing recordings of biometric information, where the third plurality of representations correspond to existing recordings associated with a second type of evaluation result. In some embodiments, the second and third plurality of representations have corresponding overlapping existing recordings, if one or more existing recordings are associated with both the first type of evaluation result and the second type of evaluation result.

In some embodiments, the first electronic device (e.g., 600A) detects, via the one or more input devices, a user selection of a first representation (e.g., 662A) of the first plurality of representations (e.g., 662A-66C) corresponding to a first existing recording corresponding to a first evaluation result. In some embodiments, in response to detecting the user selection of the first representation, the first electronic device (e.g., 600A) displays a first details view (e.g., 666) of the first existing recording.

In some embodiments, while displaying the first details view (e.g., 666) of the first existing recording, the first electronic device (e.g., 600A) detects, via the one or more input devices, a user activation of an information affordance (e.g., 670, an "i" icon). In some embodiments, in response to detecting the user activation of the information affordance (e.g., 670), the first electronic device (e.g., 600A) displays, on the display (e.g., 602), a result summary (e.g., text summarizing medical characteristics related to the respective result) and an animation from a corresponding possible result from the first portion of the tutorial (e.g., where the possible result from the tutorial corresponds to the evaluation result of the first existing recording).

In some embodiments, while displaying the first details view (e.g., 666) of the first existing recording corresponding to a first evaluation result, the first electronic device (e.g., 600A) detects, via the one or more input devices, a user activation of an export affordance (e.g., 672, marked as "share as a PDF"). In some embodiments, in response to detecting user activation of the export affordance (e.g., 672), the first electronic device (e.g., 600A) creates (and subsequently transmitting to an intended recipient) a document that includes information concerning the first existing recording (e.g., information about the user, date and time of the recording, a tachogram of the (ECG) recording, the evaluation result of the recording). In some embodiments, the biometric data (e.g., ECG data) of the recording is included in the document without any filtering (of the data from the recording). (Automatically) generating and (automatically) transmitting the document (to an intended recipient) in response to detecting the user activation of the information affordance reduces the number of inputs needed from the user to create a transmittal document summarized a recording and subsequently transmitting the document to an intended recipient. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the user-specified symptoms cannot be modified after the symptoms have been specified and saved (by the user on the second electronic device).

Note that details of the processes described above with respect to method 700 (e.g., FIGS. 7A-7C) are also applicable in an analogous manner to the methods described below. For example, method 900 optionally includes one or more of the characteristics of the various methods described above with reference to method 700. For another example, method 1100 optionally includes one or more of the characteristics of the various methods described above with reference to method 700. For another example, method 1300 optionally includes one or more of the characteristics of the various methods described above with reference to method 700. For another example, method 1500 optionally includes one or more of the characteristics of the various methods described above with reference to method 700. For brevity, these details are not repeated below.

FIGS. 8A-8S illustrate exemplary user interfaces for recording biometric information for use in health monitoring. The user interfaces in these figures are used to illustrate the processes described below, including the processes in FIGS. 9A-9B. The exemplary user interfaces in these figures relate generally to monitoring health using recorded biometric information, and are not limited to a specific type of biometric information. Only for the sake of convenience, the exemplary user interfaces in these figures are described with reference to a type of biometric information-electrocardiogram (hereinafter "ECG") information.

FIG. 8A illustrates a first electronic device 800A (e.g., corresponding to second electronic device 600B). In some embodiments, first electronic device 800A is a smartwatch. In some embodiments, first electronic device 800A has a display 802 and one or more input devices (e.g., including a touch layer of display 802 and one or more mechanical buttons, such as a rotating crown). In some embodiments, first electronic device 800A includes one or more biometric sensors (e.g., for recording ECG information, for detecting heart rhythm and heart rate of the user) comprising one or more electrodes integrated in an input device 804 (e.g., a mechanical input device, such as a depressible, rotating crown) of first electronic device 800A. In some embodiments, the one or more biometric sensors of first electronic device 800A further comprise one or more electrodes of (e.g., integrated in) a housing portion (e.g., the backplate) of first electronic device 800A, where the one or more electrodes integrated in the input device operate in conjunction with the one or more electrodes of the housing portion to capture biometric information (e.g., ECG information). Features concerning the one or more biometric sensors of first electronic device 800A used to capture biometric information (e.g., ECG information) is described in greater detail in Appendix A.

FIG. 8A illustrates first electronic device 800A displaying, on display 802, a user interface 806 of an ECG application (e.g., corresponding to user interface 644 of the ECG application described with reference to FIGS. 6A-6AE).

In some embodiments, similar to user interface 644, user interface 806 includes an animation 808 (e.g., a fluid animation, corresponding to animation 646 of user interface 644) that depicts a particular shape (e.g., a heart). In some examples, as shown in FIG. 8A, animation 808 comprises a plurality of dynamic objects (e.g., circular objects) that form the particular shape (e.g., a heart), where the shape appears three-dimensional and is visually fluid as the plurality of dynamic objects constantly move while maintaining the structure of the shape.

In some embodiments, while displaying animation 808 in the particular shape (e.g., a heart), user interface 806 displays a notification message 810 (e.g., corresponding to notification message 648 of user interface 644) indicating to the user that an action must be performed (by the user) on the device to proceed with an ECG recording (to capture heart rhythm and heart rate information). In some embodiments, notification message 810 instructs the user of the type of input (e.g., a touch or contact on the input device that is below a threshold amount such that the input does not "click" the input device) and that the input must be maintained on the input device (e.g., for the duration of the recording).

In some embodiments, prior to displaying user interface 806 of the ECG application (e.g., while first electronic device 800A is displaying a user interface of a different application or the display is off), the device detects (e.g., using a second biometric sensor that measures heart rate information without user input) heart rate information of the user for a period of time (e.g., 1 minute) and determines that the detected heart rate is above a threshold rate (e.g., above 150 BPM). In some embodiments, upon detecting that the detected heart rate is above the threshold rate for at least the period of time, the device displays, on display 802, a notification informing the user of the (continuous) high heart rate and requests that the user monitor his or her heart health using the ECG application.

Figure 8B:
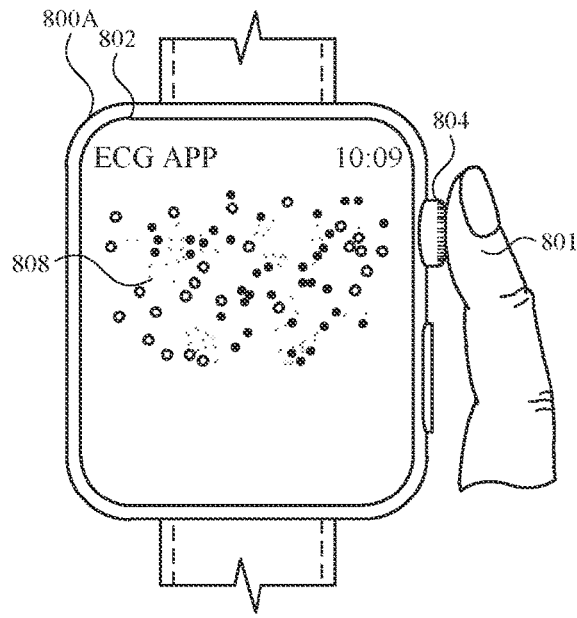

In FIG. 8B, while displaying, on display 802, user interface 806 of the ECG application, first electronic device 800A detects a user input 801 on input device 804 in accordance with the instructions from notification message 810. In some embodiments, user input 801 is a continuous touch or contact on the input device that is below a threshold amount (e.g., an input that does not "click" the input device). In some embodiments, upon detecting (and continuing to detect) user input 801 on input device 804, the plurality of dynamic objects forming animation 808 transition from their initial pattern (e.g., of a shape) towards a different pattern, as shown in FIG. 8B. In some embodiments, upon detecting (and continuing to detect) user input 801, first electronic device 800A ceases to display, on display 802, notification message 810.

Figure 8C:
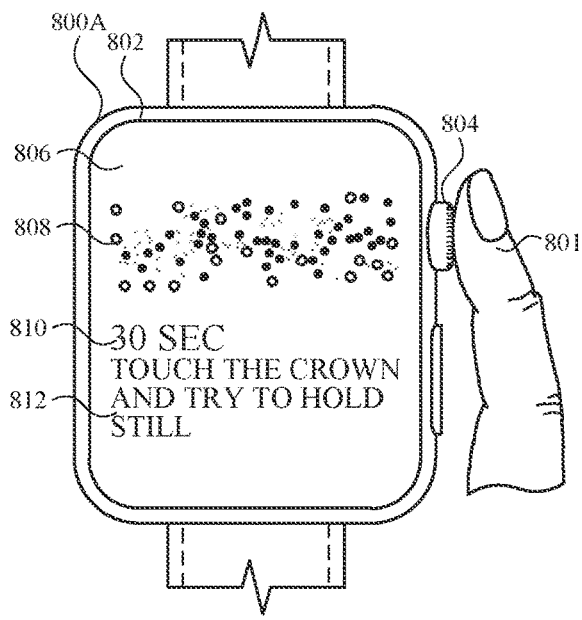

FIG. 8C illustrates first electronic device 800A continuing to detect user input 801 on input device 804. In some embodiments, while continuing to detect user input 801 on input device 804, the plurality of dynamic objects forming animation 808 continue to transition toward and begin to form a different pattern (e.g., a grid of a tachogram). In some embodiments, first electronic device 800A displays, in user interface 806 (e.g., below animation 808), a timer 810 (e.g., a countdown timer of a predetermined amount of time, such as 30 seconds) that indicates the amount of time remaining to complete the ECG recording. In some embodiments, first electronic device 800A displays, in user interface 806 (e.g., below timer 810), a notification message 812 instructing the user to maintain the input on input device 804 (e.g., stating "Touch the crown and try to hold still") to successfully complete the ECG recording.

Figure 8D:
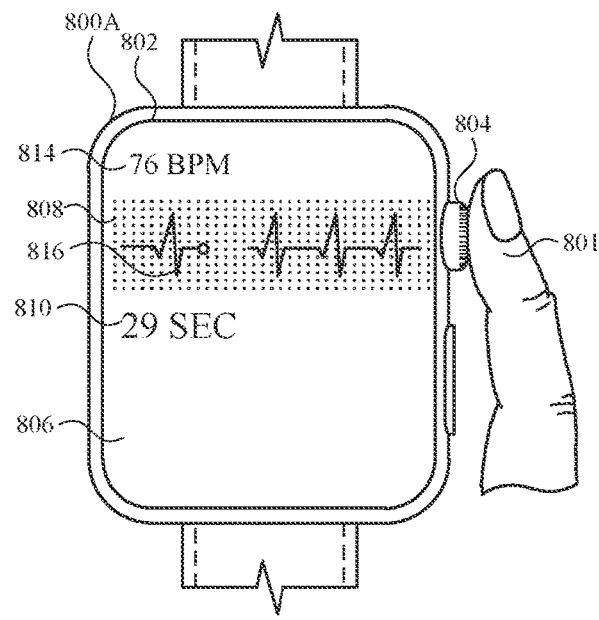

FIG. 8D illustrates first electronic device 800A further continuing to detect user input 801 on input device 804. In some embodiments, as the user continues to maintain user input 801 on input device 804, first electronic device 800A begins recording ECG information. In some embodiments, while recording the ECG information, the device displays, in user interface 806, a BPM indicator 814 showing the heart rate being detected by the recording. In some embodiments, while recording ECG information, the device further displays, over animation 808 (which, during a recording, forms a grid-like pattern), a tachogram 816 that graphically depicts the ongoing recording. In some embodiments, while recording ECG information, timer 810 continuously reflects (e.g., by counting down) the remaining time to successfully complete the recording.

Figure 8E:
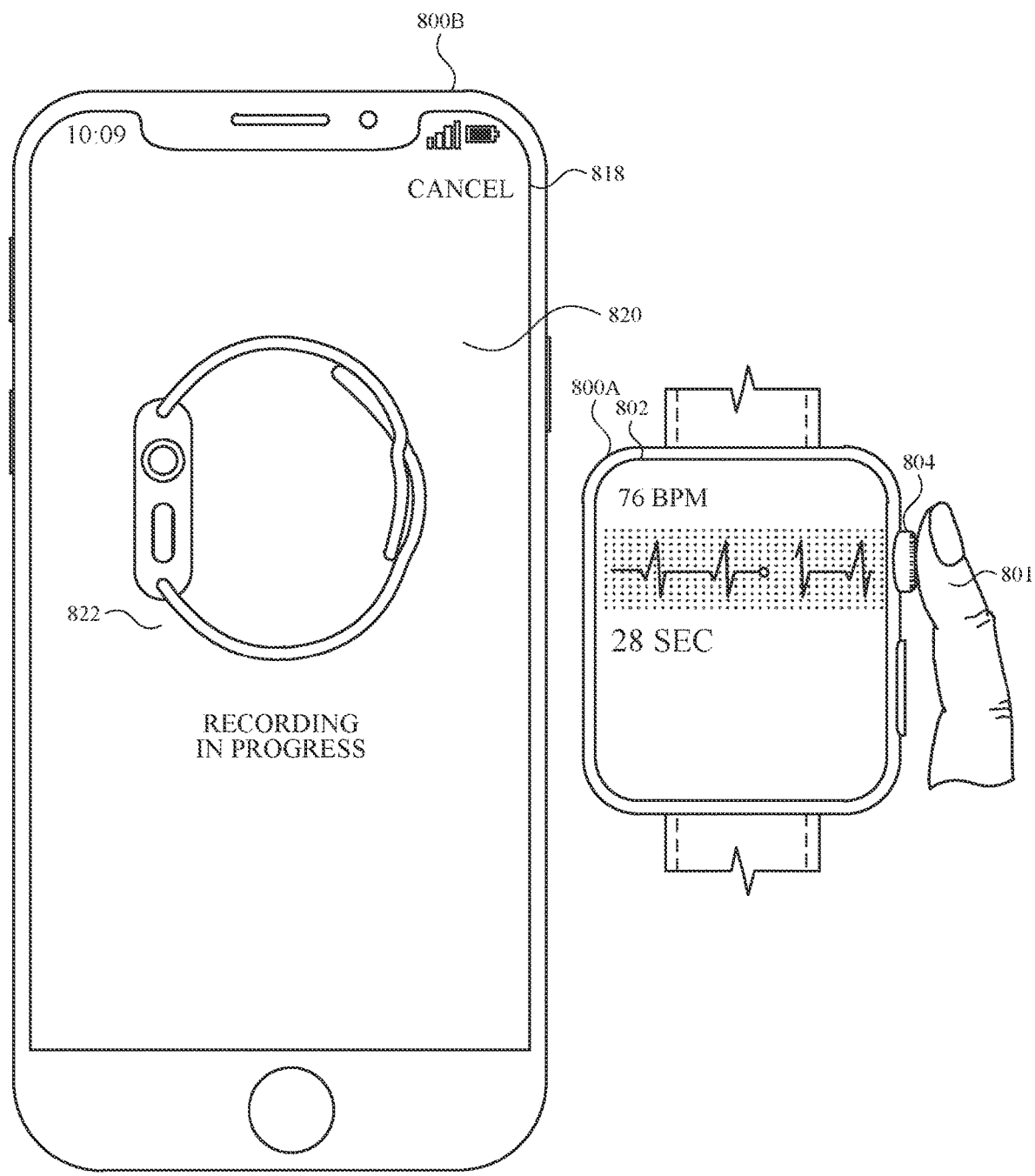

FIG. 8E illustrates a second electronic device 800B (e.g., corresponding to first electronic device 600A described with reference to FIGS. 6A-6AE). In some embodiments, second electronic device 800B is a smartphone that is paired with first electronic device 800A (e.g., via a short-range wireless communication radio connection, such as a Bluetooth connection). In FIG. 8E, second electronic device 800B is displaying, on a display 818, a user interface 820 of a health application that is associated with the ECG application running on first electronic device 800A. In some embodiments, while recording ECG information on first electronic device 800A, second electronic device 800B displays, in user interface 820 of the health application associated with the ECG application, an indication 822 that ECG recording is on-going on first electronic device 800A. In some examples, indication 822 includes a graphical indication portion (e.g., illustrating an image corresponding to the device being used to perform the recording) and a text indication portion (e.g., stating "Recording in Progress").

Figure 8F:
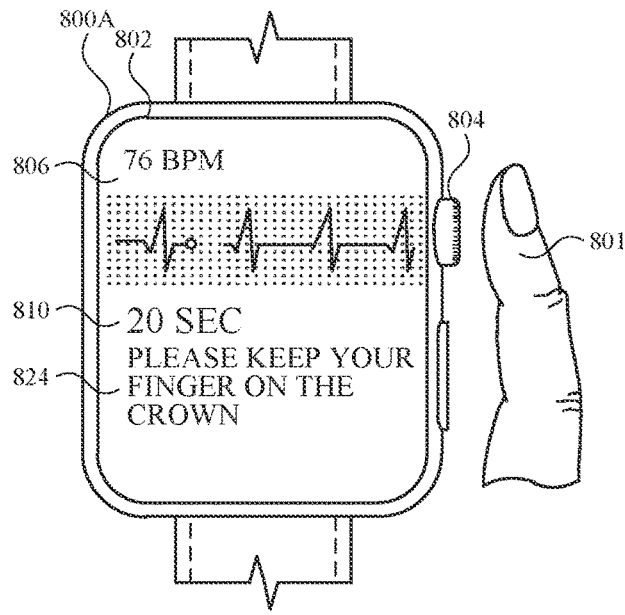

FIG. 8F illustrates first electronic device 800A displaying, on display 802, user interface 806 of the ECG application while the device is continuing to perform the ECG recording from FIG. 8E. In FIG. 8F, during the ECG recording, the device detects that user input 801 on input device 804 is lost (e.g., because the user lifted the finger used for the input away from input device 804). In some embodiments, in response to detecting that the user input on input device 804 is lost, the device displays, in user interface 806, a message indication 824 (e.g., stating "Please keep your finger on the crown") requesting that the user restore the user input on input device 804 in order to continue with the ECG recording. In some embodiments, while the user input is lost on input device 804, the device continues to count down towards the end of the recording (which is indicated by timer 810). In some embodiments, while the user input is lost on input device 804, the device pauses the recording until the user input is restored on input device 804. In some embodiments, in response to detecting that the user input is lost on the input device 804, the first electronic device 800A resets the value of timer 810 (e.g., to the initial 30 seconds value) and restarts the recording if the user input is restored (e.g., restored within a predetermined time).

In some embodiments, if the user input on input device 804 is not restored within a time limit (e.g., 5 seconds), first electronic device 800A (automatically) terminates the recording and transitions back to the initial user interface of FIG. 8A. In some embodiments, if the user input on input device 804 is restored within the time limit (e.g., 5 seconds), the device (automatically) continues the recording (e.g., and re-starts the timer, if paused). In some embodiments, the time limit (e.g., 5 seconds) for restoring the input is reset once the user input is restored. That is, if the user input is lost for a second time during a recording, the device (automatically) terminates the recording and transitions back to the initial user interface of FIG. 8A if the full time limit (e.g., 5 seconds) lapses without the user restoring the user input.

Figure 8G:
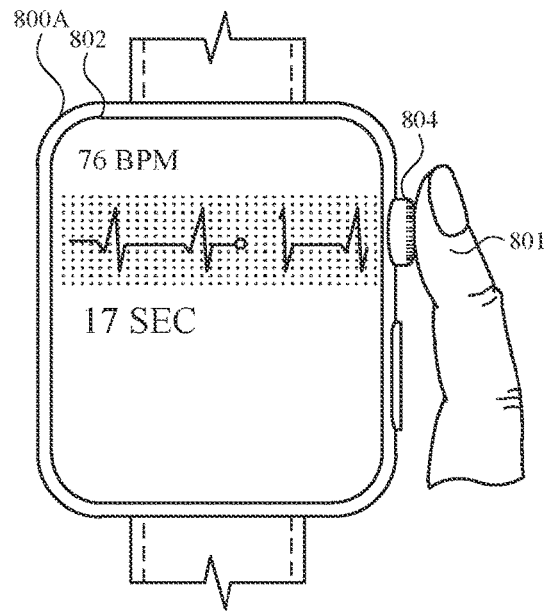

In FIG. 8G, first electronic device 800A again detects user input 801 on input device 804 before the time limit (e.g., 5 seconds) has lapsed from when the user input was lost in FIG. 8F. Because the user input on input device 804 was restored prior to expiration of the time limit (e.g., 5 seconds), the device continues the ECG recording without (automatically) terminating the recording.

Figure 8H:
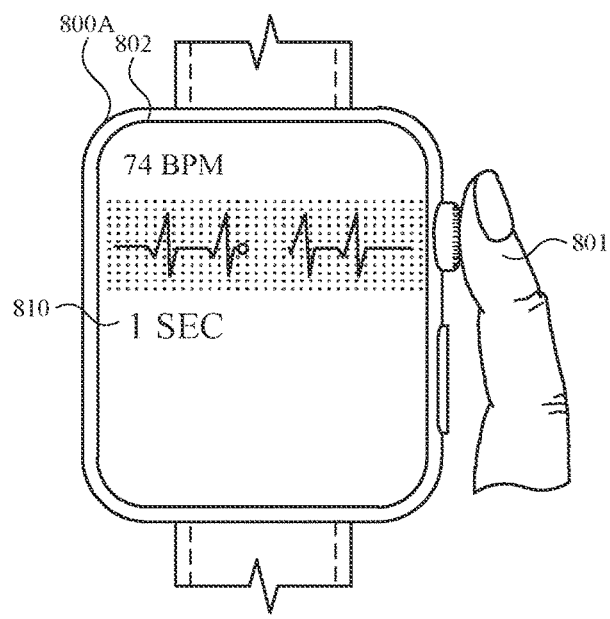

FIG. 8H illustrates first electronic device 800A continuing to detect user input 801 on input device 804 and the device continuing the ECG recording from FIG. 8G. In some embodiments, timer 810 continues to indicate the time remaining to complete the recording (e.g., "1 second").

Figure 8I:
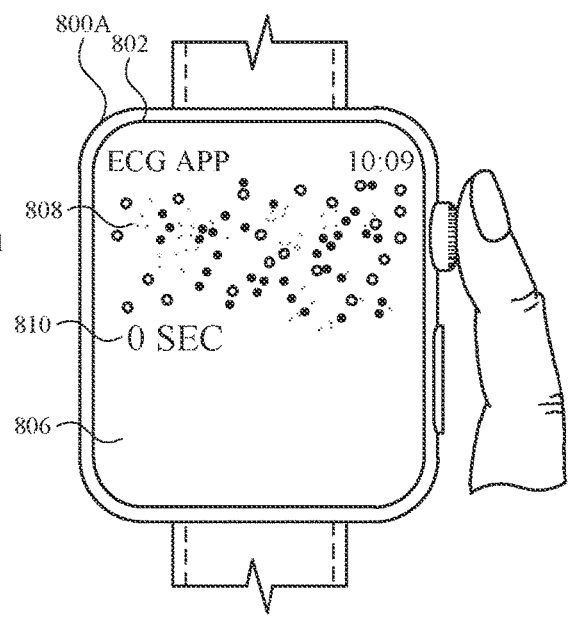

FIG. 8I illustrates user interface 806 of the ECG application upon completion of the recording (which is indicated by timer 810 showing no time remaining). In some embodiments, upon completion of a recording, the plurality of dynamic objects forming animation 808 re-transitions from the grid-like pattern during the recording toward their initial pattern (e.g., of a shape, such as heart) prior to the recording.

Figure 8J:
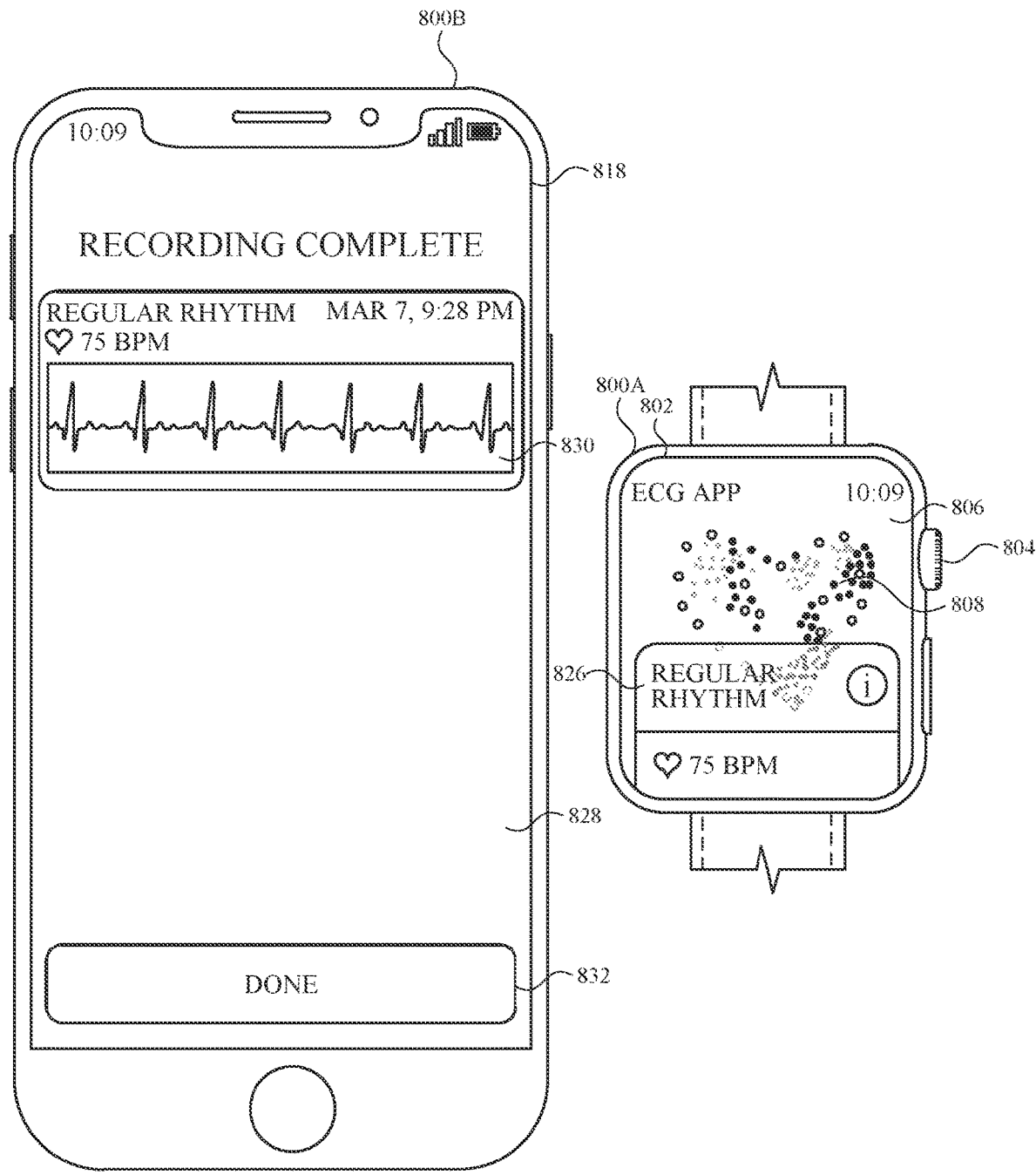

FIG. 8J illustrates first electronic device 800A and second electronic device 800B (immediately) after completing the ECG recording. In some embodiments, upon completing the ECG recording, first electronic device 800A transmits (e.g., via a Bluetooth connection) data of the ECG recording to second electronic device 800B. In some embodiments, upon completing the ECG recording, first electronic device 800A transmits (e.g., via a LTE or WiFi connection) data of the ECG recording to an external server, where the external server is also accessible by second electronic device 800B. In some embodiments, first electronic device 800A can record and locally store a plurality of ECG recordings and transmit the plurality of ECG recordings to second electronic device 800B.

In some embodiments, (immediately) after completing the ECG recording, first electronic device 800A displays, on display 802, user interface 806 of the ECG application with animation 808 in its initial pattern (e.g., a fluid heart-shaped pattern) and at least a portion of a summary page 826 that includes an evaluation result (e.g., "Regular Result") and other related information about the completed recording. In some embodiments, summary page 826 slides onto the display from an edge of the display (e.g., a bottom edge of the display).

In some embodiments, (immediately) after completing the ECG recording, second electronic device 800B displays, in the health application, a summary page 828 of the health application associated with the ECG application on second electronic device 800A, where summary page 828 includes a representation 830 of the completed recording. In some embodiments, representation 830 includes the evaluation result (e.g., "Regular Rhythm"), the heart rate reading (e.g., in BPM), and a graphical depiction (e.g., a tachogram) of the recording. In some embodiments, summary page 828 includes an affordance 832 for leaving the summary page.

Figure 8K:
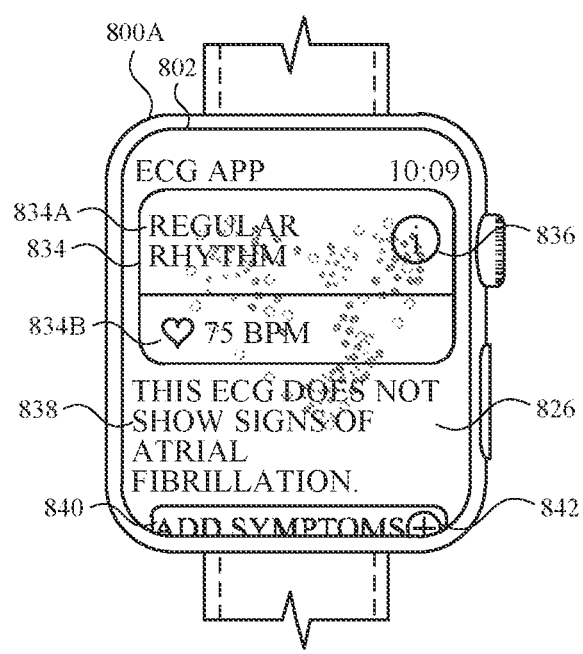

FIG. 8K illustrates first electronic device 800A displaying, on display 802, (at least a portion of) summary page 826 corresponding to the ECG recording. In some embodiments, summary page 826 includes a summary region 834 that includes an indication 834A of the evaluation result (e.g., "Regular Rhythm") and an indication 834B of the heart rate reading (e.g., in BPM). In some embodiments, summary region 834 also includes a information affordance 836 for viewing a detailed description about the respective evaluation result (e.g., where the detailed description corresponds to the text description shown in possible results page 618 of the tutorial described with reference to FIGS. 6A-6AE). In some embodiments, summary page 826 includes an indication 838 of whether a particular medical characteristic (e.g., signs of Atrial Fibrillation, signs of irregular heart rhythm) was determined from the recording. In some embodiments, summary page 826 includes a symptoms region 840 that includes an affordance 842 for associating one or more symptoms to the reading. In some embodiments, while displaying summary page 826, the device maintains display of animation 808 (e.g., in its initial shape as shown in FIG. 8A) in the background of the summary page (e.g., in a lighter shade so that the summary page is easily legible to the user).

Figure 8L:
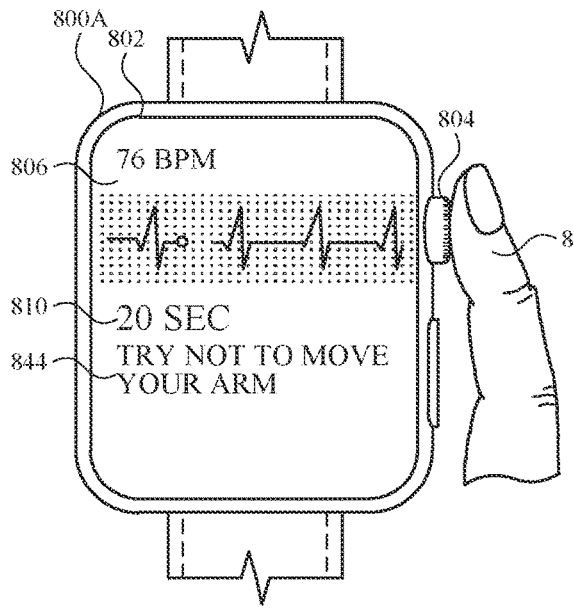

FIGS. 8L-8O illustrate a plurality of different error notification messages that can be displayed in user interface 806 of the ECG application while recording ECG information. In FIG. 8L, while performing a first ECG recording corresponding to a user input 803 on input device 804, first electronic device 800A detects movement of the user input on input device 804 above a threshold amount (e.g., there is movement with the user's contact with input device 804, where the amount of the movement is above a threshold amount of movement). In some embodiments, in response to detecting the movement of the user input on input device 804 above the threshold amount (e.g., for at least a period of time, such as 5 seconds), first electronic device 800A displays (e.g., below timer 810), a notification message 844 (e.g., stating "Try not to move your arm") requesting that the user restrict movement of user input 803 during the recording.

Figure 8M:
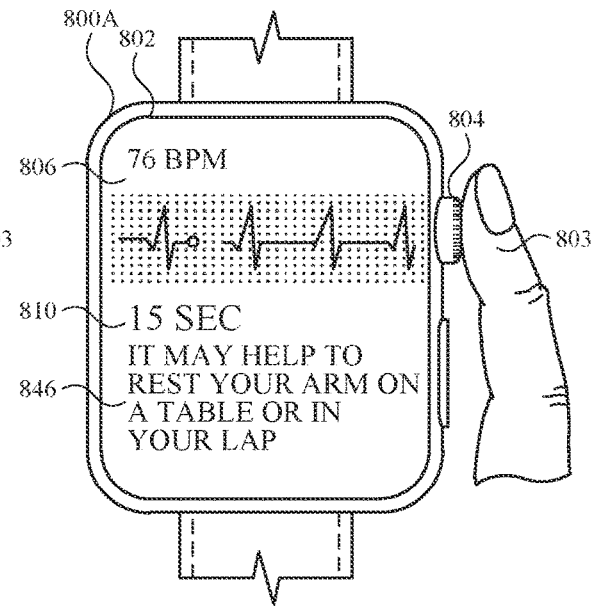

In FIG. 8M, a period of time (e.g., 5 seconds) after displaying notification message 844, and while continuing to perform the first ECG recording corresponding to user input 803 on input device 804, first electronic device 800A continues to detect movement of the user input on input device 804 above the threshold amount. In some embodiments, in response to continuing (e.g., for another period of time, such as 5 seconds, after displaying the initial notification message 844), first electronic device 800A displays (e.g., below timer 810, replaces display of notification message 844 with) a notification message 846 (e.g., stating "It may help to rest your arm on a table or in your lap") indicating that the user could try resting his/her arm on a surface to stabilize the user input on input device 804.

Figure 8N:
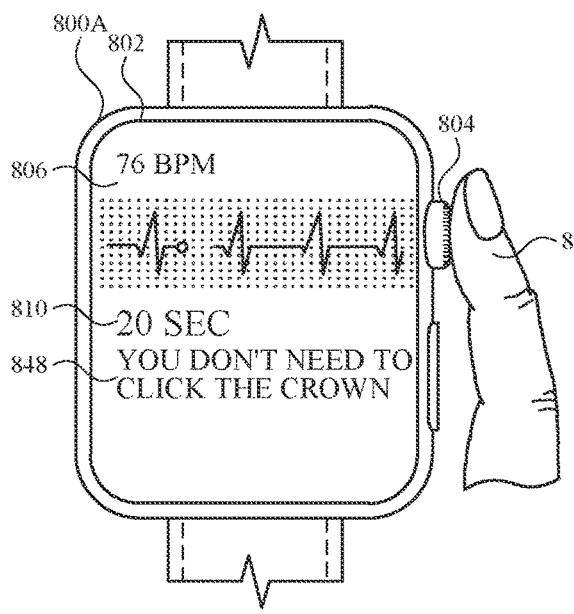

In FIG. 8N, while performing a second ECG recording corresponding to a user input 805 on input device 804, first electronic device 800A detects a press input on input device 804, where the force of the press is above a threshold amount (e.g., such that the user "clicks" input device 804). In some embodiments, in response to detecting the press input on input device 804, first electronic device 800A displays (e.g., below timer 810) a notification message 848 (e.g., stating "You do not need to click the crown") informing the user that input device 804 does not need to be "clicked" to perform the recording, and/or informing the user that less force can be used for the input on input device 804 to successfully complete the recording.

Figure 8O:
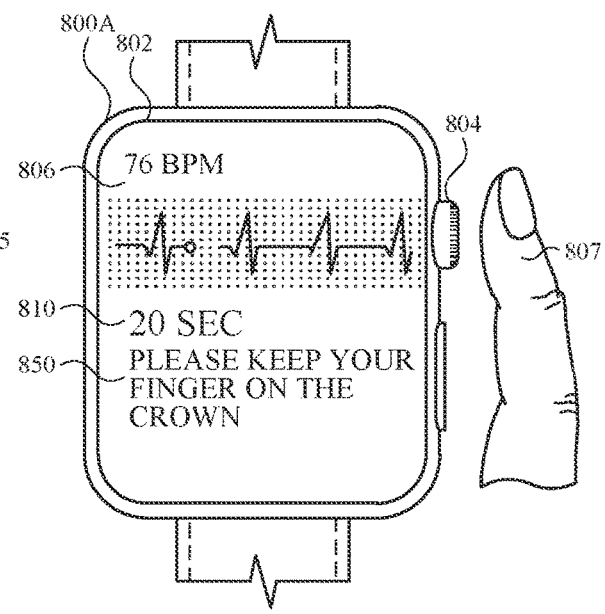

In FIG. 8O, while performing a third ECG recording corresponding to a user input 807 on input device 804, first electronic device 800A detects (e.g., as in FIG. 8F), that user input 807 on input device 804 is lost (e.g., because the user lifted the finger used for the input away from input device 804). In some embodiments, in response to detecting that the user input on (e.g., the user's contact with) input device 804 is lost, first electronic device 800A displays (e.g., below timer 810) a notification message 850 (e.g., corresponding to notification message 824, stating "Please keep your finger on the crown") requesting that the user restore the user input on input device 804 to continue with the ECG recording.

Figure 8P:
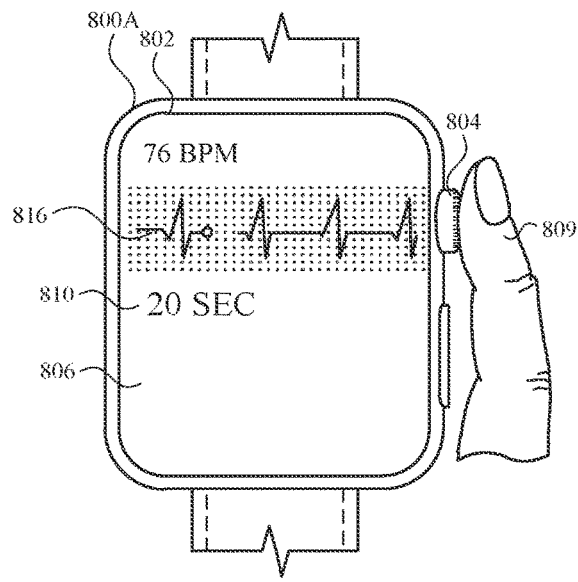

FIG. 8P illustrates first electronic device 800A displaying, on display 802, user interface 806 of the ECG application while performing an ECG recording corresponding to a user input 809 on input device 804 (e.g., after an initial threshold time period (e.g., 5 seconds) has passed from the initiation of the recording). In some embodiments, the required duration of an ECG recording is 30 seconds. As indicated by timer 810 (e.g., showing "20 seconds") in FIG. 8P, 10 seconds have passed since the initiation of the recording. In some embodiments, first electronic device 800A displays a tachogram 816 corresponding to a visual illustration of the ECG recording.

Figure 8Q:
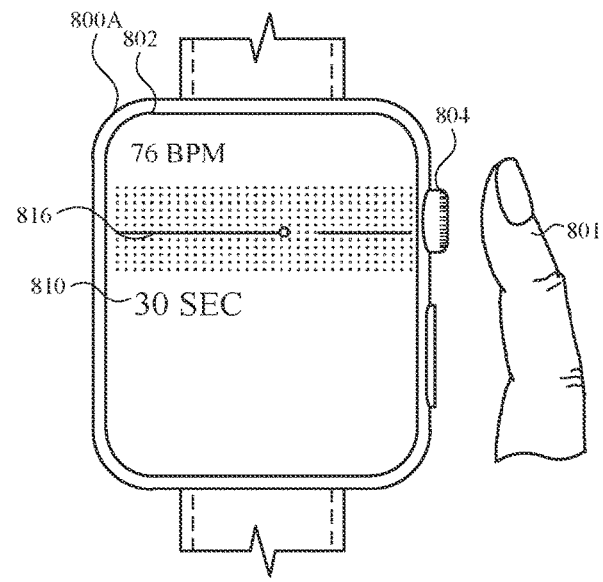

In FIG. 8Q, first electronic device 800A loses detection of user input 809 on input device 804. In some embodiments, in response to (e.g., immediately in response to or within a short period of time, such as 1 second) losing detection of the user input on input device 804, first electronic device 800A resets the ECG recording (e.g., terminates the previous recording and prepares to start a new recording), as indicated by timer 810 (e.g., which now shows "30 seconds," the full duration of a recording. In some embodiments, first electronic device 800A causes the remaining time indicated in timer 810 to "rewind" back to (e.g., count back up to) the initial duration in response to losing detection of the user input on input device 804. In some embodiments, first electronic device 800A causes tachogram 816 to show a "silent" tachogram, thereby further indicating to the user that ECG information is not being captured.

Figure 8R:
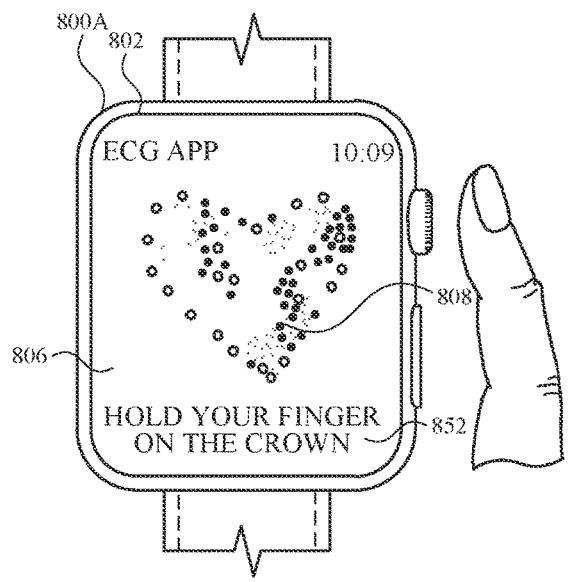

In some embodiments (e.g., after resetting the recording), upon detecting that the user input on input device 804 has not been restored for a at least a predetermined period of time (e.g., 2.5 seconds), first electronic device 800A displays, in user interface 806 of the ECG application, a notification message 852 (e.g., stating "Hold your finger on the crown") requesting that the user restore the input on input device 804, as shown in FIG. 8R. In some embodiments (e.g., in addition to displaying notification message 852), the devices displays (e.g., re-displays) animation 808 in its initial pattern (e.g., a heart shape), as first described with reference to FIG. 8A. In some embodiments, the plurality of dynamic objects forming animation 808 dynamically transition from the grid-like pattern of FIG. 8Q to its initial pattern (e.g., a heart shape) of FIG. 8R.

In some embodiments (e.g., after resetting the recording), upon detecting that the user input on input device 804 has not been restored for at least the predetermined period of time (e.g., 2.5 seconds), first electronic device 800A alternatively displays, in user interface 806 of the ECG application, animation 808 in its initial pattern (e.g., a heart shape) but forgoes displaying notification message 852, as shown in FIG. 8S.

In some embodiments, first electronic device 800A first transitions form the user interface of FIG. 8Q to the user interface of FIG. 8R upon detecting that the user input on input device 804 has not been restored for a first predetermined period of time (e.g., 2.5 seconds), and then transitions from the user interface of FIG. 8R to the user interface of FIG. 8S upon detecting that the user input on input device 804 has not been restored for a second predetermined period of time (e.g., which is the same as or different from the first predetermined period of time) after the first predetermined period of time has passed.

FIGS. 9A-9B are a flow diagram illustrating a method recording biometric information for health monitoring, in accordance with some embodiments. Method 900 is performed at a first electronic device (e.g., 100, 300, 500, 600B, 800A) with a display and one or more input devices including a biometric sensor (e.g., a set of one or more sensors, such as electrodes, configured to measure electrical activity correlated to portions of the heart of a user of the electronic device). Some operations in method 900 are, optionally, combined, the orders of some operations are, optionally, changed, and some operations are, optionally, omitted.

As described below, method 900 provides an intuitive way for managing health monitoring. The method reduces the cognitive burden on a user for managing health monitoring, thereby creating a more efficient human-machine interface. For battery-operated computing devices, enabling a user to manage health monitoring faster and more efficiently conserves power and increases the time between battery charges.

The first electronic device (e.g., 800A) displays (908), on the display (e.g., 802), a first user interface (e.g., of a health monitoring application or a health data measurement application, main user interface 806 of the ECG application, as shown in FIG. 8A) indicating that the first electronic device (e.g., 800A) is ready to detect biometric information (e.g., ECG data, BPM data, heart-related data). Displaying, on the display (e.g., 802), the first user interface indicating that the first electronic device (e.g., 800A) is ready to detect biometric information provides visual feedback by indicating that biometric information is ready to be recorded on the first electronic device. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, prior to displaying the first user interface (e.g., 806 of FIG. 8A), the first electronic device (e.g., 800A) displays (902) a homescreen (e.g., 1012) that includes an application affordance (e.g., 1014) corresponding to a health monitoring application (e.g., for monitoring heart health, such as the ECG application). Displaying, on the display (e.g., 802), the application affordance corresponding to the health monitoring application on the homescreen provides visual feedback by indicating to the user that the health monitoring application can be accessed from the homescreen of the first electronic device (e.g., 800A). Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the first electronic device (e.g., 800A) detects (904), via the one or more input devices, a user activation of the application affordance. In some embodiments, in response to detecting the user activation of the application affordance, the first electronic device (e.g., 800A) displays (906), on the display (e.g., 802), the first user interface (e.g., 806).

In some embodiments, a (text) notification (e.g., 810) requesting the first input on the biometric sensor (e.g., 804) is displayed in the first user interface (e.g., 806 of FIG. 8A) after a predetermined amount of time (e.g., 5 seconds) has passed after detecting the user activation of the application affordance. In some embodiments, the notification (e.g., 810) instructs the user to place a finger on the first input device (e.g., 804). Providing the notification (e.g., 810) requesting the first input on the biometric sensor in the first user interface after the predetermined amount of time has passed after detecting the user activation of the application affordance provides the user with more control of the device by helping the user avoid unintentionally an unintended operation (e.g., by selecting a wrong button or affordance) and simultaneously allowing the user to recognize that the input on the biometric sensor is required to proceed with the recording operation. Providing additional control of the device (without cluttering the user interface with additional displayed controls) enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the recorded biometric information includes an electrocardiogram recording derived from the biometric information detected by the biometric sensor (e.g., 804). In some embodiments, the biometric sensor (e.g., 804) is a contact-based sensor, and the first input with the biometric sensor (e.g., 804) satisfies the first criteria when a contact (e.g., from a finger of a user) is detected on the biometric sensor (e.g., 804).

The first electronic device (e.g., 800A) detects (910) a first input with the biometric sensor (e.g., 804) that satisfies first criteria (e.g., user contact with the biometric sensor, movement below a threshold, electrical interference below a threshold).

In response to detecting the first input with the biometric sensor (e.g., 804), the first electronics device (e.g., 800A) starts (912) to record biometric information detected by the biometric sensor (e.g., 804). Also in response to detecting the first input with the biometric sensor (e.g., 804), the first electronic device (e.g., 800A) displays (914), on the display (e.g., 802), a second user interface (e.g., 806 of FIG. 8D) (e.g., a measurement page of a health application) that is different from the first user interface (e.g., 806 of FIG. 8A), where the second user interface (e.g., 806 of FIG. 8D) includes an indication of progress (e.g., 810) in recording the biometric information. In some embodiments, the indication of progress (e.g., 810) is a countdown timer (e.g., showing a countdown in seconds from a predetermined start time to zero). Displaying, on the second user interface (e.g., 806 of FIG. 8D), the indication of progress (e.g., 810) in recording the biometric information improves visual feedback by indicating to the user that the recording is being carried out and the duration for which the user must maintain the input to continue with the recording. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

After recording at least a portion of the biometric information, the first electronic device (e.g., 800A) detects (912), via the one or more input devices, that the first criteria are no longer met (e.g., user contact with the biometric sensor 804 is lost).

In response to detecting that the first criteria are no longer met for a first period of time (e.g., 5 seconds), the first electronic device (e.g., 800A) resets (918) the indication of progress (e.g., 810) in recording the biometric information and maintaining display of the second user interface (e.g., 806 of FIG. 8D). Resetting the indication of progress (e.g., 810) while maintaining display of the second user interface (e.g., 806 of FIG. 8D) in response to detecting that the first criteria are no longer met for a first period of time provides the user with more control of the device by helping the user avoid unintentionally leaving the health monitoring application while simultaneously allowing the user to easily continue with the recording without having to manually re-initiate the recording or the health monitoring application. Providing additional control of the device (without cluttering the user interface with additional displayed controls) enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In response to detecting that the first criteria are no longer met for a second period of time that is longer than the first period of time (e.g., longer than 5 seconds), the first electronic device (e.g., 800A) replaces (920) display of the second user interface (e.g., 806 of FIG. 8D) with the first user interface (e.g., 806 of FIG. 8A). Replacing display of the second user interface (e.g., 806 of FIG. 8D) with the first user interface (e.g., 806 of FIG. 8A) in response to detecting that the first criteria are no longer met for a second period of time that is longer than the first period of time improves visual feedback by visually indicating to the user that the recording has been stopped and that the a new recording can be re-initiated by the user. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first user interface (e.g., 806 of FIG. 8A) includes a graphical animation (e.g., of a shape, such as a heart, 808 of FIG. 8A) indicating (to the user) that the first electronic device (e.g., 800A) is ready to detect biometric information, where the graphical animation is comprised of a plurality of moving objects (e.g., 808, circular dots) forming a first shape (e.g., a heart shape). Providing the graphical animation (e.g., 808 of FIG. 8A to the user that the first electronic device (e.g., 800A) is ready to detect biometric information provides visual feedback about the current state of the application and indicates to that the user can proceed with a recording. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the plurality of moving objects (e.g., 808) of the graphical animation transitions from the first shape (e.g., a heart shape) to a second shape (e.g., a grid shape) different from the first shape as the display transitions from the first user interface to the second user interface.

In some embodiments, further in response to detecting that the first criteria are no longer met for the first period of time, the first electronic device (e.g., 800A) transitions the plurality of moving objects (e.g., 808) of the graphical animation to an interstitial shape between the first shape (e.g., a heart shape) and the second shape (e.g., a grid shape).

In some embodiments, while displaying the second user interface (e.g., 806 of FIG. 8D) and recording the biometric information (e.g., heart rhythm information, heart rate information), the first electronic device (e.g., 800A) displays, within the graphical animation that is in the second shape (e.g., 808 of FIG. 8D, a grid), a visual representation of the recorded biometric information, where the recorded biometric information is filtered and scaled such that the visual representation of the recorded biometric information can be displayed within the graphical animation. Displaying the visual representation of the recorded biometric information while displaying the second user interface (e.g., 806 of FIG. 8D) and recording the biometric information improves visual feedback by allowing the user to view the current state and progress of the recording and indicating to the user that the recording is being carried out. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the second user interface (e.g., 806 of FIG. 8D) includes a (dynamic) graphical representation (e.g., a dynamic tachogram-like animation) that corresponds to a visualization of the biometric information from the recorded biometric information and a (countdown) timer (e.g., 810) indicating (to the user) the amount of time remaining to complete the recording of the biometric information. In some embodiments, the biometric information that is recorded is heart-related data, and the graphical representation is a dynamic animation that includes a tachogram to reflect the data obtained from the biometric sensor (e.g., 804).

In some embodiments, while recording the biometric information, the first electronic device (e.g., 800A) detects, via the one or more input devices, that second criteria are met. In some embodiments, in response to detecting that the second criteria are met, the first electronic device (e.g., 800A) displays, in the second user interface (e.g., 806 of FIG. 8D, below the indication of progress 810), a (text) notification (e.g., 824) related to the second criteria. Displaying, on the second user interface (e.g., 806 of FIG. 8D), the notification (e.g., 824) related to the second criteria in response to detecting that the second criteria are met provides the user with more control of the device by quickly indicating to the user that one or more actions need to be taken by the user to maintain a recording. Providing additional control of the device (without cluttering the user interface with additional displayed controls) enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the second criteria is met when an amount of movement (of the device caused by the user) above a threshold is detected, and the notification (e.g., 844) indicates (to the user) that the amount of movement should be decreased. In some embodiments, the notification (e.g., 844) notifies the user that too much movement is detected. In some embodiments, the notification (e.g., 844) further notifies the user to constrain his/her movements.

In some embodiments, the second criteria is met when the amount of movement (of the device caused by the user) above the threshold is detected for at least a third period of time, and the notification (e.g., 846) indicates (to the user) that the first electronic device should be moved to a resting position (e.g., on a table). In some embodiments, if the first electronic device is a smartwatch, the notification (e.g., 846) instructs the user to rest his/her arm on a table.

In some embodiments, the second criteria is met when a second input (e.g., a press input, a click input) having a type that is different from the type of the first input is detected on a first input device (e.g., 804, a crown, a mechanical button, a rotating button), and the notification (e.g., 848) indicates (to the user) that the second input should not be repeated on the first input device. In some embodiments, the biometric sensor includes one or more electrodes integrated in the first input device (e.g., 804) (e.g., operating in conjunction with one or more electrodes integrated in a housing portion (e.g., backplate) of the first electronic device (e.g., 800A). In some embodiments, the second input is a press/click input on the first input device (e.g., 804), and the notification (e.g., 848) notifies that the user should not press/click the first input device (e.g., 804).

In some embodiments, the second criteria is met when the first input is no longer detected (e.g., discontinued, interrupted) by the biometric sensor (e.g., 804) when recording of the biometric information is not yet completed, and the notification (e.g., 850) indicates (to the user) that the first input should be maintained on the biometric sensor (e.g., 804). In some embodiments, the first electronic device (e.g., 800A) detects that the first input is no longer detected when the user discontinues contact with the biometric sensor (e.g., 804) while recording of the biometric information is still ongoing. In some embodiments, the notification (e.g., 850) instructs the user to re-establish contact with (e.g., by placing his/her finger back on) the biometric sensor (e.g., 804).

In some embodiments, after taking a first recording of first biometric information and a second recording of second biometric information different from the first biometric information (e.g., where the first recording and the second recording are different recordings that were taken at different times), the first electronic device (e.g., 800A) transmits (922), to a second electronic device (e.g., 800B, a smartphone paired with the smartwatch), the recorded first biometric information and the recorded second biometric information.

In some embodiments, (e.g., while not displaying the application corresponding to the first and second user interfaces on the display) the first electronic device (e.g., 800A) detects (924) (e.g., via a second biometric sensor that measures heart rate information without user input) heart rate information (of the user) for a predetermined amount of time. In some embodiments, in accordance with a determination that the detected heart rate information meets a first condition (e.g., above a threshold, such as 150 BPM, above a threshold for a certain amount of time), the first electronic device (e.g., 800A) displays (926), on the display (e.g., 802), a notification indicating a high heart rate. Displaying, on the display (e.g., 802), the notification indicating the high heart rate in accordance with the determination that the detected heart rate information meets the first condition improves visual feedback by quickly informing the user of the high heart rate. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first electronic device (e.g., 800A) detects (928), via the one or more input devices, a user activation of the notification. In some embodiments, in response to detecting the user activation of the notification, the first electronic device (e.g., 800A) displays (930), on the display (e.g., 802), the first user interface (e.g., 806 of FIG. 8A, so that the user can check his/her electrocardiogram recording using the application corresponding to the first user interface). Displaying, on the display (e.g., 802) the first user interface (e.g., 806 of FIG. 8A) in response to detecting the user activation of the notification reduces the number of inputs needed to launch the application corresponding to the first user interface when the device detects the high heart rate of the user. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

Note that details of the processes described above with respect to method 900 (e.g., FIGS. 9A-9B) are also applicable in an analogous manner to the methods described above and below. For example, method 700 optionally includes one or more of the characteristics of the various methods described above with reference to method 900. For another example, method 1100 optionally includes one or more of the characteristics of the various methods described above with reference to method 900. For another example, method 1300 optionally includes one or more of the characteristics of the various methods described above with reference to method 900. For another example, method 1500 optionally includes one or more of the characteristics of the various methods described above with reference to method 900. For brevity, these details are not repeated below.

FIGS. 10A-10J illustrate exemplary user interfaces for health monitoring, in accordance with some embodiments. The exemplary user interfaces in these figures are used to illustrate the processes described below, including the processes in FIG. 11. The exemplary user interfaces in these figures relate generally to monitoring health using recorded biometric information, and are not limited to a specific type of biometric information. Only for the sake of convenience, the exemplary user interfaces in these figures are described with reference to a type of biometric information-electrocardiogram (hereinafter "ECG") information.

Figure 10A:
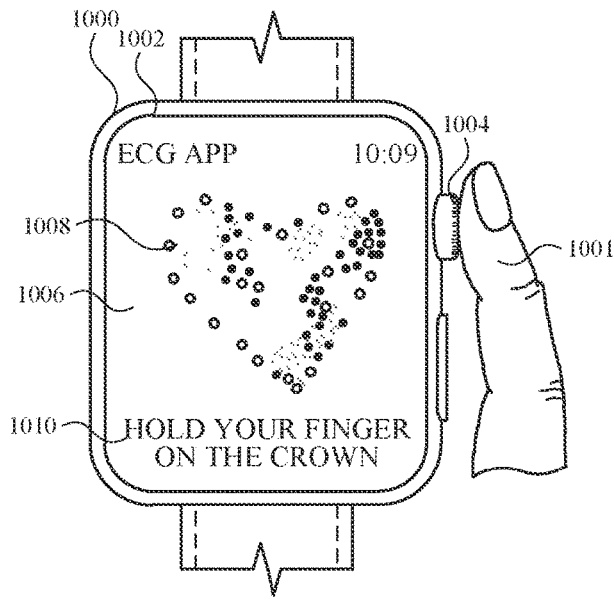
FIGS. 10A-10J illustrate exemplary user interfaces for using an input device for health monitoring.

FIG. 10A illustrates a first electronic device 1000 (e.g., corresponding to second electronic device 600B, first electronic device 800A). In some embodiments, first electronic device 1000A is a smartwatch. In some embodiments, first electronic device 1000A has a display 1002 and one or more input devices (e.g., including a touch layer of display 1002 and one or more mechanical buttons, such as a rotating crown). In some embodiments, first electronic device 1000 includes one or more biometric sensors (e.g., for recording ECG information, for detecting heart rhythm and heart rate of the user) comprising one or more electrodes integrated in an input device 1004 (e.g., a mechanical input device, such as a depressible, rotating crown) of first electronic device 1000. In some embodiments, the one or more biometric sensors of first electronic device 1000 further comprise one or more electrodes of (e.g., integrated in) a housing portion (e.g., the backplate) of first electronic device 1000, where the one or more electrodes integrated in the input device operate in conjunction with the one or more electrodes of the housing portion to capture biometric information (e.g., ECG information). Features concerning the one or more biometric sensors of first electronic device 1000 used to capture biometric information (e.g., ECG information) is described in greater detail in Appendix A.

In some embodiments, first electronic device 1000 is configured to detect and respond to activation of input device 1004 (e.g., respond by performing a first predefined operation or a second predefined operation), where the activation is different from and independent of the capture of biometric information (e.g., ECG information).

FIG. 10A illustrates first electronic device 1000 displaying, on display 1002, a user interface 1006 of an ECG application (e.g., corresponding to user interface 644 of the ECG application described with reference to FIGS. 6A-6AE and user interface 806 of the ECG application described with reference to FIGS. 8A-8S). In some embodiments, the ECG application is configured to cause first electronic device 1000 to capture biometric information without detecting the activation of input device 1004.

In some embodiments, user interface 1006 includes an animation 1008 (e.g., a fluid animation, corresponding to animation 646 of user interface 644 and animation 808 of user interface 806) that depicts a particular shape (e.g., a heart). In some examples, as shown in FIG. 10A, animation 1008 comprises a plurality of dynamic objects (e.g., circular objects) that form the particular shape (e.g., a heart), where the shape appears three-dimensional and is visually fluid as the plurality of dynamic objects constantly move while maintaining the structure of the shape. In some examples, the plurality of dynamic objects forming animation 1008 have a consistent visual characteristic (e.g., the same color).

In some embodiments, while displaying animation 1008 in the particular shape (e.g., a heart), user interface 1006 displays a notification message 1010 (e.g., corresponding to notification message 648 of user interface 644 and notification message 810 of user interface 806, stating "Hold your finger on the crown") indicating to the user that an action must be performed (by the user) on the device to proceed with recording the user's ECG information. In some embodiments, notification message 1010 instructs the user of the type of input (e.g., a touch or contact on input device 1004 that is below a threshold amount such that the input does not "click" input device 1004) and that the input must be maintained on input device 1004 (e.g., for the duration of the recording).

In some embodiments, while displaying user interface 1006 of the ECG application as shown in FIG. 10A, first electronic device 1000 detects a press input 1001 on input device 1004, where the press input is an input on input device 1004 with a pressing force above a threshold amount such that the input "clicks" input device 1004.

Figure 10B:
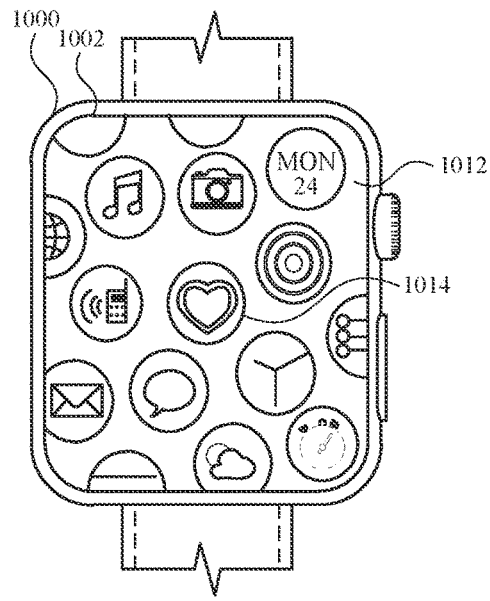

In some embodiments, in response to detecting press input 1001 while displaying user interface 1006 of the ECG application as shown in FIG. 10A, first electronic device 1000 displays, on display 1002 (e.g., replaces display of user interface 1006 with), a home user interface 1012 (e.g., a main user interface of the operating system of the device), as shown in FIG. 10B. In some embodiments, home user interface 1012 includes a plurality of icons corresponding to different applications installed on the device, including an icon 1014 corresponding to the ECG application.

Figure 10C:
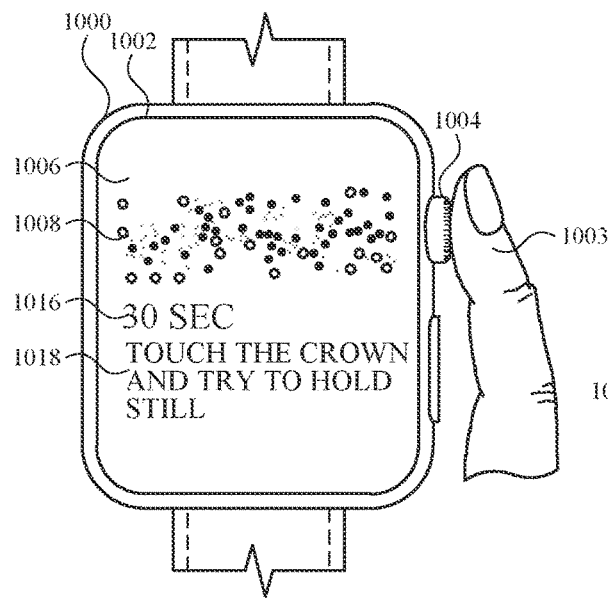

FIG. 10C illustrates first electronic device 1000, while displaying user interface 1006 of the ECG application, detecting (and maintaining) a user input 1003 (e.g., a continuous touch or contact of a finger on input device 1000) on input device 1004 to begin an ECG recording (e.g., as described with reference to FIGS. 8A-8C). In some embodiments, upon beginning the ECG recording, the dynamic plurality of objects (e.g., circular objects) of animation 1008 transitions from their initial fluid shape in FIG. 10A to a grid-like shape. In some embodiments, upon beginning the ECG recording, the device displays, in user interface 1006, a timer 1016 (e.g., below animation 1010) indicating the remaining amount of time to complete the recording (e.g., initially 30 seconds). In some embodiments, upon beginning the ECG recording, the device displays, in user interface 1006 (e.g., below timer 1016), a notification message 1018 (e.g., stating "Touch the crown and try to hold still") requesting that the user maintain (a stable) user input 1003 on input device 1004 during the recording of the ECG information.

Figure 10D:
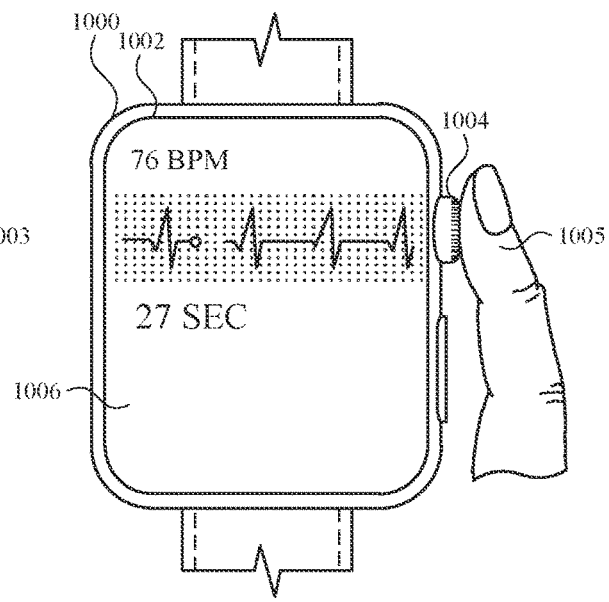

FIG. 10D illustrates first electronic device 1000 recording ECG information from the user, where a initial threshold time period (e.g., 5 seconds) has not passed since the initiation of the recording (e.g., as indicated by timer 1016, which shows that 3 seconds have passed since the initiation of the recording). In some embodiments, while the initial threshold time period has not yet passed, first electronic device 1000 detects a press input 1005 on input device 1004, where the press input is an input on input device 1004 with a pressing force above a threshold amount such that the input "clicks" input device 1004. In some embodiments, in response to detecting press input 1005 on input device 1004 while the initial threshold time period has not yet passed, first electronic device 1000 (automatically) terminates the recording and displays user interface 1006 of the ECG application as shown in FIG. 10A.

Figure 10E:
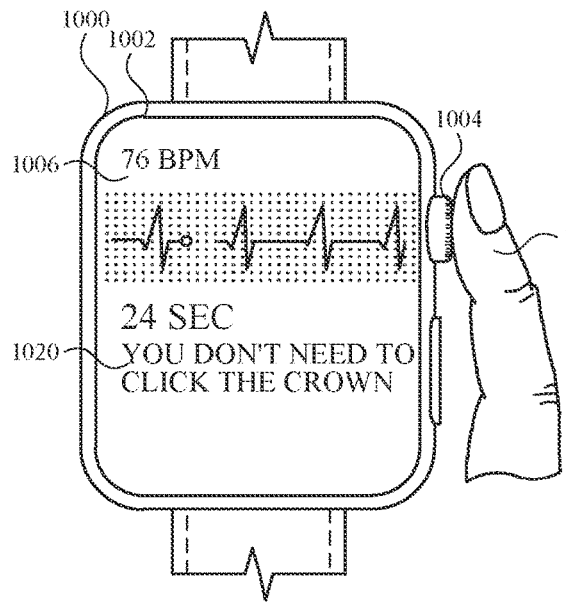

FIG. 10E illustrates first electronic device recording ECG information from the user, where the initial threshold time period (e.g., 5 seconds) has passed since the initiation of the recording (e.g., as indicated by timer 1016, which shows that 6 seconds have passed since the initiation of the recording). In some embodiments, after the initial threshold time period has passed, first electronic device 1000 detects a press input 1007 (e.g., similar to press input 1005) on input device 1004, where the press input is an input on input device 1004 with a pressing force above a threshold amount such that the input "clicks" input device 1004. In some embodiments, in response to detecting press input 1007 on input device 1004 after the initial threshold time period (e.g., 5 seconds) has passed, first electronic device 1000 does not terminate the recording. In some embodiments, (instead of terminating the recording) first electronic device 1000 displays, in user interface 1006, a notification message 1020 (e.g., stating "You do not need to click the crown") indicating that there is no need to "click" input device 1004 during the recording or to successfully complete the recording.

In some embodiments, after detecting press input 1007 on input device 1004 after the initial threshold time period (e.g., 5 seconds) has passed, in response to which first electronic device 1000 does not terminate the recording, the device detects a second press input (e.g., similar to press input 1007) after detecting press input 1007 but before a predetermined amount of time (e.g., 2.5 seconds) has passed since detecting press input 1007. In some embodiments, in response to detecting the second press input after detecting press input 1007 but before the predetermined amount of time (e.g., 2.5 seconds) has passed since detecting press input 1007, first electronic device 1000 (automatically) terminates the recording and displays user interface 1006 of the ECG application as shown in FIG. 10A.

In some embodiments, after detecting press input 1007 on input device 1004 after the initial threshold time period (e.g., 5 seconds) has passed, in response to which first electronic device 1000 does not terminate the recording, the device detects a second press input (e.g., similar to press input 1007) after detecting press input 1007 and after a predetermined amount of time (e.g., 2.5 seconds) has passed since detecting press input 1007. In some embodiments, (instead of terminating the recording) first electronic device 1000 displays, in user interface 1006, a notification message 1020 (e.g., stating "You do not need to click the crown") indicating that there is no need to "click" input device 1004 during the recording or to successfully complete the recording. In summary, in some embodiments and while recording is underway, termination of recording occurs if two inputs are received within a predetermined period (e.g., within rapid succession (e.g., within 2.5 seconds)). In contrast, in some embodiments, if two inputs are received but spaced apart by more than the predetermined period (e.g., within 2.5 seconds) the recording is not cancelled.

Figure 10F:
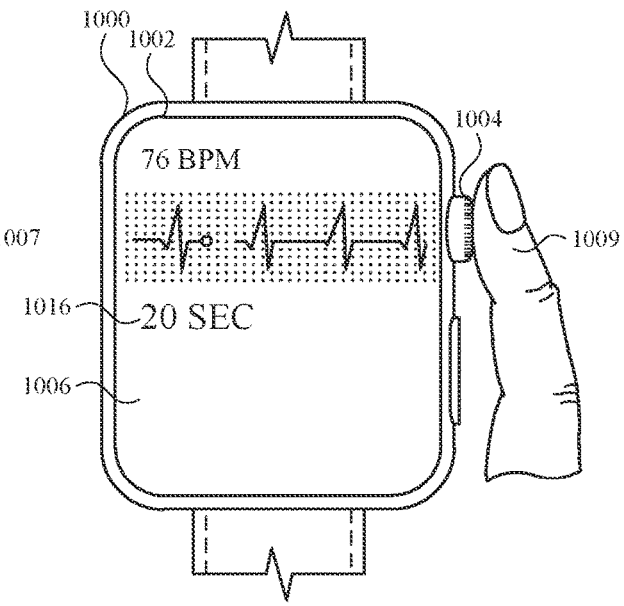

FIG. 10F illustrates first electronic device 1000 performing an ECG recording on the ECG application with, as indicated by timer 1016 of user interface 1006 (e.g., showing "20 Seconds"), 20 seconds remaining to complete the recording. In FIG. 10F, the initial threshold time period (e.g., 5 seconds) has passed since the initiation of the recording. In some embodiments, after the initial threshold time period (e.g., 5 seconds) has passed since the initiation of the recording, first electronic device 1000 detects a user input a press input 1009 (or a press-and-hold input) on input device 1004, where the press input is an input on input device 1004 with a pressing force above a threshold amount such that the input "clicks" input device 1004 (e.g., and the pressing force is maintained for at least a period of time, such as 1 second). In some embodiments, in response to detecting press input 1009 on input device 1004 after the initial threshold time period (e.g., 5 seconds) has passed, first electronic device 1000 does not terminate the recording and displays, in user interface 1006, a notification message 1020 (e.g., stating "You do not need to click the crown") indicating that there is no need to "click" input device 1004 during the recording or to successfully complete the recording.

Figure 10G:
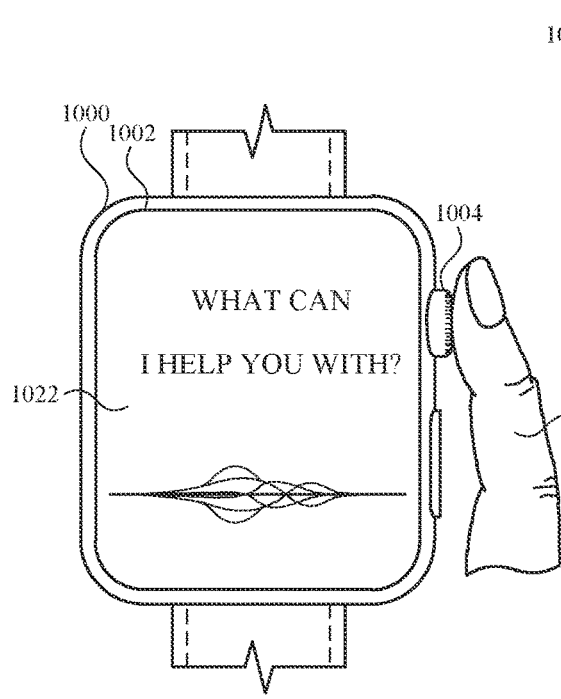

In some embodiments, at least a predetermined amount of time (e.g., 5 seconds) after detecting user input 1009, first electronic device 1000 detects a press a press-and-hold input 1011 on input device 1004, where the press-and-hold input is an input on input device 1004 with a pressing force above a threshold amount such that the input "clicks" input device 1004, and input device 1004 is "clicked" for at least a threshold period of time (e.g., 1 second). In some embodiments, in response to detecting press-and-hold input 1011 on input device 1004 while the initial threshold time period has not yet passed, first electronic device 1000 (automatically) displays, on display 1002 (e.g., replaces display of user interface 1006 of the ECG application with), a user interface 1022 of a virtual assistant (e.g., a virtual assistant controlled by the operating system of the device), as shown in FIG. 10G.

Figure 10H:
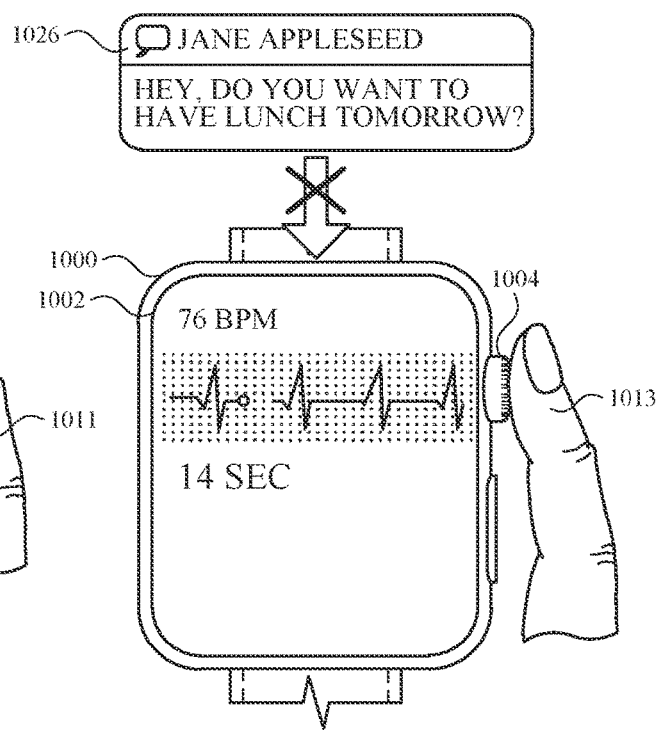
Figure 10I:
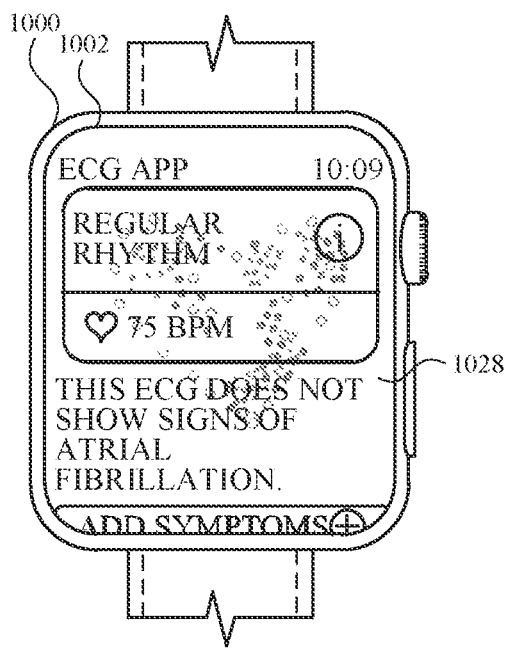
Figure 10J:
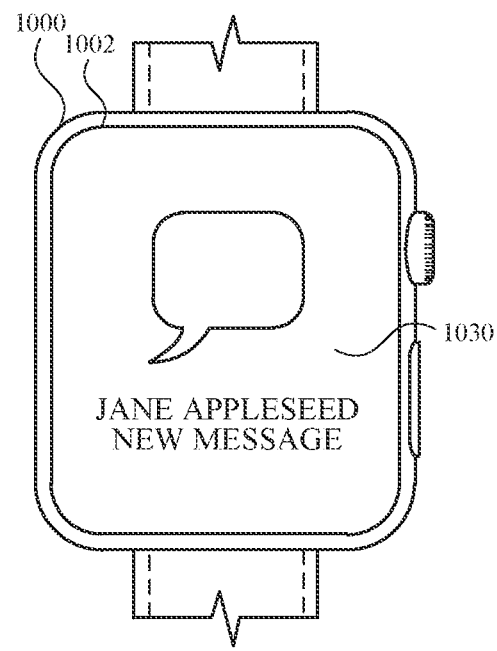

FIGS. 10H-10J illustrate first electronic device 1000 receiving an electronic communication (e.g., a phone call, a text message, an email message) while the device is performing an ECG recording. In FIG. 10H, the received electronic communication (e.g., a text message from "Jane Appleseed") is represented as a notification 1026 corresponding to the electronic communication. The electronic communication (represented as notification 1026) is received while first electronic device 1000 is performing an ECG recording (e.g., from user input 1013 on input device 1004.

FIG. 10I illustrates first electronic device 1000 displaying, on display 1002, a summary page 1028 of the ECG recording (e.g., corresponding to summary page 826 described with reference to FIGS. 8J-8K) upon completing the ECG recording. In FIG. 10J, upon (or subsequent to) completing the recording (and displaying summary page 1028 corresponding to the recording), first electronic device 1000 displays, on display 1002, a notification alert 1030 corresponding to the electronic communication (e.g., the text message from "Jane Appleseed") that was received during the recording. In some embodiments, if one or more additional electronic communications were received during the recording, the device also provides one or more notification alerts corresponding to the received electronic communications upon (or subsequent to) completing the recording.

In some embodiments, upon (or prior to) beginning an ECG recording, first electronic device 1000 automatically disables a wireless communication radio (e.g., a LTE connection) of the device. In some embodiments, upon (or in response to) completing the ECG recording, first electronic device 1000 automatically re-enables the wireless communication radio on the device.

In some embodiments, upon (or prior to) beginning an ECG recording, first electronic device 1000 automatically disables a haptic feedback controller (e.g., a haptic actuator) of the device. In some embodiments, upon (or in response to) completing the ECG recording, first electronic device 1000 automatically re-enables the haptic feedback controller of the device.

FIG. 11 is a flow diagram illustrating a method for using an input device for health monitoring, in accordance with some embodiments. Method 1100 is performed at a device (e.g., 100, 300, 500, 600B, 800A, 1000) with a display and one or more input devices including a first input device with an integrated biometric sensor (e.g., a rotatable and depressible watch crown with integrated biometric sensors comprising one or more electrodes for detecting characteristics of the user's heart). Some operations in method 1100 are, optionally, combined, the orders of some operations are, optionally, changed, and some operations are, optionally, omitted.

As described below, method 1100 provides an intuitive way for managing health monitoring. The method reduces the cognitive burden on a user for managing health monitoring, thereby creating a more efficient human-machine interface. For battery-operated computing devices, enabling a user to manage health monitoring faster and more efficiently conserves power and increases the time between battery charges.

The first electronic device (e.g., 1000) displays (1102), on the display (e.g., 1002), a user interface (e.g., 1006 of FIG. 10A) of an application (e.g., a health application, such as a health monitoring application or a health data measurement application) for capturing biometric information (e.g., ECG data, BPM data, heart-related data) from the biometric sensor (e.g., 1004).

In some embodiments, the first electronic device (e.g., 1000) is configured to detect and respond to activation of the first input device (e.g., 1004, respond by performing the predefined operation or a second predefined operation), where the activation is different from and independent of the capture of biometric information.

In some embodiments, the application is configured to cause the first electronic device (e.g., 1000) to capture the biometric information without detecting the activation of the first input device (e.g., 1004).

While displaying the user interface (e.g., 1006 of FIG. 10A) of the application for capturing biometric information from the biometric sensor (e.g., 1004), the first electronic device (e.g., 1000) detects (1104) a first activation of the first input device (e.g., 1004, a pressing of the first input device, such as a rotating crown, past a threshold amount to cause a "click" of the crown).

In response to detecting the first activation of the first input device (e.g., 1004, a press on the first input device) and while capturing biometric information from the biometric sensor (e.g., 1004), in accordance with a determination that the first activation of the first input device (e.g., 1004) was detected when first criteria are met (e.g., the device has captured less than a predetermined amount of biometric information and/or the first input device has been activated within at least a threshold amount of time, such as 5 seconds), where the first criteria are based on progress toward capturing biometric information with the biometric sensor (e.g., 1004), the first electronic device (e.g., 1000) performs (1106) a predefined operation associated with the first input device (e.g., 1004) that interrupts capture of the biometric information (e.g., scrolling of a displayed content, exiting a currently active application, activation of a digital assistant function). Performing the predefined operation associated with the first input device (e.g., 1004) that interrupts the capture of biometric information in accordance with the determination that the first activation of the first input device (e.g., 1004) was detected when the first criteria are met provides the user with more control of the device by enabling the user to interrupt the capture of biometric information in certain situations through an input on the first input device. Providing additional control options without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

Also in response to detecting the first activation of the first input device (e.g., 1004, a press on the first input device) and while capturing biometric information from the biometric sensor (e.g., 1004), in accordance with a determination that the first activation of the first input device (e.g., 1004) was detected when the first criteria are not met, the first electronic device (e.g., 1000) continues (1108) to capture the biometric information without performing the predefined operation associated with the first input device (e.g., 1004). Continuing to capture the biometric information without performing the predefined operation associated with the first input device (e.g., 1004) in accordance with the determination that the first activation of the first input device was detected when the first criteria are not met provides the user with more control of the device by enabling the user continue with the capturing of the biometric information in certain situations without having to manually re-initiate the recording process. Providing additional control options without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, prior to capturing the biometric information (e.g., while displaying an introductory animation, such as animation 808 of main user interface 806 as shown in FIG. 8A), the first electronic device (e.g., 1000) detects a second activation of the first input device (e.g., 1004). In some embodiments, in response to detecting the second activation of the first input device (e.g., 1004), the first electronic device (e.g., 1000) performs the predefined operation (e.g., performing the predefined operation without determining whether capture of biometric information is occurring).

In some embodiments, the predefined operation includes displaying, on the display (e.g., 1002), a predefined user interface (e.g., 1012, a homescreen that includes one or more affordances for launching an application). In some embodiments, displaying the predefined user interface (e.g., 1012) includes closing or suspending any currently active or running application (e.g., the application for capturing biometric information).

In some embodiments, the predefined operation includes displaying, on the display (e.g., 1002), a user interface (e.g., 1022) of a digital virtual assistant (e.g., by replacing display of the user interface (e.g., 1006) of the application for capturing biometric information).

In some embodiments, the first criteria are met when capturing the biometric information has occurred for less than a first threshold amount of time (e.g., 5 seconds).

In some embodiments, after continuing to capture the biometric information without performing the predefined operation associated with the first input device (e.g., 1004), the first electronic device (e.g., 1000) detects (1110) a second activation of the first input device (e.g., 1004). In some embodiments, in response to detecting the second activation of the first input device (e.g., 1004), in accordance with a determination that the second activation of the first input device (e.g., 1004) was detected within a predetermined time (e.g., 5 seconds) after detecting the first activation of the first input device (e.g., 1004), the first electronic device (e.g., 1000) performs (1112) the predefined operation associated with the first input device (e.g., 1004) that interrupts capture of the biometric information. Performing the predefined operation associated with the first input device (e.g., 1004) that interrupts the capture of the biometric information in accordance with the determination that the second activation of the first input device was detected within the predetermined time after detecting the first activation of the first input device provides the user with more control of the device and reduces the number of inputs needed to interrupt the capturing of the biometric information by allowing the user to quickly and easily interrupt the capturing of biometric information using the first input device. Providing additional control of the device and reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in response to detecting the second activation of the first input device (e.g., 1004), in accordance with a determination that the second activation of the first input device (e.g., 1004) was detected after the predetermined time after detecting the first activation of the first input device (e.g., 1004), the first electronic device (e.g., 1000) continues (1114) to capture the biometric information without performing the predefined operation associated with the first input device (e.g., 1004). Continuing to capture the biometric information without performing the predefined operation associated with the first input device (e.g., 1004) in accordance with the determination that the second activation of the first input device was detected after the predetermined time after detecting the first activation of the first input device provides the user with more control of the device by helping the user avoid unintentionally interrupting the capturing of the biometric information and simultaneously allowing the user to recognize that another and/or different input is required to interrupt the capturing of the biometric information. Providing additional control of the device (without cluttering the user interface with additional displayed controls) enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, upon (or prior to) capturing the biometric information (e.g., heart rhythm information, heart rate information) from the biometric sensor (e.g., 1004), the first electronic device (e.g., 1000) automatically disables a haptic feedback controller (e.g., a haptic actuator associated with the first input device) of the first electronic device (e.g., 1000). In some embodiments, upon (or in response to) completing capturing the biometric information, the first electronic device (e.g., 1000) automatically re-enables the haptic feedback controller.

In some embodiments, upon (or prior to) capturing the biometric information (e.g., heart rhythm information, heart rate information) from the biometric sensor, the first electronic device (e.g., 1000) automatically disables a wireless communication radio (e.g., LTE connection) of the first electronic device (e.g., 1000) and prevents a first type of notification (e.g., 1026, of a message, of an alert, a type of notification other than a timer notification) from being displayed, where the first type of notification includes a notification corresponding to an electronic communication (e.g., a text message, an email, a phone call) received while the capturing the biometric information. In some embodiments, the notifications that are prevented from being displayed do not include a timer notification. In some embodiments, upon (or in response to) completing capturing the biometric information, the first electronic device (e.g., 1000) automatically re-enables the wireless communication radio and allows the first type of notification (e.g., 1030) to be displayed.

Note that details of the processes described above with respect to method 1100 (e.g., FIG. 11) are also applicable in an analogous manner to the methods described above and below. For example, method 700 optionally includes one or more of the characteristics of the various methods described above with reference to method 1100. For another example, method 900 optionally includes one or more of the characteristics of the various methods described above with reference to method 1100. For example, method 1300 optionally includes one or more of the characteristics of the various methods described above with reference to method 1100. For example, method 1500 optionally includes one or more of the characteristics of the various methods described above with reference to method 1100. For brevity, these details are not repeated below.

FIGS. 12A-12S illustrate exemplary user interfaces for managing aspects of health monitoring. The user interfaces in these figures are used to illustrate the processes described below, including the processes in FIGS. 13A-13B. The exemplary user interfaces in these figures relate generally to monitoring health using recorded biometric information, and are not limited to a specific type of biometric information. Only for the sake of convenience, the exemplary user interfaces in these figures are described with reference to a type of biometric information-electrocardiogram (hereinafter "ECG") information.

FIG. 12A illustrates a first electronic device 1200 (e.g., corresponding to second electronic device 600B, first electronic device 800A, and/or first electronic device 1000). In some embodiments, first electronic device 1200 is a smartwatch. In some embodiments, first electronic device 1200 has a display 1202 and one or more input devices (e.g., including a touch layer of display 1202 and one or more mechanical buttons, such as a rotating crown). In some embodiments, first electronic device 1200 includes one or more biometric sensors (e.g., for recording ECG information, for detecting heart rhythm and heart rate of the user) comprising one or more electrodes integrated in an input device 1204 (e.g., a mechanical input device, such as a depressible, rotating crown) of first electronic device 1200. In some embodiments, the one or more biometric sensors of first electronic device 1200 further comprise one or more electrodes of (e.g., integrated in) a housing portion (e.g., the backplate) of first electronic device 1200, where the one or more electrodes integrated in the input device operate in conjunction with the one or more electrodes of the housing portion to capture biometric information (e.g., ECG information). Features concerning the one or more biometric sensors of first electronic device 1200 used to capture biometric information (e.g., ECG information) is described in greater detail in Appendix A.

In FIG. 12A, first electronic device 1200 displays, on display 1202, a summary page 1206 (e.g., corresponding to summary page 826 and summary page 1028) of an ECG application for a completed ECG recording, where the evaluation result of the completed ECG recording is a "regular rhythm" result, as indicated by indication 1208A of summary region 1208. In some embodiments, summary region 1208 also includes an indication 1208B of a heart rate reading (e.g., in BPM) of the completed ECG recording. In some embodiments, while displaying summary page 1206, the device displays (e.g., maintains display of) an animation (e.g., corresponding to animation 808 shown in FIG. 8A, in its initial shape as shown in FIG. 8A) in the background of the summary page (e.g., in a lighter shade so that the summary page is easily legible to the user).

In some embodiments, summary region 1208 also includes a information affordance 1210 for viewing a detailed description about the respective evaluation result. In some embodiments, while displaying summary page 1206, first electronic device 1200 detects (e.g., via a touch input) a user activation 1201 of information affordance 1210.

Figure 12B:
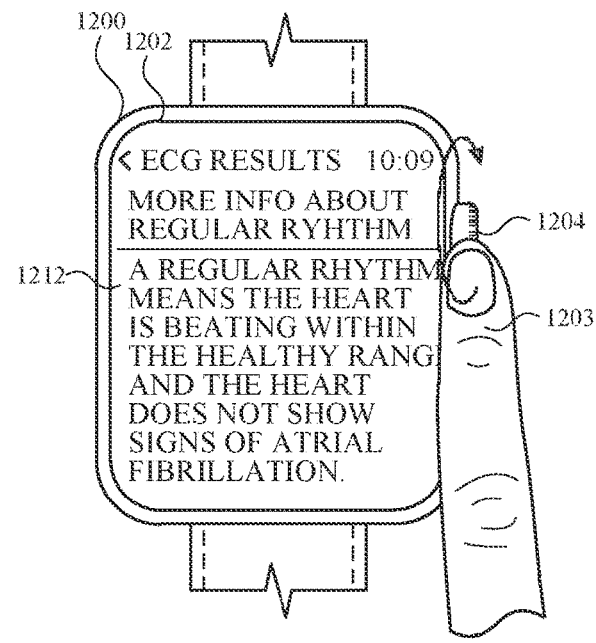

FIG. 12B illustrates first electronic device 1200 displaying, on display 1202, at least a portion of a information page 1212 that includes description about medical characteristics of its respective result. In some embodiments, the description included in information page 1212 corresponds to the text description shown in possible results page 618 of the tutorial described with reference to FIGS. 6A-6AE. In FIG. 12B, first electronic device 1200 detects a scrolling input 1203 on input device 1204 (e.g., a rotating of input device 1204, a rotating crown) in the direction of the bottom of the page. In some embodiments, the page can be scrolled via a scrolling touch gesture on the display. In response to detecting the scrolling input, first electronic device 1200 scrolls information page 1212 towards the bottom of the page.

Figure 12C:
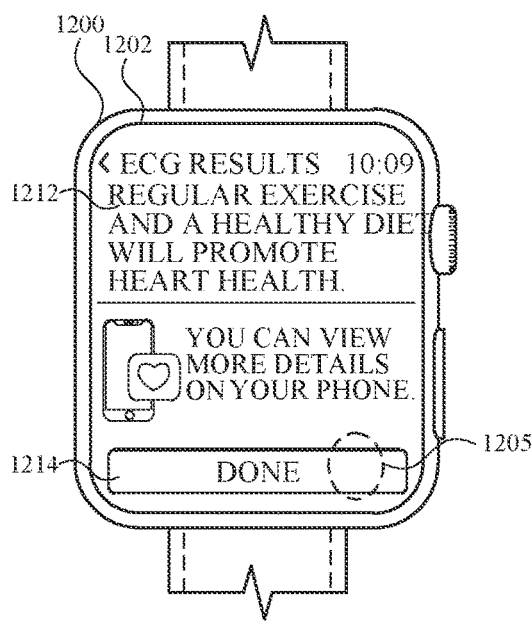

FIG. 12C illustrates first electronic device 1200 displaying, on display 1202, the bottom portion of information page 1212 of the ECG application. In some embodiments, information page 1212 includes (e.g., at the end of the page), a return affordance 1214 for returning to the previous page of the ECG application. In some embodiments, while displaying information page 1212, first electronic device 1200 detects (e.g., via a touch input) a user activation 1205 of return affordance 1214. In response to detecting user activation 1205 of return affordance 1214, first electronic device 1200 again displays, on display 1202 (e.g., replaces display of information page 1212 with), summary page 1206, as shown in FIG. 12D.

Figure 12D:
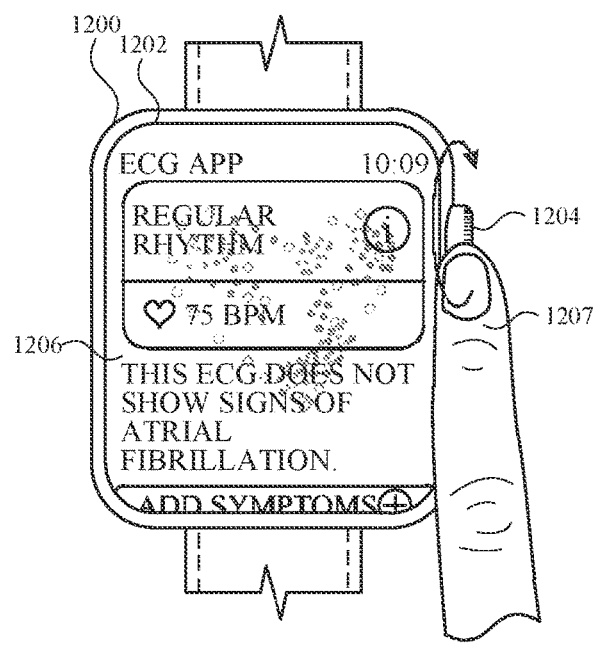

In FIG. 12D, while displaying, on display 1202, summary page 1206, first electronic device 1200 detects a scrolling input 1207 on input device 1204 (e.g., a rotating of the input device, a rotating crown). In some embodiments, in response to detecting scrolling input 1207 on input device 1204, first electronic device 1200 scrolls summary page 1206 to reveal additional items of the page, as shown in FIG. 12E.

Figure 12E:
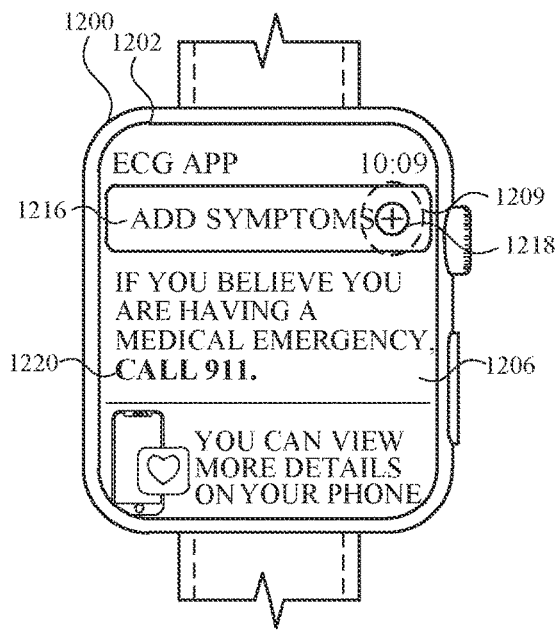

In some embodiments, as shown in FIG. 12E, summary page 1206 includes a symptoms region 1216 that includes an affordance 1218 for associating (e.g., via user selection from a list of symptoms) one or more symptoms to the ECG recording represented by the summary page. In some embodiments, as also shown in FIG. 12E, summary page 1206 includes an emergency contact affordance 1220 (e.g., for seeking immediate medical care, for contacting 911). In some embodiments, in response to detecting a user selection of emergency contact affordance 1220, first electronic device 1200 initiates a phone call to an emergency contact (e.g., 911).

Figure 12F:
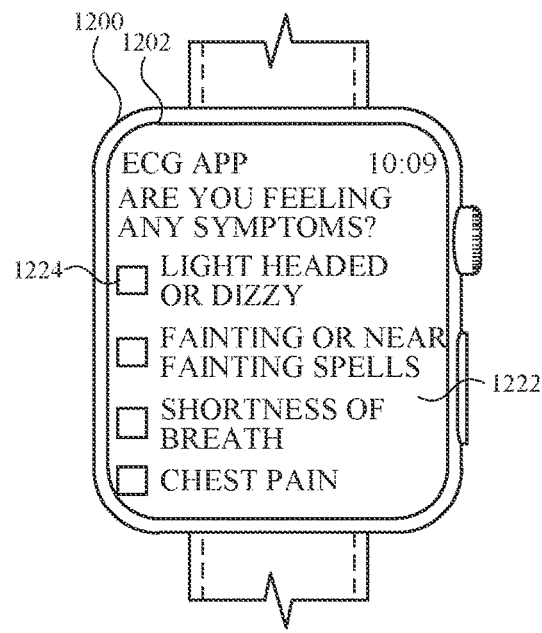

In FIG. 12E, while displaying symptoms region 1216 of summary page 1206, first electronic device 1200 detects (e.g., via a touch input) a user activation 1209 of affordance 1218 for associating one or more symptoms to the ECG recording. In some embodiments, in response to detecting user activation 1209 of affordance 1218, first electronic device 1200 displays, on display 1202 (e.g., replaces display of summary page 1206 with), a symptoms page 1222, as shown in FIG. 12F.

In some embodiments, symptoms page 1222 includes a selectable symptoms list 1224 that includes a plurality of symptoms options, of which one or more of the listed symptoms can be selected by the user from the list. In some examples, a symptom option of selectable symptoms list 1224 is a "Light headed or dizzy" option. In some examples, a symptom option of selectable symptoms list 1224 is a "Fainting or near fainting spells" option. In some examples, a symptom option of selectable symptoms list 1224 is a "Shortness of breath" option. In some examples, a symptom option of selectable symptoms list 1224 is a "Chest pain" option. In some examples, a symptom option of selectable symptoms list 1224 is an "Other" option (e.g., for indicating one or more symptoms that are not listed in the selectable symptoms list). In some examples, a symptom option of selectable symptoms list 1224 is a "None" option (e.g., for indicating that the user is not experiencing (or was not experiencing during the time of the ECG recording) any abnormal symptoms).

Figure 12G:
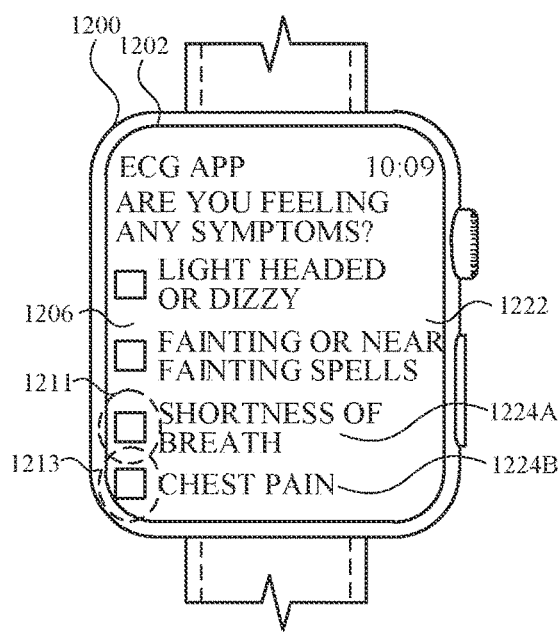
Figure 12H:
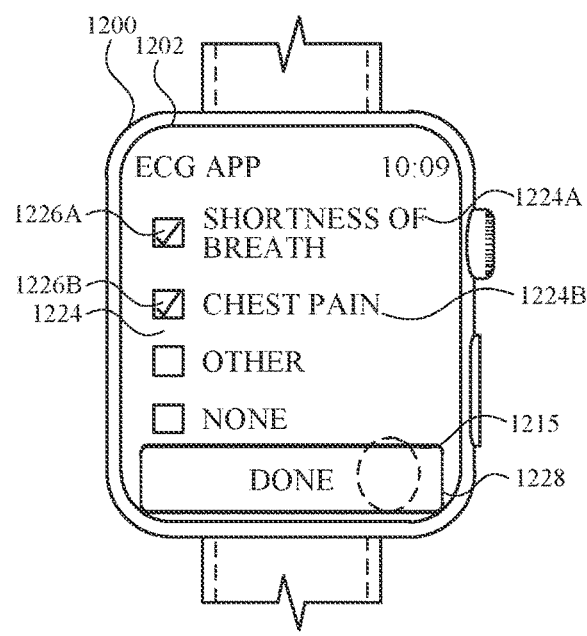

In FIG. 12G, while displaying, on display 1202, selectable symptoms list 1224 of symptoms page 1222, first electronic device 1200 detects (e.g., via touch inputs) a user selection 1211 of a first symptom option 1224A (e.g., a "Shortness of breath" option) and a user selection of 1213 of a second symptom option 1224B (e.g., a "Chest pain" option). In response to detecting user selection 1211 of first symptom option 1224A and user selection 1213 of second symptom option 1224B, first electronic device 1200 displays, in selectable symptoms list 1224, an indication 1226A (e.g., a marking of the option, such as a checkmark) of first symptom option 1224A and an indication 1226B (e.g., a marking of the option, such as a checkmark) of second symptom option 1224B, as shown in FIG. 12H. In some embodiments, user-specified symptoms can be added (via symptoms page 1222) to evaluation results that correspond to "regular" results, as is the case in FIGS. 12A-12H.

In some embodiments, first electronic device 1200 detects a scrolling gesture (e.g., via a scrolling touch gesture, via a rotating input on input device 1204, a rotating crown) on symptoms page 1222 and, in response to the scrolling gesture, scrolls the page to reveal a bottom portion of the page. In some embodiments, as shown in FIG. 12H, symptoms page 1222 includes (e.g., at the bottom of the page) a return affordance 1228 for confirming the selection of symptoms from selectable symptoms list 1224 to associate with the ECG recording and for returning to summary page 1206. In FIG. 12H, first electronic device 1200 detects (e.g., via a touch input) a user activation 1215 of return affordance 1228.

Figure 12I:
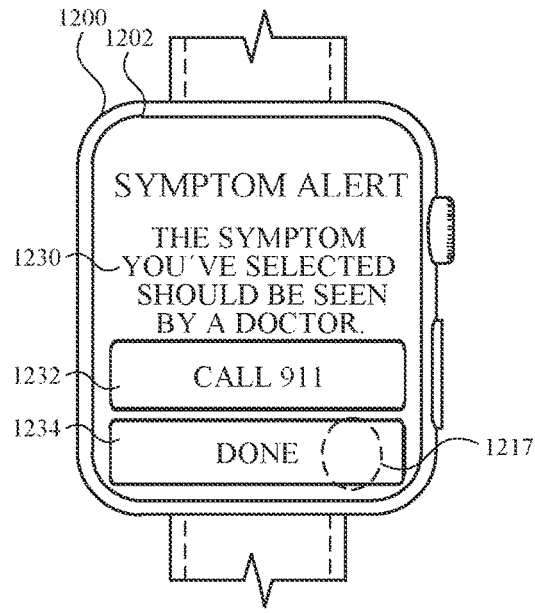

In some embodiments, in response to detecting user activation 1215 of return affordance 1228, if at least one of the user-specified symptoms are determined to be "serious" symptoms (e.g., symptoms that may require immediate medical attention), first electronic device 1200 displays, on the display 1202, an alert page 1230, as shown in FIG. 12I. In some embodiments, alert page 1230 includes an emergency contact affordance 1232 which, when activated by the user, causes the device to initiate a process for seeking immediate medical attention (e.g., by initiating an emergency call to an emergency contact, by initiating a 911 call). In some embodiments, alert page 1230 includes a return affordance 1234 for returning to summary page 1206 (e.g., without contacting an emergency contact).

In some embodiments, in response to detecting user activation 1215 of return affordance 1228, if none of the user-specified symptoms are determined to be "serious" symptoms (e.g., symptoms that may require immediate medical attention), first electronic device 1200 (automatically) displays summary page 1206 without displaying alert page 1230.

In FIG. 12I, while displaying, on display 1202, alert page 1230, first electronic device detects (e.g., via a touch input) a user activation 1217 of return affordance 1234 from alert page 1230. In some embodiments, in response to detecting user activation 1217 of return affordance 1234, first electronic device 1200 again displays, on display 1202 (e.g., replaces display of alert page 1230 with), an updated symptoms region 1236 (e.g., corresponding to previous symptoms region 1216) of summary page 1206, as shown in FIG. 12J, where updated symptoms region 1236 includes a list of the user-specified symptoms from selectable symptoms list 1224.

In some embodiments, updated symptoms region 1236 further includes an edit affordance 1238 for returning to symptoms page 1222 to modify the user-specified symptoms from selectable symptoms list 1224. In some embodiments, the user-specified symptoms of an ECG recording cannot be modified (either at first electronic device 1200 or at a second electronic device paired to first electronic device 1200, such as a smartphone) upon leaving the ECG application while on that recording.

Figure 12J:
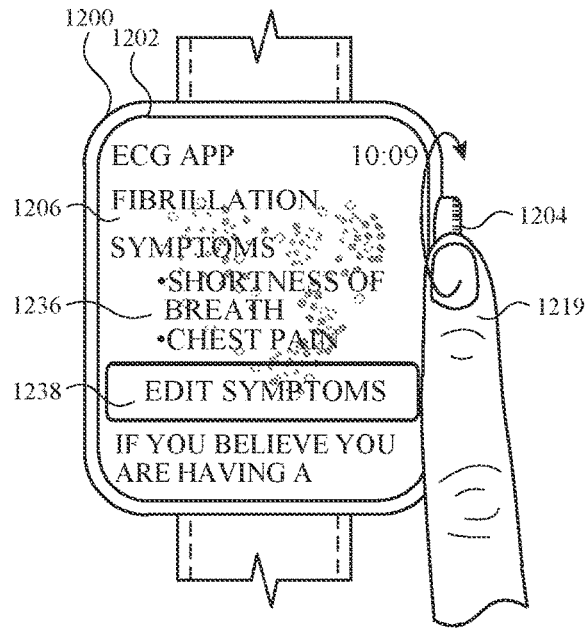

In FIG. 12J, while displaying updated symptoms region 1236 in summary page 1206 (after having received user-specified symptoms for the recording), first electronic device 1200 detects a scrolling input 1219 on input device 1204 (e.g., a rotating of input device 1204, a rotating crown) towards the bottom of summary page 1206. In some embodiments, in response to detecting scrolling input 1219 on input device 1204, first electronic device 1200 scrolls summary page towards the bottom of the page.

Figure 12K:
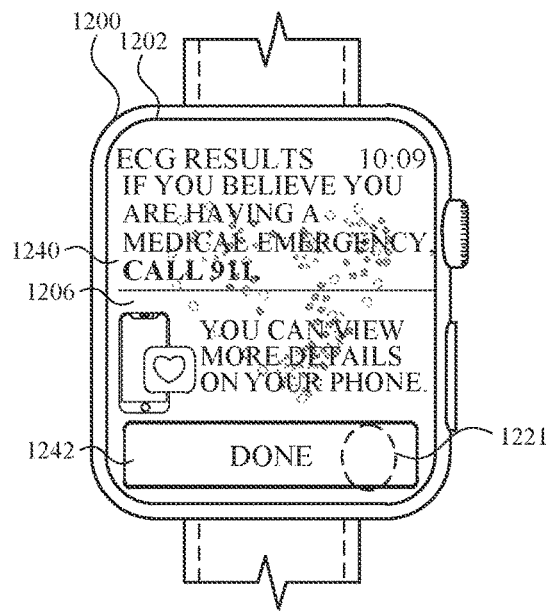
Figure 12L:
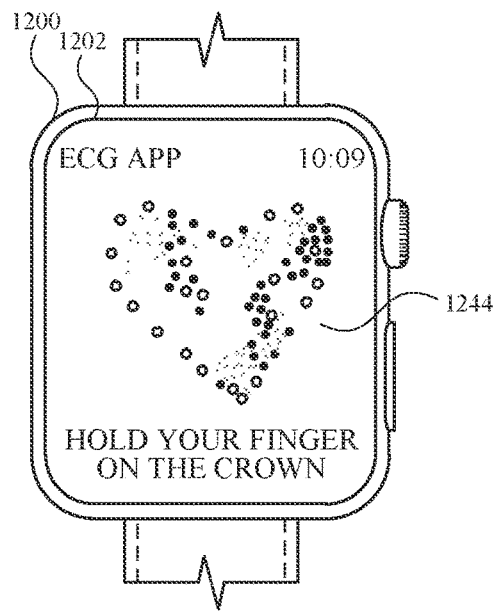

FIG. 12K illustrates first electronic device 1200 displaying, on display 1202, a bottom portion of summary page 1206. In some embodiments, summary page 1206 includes an emergency contact affordance 1240 for initiating a process for seeking immediate medical attention (e.g., initiating an emergency call to an emergency contact, initiating a 911 call). In some embodiments, summary page 1206 includes a return affordance 1242 for confirming selections (e.g., user specified symptoms) made via summary page 1206 and for returning to a mina user interface 1244 of the ECG application (e.g., corresponding to user interface 644 described with reference to FIGS. 6A-6AE, user interface 806 described with reference to FIGS. 8A-8S, and user interface 1006 described with reference to FIGS. 10A-10J), as shown in FIG. 12L.

Figure 12M:
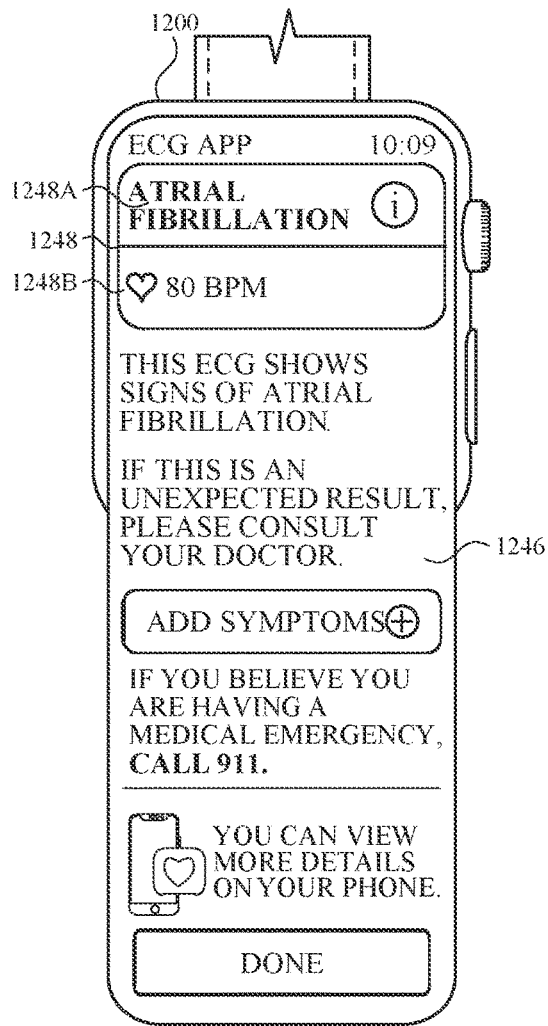

In some embodiments, within a summary region (e.g., 1248) of a summary page (e.g., 1206), an indication of the evaluation result of an ECG recording (e.g., "regular," "Atrial Fibrillation," "high heart rate," "low heart rate," "inconclusive") is highlighted with a warning visual characteristic (e.g., a warning color, such as yellow) if the result is an abnormal result (e.g., "Atrial Fibrillation," "high heart rate," "low heart rate") different from a default visual characteristic (e.g., a default color). Similarly, in some embodiments, within a summary region of a summary page, an indication of the heart rate measurement of an ECG recording (e.g., the BPM) is highlighted with the warning visual characteristic (e.g., a warning color, such as yellow) if the heart rate is abnormal high (e.g., above 100 BPM) or abnormally low (e.g., below 50 BPM). In some embodiments, if one of the evaluation result or heart rate measurement is abnormal, both the indication of the evaluation result and the indication of the heart rate measurement are displayed with warning visual characteristic FIG. 12M illustrates a full expanded view of an example summary page 1246 corresponding to a first ECG recording performed using first electronic device 1200. As indicated by a summary region 1248, the first ECG recording has an Atrial Fibrillation result (an abnormal result), as shown by an evaluation result indication 1248A (e.g., showing "Atrial Fibrillation"), with a normal heart rate (e.g., between 50-100 BPM), as shown by a BPM indication 1248B (e.g., showing "80 BPM"). In some embodiments, evaluation result indication 1248A is highlighted with the warning visual characteristic (e.g., text "Atrial Fibrillation" is displayed in a warning color, such as yellow, instead of a default color) and BPM indication 1248B is not highlighted with the warning visual characteristic (e.g., text "80 BPM" is displayed in a default color, such as white).

Figure 12N:
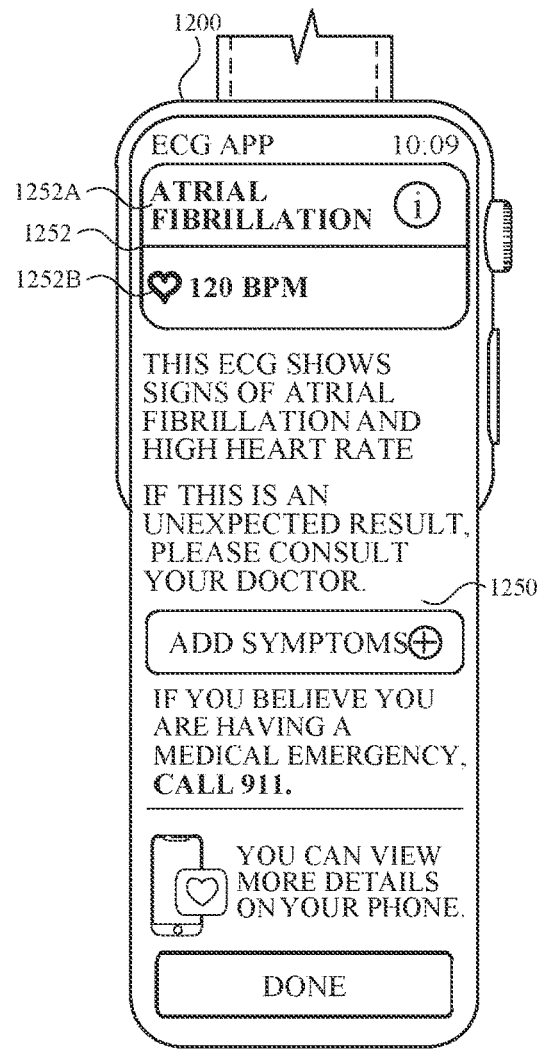

FIG. 12N illustrates a full expanded view of an example summary page 1250 corresponding to a second ECG recording performed using first electronic device 1200. As indicated by a summary region 1252, the second ECG recording has an Atrial Fibrillation result (an abnormal result), as shown by an evaluation result indication 1252A (e.g., showing "Atrial Fibrillation"), with a high heart rate (e.g., over 100 BPM), as shown by a BPM indication 1252B (e.g., showing "120 BPM"). In some embodiments, evaluation result indication 1252A is highlighted with the warning visual characteristic (e.g., text "Atrial Fibrillation" is displayed in a warning color, such as yellow, instead of a default color) and BPM indication 1252B is also highlighted with the warning visual characteristic (e.g., text "120 BPM" is displayed in the warning color, such as yellow).

Figure 12O:
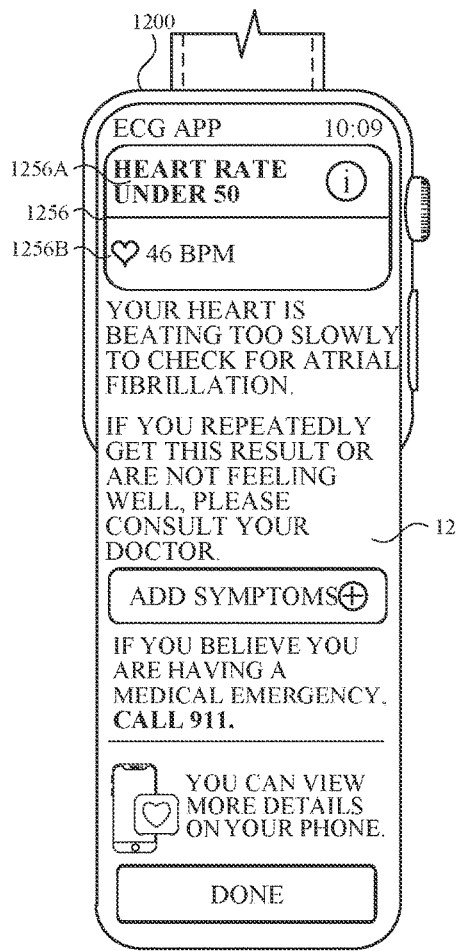

FIG. 12O illustrates a full expanded view of an example summary page 1254 corresponding to a third ECG recording performed using first electronic device 1200. As indicated in summary page 1254, the measured heart rate of the third ECG recording was too low (e.g., below 50 BPM) to check for Atrial Fibrillation. An evaluation result indication 1256A (e.g., showing "Heart rate under 50") of a summary region 1256 indicates a low heart rate result (an abnormal result) with a BPM indication 1256B (e.g., showing "46 BPM") of summary region 1256 showing the low heart rate. In some embodiments, evaluation result indication 1256A is highlighted with the warning visual characteristic (e.g., text "Heart rate under 50" is displayed in a warning color, such as yellow) and BPM indication 1256B is also highlighted with the warning visual characteristic (e.g., text "46 BPM" is displayed in the warning color, such as yellow).

Figure 12P:
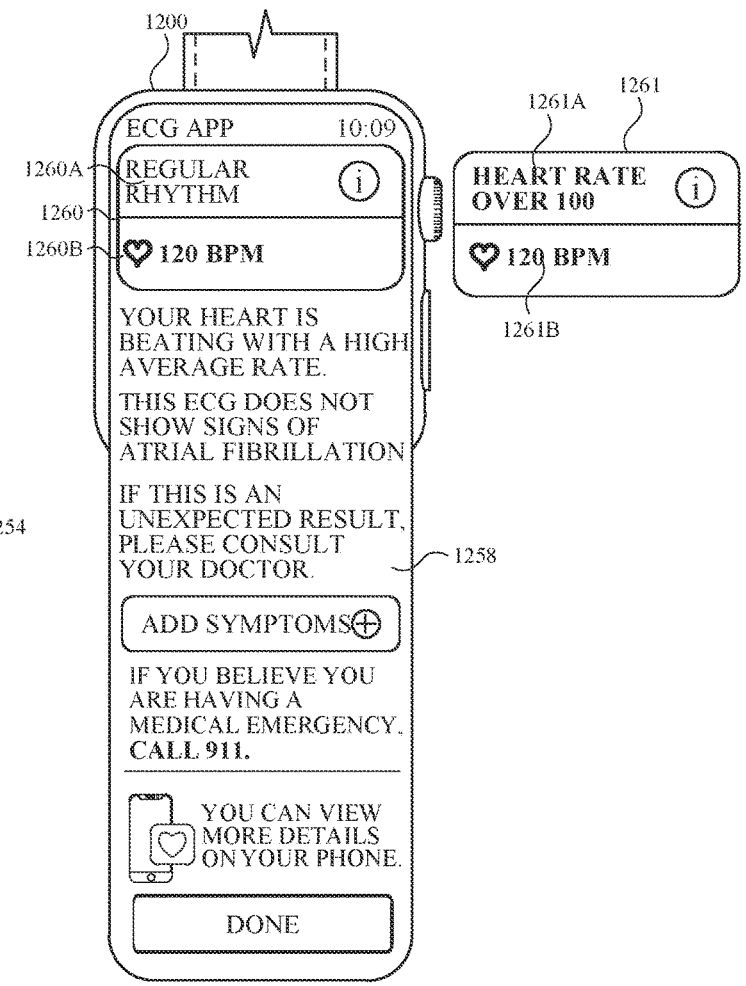

FIG. 12P illustrates a full expanded view of an example summary page 1258 corresponding to a fourth ECG recording performed using first electronic device 1200. As indicated by a summary region 1260, the fourth ECG recording has a regular rhythm result (a normal result, a non-Atrial Fibrillation result), as shown by an evaluation result indication 1260A (e.g., showing "Regular Rhythm"), with a high heart rate (e.g., over 100 BPM), as shown by a BPM indication 1260B (e.g., showing "120 BPM"). In some embodiments, evaluation result indication 1260A is not highlighted with the warning visual characteristic (e.g., text "Regular Rhythm" is displayed in a default color, such as white) and BPM indication 1260B is highlighted with the warning visual characteristic (e.g., text "120 BPM" is displayed in the warning color, such as yellow).

In some embodiments, as indicated by an alternate summary region 1261, if the heart rhythm result is a normal result (e.g., a non-Atrial Fibrillation result) and the heart rate result is an abnormal result (e.g., a high or low heart rate result), evaluation result 1261A of summary region 1261 indicates the abnormal heart rate result (e.g., by stating "Heart rate over 100," "Heart rate over 150," "Heart rate below 50") while BPM indication 1261B is maintained. In some embodiments, evaluation result indication 1261A is highlighted with the warning visual characteristic (e.g., text "Heart rate over 100" is displayed in a warning color, such as yellow) and BPM indication 1261B is highlighted with the warning visual characteristic (e.g., text "120 BPM" is displayed in the warning color, such as yellow).

FIG. 12Q illustrates a full expanded view of an example summary page 1262 corresponding to a fifth ECG recording performed using first electronic device 1200. As indicated in summary page 1262, the measured heart rate of the fifth ECG recording was too high (e.g., over 150 BPM) to check for Atrial Fibrillation. An evaluation result indication 1264A (e.g., showing "Heart rate over 150") of a summary region 1264 indicates a high heart rate result (an abnormal result) with a BPM indication 1264B (e.g., showing "152 BPM") of summary region 1264 showing the high heart rate. In some embodiments, evaluation result indication 1264A is highlighted with the warning visual characteristic (e.g., text "Heart rate over 150" is displayed in the warning color, such as yellow) and BPM indication 1264B is also highlighted with the warning visual characteristic (e.g., text "152 BPM" is displayed in the warning color, such as yellow).

FIG. 12R illustrates a full expanded view of an example summary page 1266 corresponding to a sixth ECG recording performed using first electronic device 1200. As indicated by a summary region 1268, the sixth ECG recording has a regular result (a normal result, a non-Atrial Fibrillation result), as shown by an evaluation result indication 1268A (e.g., showing "Regular Rhythm"), with a normal heart rate (e.g., 50-100 BPM), as shown by a BPM indication 1268B (e.g., showing "80 BPM"). In some embodiments, evaluation result indication 1268A is not highlighted with the warning visual characteristic (e.g., text "Regular Rhythm" is displayed in the default color, such as white) and BPM indication 1268B is also not highlighted with the warning visual characteristic (e.g., text "80 BPM" is displayed in the default color, such as white).

FIG. 12S illustrates a full expanded view of an example summary page 1270 corresponding to a seventh ECG recording performed using first electronic device 1200. As indicated by a summary region 1272, the seventh ECG recording has an inconclusive result (e.g., due to a poor reading), as shown by an evaluation result indication 1272A (e.g., showing "Inconclusive"), with an inconclusive heart rate, as shown by a BPM indication 1272B. In some embodiments, evaluation result indication 1272A is not highlighted with the warning visual characteristic (e.g., text "Inconclusive" is displayed in the default color, such as white) and BPM indication 1272B is also not highlighted with the warning visual characteristic (e.g., text "-BPM" is displayed in the default color, such as white). In some embodiments, summary page 1270 of an inconclusive results includes a text description explaining to the user why the evaluation was inconclusive.

FIGS. 13A-13B are a flow diagram illustrating a method for managing aspects of health monitoring, in accordance with some embodiments. Method 1300 is performed at a device (e.g., 100, 300, 500, 600B, 800A, 1000, 1200) with a display and one or more input devices (e.g., a rotatable and depressible watch crown with integrated biometric sensors (e.g., comprising one or more electrodes) for detecting characteristics of the user's heart (e.g., 1204), a touchscreen of the display, a mechanical button, a biometric sensor). Some operations in method 1300 are, optionally, combined, the orders of some operations are, optionally, changed, and some operations are, optionally, omitted.

As described below, method 1300 provides an intuitive way for managing health monitoring. The method reduces the cognitive burden on a user for managing health monitoring, thereby creating a more efficient human-machine interface. For battery-operated computing devices, enabling a user to manage health monitoring faster and more efficiently conserves power and increases the time between battery charges.

The first electronic device (e.g., 1200) captures (1302) biometric information with a biometric sensor that is in communication with the first electronic device (e.g., comprising one or more electrodes integrated an input device (e.g., 1204) operating in conjunction with one or more electrodes of a housing portion (e.g., backplate) of the first electronic device).

The first electronic device (e.g., 1200) displays (1304), on the display (e.g., 1202), a representation (e.g., 1208) of an evaluation of a medical characteristic (e.g., related to heart health) determined based on the biometric information (e.g., ECG data, BPM data, heart-related data) captured by the biometric sensor. Displaying, on the display (e.g., 1202), the representation of the evaluation of the medical characteristic improves visual feedback by enabling the user to quickly and easily see the result of the evaluation based on the captured biometric information. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, upon (or prior to) capturing the biometric information with the biometric sensor, the first electronic device (e.g., 1200) automatically disables a wireless communication radio (e.g., RF circuitry 108, a LTE connection) of the first electronic device and prevents notifications (e.g., of a message, of an alert) from being displayed. Automatically disabling the wireless communication radio of the first electronic device (e.g., 1200) and preventing notifications from being displayed enables the user to perform more accurate recordings of biometric information without manually disabling certain other functions of the device that may interrupt or interfere with the capturing of the biometric information. Performing an operation without requiring user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the notifications that are prevented from being displayed do not include a timer notification.

In some embodiments, upon (or in response to) completing capture of the biometric information, the first electronic device (e.g., 1200) automatically re-enables the wireless communication radio (e.g., RF circuitry 108, a LTE connection) and allows notifications to be displayed. Automatically re-enabling the wireless communication radio and allowing notifications to be displayed upon completing capture of the biometric information reduces the number of inputs required from the user to control the device by enabling the user to bypass having to manually re-enable the wireless communication radio and allow notifications to be displayed. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the medical characteristic includes a heart rhythm characteristic (e.g., a characteristic corresponding to 1208A) and a heart rate characteristic (e.g., a characteristic corresponding to 1208B), and the displayed representation of the evaluation of the medical characteristic includes a heart rhythm evaluation (e.g., a electrocardiogram evaluation, 1208*a*) summary and a heart rate evaluation (e.g., a BPM reading, 1208B) summary.

In some embodiments, the heart rhythm evaluation summary (e.g., 1252A) is displayed with a first visual characteristic (e.g., a first color, a warning color such as yellow) and the heart rate evaluation summary (e.g., 1252B) is displayed with the first visual characteristic when the heart rhythm evaluation corresponds to an abnormal result and the heart rate evaluation corresponds to an abnormal result. Displaying the heart rhythm evaluation summary (e.g., 1252A) with the first visual characteristic and the heart rate evaluation summary (e.g., 1252B) with the first visual characteristic when the heart rhythm evaluation corresponds to an abnormal result and the heart rate evaluation corresponds to an abnormal result improves visual feedback by enabling the user to quickly and easily recognize the out of the evaluation result and whether the evaluation result should be paid closer attention to (e.g., for further medical attention). Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the heart rhythm analysis evaluation (e.g., 1252A) corresponds to an abnormal result if an abnormal rhythm pattern is detected (e.g., signs of Atrial Fibrillation). In some embodiments, the heart rate evaluation (e.g., 1252B) corresponds to an abnormal result if the rate is greater than a high limit number (e.g., 100 BPM).

In some embodiments, the heart rhythm evaluation summary (e.g., 1248A) is displayed with the first visual characteristic and the heart rate evaluation summary (e.g., 1248B) is not displayed with the first visual characteristic when the heart rhythm evaluation corresponds to an abnormal result (e.g., signs of Atrial Fibrillation) and the heart rate evaluation corresponds to a normal result (e.g., 60-100 BPM). Displaying the heart rhythm evaluation summary (e.g., 1248A) with the first visual characteristic and not displaying the heart rate evaluation summary (e.g., 1248B) with the first visual characteristic when the heart rhythm evaluation corresponds to an abnormal result and the heart rate evaluation corresponds to a normal result improves visual feedback by enabling the user to quickly and easily recognize and differentiate between an abnormal result and a normal result, and whether an evaluation result should be paid closer attention to (e.g., for further medical attention). Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the heart rate evaluation summary (e.g., 1260A) is displayed with the first visual characteristic and the heart rhythm evaluation summary (e.g., 1260B) is not displayed with the first visual characteristic when the heart rate evaluation corresponds to an abnormal result (e.g., BPM below 50 or above 100) and the heart rhythm evaluation (e.g., 1260A) corresponds to a normal result. Displaying heart rate evaluation summary (e.g., 1260A) with the first visual characteristic and not displaying the heart rhythm evaluation summary (e.g., 1260B) with the first visual characteristic when the heart rate evaluation corresponds to an abnormal result (e.g., BPM below 50 or above 100) and the heart rhythm evaluation corresponds to a normal result improves visual feedback by enabling the user to quickly and easily recognize and differentiate between an abnormal result and a normal result, and whether an evaluation result should be paid closer attention to (e.g., for further medical attention). Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the heart rate evaluation summary (e.g., 1264A) is displayed with a first visual characteristic and the heart rhythm evaluation summary (e.g., 1264B) is displayed with the first visual characteristic when the heart rate evaluation corresponds to a highly abnormal result (e.g., BPM over 150 or below 50) such that a determination cannot be made on the heart rhythm evaluation. Displaying the heart rate evaluation summary (e.g., 1264A) and the heart rhythm evaluation summary (e.g., 1264B) with the first visual characteristic when the heart rate evaluation corresponds to a highly abnormal result (e.g., BPM over 150 or below 50) such that a determination cannot be made on the heart rhythm evaluation improves visual feedback by enabling the user to quickly and easily recognize that the result corresponds to a highly abnormal result and that the evaluation result should be paid closer attention to (e.g., for further medical attention). Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in accordance with a determination that the evaluation of the medical characteristic cannot be determined (e.g., because the biometric information captured by the biometric sensor is incomplete or is of poor quality), the first electronic device (e.g., 1200) displays (1306), in the representation of the evaluation, an indication that the evaluation was inconclusive (e.g., 1272A). In some embodiments, the evaluation also includes a text description (e.g., 1270) explaining to the user why the evaluation was inconclusive (e.g., due to a poor reading from the biometric sensor). Providing the text description explaining to the user why the evaluation result was inconclusive improves visual feedback and provides the user with more control of the device by enabling the user to easily understand why the evaluation result and inconclusive (e.g., such that the user can take a new recording that addresses a reason for the inconclusive result). Improving visual feedback to the user and providing additional control of the device (without cluttering the user interface with additional displayed controls) enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

While displaying the representation (e.g., 1208) of the evaluation of the medical characteristic, the first electronic device (e.g., 1200) detects (1308), via the one or more input devices, a sequence of one or more inputs (e.g., a sequence of one or more touch inputs on a touchscreen of the display (e.g., 1209, 1211, 1213)) to add user-specified symptoms (e.g., 1224) to the evaluation of the medical characteristic. In some embodiments, one or more symptoms are displayed in a list for user selection. Providing one or more symptoms as a list for user selection reduces the number of inputs required from the user to provide the one or more symptoms (e.g., allows the user to not have to type the one or more symptoms). Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the user selects one or more symptoms from the provided list of symptoms.

In some embodiments, while displaying, on the display (e.g. 1202), the representation (e.g., 1208) of the evaluation of the medical characteristic (e.g., a result of the evaluation, data from the evaluation, such as BPM), the first electronic device (e.g., 1200) detects, via a first input device (e.g., 1204), a scrolling input (e.g., 1207). In some embodiments, the first input device is a rotating crown (e.g., 1204) and the scrolling input is a rotation of the rotating crown (e.g., 1207). In some embodiments, the first input device is the touch layer of the display and the scrolling input is a scrolling touch gesture on the display (e.g., 1202). Further in such embodiments, in response to detecting the scrolling input, the first electronic device (e.g., 1200) scrolls a second user interface (e.g., 1206) that includes the representation of the evaluation of the medical characteristic. Additionally in such embodiments, the first electronic device (e.g., 1200) displays, on the display (e.g., 1202), an add-symptoms affordance (e.g., 1216) for adding the user-specified symptoms to the evaluation. Displaying, on the display (e.g., 1202), the add-symptoms affordance for adding the user-specified symptoms to the evaluation provides visual feedback by allowing the user to quickly recognize how to add one or more symptoms to an evaluation result. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the user-specified symptoms include a first symptom (e.g., 1226B) corresponding to a serious symptom (e.g., a symptom that may require immediate medical attention), and a first representation of the one or more representations of user-specified symptoms corresponding to the first symptom is displayed with a first visual characteristic (e.g., a warning color, such as yellow). In some embodiments, the user-specified symptoms include a second symptom (e.g., 1226A) corresponding to a non-serious symptom, and a second representation of the one or more representations of user-specified symptoms corresponding to the second symptom is displayed with a second visual characteristic (e.g., a non-warning color, a default color) that is different from the first visual characteristic.

In some embodiments, the evaluation of the medical characteristic is a normal result (no abnormalities detected, e.g., a normal result as discussed above with respect to method 700 and FIG. 6H) and the sequence of one or more inputs (e.g., 1209, 1211, 1213) to add the user-specified symptoms is detected while displaying the representation of the evaluation corresponding to the normal result. Thus, in some embodiments, one or more symptoms can be added to an evaluation with no abnormal results.

In some embodiments, while displaying the representation (e.g., 1208) of the evaluation of the medical characteristic, the first electronic device (e.g., 1200) detects, via the one or more input devices (e.g., 1202), a user activation of an information affordance (e.g., 1210). In such embodiments, in response to detecting the user activation of the information affordance, the first electronic device (e.g., 1200) displays, on the display (e.g., 1202), text information (e.g., 1212) related to the evaluation. Displaying, on the display (e.g., 1202), the text information (e.g., 1212) related to the evaluation in response to detecting the user activation of the information affordance provides more control of the device by enabling the user to easily access more information related to the evaluation result. Providing additional control options (without cluttering the user interface with additional displayed controls) enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the displayed text information related to the evaluation corresponds to the text information presented for the same type of evaluation during the onboarding process, as described in method 700 (e.g., FIGS. 6F-6L).

In response to detecting the sequence of one or more inputs (e.g., 1209, 1211, 1213), in accordance with a determination that at least one of the user-specified symptoms meet respective criteria, the first electronic device (e.g., 1200) displays (1310), on the display (e.g., 1202), a first user interface (e.g., a Symptom Alert user interface 1230) that includes an affordance (e.g., 1232) that, when activated, initiates a process for seeking immediate medical attention (e.g., initiating an emergency call, initiating a 911 call). Displaying, on the display (e.g., 1202), the first user interface (e.g., 1230) that includes the affordance that, when activated, initiates the process for seeking immediate medical attention improves user control of the device by enabling the user to quickly and easily recognize that immediate medical attention may be necessary and enables the user to easily and conveniently initiate a process for seeking immediate medical attention. Providing additional control options and reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In response to detecting the sequence of one or more inputs (e.g., 1209, 1211, 1213), in accordance with a determination that (all of) the user-specified symptoms do not meet the respective criteria, the first electronic device (e.g., 1200) displays (1312), on the display (e.g., 1202), the representation of the evaluation of the medical characteristic and one or more representations of user-specified symptoms without displaying the first user interface (e.g., without displaying interface 1230). Displaying, on the display (e.g., 1202), the representation of the evaluation of the medical characteristic and the one or more representations of the user-specified symptoms without displaying the first user interface (e.g., 1230) improves visual feedback by enabling the user to easily view the evaluation and the user-specified symptoms upon user selection of the symptoms. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, further in accordance with a determination that (all of) the user-specified symptoms do not meet the respective criteria, the first electronic device (e.g., 1200) detects (1312), via the one or more input devices (e.g., 1204), a scrolling gesture (e.g., a rotation of a rotating crow (e.g., 1219), a scrolling input on the touch layer of the display). In some embodiments, in response to detecting, via the one or more input devices, the scrolling gesture, the first electronic device (e.g., 1200) displays (1314), on the display (e.g., 1202), an option for seeking medical attention (e.g., a selectable text allowing the user to initiate a process for contacting 911 (e.g., 1240)). Displaying, on the display (e.g., 1202), the option for seeking medical attention in response to detecting the scrolling gesture improves user control of the device by providing the user with a quick and easy method for seeking medical attention, if the user determines that medical attention is needed. Providing additional control options (without cluttering the user interface with additional displayed controls) enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, subsequent to detecting the sequence of one or more inputs (e.g., 1209, 1211, 1213), the first electronic device (e.g., 1200) detects (1316) a user activation (e.g., 1221) of a confirmation button (e.g., 1242). In such embodiments, in response to (or subsequent to) detecting the user activation of the confirmation button, the first electronic device (e.g., 1200) transmits (1318) (e.g., via a wireless communication radio of the device) the evaluation of the medical characteristic from the first electronic device (e.g., 1200) to a second electronic device (e.g., 100, 300, 500, 600A), a smartphone that is paired with the first electronic device) for display of a corresponding representation of the evaluation of the medical characteristic on the second electronic device.

In some embodiments, the user-specified symptoms (e.g., 1226A, 1226B) cannot be modified after detecting the user activation of the confirmation button.

Note that details of the processes described above with respect to method 1300 (e.g., FIGS. 13A-13B) are also applicable in an analogous manner to the methods described above and below. For example, method 700 optionally includes one or more of the characteristics of the various methods described above with reference to method 1300. For another example, method 900 optionally includes one or more of the characteristics of the various methods described above with reference to method 1300. For another example, method 1100 optionally includes one or more of the characteristics of the various methods described above with reference to method 1300. For another example, method 1500 optionally includes one or more of the characteristics of the various methods described above with reference to method 1300. For brevity, these details are not repeated below.

FIGS. 14A-14I illustrate exemplary user interfaces for providing a health condition alert. The user interfaces in these figures are used to illustrate the processes described below, including the processes in FIG. 15. The exemplary user interfaces in these figures relate generally to providing a health condition alert, such as a heart condition alert, and are not limited to providing a specific type of health condition-related alert. Only for the sake of convenience, the exemplary user interfaces in these figures are described with reference to a type of heart-related condition—Atrial Fibrillation.

Figure 14A:
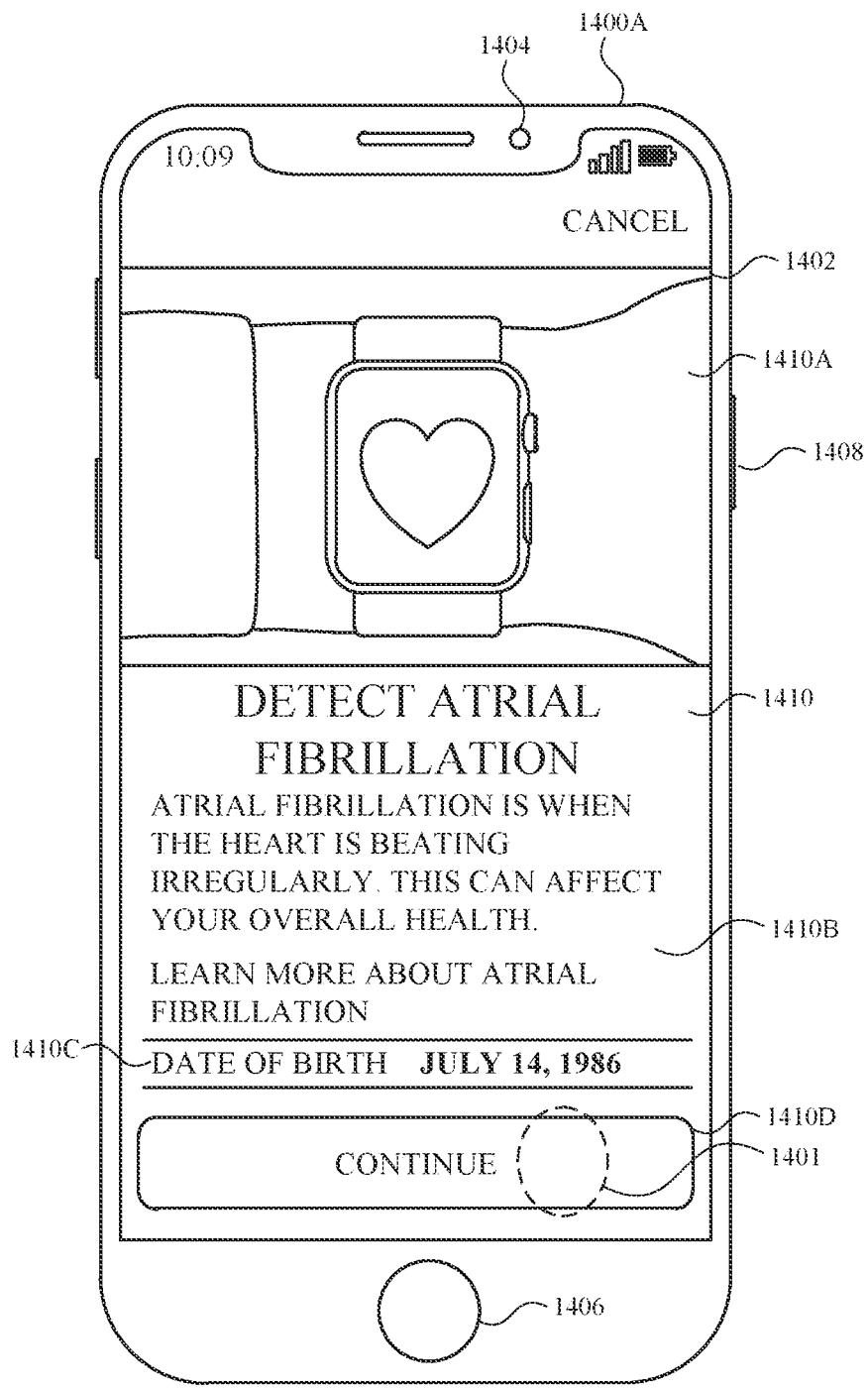
FIGS. 14A-14I illustrate exemplary user interfaces for providing a health condition alert.

FIG. 14A illustrates a first electronic device 1400A (e.g., a smartphone similar to first electronic device 600A) with a display 1402 and one or more input devices. In some embodiments, the one or more input devices include a touch layer of display 1402 for detecting touch input, one or more image sensors 1404 (e.g., a camera, a depth sensor), a first mechanical button 1406 configured to perform one or more operations (e.g., and including an integrated biometric sensor, such as a fingerprint sensor), and a second mechanical button 1408 configured to perform one or more operations. In some embodiments, first electronic device 1400A includes a wireless communication radio (e.g., for LTE, Bluetooth, WiFi connections). In some embodiments, first electronic device 1400A is paired with a second electronic device (e.g., a smartwatch). In some embodiments, the second electronic device corresponds to second electronic device 1400B described below with reference to FIGS. 14H-14J. In some embodiments, second electronic device 1400B includes a plurality of biometric sensors, including a biometric sensor (comprising one or more photodiode sensors) enclosed in a housing of the second electronic device and an integrated biometric sensor (e.g., integrated with an input device, such as a rotatable input device, of the second electronic device).

FIG. 14A illustrates first electronic device 1400A displaying, on display 1402, a first page 1410 of a setup process for performing initial setup of Atrial Fibrillation-detection management features (e.g., of an associated health application), where heart-related information (e.g., heart rhythm information) used to determine Atrial Fibrillation is captured using a second electronic device (e.g., second electronic device 1400B) paired with first electronic device 1400A. In some embodiments, first page 1410 of the setup process includes a graphical indication region 1410A that graphically indicates (e.g., via a static image, via an animation) a function of the Atrial Fibrillation-detection management features (e.g., recording heart rhythm information). In some embodiments, first page 1410 of the setup process includes a text description region 1410B describing background information relevant to the use of the Atrial Fibrillation-detection management features.

In some embodiments, first page 1410 of the setup process includes a date of birth entry field 1410C for receiving a user input corresponding to the user's date of birth, where the user's date of birth is used to determine whether the user meets a minimum age requirement (e.g., 22 years of age) to use the Atrial Fibrillation-detection management features. In some embodiments, date of birth entry field 1410C indicates (e.g., by stating "Required") that the user's date of birth must be entered in order to proceed with the setup process. In some embodiments, date of birth entry field 1410C includes scrollable month, day, and year fields.

In some embodiments, first page 1410 of the setup process does not include date of birth entry field 1410C. In some embodiments, first page 1410 of the setup process includes (e.g., in addition to or alternatively to date of birth entry field 1410C) an age restriction message (e.g., stating "You must be 22 years or older") indicating to the user that the user must meet the minimum age requirement.

In some embodiments, first page 1410 of the setup process includes an affordance 1410D for proceeding with the tutorial. In FIG. 14A, while displaying first page 1410 of the Atrial Fibrillation-detection management setup process and after having received an input corresponding to the user's date of birth in entry field 1410C, first electronic device 1400A detects (e.g., via a touch input) a user activation 1401 of affordance 1410D for proceeding with the setup process.

In some embodiments, in accordance with a determination that the minimum age requirement is not met (e.g., a determination made in response to detecting user activation 1401), first electronic device 1400A displays, on display 1402, an error notification (e.g., stating "The Atrial Fibrillation-detection management features are not intended for use by people under 22") indicating that the user does not meet the requisite minimum age requirement. In some embodiments, the error notification is overlaid on first page 1410 of the setup process. In some embodiments, while displaying the error notification, the background of the display (displaying first page 1410) is dimmed (thereby emphasizing the displayed error notification).

Figure 14B:
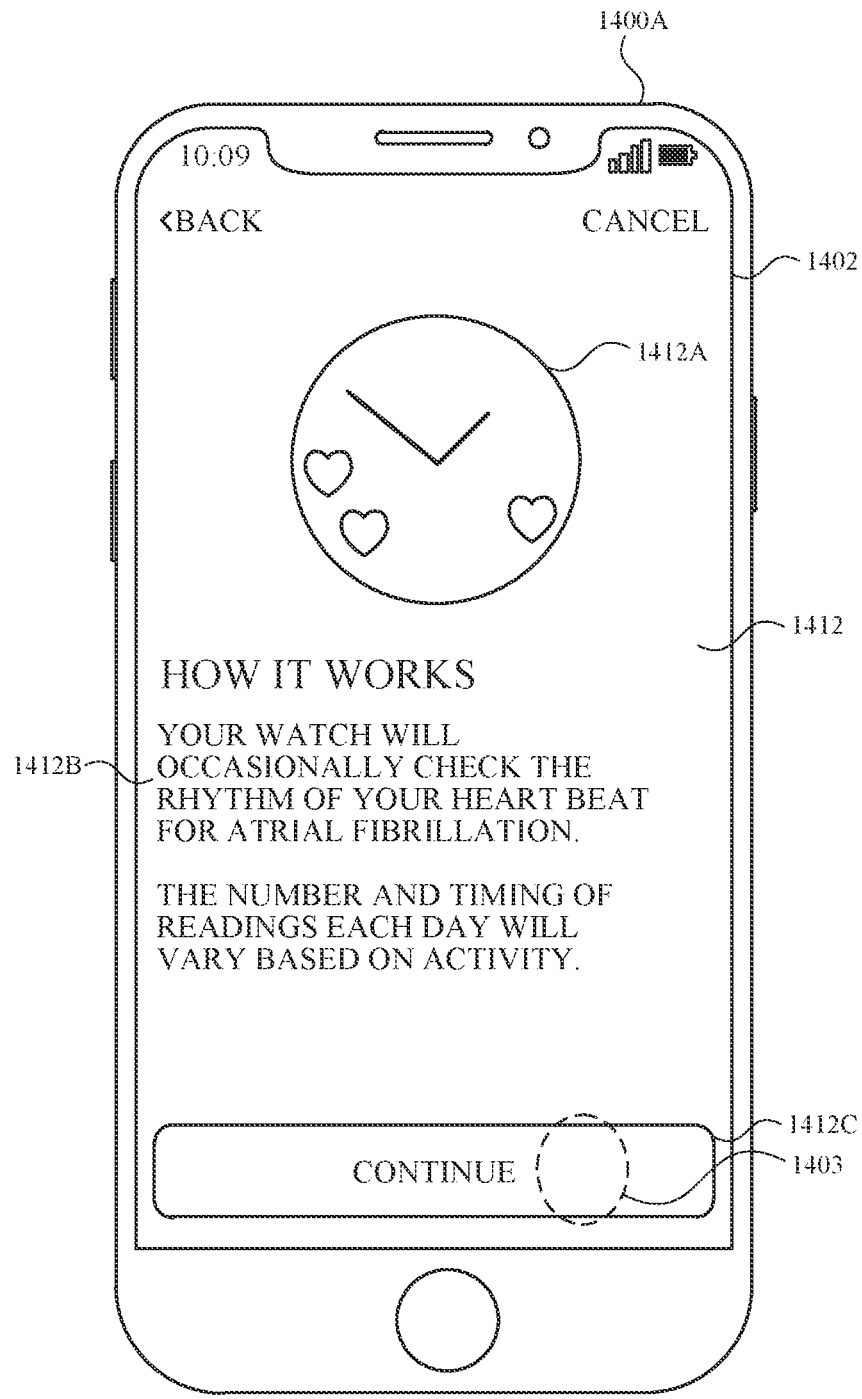

In some embodiments, in response to detecting user activation 1401 (and in accordance with a determination that the minimum age requirement is met), first electronic device 1400A displays, on display 1402 (e.g., replaces display of first page 1410 with), a second page 1412 of the setup process, as shown in FIG. 14B.

FIG. 14B illustrates first electronic device 1400A displaying, on display 1402, second page 1412 of the setup process for enabling Atrial Fibrillation-detection management features. In some embodiments, second page 1412 of the setup process includes an animation region 1412A that graphically indicates (e.g., via a static image, via an animation) a feature of Atrial Fibrillation detection (e.g., that heart-related information can be captured at several different times during time period to determine whether Atrial Fibrillation exists). In some embodiments, second page 1412 of the setup process includes a text description region 1412B that describes how the Atrial Fibrillation-detection features are implemented (using a second electronic device, such as second electronic device 1400B). In some embodiments, second page 1412 of the setup process includes an affordance 1412C for proceeding with the setup process.

In FIG. 14B, while displaying second page 1412 of the Atrial Fibrillation-detection management setup process, first electronic device 1400A detects (e.g., via a touch input) a user activation 1403 of affordance 1412C for proceeding with the setup process. In some embodiments, in response to detecting user activation 1403, first electronic device 1400A displays, on display 1402 (e.g., replaces display of second page 1412 with), a third page 1414 of the setup process, as shown in FIG. 14C.

In some embodiments, third page 1414 of the setup process indicates to the user (e.g., via a text description) one or more limitations of Atrial-Fibrillation evaluation results that are determined from heart-related information captured using the second electronic device (e.g., second electronic device 1400B) (e.g., using a biometric sensor of the second electronic device comprising one or more photodiode sensors). In some examples, third page 1414 of the setup process includes a list 1414A of one or more functional characteristics of the Atrial Fibrillation-detection features and/or medical characteristics that cannot be determined from the captured heart-related information (e.g., heart attack, blood clots/stroke). In some embodiments, third page 1414 of the setup process includes (e.g., at the bottom of the page), an affordance 1414B for proceeding with the tutorial.

Figure 14C:
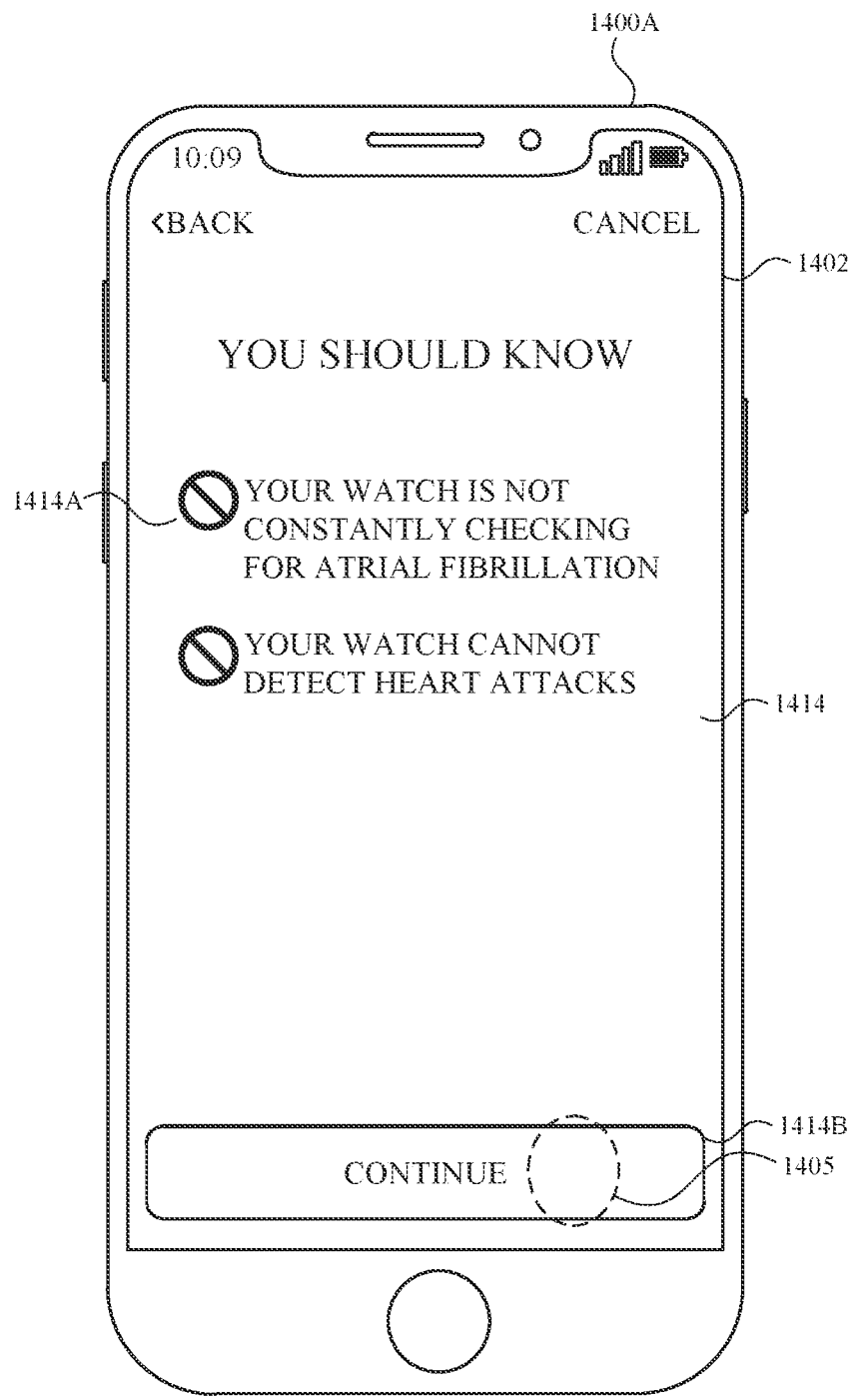

In FIG. 14C, while displaying, on display 1402, third page 1414 of the setup process, first electronic device 1400A detects (e.g., via a touch input) a user activation 1405 of affordance 1414B for proceeding with the setup process. In some embodiments, in response to detecting user activation 1405 of affordance 1414B, the device displays, on display 1402, a fourth page 1416 of the setup process, as shown in FIG. 14D.

Figure 14D:
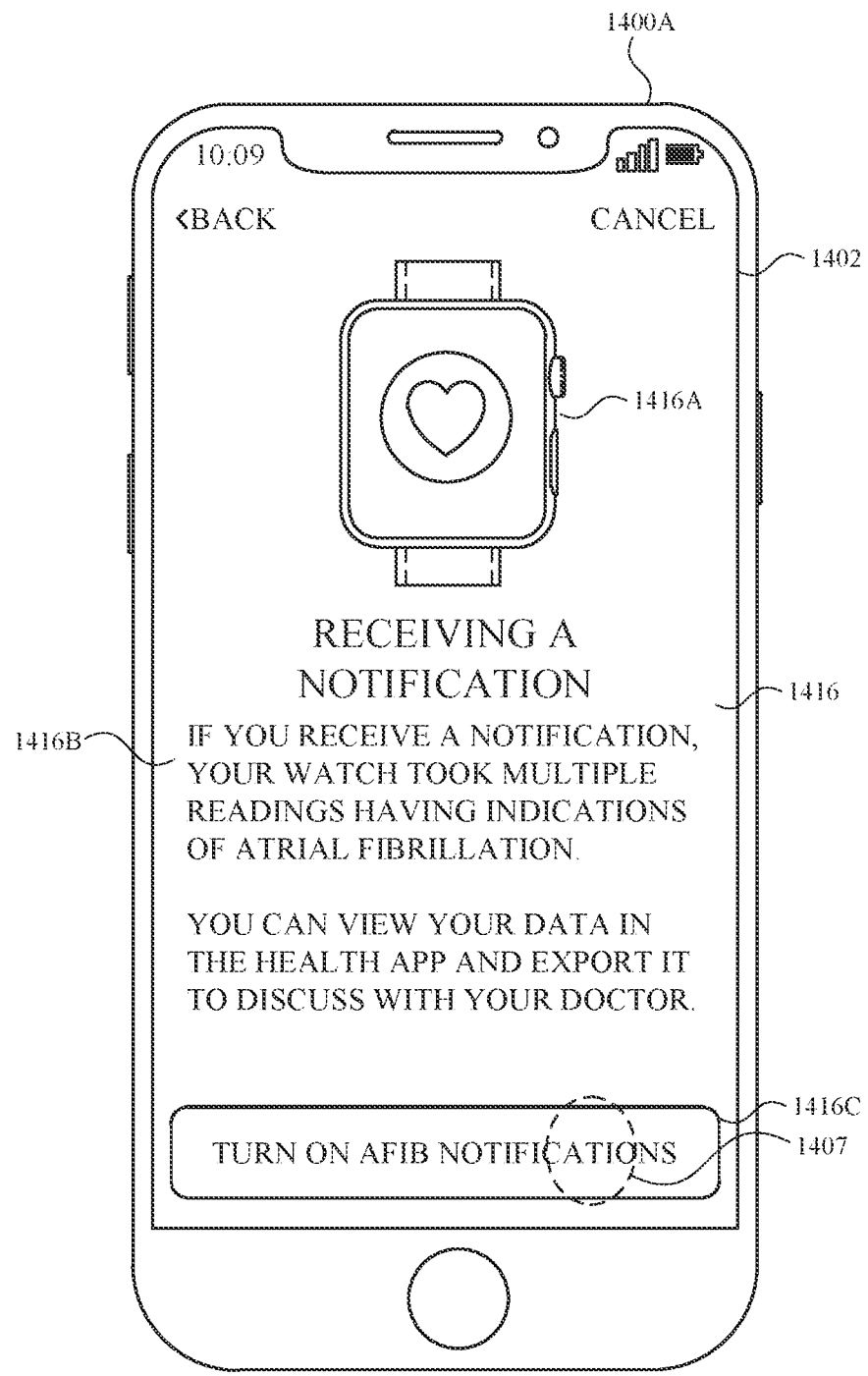

FIG. 14D shows first electronic device 1400A displaying, on display 1402, fourth page 1416 of the setup process. In some embodiments, fourth page 1416 of the setup process includes a graphical indication region 1416A and a text indication region 1416B that provides instructions on how to view and manage Atrial Fibrillation-detection features when Atrial Fibrillation is determined based on heart-related information (e.g., captured at different times) captured using the second electronic device (e.g., second electronic device 1400B).

In some embodiments, fourth page 1416 of the setup process includes a notification activation affordance 1416C (e.g., showing "Turn on AFib Notifications") for enabling notifications on first electronic device 1400A and/or second electronic device 1400B when Atrial Fibrillation is determined (using heart-related information captured using the second electronic device). In some embodiments, while displaying fourth page 1416 of the setup process, first electronic device 1400A detects (e.g., via a touch input) a user activation 1407 of notification activation affordance 1416C. In some embodiments, in response to detecting user activation 1407, first electronic device 1400A activates notifications to be displayed on first electronic device 1400A and/or second electronic device 1400B when Atrial Fibrillation is determined.

Figure 14E:
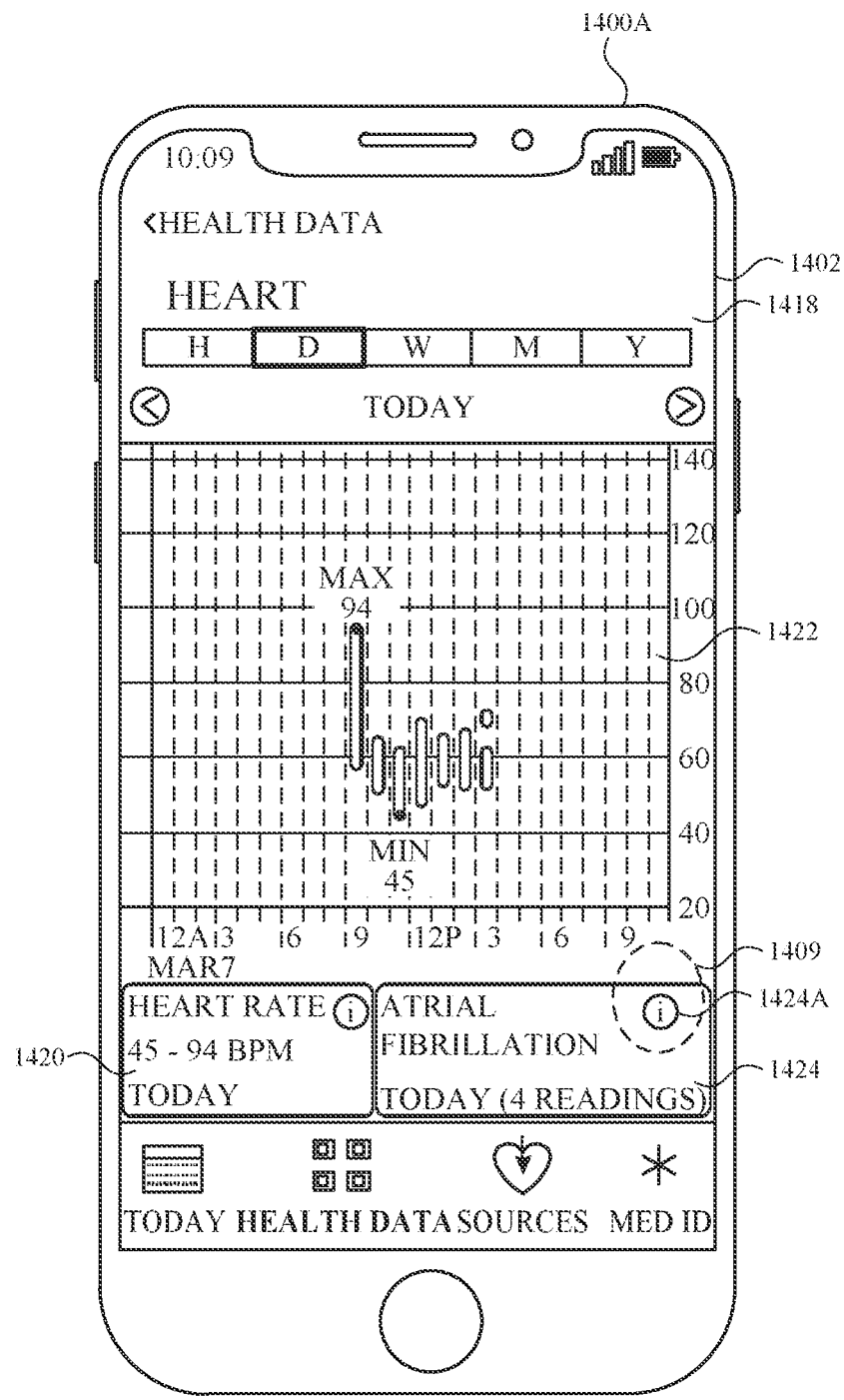

FIG. 14E illustrates first electronic device 1400A displaying, on display 1402, a heart data user interface 1418 of a health application associated with the Atrial Fibrillation-detection features (e.g., operating after activation of notifications as described with respect to FIGS. 14A-14D). In some embodiments, the health application is accessible via a corresponding icon on a home user interface of the operating system of first electronic device 1400A.

In some embodiments, heart data user interface 1418 of the health application includes a heart rate affordance 1420. In some embodiments, heart rate affordance 1420 includes an indication of a range of the user's heart rate measured (e.g., via second electronic device 1400B) during a certain period of time (e.g., today). In some embodiments, in response to detecting a user selection on heart rate affordance 1420, heart data user interface 1418 displays a graphical depiction of the heart rate information summarized by heart rate affordance 1420 within a graphical depiction region 1422 of the user interface (and further highlights the affordance with a particular visual characteristic, such as a different color, to indicate to the user that the heart rate affordance is currently selected by the user).

In some embodiments, heart data user interface 1418 of the health application includes an Atrial Fibrillation affordance 1424. In some embodiments, Atrial Fibrillation affordance 1424 includes an indication of the number of heart-related readings taken during a certain period of time (e.g., "Today (4 Readings)") by the second electronic device (e.g., second electronic device 1400B) (e.g., using a biometric sensor comprising one or more photodiode sensors of the second electronic device). In some embodiments, Atrial Fibrillation affordance 1424 includes an information affordance 1424A for viewing and managing information about existing heart-related recordings taken by the second electronic device (e.g., using a biometric sensor comprising one or more photodiode sensors) to detect Atrial Fibrillation.

In FIG. 14E, while displaying heart data user interface 1418 with Atrial Fibrillation affordance 1424 visible on display 1402, first electronic device 1400A detects (e.g., via a touch input) a user activation 1409 of information affordance 1424A of Atrial Fibrillation affordance 1424. In some embodiments, in response to detecting user activation 1409 of information affordance 1424A, first electronic device 1400A displays, on display 1402, an Atrial Fibrillation management user interface 1426, as shown in FIG. 14F.

Figure 14F:
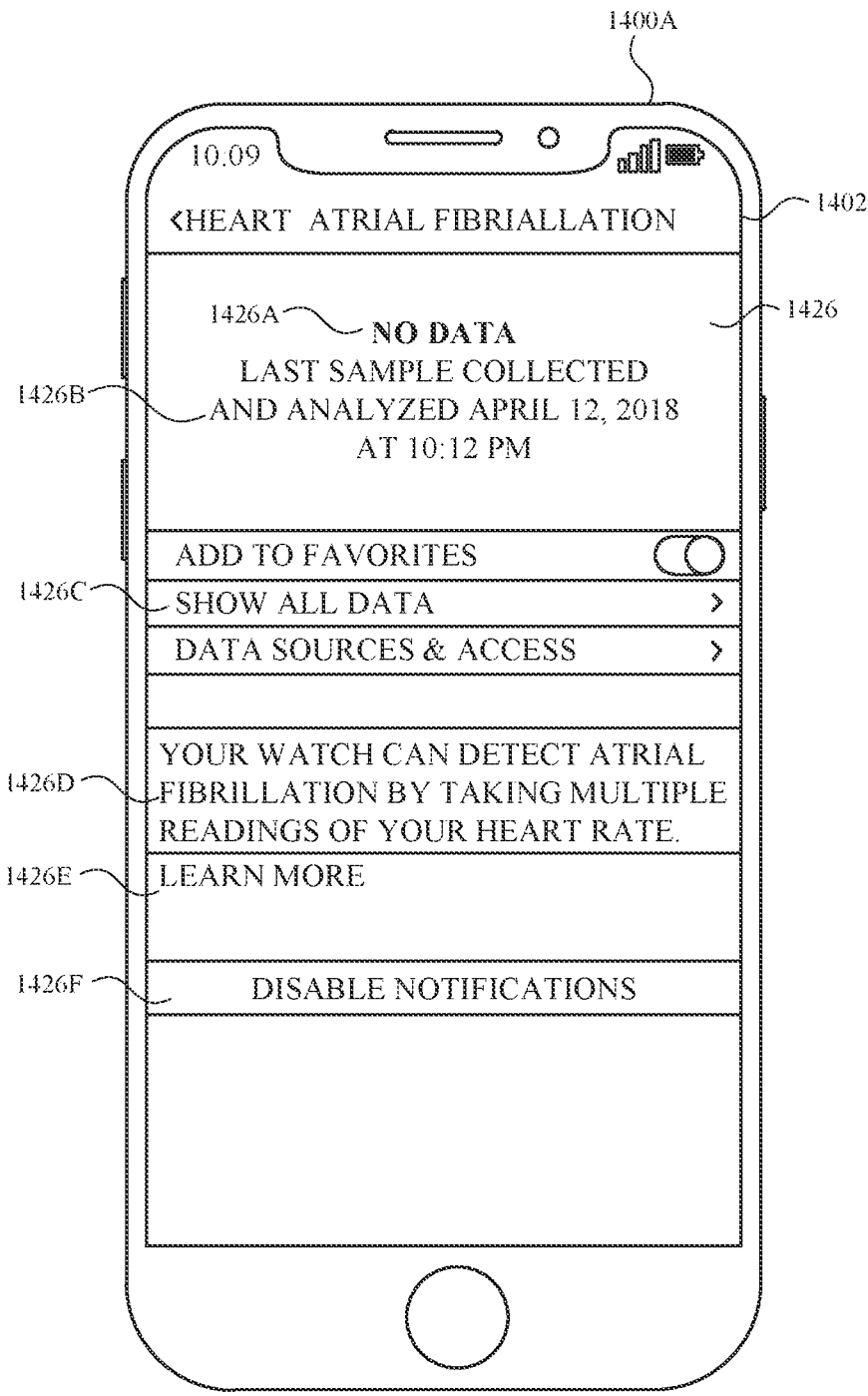

FIG. 14F illustrates first electronic device 1400A displaying, on display 1402, an Atrial Fibrillation management user interface 1426. In some embodiments, Atrial Fibrillation management user interface 1426 includes an alert log indication region 1426A indicating Atrial Fibrillation alerts (if any) that have been generated upon detection of the condition using the second electronic device (e.g., second electronic device 1400B). In some embodiments, if Atrial Fibrillation has not yet been detected (and thus no Atrial Fibrillation alerts have been generated), alert log indication region 1426A indicates (e.g., by stating "No data") that alerts have not yet been generated for Atrial Fibrillation detection.

In some embodiments, Atrial Fibrillation management user interface 1426 includes a recent analysis indication 1426B indicating the time(s) of one or more most recent measurements of heart-related information made by the second electronic device (e.g., second electronic device 1400B) (e.g., using a biometric sensor comprising one or more photodiode sensors of the second electronic device). In some embodiments, the one or more recent measurements shown in recent analysis indication 1426B only include heart-related information captured after an Atrial Fibrillation alert has been presented (if any) by first electronic device 1400A and/or second electronic device 1400B.

In some embodiments, Atrial Fibrillation management user interface 1426 includes a show all affordance 1426C for viewing a record of all past measurements of heart-related information using the second electronic device (e.g., second electronic device 1400B) (e.g., using a biometric sensor comprising one or more photodiode sensors of the second electronic device).

In some embodiments, Atrial Fibrillation management user interface 1426 includes an indication 1426D (e.g., a brief textual description) of how Atrial Fibrillation is detected by the second electronic device (e.g., second electronic device 1400B). In some embodiments, Atrial Fibrillation management user interface 1426 includes a learn more affordance 1426E for viewing additional information (e.g., expounding upon the description shown in indication 1426D) about the Atrial Fibrillation-detection features.

In some embodiments, Atrial Fibrillation management user interface 1426 includes a disable notifications affordance 1426F for disabling notifications from being presented (on first electronic device 1400A and/or second electronic device 1400B) when Atrial Fibrillation is detected.

Figure 14G:
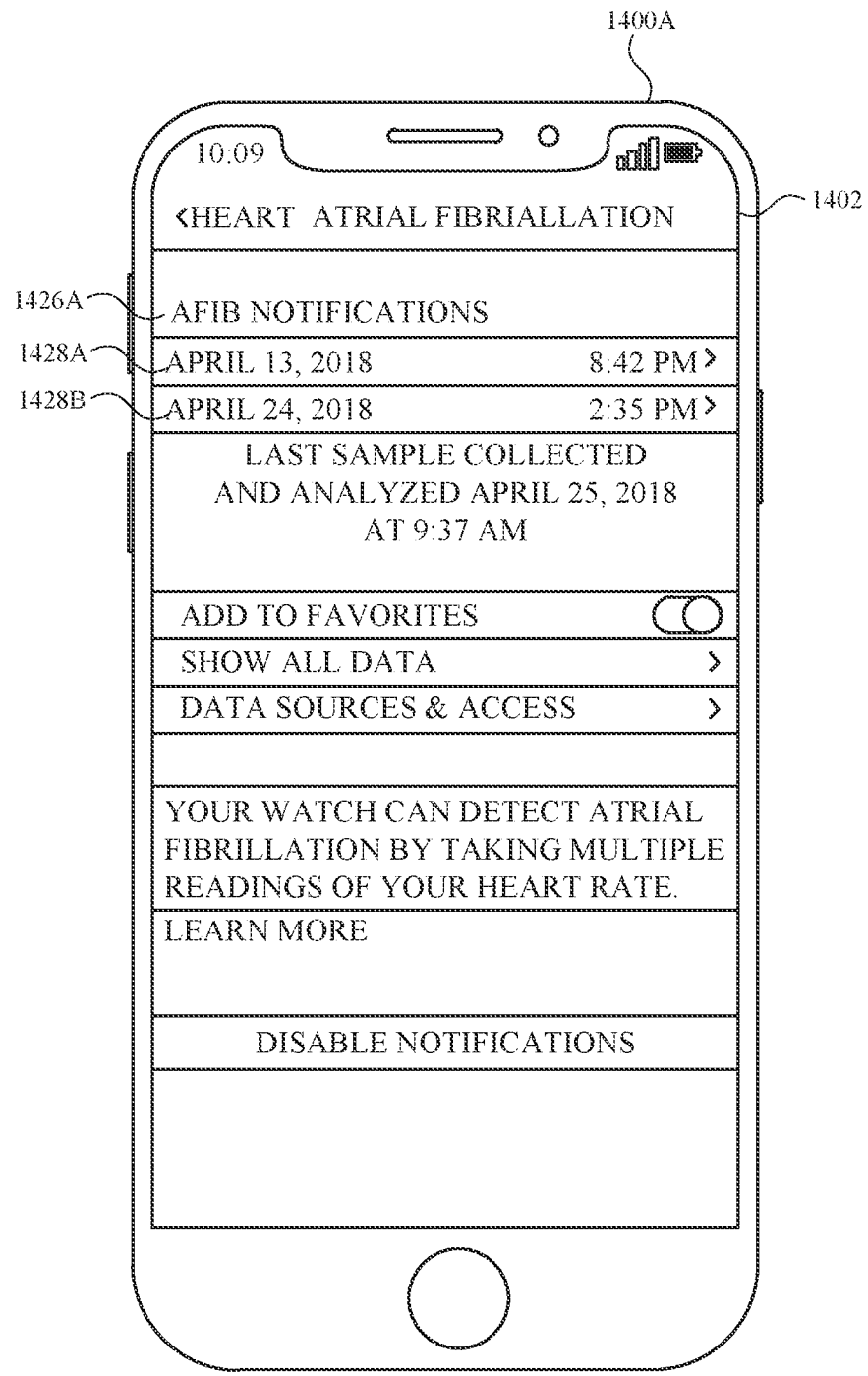

FIG. 14G illustrates first electronic device 1400A displaying, on display 1402, Atrial Fibrillation management user interface 1426 after two previous Atrial Fibrillation alerts have been presented at first electronic device 1400A and/or second electronic device 1400B, as indicated in alert log indication region 1426A. In FIG. 14G, alert log indication region 1426A includes a first alert log 1428A corresponding to a first Atrial Fibrillation alert (upon a first detection of Atrial Fibrillation) and a second alert log 1428B corresponding to a second Atrial Fibrillation alert (upon a second detection of Atrial Fibrillation different from/separate from the first detection of Atrial Fibrillation).

In some embodiments, an alert log (e.g., first alert log 1428A and second alert log 1428B) includes a time at which the alert was generated. In some embodiments, in response to detecting a user activation of an alert log, first electronic device 1400A displays, on display 1402, a detailed alert log page that includes more detailed information about the captured heart-related information corresponding to the alert log (e.g., heart rate information, separate non-contiguous number of times during which the heart-related information was captured).

Figure 14H:
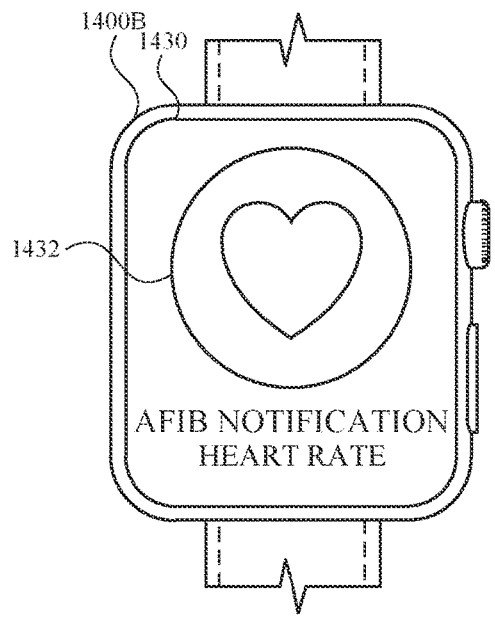
Figure 14I:
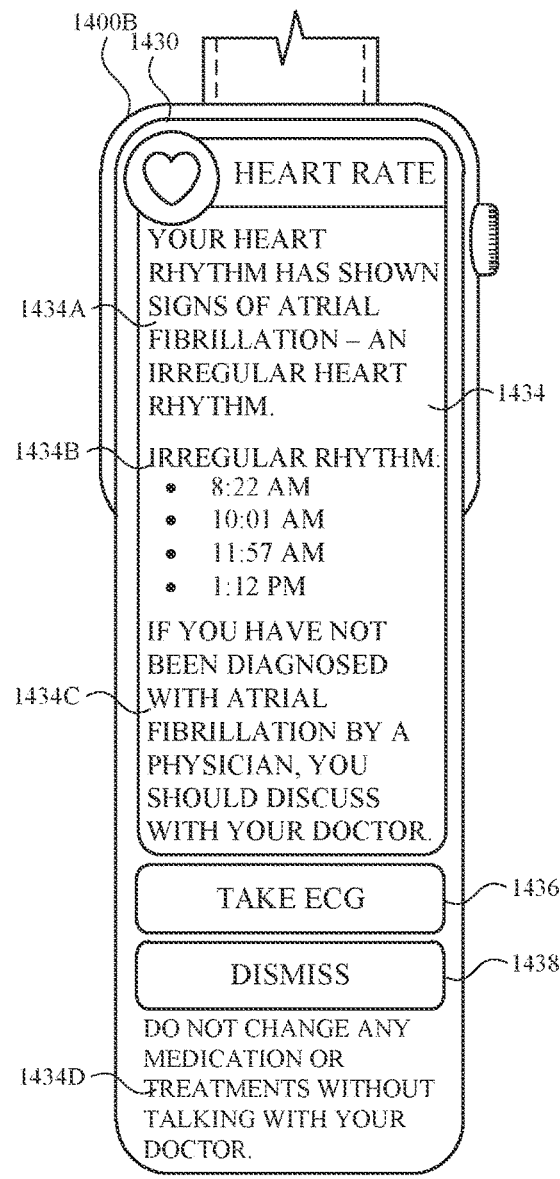
Figure 15:
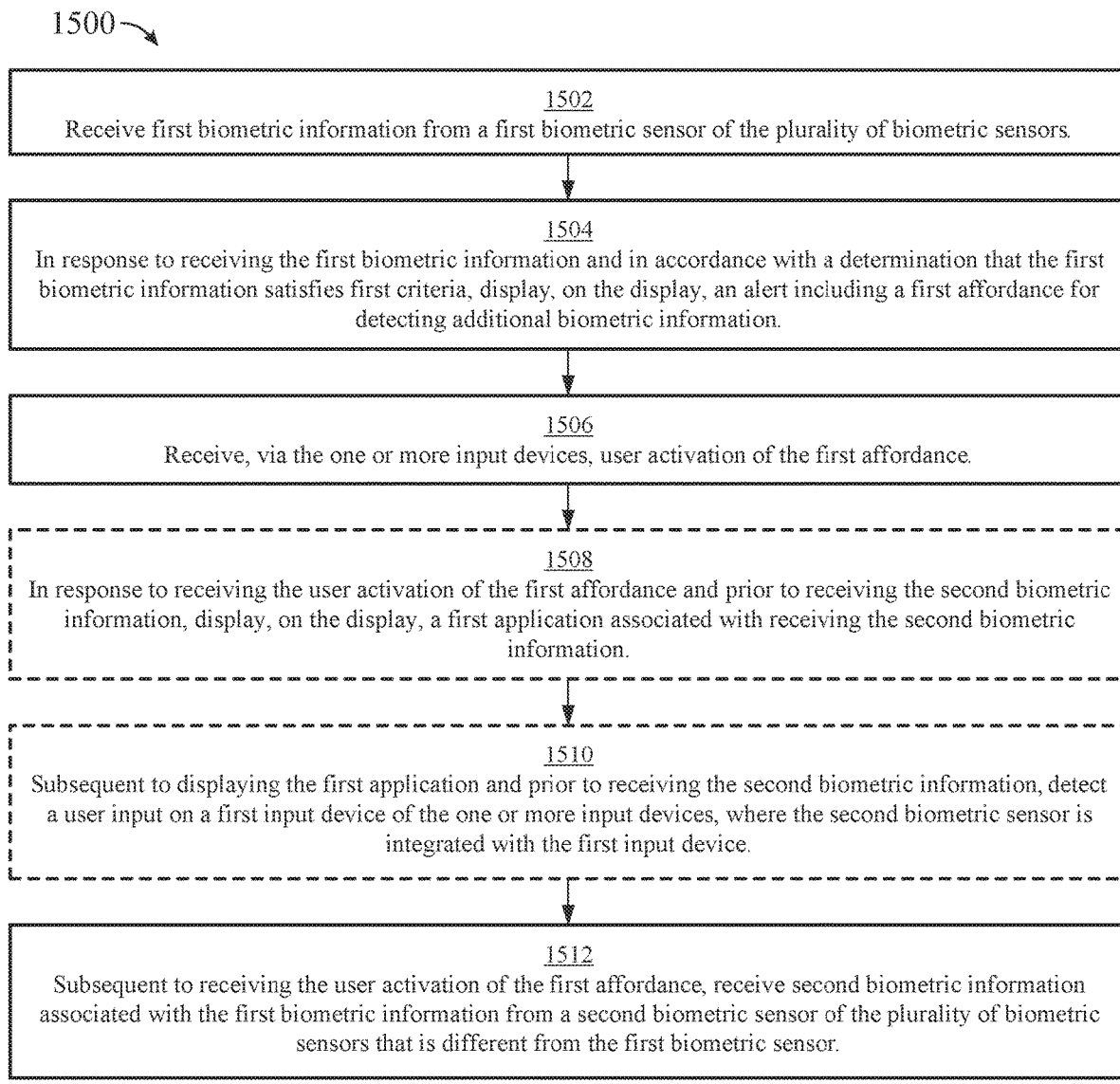
FIG. 15 illustrates a flow diagram for providing a health condition alert, in accordance with some embodiments.

FIG. 14H illustrates second electronic device 1400B (e.g., paired with first electronic device 1400A and including a biometric sensor comprising one or more photodiode sensors for detecting heart-related information) displaying, on a display 1430, an Atrial Fibrillation notification 1432 corresponding to a received Atrial Fibrillation alert. In some embodiments, in response to detecting a user activation (e.g., via a touch input on display 1430 or via a scrolling gesture (e.g., a rotation of a rotating input device of second electronic device 1400B or a scrolling input on display 1430 of second electronic device 1400B)) of Atrial Fibrillation notification 1432, second electronic device 1400B displays, on display 1430, an Atrial Fibrillation alert 1434, as shown in FIG. 14I.

In some embodiments, Atrial Fibrillation alert 1434 includes an indication 1434A (e.g., a textual description) describing the reason for the alert (e.g., a detection of Atrial Fibrillation) and an explanation of the medical condition (e.g., Atrial Fibrillation) associated with the alert. In some embodiments, Atrial Fibrillation alert 1434 includes an indication 1434B listing the one or more times (corresponding to measurements of heart-related information taken by second electronic device 1400B (e.g., using a biometric sensor comprising one or more photodiode sensors)) during which Atrial Fibrillation was detected by the device. In some embodiments, indication 1434B includes (not shown in FIG. 14I) one or more times and dates (e.g., within the previous 48 hours) during which Atrial Fibrillation was detected by the device. In some embodiments, Atrial Fibrillation alert 1434 includes an indication 1434C indicating that medical attention may be required (e.g., stating "If you have not been diagnosed with Atrial Fibrillation by a physician, you should discuss with your doctor"). In some embodiments, Atrial Fibrillation alert 1434 includes an indication 1434D warning that the user should not take a medical action (e.g., changing medication or treatments) without consulting a physician.

In some embodiments, Atrial Fibrillation alert 1434 includes an ECG affordance 1436 for taking more detailed heart-related information using an ECG application of second electronic device 1400B (e.g., corresponding to the ECG application discussed above with respect to FIGS. 6A-6AE, 8A-8S, 10A-10J, and 12A-12S). In some embodiments, the more detailed heart-related information captured using the ECG application relates to the condition (e.g., Atrial Fibrillation) detected by second electronic device 1400B without using the ECG application. In some embodiments, using the ECG application, the more detailed heart-related information is captured by one or more biometric sensors of second electronic device 1400B that comprise one or more electrodes of (e.g., integrated in) an input device (e.g., a rotatable and depressible input device) of second electronic device 1400B and one or more electrodes of (e.g., integrated in) a housing portion (e.g., the backplate) of second electronic device 1400B, where the one or more electrodes integrated in the input device operate in conjunction with the one or more electrodes of the housing portion to capture the more detailed heart-related information (e.g., ECG information). Features concerning the one or more biometric sensors of second electronic device 1400B used to capture the more detailed heart-related information (e.g., ECG information) is described in greater detail in Appendix A. In some embodiments, Atrial Fibrillation alert 1434 includes a dismiss affordance 1438 for dismissing the alert (e.g., without proceeding to the ECG application to record more detailed heart-related information).

FIG. 15 is a flow diagram illustrating a method for providing a health condition alert, in accordance with some embodiments. Method 1500 is performed at a device (e.g., 100, 300, 500, 600B, 800A, 1000, 1200, 1400B) with a display and one or more input devices (e.g., a rotatable and depressible input device with an integrated biometric sensor(s) (e.g., comprising one or more electrodes) for detecting characteristics of the user's heart (e.g., 1204), a touch-sensitive surface, a mechanical button). The device is operably connected to a plurality of biometric sensors (e.g., a physical activity tracking sensor; a sensor integrated into electronic device; a plurality of sensors discrete from the electronic device that are connected (e.g., wireless connected) to the device). Some operations in method 1500 are, optionally, combined, the orders of some operations are, optionally, changed, and some operations are, optionally, omitted.

As described below, method 1500 provides an intuitive way for providing a health condition alert. The method reduces the cognitive burden on a user for managing a health condition, thereby creating a more efficient human-machine interface. For battery-operated computing devices, enabling a user to manage health monitoring faster and more efficiently conserves power and increases the time between battery charges.

The electronic device (e.g., 1400B) receives (1502) (e.g., via an internal connection from an integrated sensor of the electronic device (e.g., 1400), via a wireless connection from a discrete sensor) first biometric information from a first biometric sensor of the plurality of biometric sensors. In some embodiments, the first biometric sensor comprises one or more photodiode sensors (e.g., enclosed in a housing of the electronic device). In some embodiments, the first biometric information comprises biometric information recorded at a first time and biometric information recorded at a second time different from (e.g., spaced apart from, non-contiguous with) the first time (e.g., a common time on a different day of the week).

In response to receiving the first biometric information and in accordance with a determination that the first biometric information satisfies first criteria (e.g., because the first biometric information includes heart rate or rhythm information that is abnormal and, optionally, because during a predetermined period of time (e.g., 48 hours), the electronic device (e.g., 1400B) has detected a threshold number of readings (e.g., five readings) having indications of irregular heart rate or rhythm), the electronic device (e.g., 1400B) displays (1504), on the display (e.g., 1430), an alert (e.g., 1434) including a first affordance (e.g., 1436) for detecting additional biometric information (e.g., using an ECG application on the electronic device). Displaying an alert that includes a first affordance for detecting additional biometric information in response to receiving the first biometric information and in accordance with a determination that the first biometric information satisfies first criteria improves visual feedback by quickly (and in an easily-recognizable method) indicating to the user that an action (e.g., measuring additional biometric information) can be taken on the device. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the biometric information relates to heart-related information. In some embodiments, the first criteria comprises abnormal heart rhythm information.

In some embodiments, the alert (e.g., 1434) includes one or more times (e.g., 1434B) during which the first biometric information was recorded by the electronic device. In some embodiments, the alert includes an indication (e.g., 1434A, a text description) of a medical condition (e.g., abnormal heart rhythm, Atrial Fibrillation) identified based on the first biometric information. In some embodiments, the alert includes an indication (e.g., 1434C, a text description) to seek medical attention. Including an indication to seek medical attention enhances the operability of the device by quickly and efficiently indicating to the user an action relating to information provided by the device can be taken. Enhancing the operability of the device makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

The electronic device (e.g., 1400B) receives (1506), via the one or more input devices, user activation of the first affordance (e.g., 1436).

Subsequent to receiving the user activation of the first affordance (e.g., 1436), the electronic device (e.g., 1400B) receives (1512) (e.g., using the ECG application) second biometric information (e.g., more detailed heart rhythm information, ECG information) associated with the first biometric information from (at least) a second biometric sensor (e.g., a biometric sensor integrated with an input device (e.g., 636, 804, 1004, 1204, such as a rotatable input device) of the plurality of biometric sensors that is different from the first biometric sensor. In some embodiments, the second biometric sensor is integrated with a first input device (e.g., 636, 804, 1004, 1204, a rotatable and depressible input device) of the one or more input devices. In some embodiments, a first type of input on the first input device (e.g., 629, 801, 1005, such as a non-press input or a contact input, activates a feature(s) associated with activation of the second biometric sensor but does not activate a feature(s) associated with activation of the first input device.

In some embodiments, in response to receiving the user activation of the first affordance (e.g., 1436) and prior to receiving the second biometric information, the electronic device (e.g., 1400B) displays (1508), on the display (e.g., 1430), a first application (e.g., 806, 1006, an ECG application) associated with receiving the second biometric information. Displaying the first application associated with receiving the second biometric information in response to receiving the user activation of the first affordance and prior to receiving the second biometric information improves visual feedback by enabling the user to quickly and easily recognize that the second biometric information to be captured relates to features of the first application. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, subsequent to displaying the first application (e.g., 806, 1006, an ECG application) and prior to receiving the second biometric information, the electronic device (e.g., 1400B) detects (1510) a user input (e.g., 629, 801, 1005, a non-press input, a contact input) on a first input device (e.g., 636, 804, 1004, 1204, a rotatable and depressible input device) of the one or more input devices, where the second biometric sensor is integrated with the first input device. In some embodiments, in response to detecting the user input, the electronic device receives the second biometric information from the second biometric sensor.

In some embodiments, the second biometric information is received from the second biometric sensor while the user input (e.g., 629, 801, 1005, a non-press input, a contact input) is maintained on the first input device (e.g., 636, 804, 1004, 1204, a rotatable and depressible input device). In some embodiments, in response to detecting that the user input is no longer maintained on the first input device, the electronic device (e.g., 1400B) ceases receiving the second biometric information from the second biometric sensor. In some embodiments, if the user input is restored within a predetermined period of time, the electronic device resumes receiving the second biometric information from the second biometric sensor.

Note that details of the processes described above with respect to method 1500 (e.g., FIG. 15) are also applicable in an analogous manner to the methods described above. For example, method 700 optionally includes one or more of the characteristics of the various methods described above with reference to method 1500. For another example, method 900 optionally includes one or more of the characteristics of the various methods described above with reference to method 1500. For another example, method 1100 optionally includes one or more of the characteristics of the various methods described above with reference to method 1500. For another example, method 1300 optionally includes one or more of the characteristics of the various methods described above with reference to method 1500. For brevity, these details are not repeated below.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the delivery to users of invitational content or any other content that may be of interest to them.

The present disclosure contemplates that in some instances, this gathered data may include personal information data that uniquely identifies or can be used to contact or locate a specific person. Such personal information data can include demographic data, location-based data, telephone numbers, email addresses, home addresses, or any other identifying information.

The present disclosure recognizes that the use of such personal information data, in the present technology, can be used to the benefit of users. For example, the personal information data can be used to deliver targeted content that is of greater interest to the user. Accordingly, use of such personal information data enables calculated control of the delivered content. Further, other uses for personal information data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services. In another example, users can select not to provide location information for targeted content delivery services. In yet another example, users can select to not provide precise location information, but permit the transfer of location zone information.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publically available information.

What is claimed is:

1. A first electronic device, comprising:
   a display;
   one or more input devices including a biometric sensor;
   one or more processors; and
   memory storing one or more programs configured to be executed by the one or more processors, the one or more programs including instructions for:
   displaying, on the display, a first user interface indicating that the first electronic device is ready to detect biometric information;
   detecting a first input with the biometric sensor, wherein the first input satisfies a first set of criteria, the first set of criteria including a first criterion that is satisfied when the first input remains in contact with the biometric sensor for a threshold period of time, and a second criterion that is satisfied when an amount of movement is below a predetermined threshold;
   in response to detecting the first input with the biometric sensor:
      starting to record biometric information detected by the biometric sensor; and
      displaying, on the display, a second user interface that is different from the first user interface, wherein the second user interface includes an indication of progress in recording the biometric information;
   after recording at least a portion of the biometric information, detecting, via the one or more input devices, that the first set of criteria are no longer met;
   in response to detecting that the first criterion is no longer met, replacing display of the second user interface with the first user interface; and
   in response to detecting that the second criterion is no longer met, resetting the indication of progress in recording the biometric information and maintaining display of the second user interface.

2. The first electronic device of claim 1, wherein the recorded biometric information includes an electrocardiogram recording derived from the biometric information detected by the biometric sensor.

3. The first electronic device of claim 1, wherein the one or more programs further include instructions for:
   prior to displaying the first user interface, displaying a home user interface that includes an application affordance corresponding to a health monitoring application;
   detecting, via the one or more input devices, a user activation of the application affordance; and
   in response to detecting the user activation of the application affordance, displaying, on the display, the first user interface.

4. The first electronic device of claim 1, wherein the biometric sensor is a contact-based sensor.

5. The first electronic device of claim 1, wherein the first user interface includes a graphical animation indicating that the first electronic device is ready to detect biometric information.

6. The first electronic device of claim 5, wherein the one or more programs further include instructions for:
   while displaying the second user interface and recording the biometric information, displaying a visual representation of the recorded biometric information, wherein the recorded biometric information is filtered and scaled such that the visual representation of the recorded biometric information can be displayed within the graphical animation.

7. The first electronic device of claim 1, wherein the second user interface includes a graphical representation that corresponds to a visualization of the biometric information from the recorded biometric information and a timer indicating an amount of time remaining to complete the recording of the biometric information.

8. The first electronic device of claim 1, wherein the second criterion is met when an amount of detected movement of the first electronic device is below the predetermined threshold.

9. The first electronic device of claim 1, wherein the second criterion is met when an amount of detected movement of the first input is below the predetermined threshold.

10. The first electronic device of claim 1, wherein the one or more programs further include instructions for:
after taking a first recording of first biometric information and a second recording of second biometric information different from the first biometric information, transmitting, to a second electronic device, the recorded first biometric information and the recorded second biometric information.

11. The first electronic device of claim 1, wherein the indication of progress is a countdown timer.

12. A non-transitory computer-readable storage medium storing one or more programs configured to be executed by one or more processors of a first electronic device with a display and one or more input devices including a biometric sensor, the one or more programs including instructions for:
displaying, on the display, a first user interface indicating that the first electronic device is ready to detect biometric information;
detecting a first input with the biometric sensor, wherein the first input satisfies a first set of criteria, the first set of criteria including a first criterion that is satisfied when the first input remains in contact with the biometric sensor for a threshold period of time, and a second criterion that is satisfied when an amount of movement is below a predetermined threshold;
in response to detecting the first input with the biometric sensor:
starting to record biometric information detected by the biometric sensor; and
displaying, on the display, a second user interface that is different from the first user interface, wherein the second user interface includes an indication of progress in recording the biometric information;
after recording at least a portion of the biometric information, detecting, via the one or more input devices, that the first set of criteria are no longer met;
in response to detecting that the first criterion is no longer met, replacing display of the second user interface with the first user interface; and
in response to detecting that the second criterion is no longer met, resetting the indication of progress in recording the biometric information and maintaining display of the second user interface.

13. The non-transitory computer-readable storage medium of claim 12, wherein the recorded biometric information includes an electrocardiogram recording derived from the biometric information detected by the biometric sensor.

14. The non-transitory computer-readable storage medium of claim 12, wherein the one or more programs further include instructions for:
prior to displaying the first user interface, displaying a home user interface that includes an application affordance corresponding to a health monitoring application;
detecting, via the one or more input devices, a user activation of the application affordance; and
in response to detecting the user activation of the application affordance, displaying, on the display, the first user interface.

15. The non-transitory computer-readable storage medium of claim 12, wherein the biometric sensor is a contact-based sensor.

16. The non-transitory computer-readable storage medium of claim 12, wherein the first user interface includes a graphical animation indicating that the first electronic device is ready to detect biometric information.

17. The non-transitory computer-readable storage medium of claim 16, wherein the one or more programs further include instructions for:
while displaying the second user interface and recording the biometric information, displaying a visual representation of the recorded biometric information, wherein the recorded biometric information is filtered and scaled such that the visual representation of the recorded biometric information can be displayed within the graphical animation.

18. The non-transitory computer-readable storage medium of claim 12, wherein the second user interface includes a graphical representation that corresponds to a visualization of the biometric information from the recorded biometric information and a timer indicating an amount of time remaining to complete the recording of the biometric information.

19. The non-transitory computer-readable storage medium of claim 12, wherein the second criterion is met when an amount of detected movement of the first electronic device is below the predetermined threshold.

20. The non-transitory computer-readable storage medium of claim 12, wherein the second criterion is met when an amount of detected movement of the first input is below the predetermined threshold.

21. The non-transitory computer-readable storage medium of claim 12, wherein the one or more programs further include instructions for:
after taking a first recording of first biometric information and a second recording of second biometric information different from the first biometric information, transmitting, to a second electronic device, the recorded first biometric information and the recorded second biometric information.

22. The non-transitory computer-readable storage medium of claim 12, wherein the indication of progress is a countdown timer.

23. A method, comprising:
at a first electronic device with a display and one or more input devices including a biometric sensor:
displaying, on the display, a first user interface indicating that the first electronic device is ready to detect biometric information;
detecting a first input with the biometric sensor, wherein the first input satisfies a first set of criteria, the first set of criteria including a first criterion that is satisfied when the first input remains in contact with the biometric sensor for a threshold period of time, and a second criterion that is satisfied when an amount of movement is below a predetermined threshold;

in response to detecting the first input with the biometric sensor:
  starting to record biometric information detected by the biometric sensor; and
  displaying, on the display, a second user interface that is different from the first user interface, wherein the second user interface includes an indication of progress in recording the biometric information;
after recording at least a portion of the biometric information, detecting, via the one or more input devices, that the first set of criteria are no longer met;
in response to detecting that the first criterion is no longer met, replacing display of the second user interface with the first user interface; and
in response to detecting that the second criterion is no longer met, resetting the indication of progress in recording the biometric information and maintaining display of the second user interface.

24. The method of claim 23, wherein the recorded biometric information includes an electrocardiogram recording derived from the biometric information detected by the biometric sensor.

25. The method of claim 23, further comprising:
prior to displaying the first user interface, displaying a home user interface that includes an application affordance corresponding to a health monitoring application;
detecting, via the one or more input devices, a user activation of the application affordance; and
in response to detecting the user activation of the application affordance, displaying, on the display, the first user interface.

26. The method of claim 23, wherein the biometric sensor is a contact-based sensor.

27. The method of claim 23, wherein the first user interface includes a graphical animation indicating that the first electronic device is ready to detect biometric information.

28. The method of claim 27, further comprising:
while displaying the second user interface and recording the biometric information, displaying a visual representation of the recorded biometric information, wherein the recorded biometric information is filtered and scaled such that the visual representation of the recorded biometric information can be displayed within the graphical animation.

29. The method of claim 23, wherein the second user interface includes a graphical representation that corresponds to a visualization of the biometric information from the recorded biometric information and a timer indicating an amount of time remaining to complete the recording of the biometric information.

30. The method of claim 23, wherein the second criterion is met when an amount of detected movement of the first electronic device is below the predetermined threshold.

31. The method of claim 23, wherein the second criterion is met when an amount of detected movement of the first input is below the predetermined threshold.

32. The method of claim 23, further comprising:
after taking a first recording of first biometric information and a second recording of second biometric information different from the first biometric information, transmitting, to a second electronic device, the recorded first biometric information and the recorded second biometric information.

33. The method of claim 23, wherein the indication of progress is a countdown timer.

* * * * *